(12) United States Patent
Yang et al.

(10) Patent No.: US 10,752,673 B2
(45) Date of Patent: Aug. 25, 2020

(54) HIGH-THROUGHPUT SCREENING OF FUNCTIONAL ANTIBODY FRAGMENTS, IMMUNOCONJUGATE COMPRISING THE SAME, AND ADAPTOR-DRUG CONJUGATE FOR SCREENING

(71) Applicant: Academia Sinica, Taipei (TW)

(72) Inventors: An-Suei Yang, Emeryville, CA (US); Hong-Sen Chen, Taipei (TW); Chung-Ming Yu, Taipei (TW); Shin-Chen Hou, Taipei (TW); Wei-Ying Kuo, Taipei (TW); Yi-Kai Chiu, Taipei (TW); Yueh-Liang Tsou, Taipei (TW); Hung-Ju Hsu, Taipei (TW); Hwei-Jiung Wang, Taipei (TW); Shih-Hsien Chuang, New Taipei (TW); Chao-Pin Lee, New Taipei (TW)

(73) Assignee: ACADEMIA SINICA, Taipei (TW)

( * ) Notice: Subject to any disclaimer, the term of this patent is extended or adjusted under 35 U.S.C. 154(b) by 184 days.

(21) Appl. No.: 15/619,835

(22) Filed: Jun. 12, 2017

(65) Prior Publication Data
US 2017/0355750 A1    Dec. 14, 2017

Related U.S. Application Data

(60) Provisional application No. 62/348,860, filed on Jun. 11, 2016.

(51) Int. Cl.
| | |
|---|---|
| *A61K 39/395* | (2006.01) |
| *A61K 39/00* | (2006.01) |
| *A61K 39/02* | (2006.01) |
| *C07K 16/00* | (2006.01) |
| *A61K 47/68* | (2017.01) |
| *A61P 35/00* | (2006.01) |
| *C07K 16/32* | (2006.01) |
| *C07K 19/00* | (2006.01) |

(52) U.S. Cl.
CPC ........ *C07K 16/005* (2013.01); *A61K 47/6817* (2017.08); *A61K 47/6829* (2017.08); *A61K 47/6851* (2017.08); *A61P 35/00* (2018.01); *C07K 16/32* (2013.01); *C07K 19/00* (2013.01); *A61K 2039/505* (2013.01); *C07K 2317/10* (2013.01); *C07K 2317/35* (2013.01); *C07K 2317/55* (2013.01); *C07K 2317/622* (2013.01); *C07K 2317/73* (2013.01); *C07K 2317/77* (2013.01); *C07K 2317/92* (2013.01); *C07K 2317/94* (2013.01); *C07K 2319/04* (2013.01); *C07K 2319/55* (2013.01)

(58) Field of Classification Search
CPC ............ A61K 47/6851; A61K 47/6829; A61K 47/6817
USPC ......... 424/130.1, 133.1, 134.1, 138.1, 184.1, 424/234.1, 236.1
See application file for complete search history.

(56) References Cited

PUBLICATIONS

Yu et al. "Rationalization and Design of the Complementarity Determining Region Sequences in an Antibody-Antigen Recognition Interface", vol. 7, Issue 3, Mar. 2012, pp. 1-15.
Hou et al. "High throughput cytotoxicity screening of anti-HER2 immunotoxins conjugated with antibody fragments fro phagedisplayed synthetic antibody libraries", Scientific Reports, Aug. 23, 2016.
Chen et al. "Predominant structural configuration of natural antibody repertoires enables potent antibody responses against protein antigens", Scientific Reports, Jul. 23, 2015.

*Primary Examiner* — Rodney P Swartz

(57) ABSTRACT

Disclosed herein are methods for high-throughput screening of a functional antibody fragment for an immunoconjugate that targets a protein antigen. The method combines a phage-displayed synthetic antibody library and high-throughput cytotoxicity screening of non-covalently assembled immunotoxins or cytotoxic drug to identify highly functional synthetic antibody fragments for delivering toxin payloads.

11 Claims, 39 Drawing Sheets
(2 of 39 Drawing Sheet(s) Filed in Color)
Specification includes a Sequence Listing.

HIGH-THROUGHPUT SCREENING OF FUNCTIONAL ANTIBODY FRAGMENTS, IMMUNOCONJUGATE COMPRISING THE SAME, AND ADAPTOR-DRUG CONJUGATE FOR SCREENING

CROSS-REFERENCE TO RELATED APPLICATION

This application relates to and claims the benefit of U.S. Provisional Application No. 62/348,860, filed Jun. 11, 2016, the contents of said application are incorporated herein by reference in its entirety.

STATEMENT REGARDING PRIOR DISCLOSURES BY THE INVENTOR OR A JOINT INVENTOR UNDER 37 C.F.R. 1.77(B)(6)

Most of the subject matter of the invention described in the present application was published by the inventors, An-Suei Yang, Shin-Chen Hou, Hong-Sen Chen, and Chung-Ming Yu in an article titled "HIGH THROUGHPUT CYTOTOXICITY SCREENING OF ANTI-HER2 IMMUNOTOXINS CONJUGATED WITH ANTIBODY FRAGMENTS FROM PHAGE-DISPLAYED SYNTHETIC ANTIBODY." The article was published on Aug. 23, 2016 on Scientific Reports 6, Article number: 31878 (2016). The publication was made by and/or originated from all member of the inventive entity of the present invention I, and the entirety of this article is incorporated herein by reference. A copy of the article is provided in a concurrently filed Information Disclosure Statement pursuant to the guidance of 78 Fed. Reg. 11076 (Feb. 14, 2013).

BACKGROUND OF THE INVENTION

1. Field of the Invention

The present disclosure relates to method of screening of functional antibody fragment.

2. Description of Related Art

Immunoconjugates are becoming a mainstay in antibody-based therapeutics. In particular, immunoconjugates with antibody fragments as targeting modules and protein toxins as therapeutic payloads (i.e., immunotoxins), instead of chemo-toxins as in ADCs, have made a promising class of anti-cancer therapeutics. The first therapeutic application of protein toxin (diphtheria toxin) was approved by the US Food and Drug Administration in 1999 for denileukin diftitox in treating cutaneous T-cell lymphoma. Currently, around 10 immunotoxins are under clinical development. While the side-effects of immunotoxins, including vascular leak syndrome and the immunogenicity due to the protein toxins, remain challenging, substantial progresses have nevertheless been made in decreasing immunogenicity and toxicity of the protein toxin payloads in the next-generation immunotoxins.

About half of current immunotoxins in human trails employ the cytotoxic payload derived from *Pseudomonas* Exotoxin A (PE). PE is an A-B class cytotoxic protein produced by *Pseudomonas aeruginosa* and is known to follow the common retrograde trafficking route to cytosol. The B subunit of PE binds to human cell surface receptor LRP1 or LRP1B (low density lipoprotein receptor-related protein 1/1B), inducing receptor-mediated endocytosis. In endosome, the peptide linkage between A-B subunits is cleaved by membrane-bound endoprotease furin. The cleaved toxin trafficked to Golgi binds to KDEL receptor, which subsequently transports the toxin to the endoplasmic reticulum (ER), where the protein disulfide isomerase (PDI) cleaves the disulfide bond linking the A-B subunits and only the A subunit of the PE is transported to cytosol, perhaps through the Sec61 translocon. In cytosol, the A subunit catalyzes the inactivation of eukaryotic elongation factor 2 (eEF2) by transferring an ADP-ribosyl group from NAD+ to the highly conserved post-translationally modified diphthamide-histidine residue on eEF2. The inactivation of eEF2 arrests the protein synthesis machinery, resulting in apoptosis of the cell. It has been estimated that one molecule of the PE A subunit in cytosol is sufficient to induce apoptosis of the cell. By the same token, immunotoxin composed of the A subunit of PE and an antibody fragment targets a specific cell surface antigen through the antibody-antigen interaction. However, only when the immunotoxin is internalized and adequately processed as the consequence of the antibody-antigen interaction, the A subunit of PE is able to effectively exploit the same retrograde trafficking route as the native toxin and kills the cell with potent cytotoxicity.

The cytotoxicity of an immunotoxin is effectuated by the antibody-based targeting module inducing receptor-mediated endocytosis and delivering the toxin payload to proper subcellular locations for optimal cytotoxicity. Receptor-mediated endocytosis, especially via clathrin-coated pits, has been well established as a mechanism to control the receptor-dependent signaling by adjusting the cell surface receptor distributions according to the overall activation state of the cells. Immunotoxin internalization occurs when antibody-receptor interaction induces the receptor-mediated endocytosis through various endocytic mechanisms. Although antibody-mediated receptor crosslinking and antibody binding location on the receptor have been demonstrated as predominant determinants affecting the efficiency of immunoconjugate-induced endocytosis, the mechanisms for the internalization of the immunoconjugates and the delivery of the toxin payloads remain limitedly understood.

In view of the foregoing, the discovery of suitable antibodies for delivering cytotoxic payloads through interacting with a specific cell surface target has relied on screening of large number of candidate antibodies, which is both time consuming and labor intensive. Accordingly, there exists a need in the art for providing a method for high-throughput screening of functional antibody fragments for use as the targeting module of an immunoconjugate.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a method for high-throughput screening of a functional antibody fragment for an immunoconjugate that targets a protein antigen.

According to one embodiment of the present disclosure, the method comprises the steps of, (a) providing a phage-displayed synthetic single-chain variable fragment (scFv) library that comprises a plurality of phage-displayed scFvs, wherein the VH domain of each of the plurality of phage-displayed scFvs has a binding affinity to protein A, and the VL domain of each of the plurality of phage-displayed scFvs has a binding affinity to protein L;

(b) selecting, from the phage-displayed synthetic scFv library of the step (a), a plurality of phages that express scFvs specific for the protein antigen;

(c) preparing a plurality of secreted scFvs respectively from the plurality of phages selected in the step (b);

(d) allowing the formation of a plurality of scFv-adaptor-drug complexes by contacting an adaptor-drug conjugate with the plurality of secreted scFvs prepared in the step (c), respectively, wherein the adaptor-drug conjugate comprises a drug and an adaptor that comprises at least one AL module comprising a protein A fragment at the N-terminus and a protein L fragment at the C-terminus;

(e) culturing a plurality of cells presenting the protein antigen in the presence of the plurality of scFv-adaptor-drug complexes formed in the step (d), respectively;

(f) determining the respective efficacy of the plurality of scFv-adaptor-drug conjugates in the plurality of cells presenting the protein antigen cultured in the step (e);

(g) selecting the functional antibody fragment for the immunoconjugate based on the results determined in the step (f), wherein the respective scFv of one or more scFv-adaptor-drug complexes of the plurality of scFv-adaptor-drug complexes that exhibit superior efficacy over the other scFv-adaptor-drug complexes of the plurality of scFv-adaptor-drug complexes—is selected as the functional antibody fragment for the immunoconjugate.

According to some embodiments, the protein antigen is human epidermal growth factor receptor 2 (HER2), maltose-binding protein, bovine serum albumin, human serum albumin, lysozyme, interleukin-1 beta (IL-1β), hemagglutinin of influenza virus, vascular endothelial growth factor (VEGF), epidermal growth factor receptor 1 (EGFR1), epidermal growth factor receptor 3 (EGFR3), glucagon receptor, programmed death-ligand 1 (PD-L1), sialic acid binding Ig-like lectin 3 (SIGLEC 3) or rituximab. In certain embodiments, the protein antigen is HER2.

In certain optional embodiments, the drug comprises a drug motif, which is an immunotoxin, immunoliposome, or cytotoxic drug. In some embodiments, the drug motif is an immunotoxin, such as an exotoxin. For example, the exotoxin is or is derived from *Pseudomonas* Exotoxin (PE) A. In certain embodiments, the immunotoxin comprises a truncated form of PE A subunit toxin. In further embodiments, the drug further comprises an endoplasmic reticulum (ER) retention motif at the C-terminus of the PE A subunit toxin. For example, the ER retention motif comprises the sequence of KDEL.

In some optional embodiments, the step (f) is determined by measuring the respective cell viability of the plurality of cells presenting the protein antigen cultured in the step (e).

In another aspect, the present disclosure is directed to a method for high-throughput screening of a functional antibody fragment for an immunoconjugate that targets human epidermal growth factor receptor 2 (HER2).

According to various embodiments, the method comprises the steps of, (a) providing a phage-displayed synthetic single-chain variable fragment (scFv) library that comprises a plurality of phage-displayed scFvs, wherein the VH domain of each of the plurality of phage-displayed scFvs has a binding affinity to protein A, and the VL domain of each of the plurality of phage-displayed scFvs has a binding affinity to protein L;

(b) selecting, from the phage-displayed synthetic scFv library of the step (a), a plurality of phages that express scFvs specific for HER2;

(c) preparing a plurality of secreted scFvs respectively from the plurality of phages selected in the step (b);

(d) allowing the formation of a plurality of scFv-adaptor-drug complexes by contacting an adaptor-drug conjugate with the plurality of secreted scFvs prepared in the step (c), respectively, wherein the adaptor-drug conjugate comprises (i) a protein drug that comprises an exotoxin, and (ii) an adaptor that comprises at least one AL module comprising a protein A fragment at the N-terminus, a protein L fragment at the C-terminus, and a first polypeptide linker connecting the protein A fragment and the protein L fragment;

(e) culturing a plurality of cells presenting HER2 in the presence of the plurality of scFv-adaptor-drug complexes formed in the step (d), respectively;

(f) determining the respective cell viability of the plurality of scFv-adaptor-drug complexes in the plurality of cells presenting HER2 cultured in the step (e);

(g) selecting the functional antibody fragment for the immunoconjugate based on the results determined in the step (f), wherein the respective scFv of one or more scFv-adaptor-drug complexes of the plurality of scFv-adaptor-drug complexes that resulted in lower cell viability than the other scFv-adaptor-drug complexes of the plurality of scFv-adaptor-drug complexes is selected as the functional antibody fragment for the immunoconjugate.

In certain optional embodiments, the exotoxin is or is derived from *Pseudomonas* Exotoxin (PE) A; for example, the protein drug comprises a truncated form of PE A subunit toxin. In further embodiments, the protein drug further comprises an endoplasmic reticulum (ER) retention motif at the C-terminus of the PE A subunit toxin. For example, the ER retention motif comprises the sequence of KDEL.

In yet another aspect, the present disclosure is directed to an immunoconjugate that targets a protein antigen or a pharmaceutical composition comprising the same.

According to some embodiments, the immunoconjugate comprises a drug and a targeting module, wherein the targeting module comprises a functional antibody fragment selected using the method according to any aspect/embodiment of the present disclosure. Also, the drug comprises a drug motif, which can be an immunotoxin, immunoliposome, or cytotoxic drug.

As to the pharmaceutical composition according to embodiments of the present disclosure, the pharmaceutical composition comprises an effective amount of the immunoconjugate and a pharmaceutically acceptable excipient for the immunoconjugate.

In still another aspect, the present disclosure is directed to a method for treating a subject in need thereof, comprising the step of administering to the subject an effective amount of an immunoconjugate or pharmaceutical composition according to any aspect/embodiment of the present disclosure.

In still yet another aspect, the present disclosure is directed to an adaptor-drug conjugate for use in the high-throughput screening method according to any aspect/embodiment of the present disclosure.

According to some embodiments, the adaptor-drug conjugate comprises (1) an adaptor that comprises at least one AL module, wherein each AL module comprises a protein A fragment at the N-terminus, a protein L fragment at the C-terminus, and a first polypeptide linker connecting the protein A fragment and the protein L fragment; (2) a drug;

and (3) a second polypeptide linker connecting the drug to the C-terminus of the adaptor.

In certain optional embodiments, the drug comprises a drug motif, which can be an immunotoxin, immunoliposome, or cytotoxic drug. In some embodiments, the drug motif is an immunotoxin, such as an exotoxin. For example, the exotoxin is or is derived from *Pseudomonas* Exotoxin (PE) A. In certain embodiments, the immunotoxin comprises a truncated form of PE A subunit toxin. In further embodiments, the drug further comprises an endoplasmic reticulum (ER) retention motif at the C-terminus of the PE A subunit toxin. For example, the ER retention motif comprises the sequence of KDEL.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings. A brief description of the drawings is summarized below.

FIG. 9A: scFvs randomly selected from the top 25% of scFvs in Table 2 without histidine in the CDR-H3 sequence; FIG. 9B: scFvs randomly selected from the top 25% of scFvs in Table 2 with histidine(s) in the CDR-H3 sequence; FIG. 9C: scFvs randomly selected from the bottom 25% of scFvs in Table 2 without histidine in the CDR-H3 sequence; FIG. 9D: scFvs randomly selected from the bottom 25% of scFvs in Table 2 with histidine(s) in the CDR-H3 sequence.

The expression levels were analyzed by Western blot, where GAPDH was detected as internal control. The expression levels were measured with three independent experimental repeats.

Figure 12A:
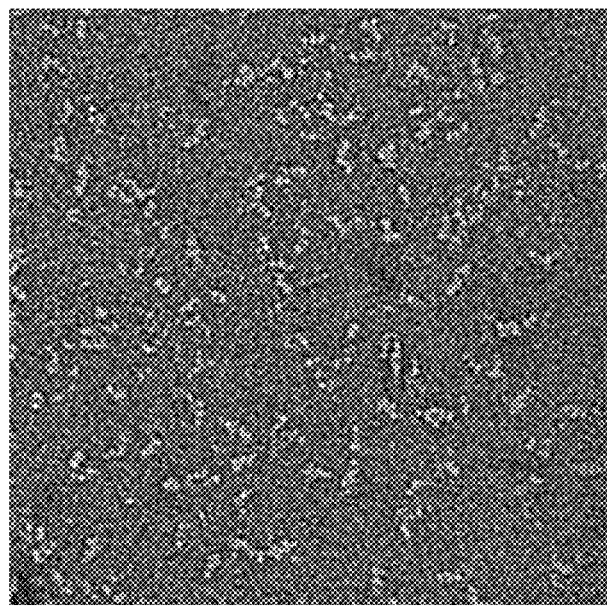
Figure 12B:
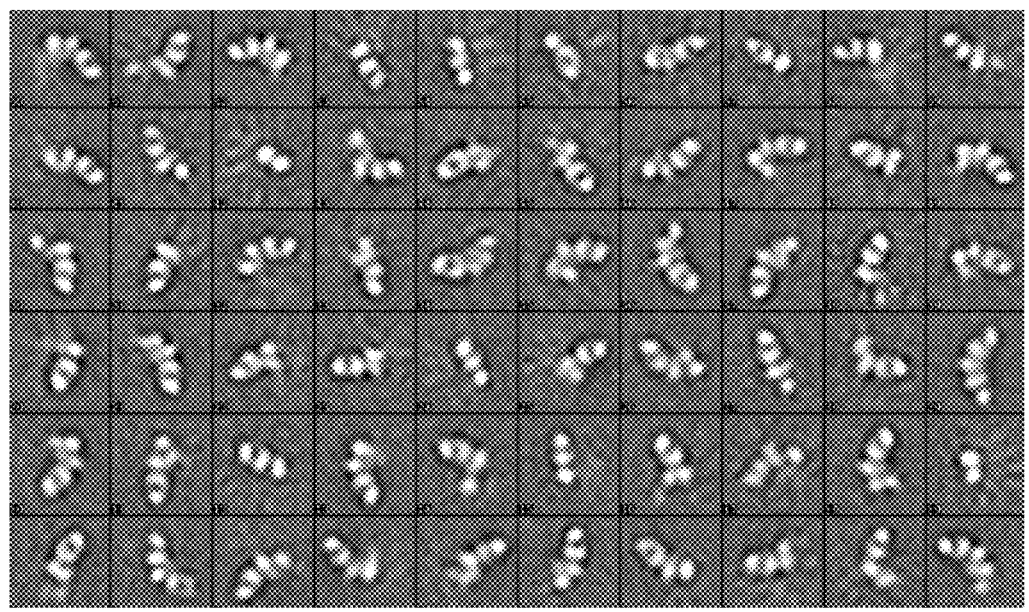
Figure 12C:
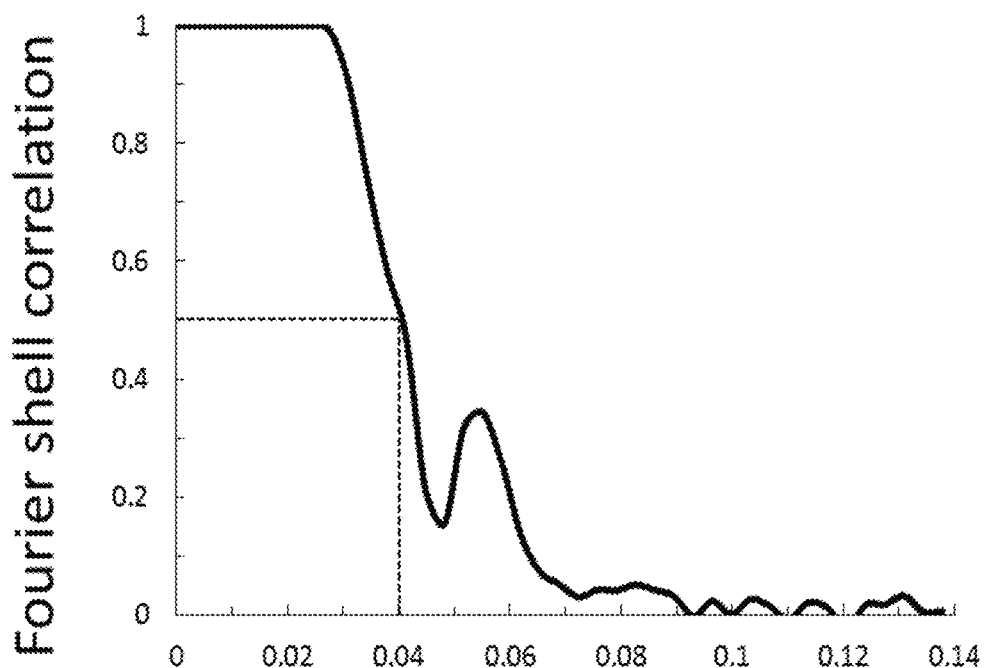

FIGS. 12A to 12C show the negative stain EM reconstruction of Fab(H32)-HER2-ECD complexes. FIG. 12A is a representative micrograph of negative stain EM of HER2 ECD-Fab(H32) complexes. FIG. 12B is a representative 2D class averages analyzed by ISAC software. FIG. 12C shows a Gold standard FSC curve of the 3D model with 0.5 cutoff marked by dash lines. Details of the EM structure determination are described in Methods.

Figure 13A:
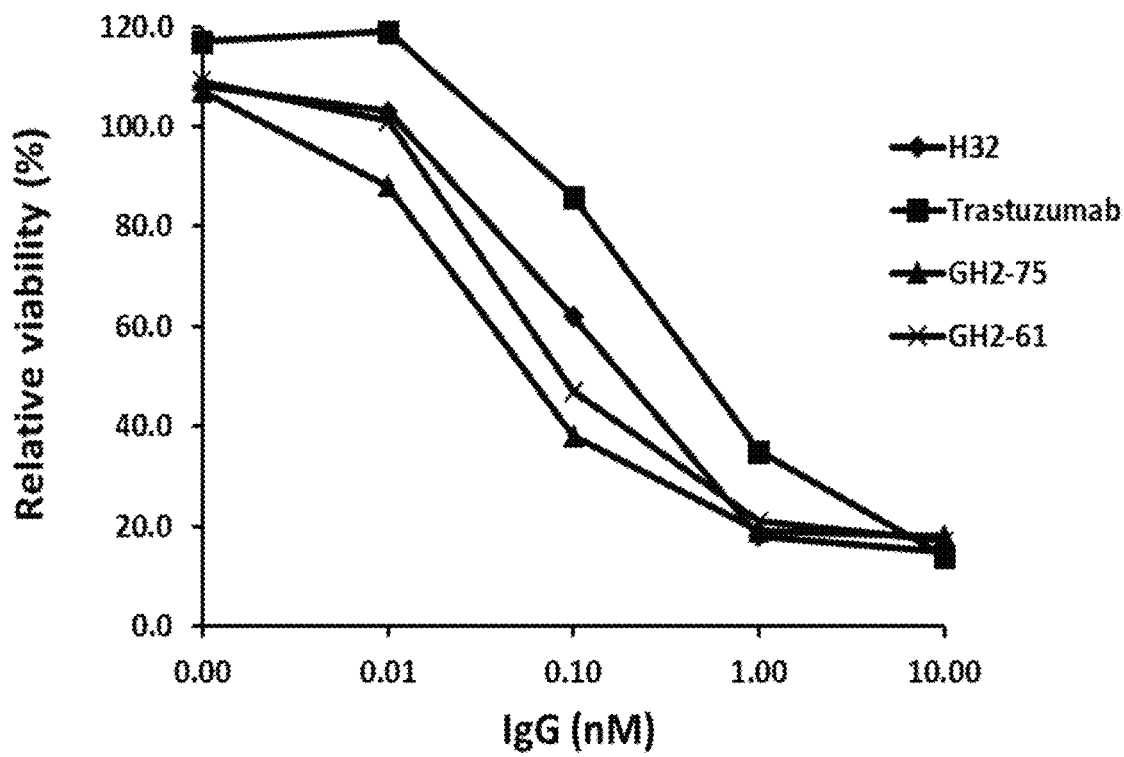
Figure 13B:
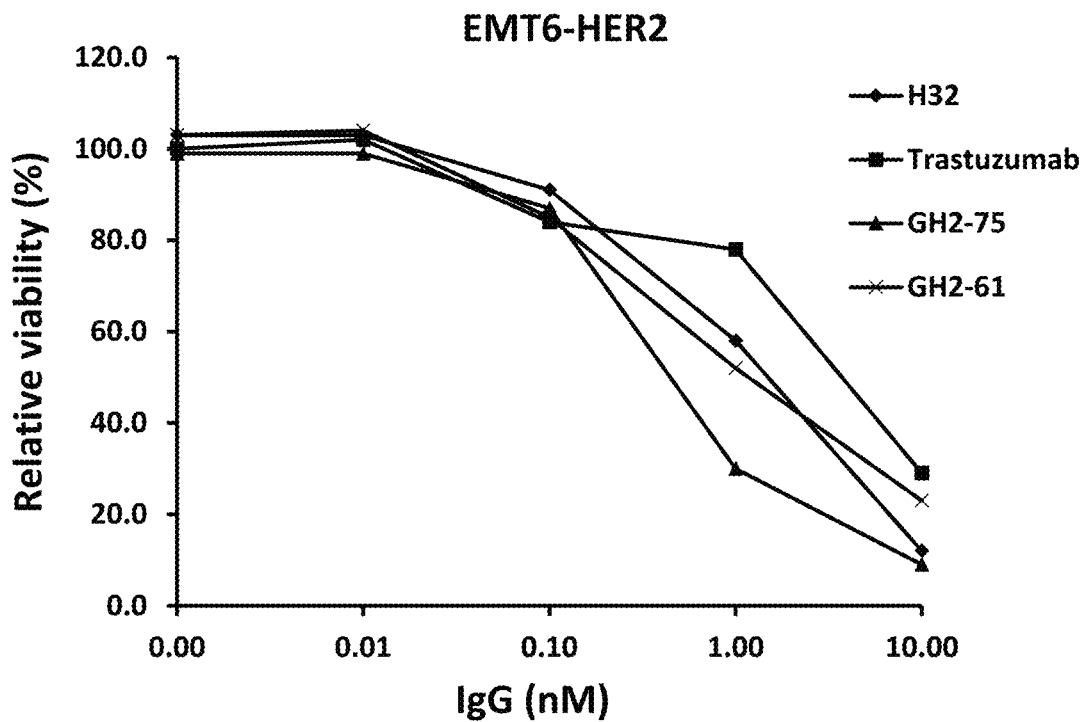
Figure 13C:
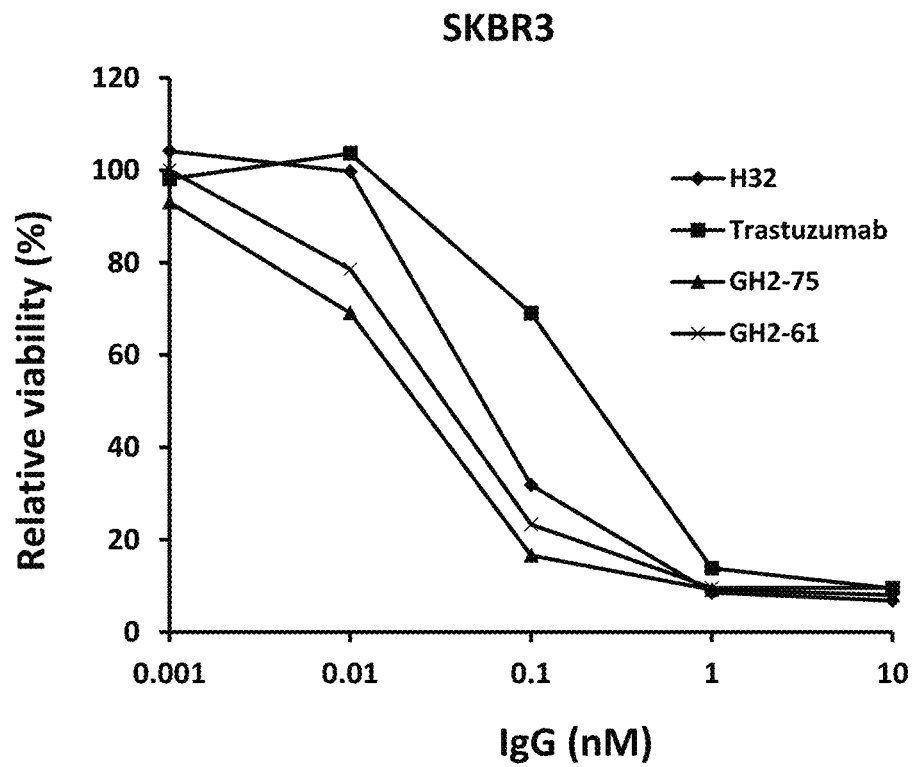

FIGS. 13A to 13C show that the non-covalently assembled IgG and AL1-PE38KDEL (i.e., IgG-AL1-PE38KDEL immunotoxin) can be potent immunotoxins to the human gastric cancer cell line N87 (FIG. 13A), the HER2-expressing mouse breast cancer cell line EMT6-HER2 (FIG. 13B), and the human breast cancer cell line SKBR3 cells (FIG. 13C).

Figure 14A:
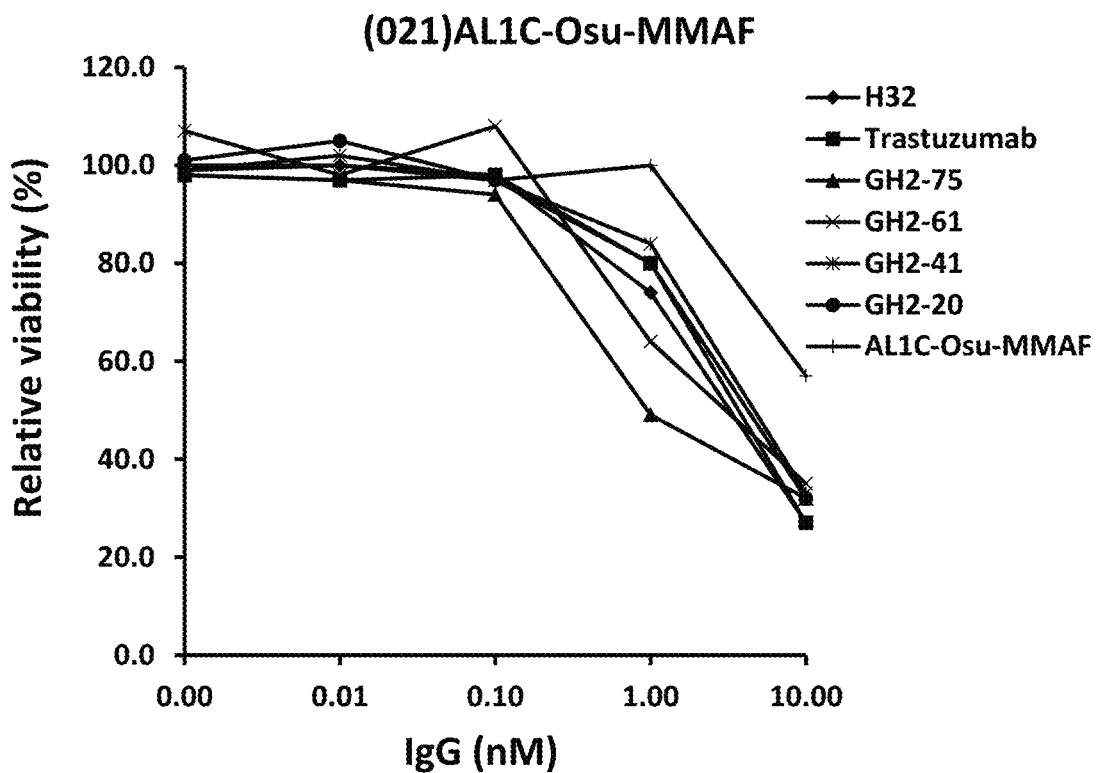
Figure 14B:
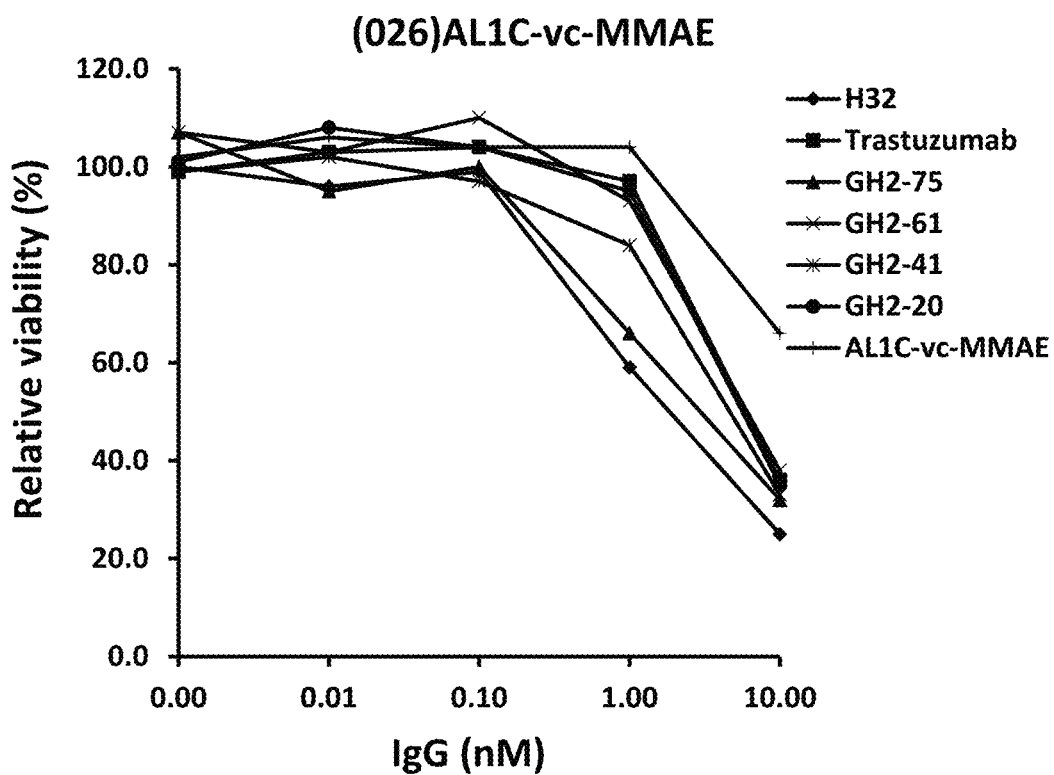
Figure 14C:
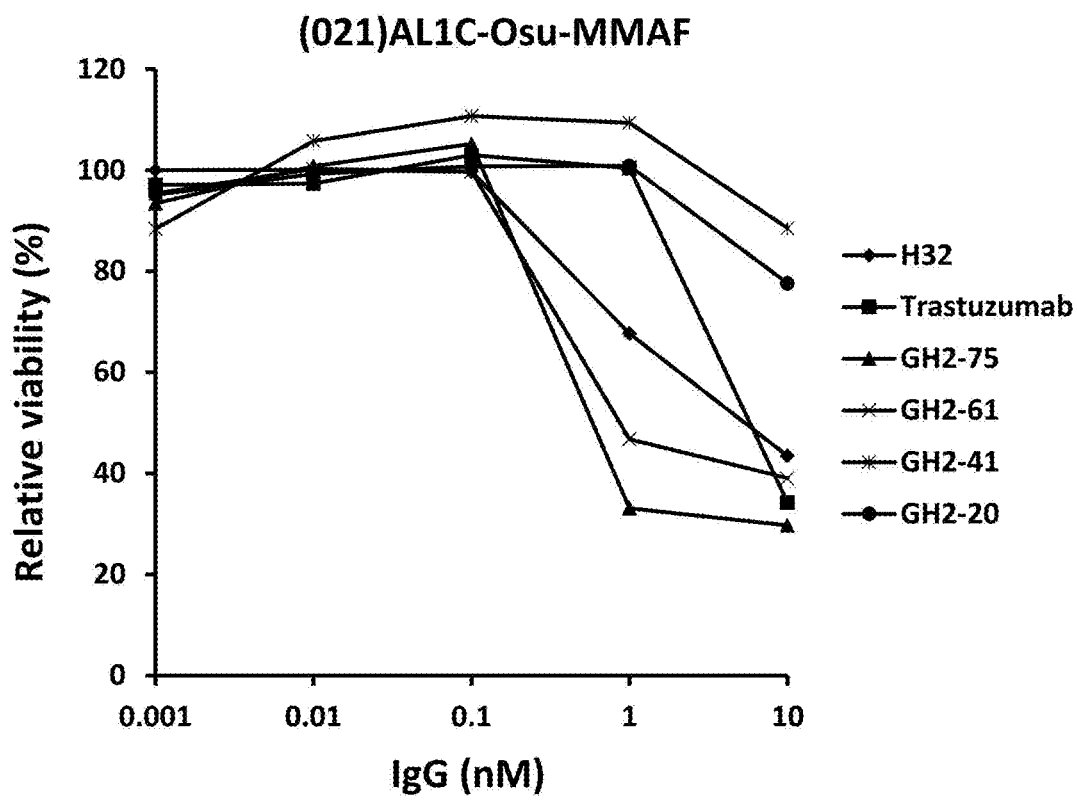
Figure 14D:
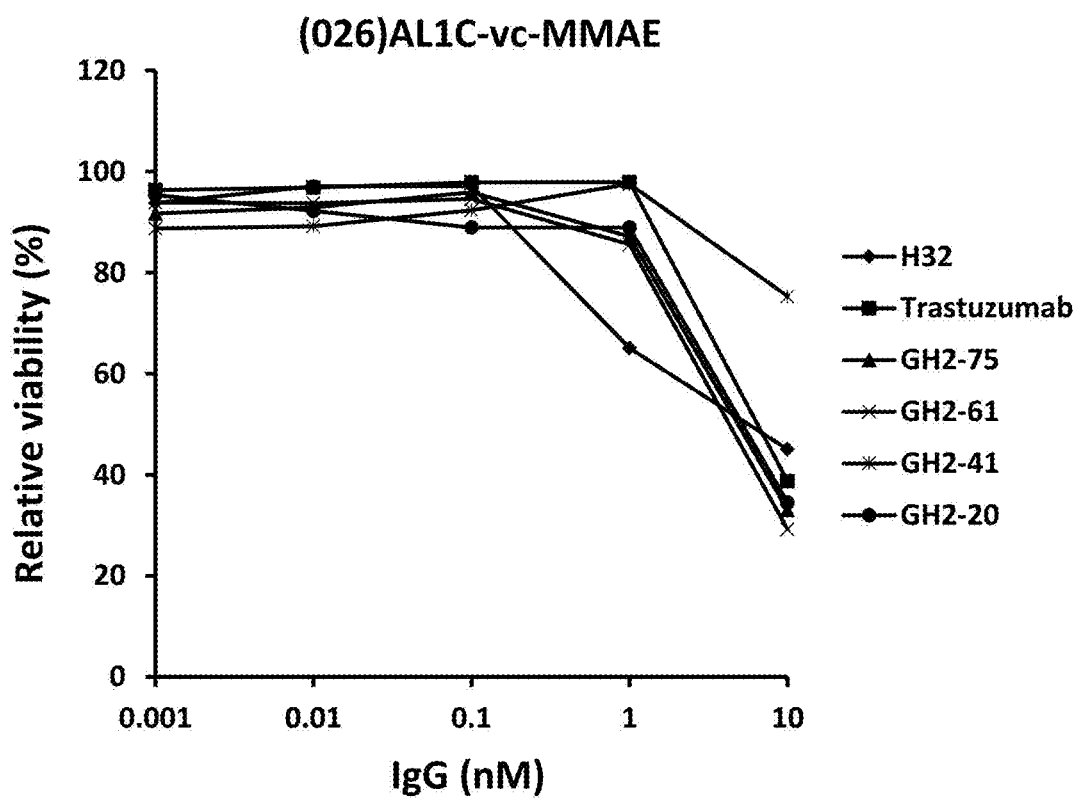

FIGS. 14A to 14D show the cytotoxicity of IgG bound with the adaptor-toxin fusion protein AL1C-Osu-MMAF/AL1C-vc-MMAE (i.e., IgGs-AL1C-Osu-MMAF (AL1C-021) and IgGs-AL1C-vc-MMAE (AL1C-026) complexes) to N87 cells (FIGS. 14A and 14B) and SKBR3 cells (FIGS. 14C and 14D).

Figure 15A:
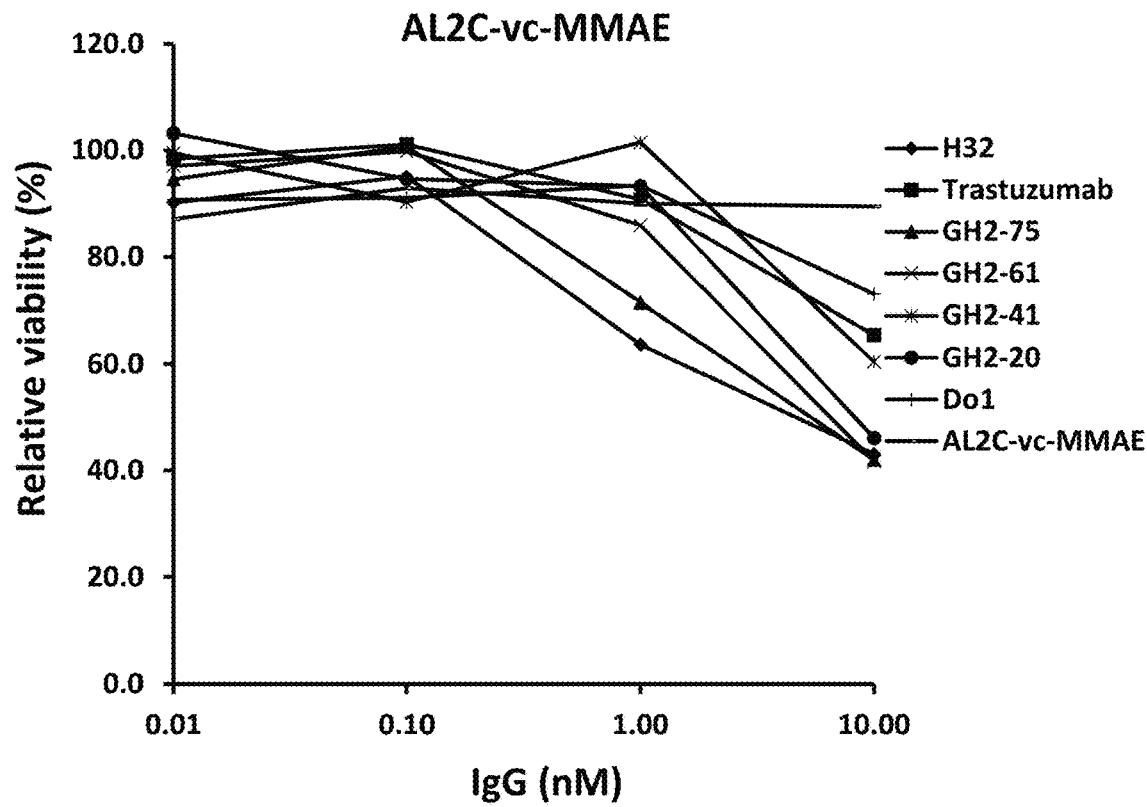
Figure 15B:
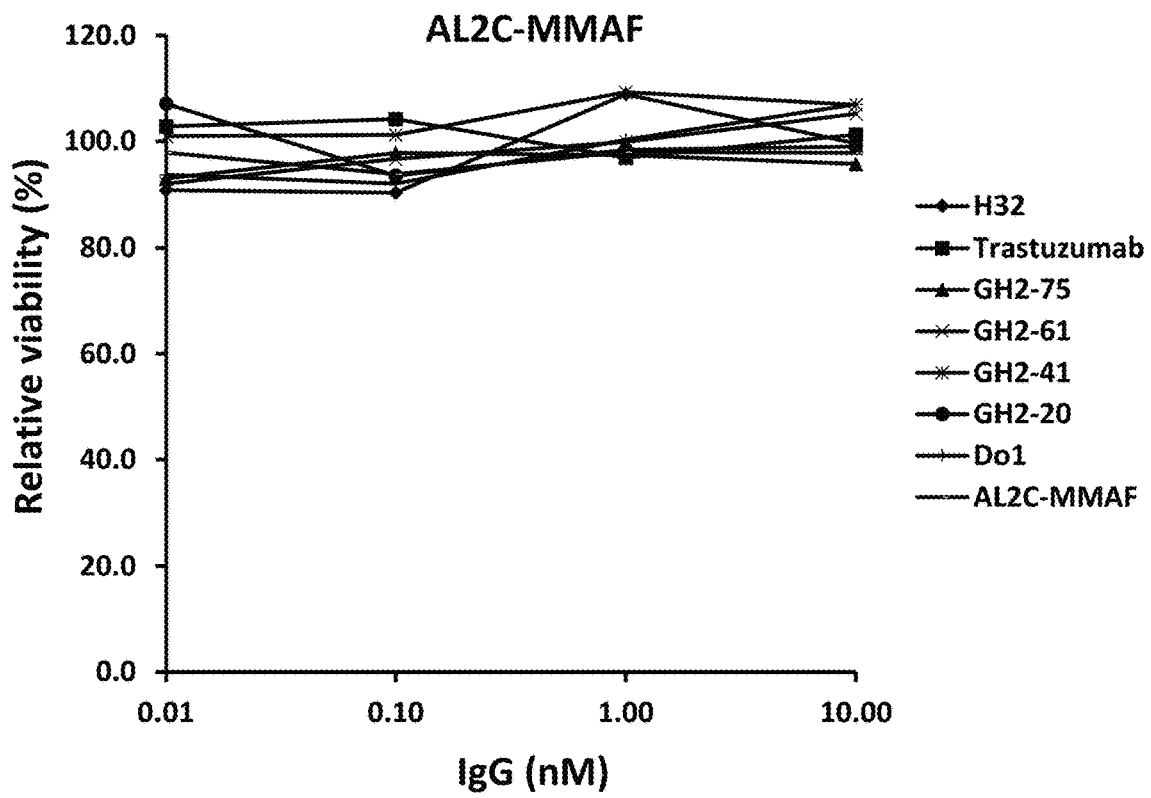
Figure 15C:
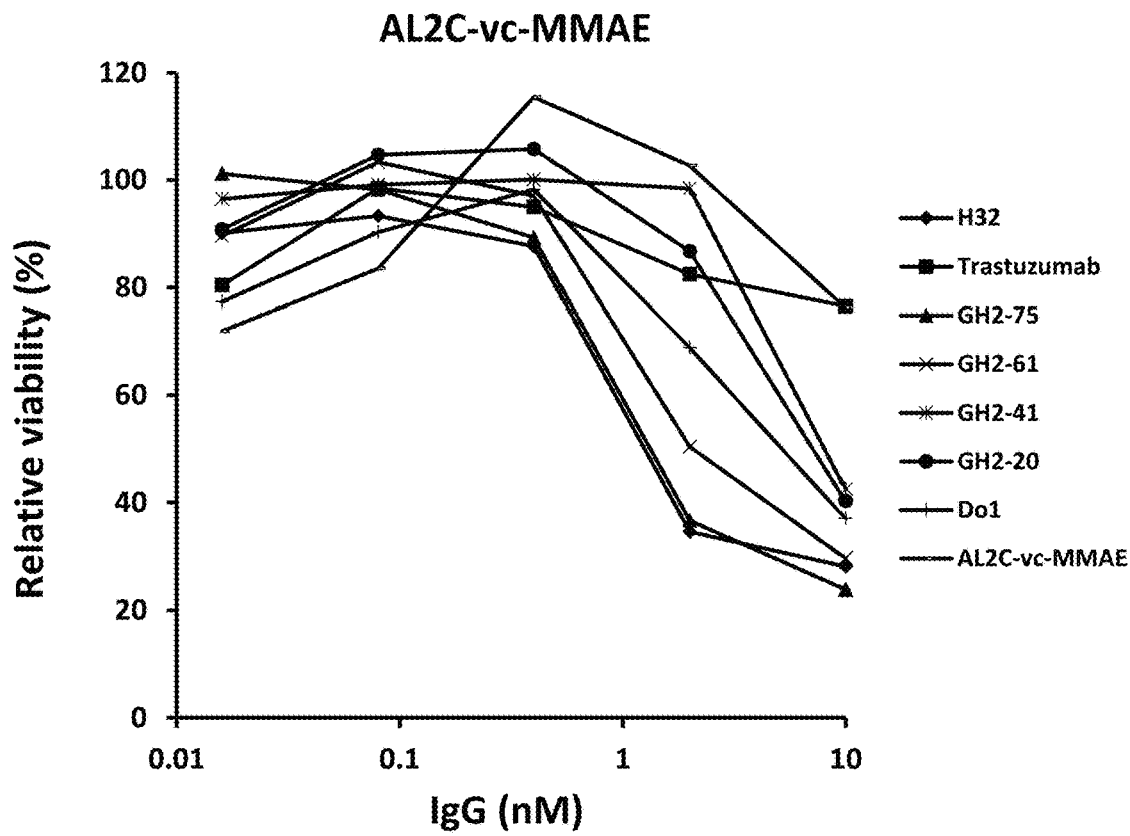
Figure 15D:
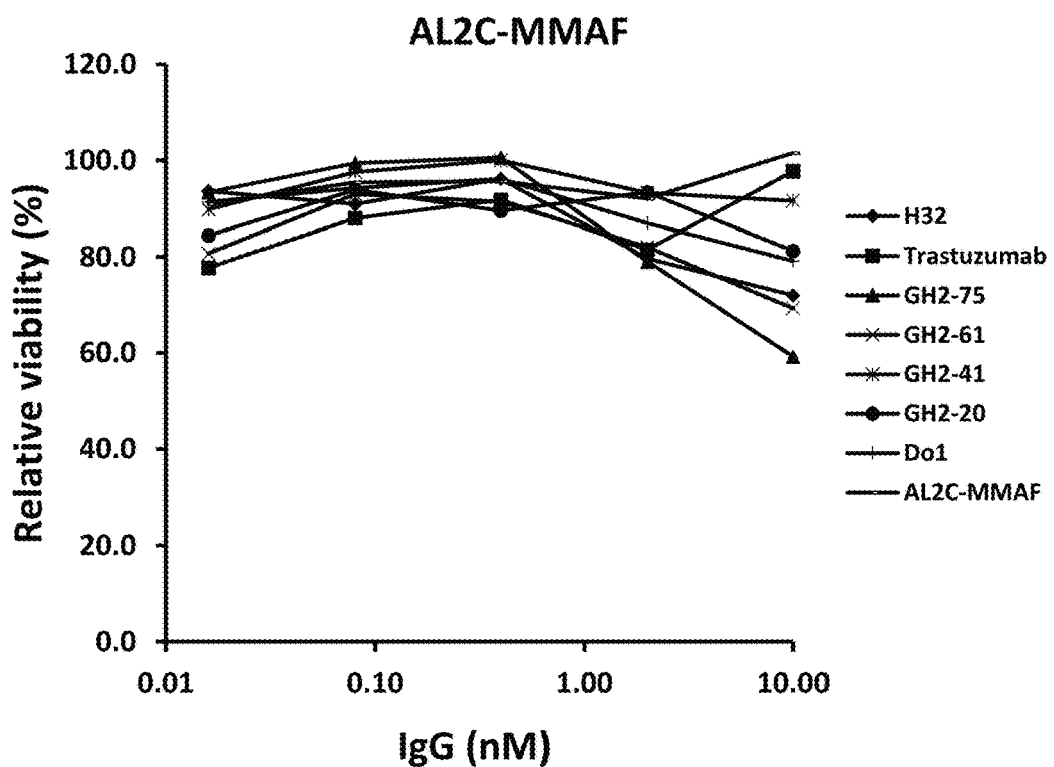

FIGS. 15A to 15D show the cytotoxicity of IgG bound with the adaptor-toxin fusion protein AL2C-vc-MMAE/AL2C-MMAF (i.e., IgGs-AL2C-vc-MMAE (AL2C-002) and IgGs-AL2C-MMAF (AL2C-004) complexes) to N87 cells (FIGS. 15A and 15B) and breast cancer BT474 cells (FIGS. 15C and 15D).

Figure 16A:
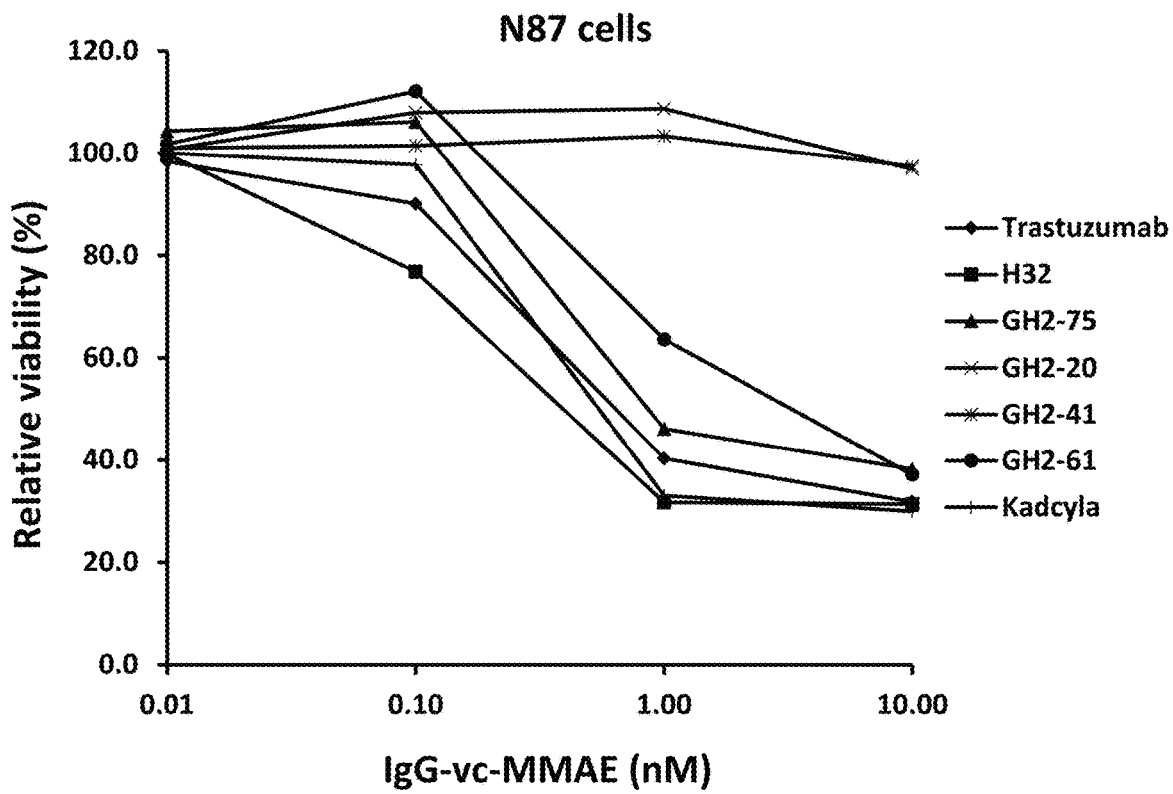
Figure 16B:
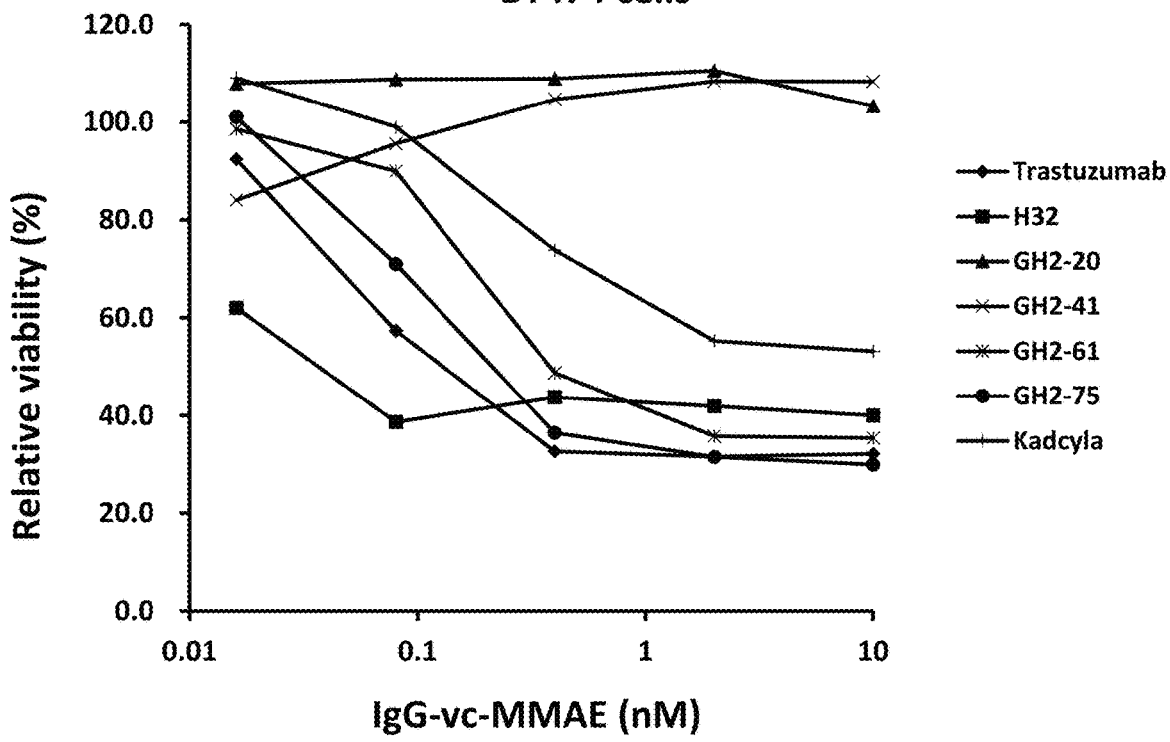

FIGS. 16A and 16B show the cytotoxicity of six anti-HER2 IgG-vc-MMAE conjugates to the gastric cancer N87 cells (FIG. 16A) and the breast cancer BT474 cells (FIG. 16B); KADCYLA, Herceptin-SMCC-DM1, was used as the positive control.

Figure 17A:
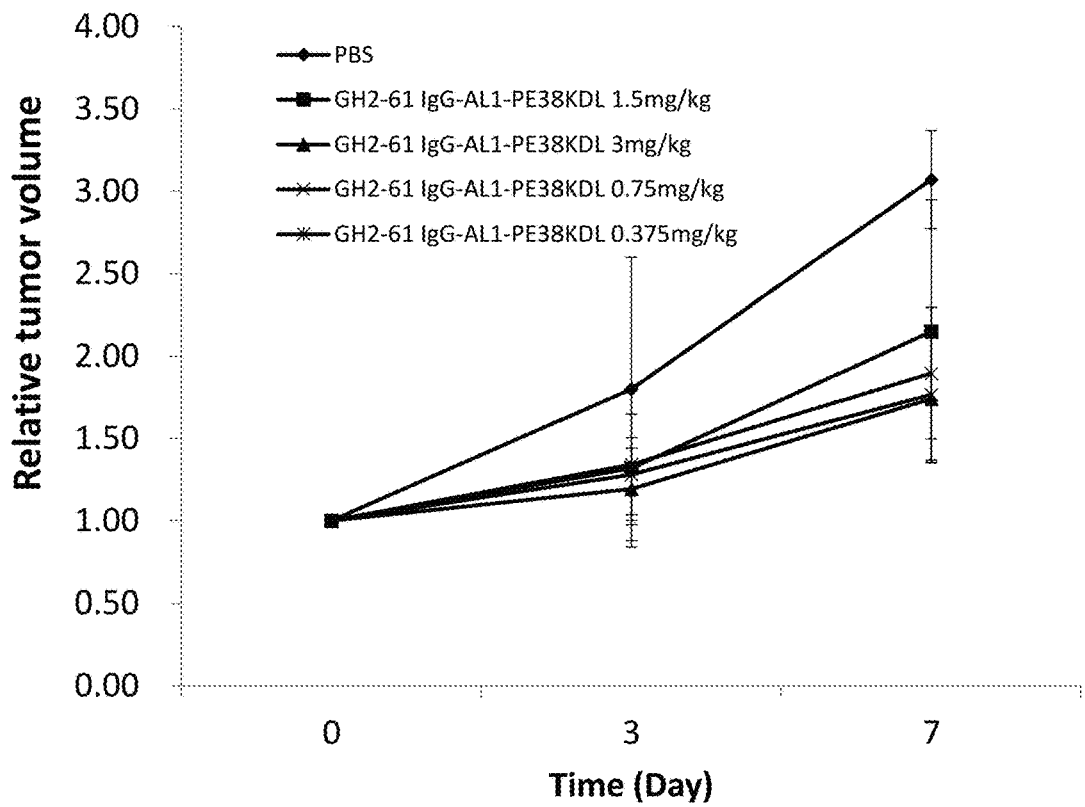
Figure 17B:
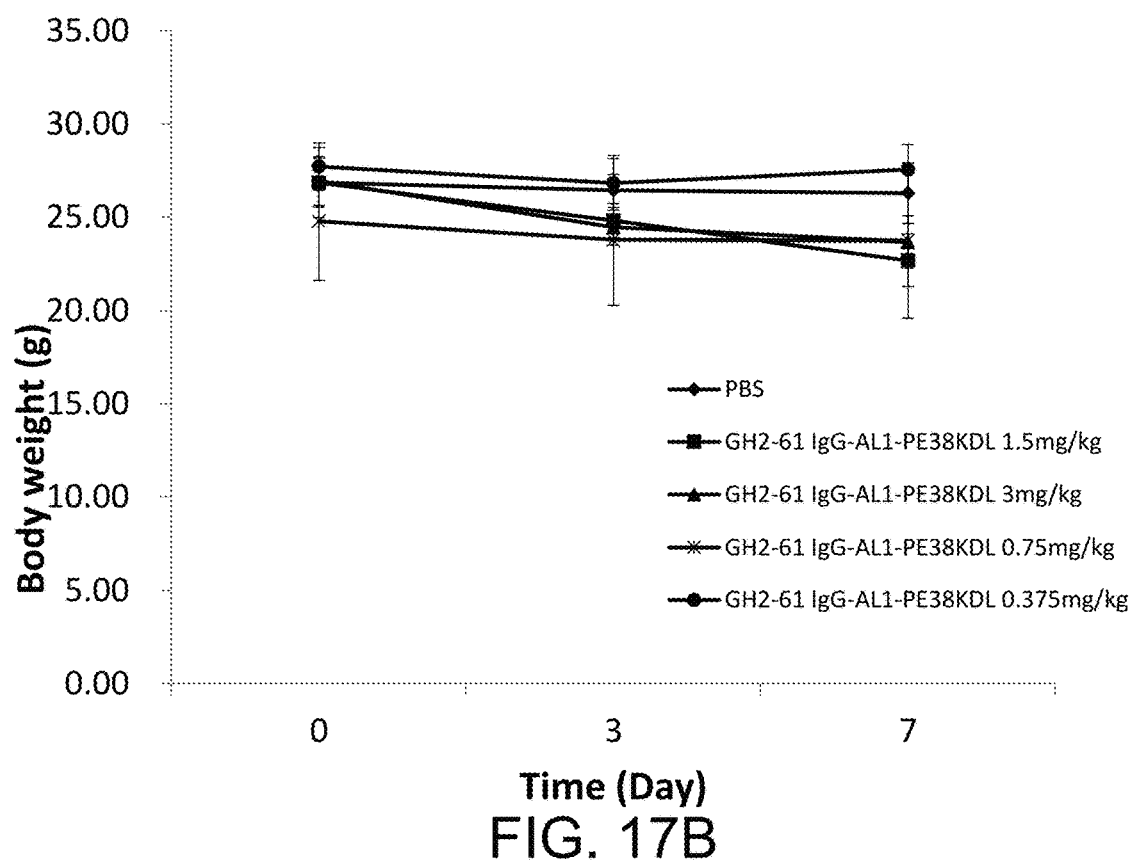

FIGS. 17A and 17B show the dose-dependent effect of GH2-61 IgG-AL1-PE38KDEL immunotoxins on tumor growth.

Figure 18A:
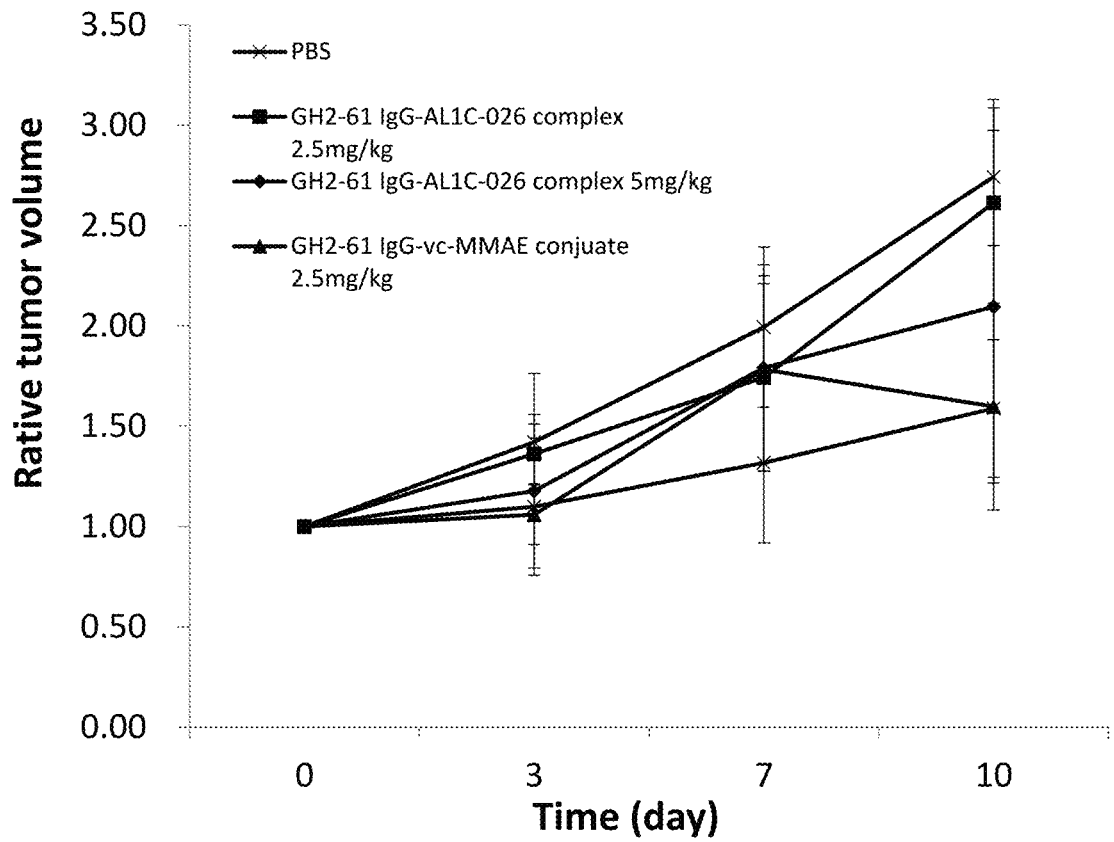
Figure 18B:
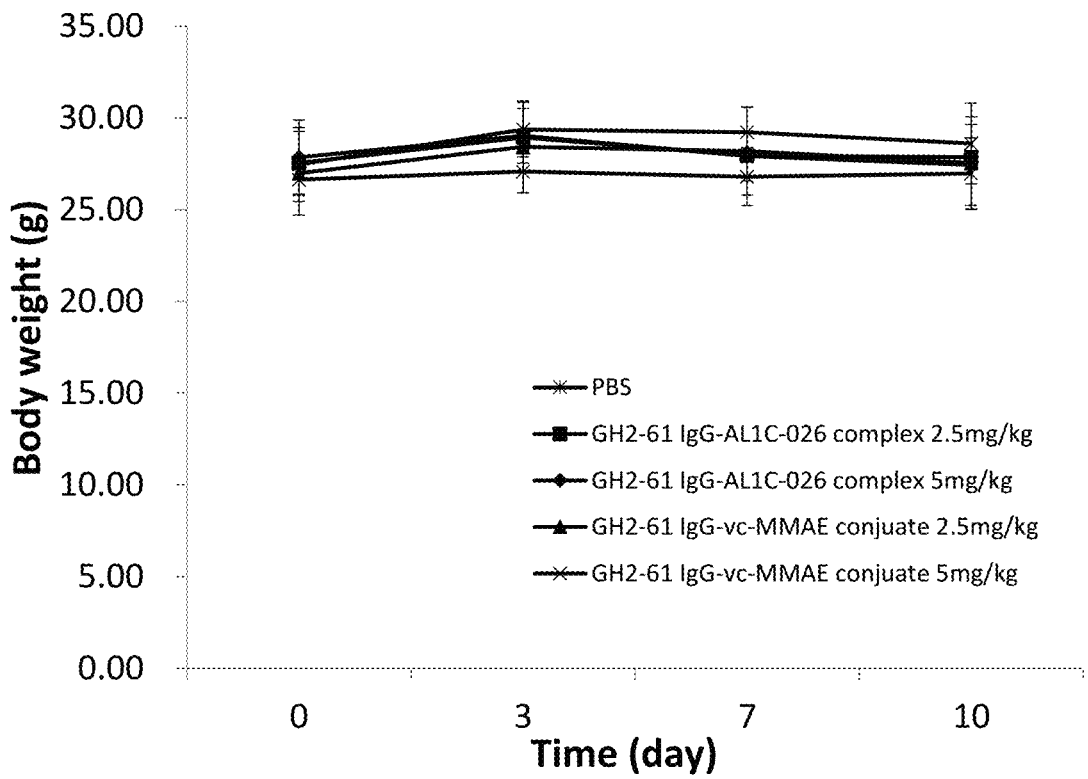

FIGS. 18A and 18B show the in vivo antitumor activity of GH2-61 IgG-vc-MMAE conjugates in N87 xenograft model.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleic acid sequence or a partial nucleic acid sequence encoding a protein that elicits an immune response, therefore encodes an "antigen" as that term is used herein. Furthermore, one skilled in the art will understand that an antigen needs not be encoded solely by a full length nucleic acid sequence of a gene; it can also be encoded by partial nucleic acid sequences of more than one gene and that these nucleic acid sequences are arranged in various combinations to elicit the desired immune response. Moreover, a skilled artisan will understand that an antigen needs not to be encoded by a "gene" at all; it is readily apparent that an antigen can be synthesized or can be derived from a biological sample. Such a biological sample can include, but is not limited to, a tissue sample, a tumor sample, a cell, or a biological fluid.

The term "antibody" is used in the broadest sense and specifically covers monoclonal antibodies (including full length monoclonal antibodies), polyclonal antibodies, multi-specific or multivalent antibodies (e.g., bi-specific antibodies), and antibody fragments so long as they exhibit the desired biological activity. "Antibody fragments" comprise a portion of a full-length antibody, generally the antigen binding or variable region thereof. Examples of antibody fragments include Fab, Fab', F(ab')2, and Fv fragments; diabodies; linear antibodies; single-chain antibody molecules; and multi-specific antibodies formed from antibody fragments.

The term "antibody library" refers to a collection of antibodies and/or antibody fragments displayed for screening and/or combination into full antibodies. The antibodies and/or antibody fragments may be displayed on a ribosome; on a phage; or on a cell surface, in particular a yeast cell surface.

As used herein, the term "single-chain variable fragment" or "scFv" is a fusion protein comprising the variable regions of the heavy (VH) and light chains (VL) of an immunoglobulin, in which the VH and VL are covalently linked to form a VH:VL heterodimer. The VH and VL are either joined directly or joined by a peptide-encoding linker, which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL-encoding sequences.

The term "complementarity determining region (CDR)" used herein refers to the hypervariable region of an antibody molecule that forms a surface complementary to the 3-dimensional surface of a bound antigen. Proceeding from N-terminus to C-terminus, each of the antibody heavy and light chains comprises three CDRs (CDR 1, CDR 2, and CDR3). A HLA-DR antigen-binding site, therefore, includes a total of six CDRs that comprise three CDRs from the variable region of a heavy chain and three CDRs from the variable region of a light chain. The amino acid residues of CDRs are in close contact with bound antigen, wherein the closest antigen contact is usually associated with the heavy chain CDR3.

The term "$EC_{50}$," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, the term "association rate constant ($k_{on}$)" refers to a value representing the intensity (degree) of association of the antibody with the target antigen thereof, which is determined based on the kinetics of the antigen-antibody reaction. The term "dissociation rate constant ($k_{off}$)" refers to a value representing the intensity (degree) of dissociation of the antibody from the target antigen thereof, which is determined based on the kinetics of the antigen-antibody reaction. The term "dissociation constant ($K_d$)" is calculated by dividing the "dissociation rate constant ($k_{off}$)" with the "association rate constant ($k_{on}$)." These constants are used as indexes representing the affinity of an antibody for its antigen and its activity neutralizing the antigen.

The term "phagemid" refers to a vector, which combines attributes of a bacteriophage and a plasmid. A bacteriophage is defined as any one of a number of viruses that infect bacteria.

The terms "nucleic acid sequence", "nucleotide sequence", "polynucleotide" or "nucleic acid" can be used interchangeably and are understood to mean, according to the present disclosure, either a double-stranded DNA, a single-stranded DNA or a product of transcription of said DNA (e.g., RNA molecule). It should also be understood that the present disclosure does not relate to genomic polynucleic acid sequences in their natural environment or natural state. The nucleic acid, polynucleotide, or nucleic acid sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

All degenerate nucleotide sequences are included within the scope of the invention as long as the peptide/polypeptide/protein (e.g., the present CDR) encoded by the nucleotide sequence maintains the desired activity or function. The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The terms "coding sequence" and "coding region" as used herein are interchangeable and refer to nucleotide sequences and nucleic acid sequences, including both RNA and DNA, that encode genetic information for the synthesis of an RNA, a protein, or any portion of an RNA or protein. Nucleotide sequences that are not naturally part of a particular organism's genome are referred to as "foreign nucleotide sequences", "heterologous nucleotide sequences", or "exogenous nucleotide sequences". "Heterologous proteins" are proteins encoded by foreign, heterologous, or exogenous nucleotide sequences and therefore are often not naturally expressed in the cell. A nucleotide sequence that has been isolated and then reintroduced into the same type (e.g., same species) of organism is not considered to be a naturally occurring part of a particular organism's genome and is therefore considered exogenous or heterologous.

"Percentage (%) sequence identity" with respect to any nucleotide sequence or amino acid sequence identified herein is defined as the percentage of nucleotide residues or amino acid residues in a candidate sequence that are identical with the nucleotide residues amino acid residues in the specific nucleotide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two nucleotide sequences was carried out by computer program Blastn (nucleotide-nucleotide BLAST) provided online by Nation Center for Biotechnology Information (NCBI). For purposes herein, sequence comparison between two amino acid sequences was carried out by computer program Blastp (protein-protein BLAST) provided online by Nation Center for Biotechnology Information (NCBI). The percentage sequence identity of a given sequence A to a subject sequence B (which can alternatively be phrased as a given sequence A that has a certain % sequence identity to a given sequence B) is calculated by the formula as follows:

$$\frac{X}{Y} \times 100\%$$

where X is the number of nucleic acid or amino acid residues scored as identical matches by the sequence alignment program BLAST in that program's alignment of A and B, and where Y is the total number of nucleic acid or amino acid residues in the subject sequence B.

The phrase "pharmaceutically acceptable excipient" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each excipient must be "acceptable" in the sense of being compatible with the other ingredients of the formulation. The pharmaceutical formulation contains an active ingredient of the invention in combination with one or more pharmaceutically acceptable ingredients. The excipient can be in the form of a solid, semi-solid, or liquid diluent, cream or a capsule. These pharmaceutical preparations are a further object of the invention. Usually, the amount of the active ingredient is between 0.1-95% by weight of the preparation, and preferably between 0.2-20% by weight in preparations for parenteral use. For the clinical use of the methods of the present invention, the pharmaceutical composition of the invention is formulated into formulations suitable for the intended route of administration.

The present disclosure is directed to a high-throughput screening method for identifying a functional antibody (or a fragment thereof) that can be used as a targeting module for delivering an immunoconjugate comprising said functional antibody to the targeted site of a subject. In the present application, immunotoxins targeting HER2-overexpressed cells were used as a model system to evaluate the applicability of synthetic antibody libraries in developing immunoconjugates. Antibodies used as targeting modules in immunoconjugates are more likely to result in optimally functional therapeutics by satisfying the following criteria: adequate affinity and specificity to the target receptor; capable of inducing receptor-mediated endocytosis; capable of deliver the toxin payload to subcellular locations for optimal cytotoxicity; of human origin to reduce immunogenicity; easy to manufacture with high expression efficiency and protein stability. To this end, we have constructed a phage-displayed synthetic antibody library (GH2) with a single human variable domain antibody germline framework: IGKV1-NL1*01/IGHV3-23*04, on which the antibody libraries were designed based on the antibody-protein interaction principles derived from computational and experimental analyses. On the order of hundreds of antibodies binding to HER2-ECD with high affinity and specificity have been discovered from the GH2 library with phage display-based selection and screening. The GH2 antibody epitopes on HER2-ECD are broadly distributed over the HER2-ECD molecular surface and many of the epitopes were novel. Moreover, overwhelmingly majority of the GH2 antibodies in both scFv and IgG forms can be expressed with high efficiency and high protein stability. As such, the groundwork has been established to explore the applicability of these HER-ECD-specific GH2 antibodies as targeting modules for toxin payloads.

The purpose of this study is to identify the optimally functional antibodies used in immunotoxins from a large number of target-specific antibodies, so as to understand the principles governing the efficiency of the antibodies as targeting modules for cytotoxic drug delivery. We developed an adaptor-toxin fusion proteins AL1-PE38KDEL and AL2-PE38KDEL for high throughput screening of the GH2 antibodies as targeting modules for delivering PE38KDEL, which is a truncated form of PE A subunit toxin. The GH2 library had been constructed with protein A and protein L selections so as to ensure that the IGKV1-NL1*01/IGHV3-23*04 framework of the VH and VL domains in a GH2 scFv simultaneously binds to protein A and protein L respectively. The AL1 fragment contains consecutive protein A and protein L separated by a polypeptide linker enabling the protein A and protein L binding to a GH2 scFv simultaneously; the AL2 fragment is composed of two consecutive AL1 modules separated by another polypeptide linker with length designed to promote two GH2 scFvs binding simultaneously to the AL2 fragment. While the scFv-AL1-PE38KDEL is designed as 1:1 for the antibody:toxin in one immunoconjugate complex, the scFv-AL2-PE38KDEL is designed to mimic the bivalent antigen binding of IgG with 2 scFvs in one immunoconjugate complex. Ninety-two GH2 scFvs that bind to HER2-ECD with high specificity and affinity were tested as the targeting modules combining with the AL1-PE38KDEL and AL2-PE38KDEL adaptor-toxin fusion proteins.

The results, as summarized below, proved that different scFvs, when conjugate with PE38KDEL, lead to strikingly different cytotoxicity. The bivalent binding promotes superior toxin delivery in some scFvs but shows no obvious difference comparing with monovalent binding in other scFvs. Epitope location on the target receptor determines the efficiency in receptor-mediated endocytosis and/or toxin delivery to certain extent; amino acid types on the antibody paratopes could also be a prominent determinant affecting the subcellular toxin delivery location. The density of the target receptors on the cell surface determines the cytotoxic efficacies of the immunoconjugates. These results indicate that the cytotoxicity of the immunotoxins is decisively dependent on the target cells and the antibodies as the targeting modules; screening of a large pool of candidate antibodies as the targeting module is a viable strategy to optimize the antibodies in immunoconjugate developments. While a large pool of candidate antibodies can be difficult to attain from natural antibody repertoires, synthetic antibody libraries can provide functional antibodies without being restricted by natural antibody responses. Combining the synthetic antibody libraries with the high throughput screening platform developed in this work enables better engineering capabilities for optimally functional antibody-based targeting modules in immunoconjugates.

In view of the foregoing, the first aspect of the present disclosure is directed to a method for high-throughput screening of a functional antibody fragment for an immunoconjugate that targets a protein antigen. The steps of the present method are discussed below.

First, in step (a), a phage-displayed synthetic single-chain variable fragment (scFv) library is provided. The phage-displayed synthetic scFv library comprises a plurality of phage-displayed scFvs. In particular, the phage-displayed synthetic scFv library is constructed with protein A and protein L selection, so that each of the plurality of phage-displayed scFvs has a VH domain capable of binding to protein A, and a VL domain capable of binding to protein L. This phage-displayed synthetic scFv library can be constructed using the method described in the co-pending PCT application, PCT/US2016/19128.

Next, in step (b), a plurality of phages that express scFvs specific for the protein antigen to be targeted were selected from the phage-displayed synthetic scFv library of the step (a). For example, the protein antigen is first immobilized on a matrix (such as an agarose resin or polyacrylamide) and mixed with the present phage-displayed scFv library. The phages that express scFvs capable of binding to the protein antigen are then treated with an elution buffer (such as, a glycine solution, pH 2.2) so as to disrupt the binding between the immobilized protein antigen and phage-display antibody. In this way, a plurality of phages that express scFvs specific for the protein antigen are collected.

Thereafter, in step (c), a plurality of secreted soluble scFvs are respectively prepared from the plurality of phages selected in the step (b). This preparation step can be performed using methods known to persons having ordinary skill in the art.

According to some embodiments, the protein antigen is human epidermal growth factor receptor 2 (HER2), maltose-binding protein, bovine serum albumin, human serum albumin, lysozyme, interleukin-1 beta (IL-1β), hemagglutinin of influenza virus, vascular endothelial growth factor (VEGF), epidermal growth factor receptor 1 (EGFR1), epidermal growth factor receptor 3 (EGFR3), glucagon receptor, programmed death-ligand 1 (PD-L1), sialic acid binding Ig-like lectin 3 (SIGLEC 3) or rituximab. In certain embodiments, the protein antigen is HER2.

According to some optional embodiments, the secreted soluble scFvs prepared in the step (c) are further screened against the same protein antigen to identify soluble scFvs that exhibit higher binding affinity and specificity to the protein antigen (step (c1)).

Then, in step (d), the secreted soluble scFvs from the step (c) or from the optional step (c1) are respectively mixed with an adaptor-drug conjugate.

According to the embodiments of the present disclosure, the adaptor-drug conjugate comprises a drug and an adaptor. The adaptor comprises an AL module that comprises a protein A fragment at the N-terminus and a protein L fragment at the C-terminus. In this way, the adaptor of the adaptor-drug conjugate is capable of non-covalently binding with the secreted soluble scFvs, thereby forming a plurality of scFv-adaptor-drug complexes.

In some optional embodiments, the AL module further comprises a first polypeptide linker connecting the protein A fragment and the protein L fragment. Still optionally, the adaptor-drug conjugate further comprises a second polypeptide linker connecting the drug to the C-terminus of the adaptor.

In some optional embodiments, the adaptor comprises two AL modules and further comprises a third polypeptide linker connecting the two AL modules.

As could be appreciated, the above-mentioned adaptor is specifically designed for use in the present high-throughput screening method, and accordingly, the adaptor is also a subject matter of the present invention for which the protection is sought.

In certain optional embodiments, the drug comprises a small molecule cytotoxic drug or an immunotoxin (such as, an exotoxin). For example, the exotoxin is or is derived from *Pseudomonas* Exotoxin (PE) A. In certain embodiments, the immunotoxin comprises a truncated form of PE A subunit toxin. In further embodiments, the immunotoxin further comprises an endoplasmic reticulum (ER) retention motif at the C-terminus of the PE A subunit toxin. For example, the ER retention motif comprises the sequence of KDEL.

After the formation of scFv-adaptor-drug complexes in the step (d), the present method proceeds to step (e), in which a plurality of cells presenting the protein antigen are cultured in the presence of the plurality of scFv-adaptor-drug complexes formed in the step (d), respectively. Protocols for culturing cells presenting various protein antigens are well known to persons having ordinary skill in the art.

Then, in step (f), the respective efficacy of the plurality of scFv-adaptor-drug complexes in the plurality of cells presenting the protein antigen cultured in the step (e) is determined.

In some optional embodiments, the step (f) is determined by measuring the respective cell viability of the plurality of cells presenting the protein antigen cultured in the step (e); however, the present disclosure is not limited thereto. Rather, one or more suitable quantitative or qualitative analyses can be performed depending on the intended therapeutic effect that the drug exerts on the cells.

Next, in step (g), the functional antibody fragment for the immunoconjugate is selected based on the results determined in the step (f). Specifically, the respective scFv of one or more scFv-adaptor-drug complexes of the plurality of scFv-adaptor-drug complexes that exhibit superior efficacy over the other scFv-adaptor-drug complexes of the plurality of scFv-adaptor-drug complexes is selected as the functional antibody fragment for the immunoconjugate.

The present high-throughput screening method is advantageous at least in that it eliminates the labor- and material-intensive sub-cloning and purification steps of the immunoconjugates. Consequently, the throughput rate in discovering and optimizing the targeting antibodies is substantially improved.

Once a suitable targeting module is identified using the high-throughput screening method provided herein, it is feasible to prepare an immunoconjugate comprising the targeting module. Methods for conjugating a drug (including an exotoxin) with a functional antibody fragment are well known in the art. As could be appreciated, these immunoconjugates and pharmaceutical compositions comprising the same are also within the scope of the present disclosure.

According to some embodiments, the immunoconjugate comprises a drug and a targeting module, wherein the targeting module comprises a functional antibody fragment selected using the method according to any aspect/embodiment of the present disclosure.

As to the pharmaceutical composition according to embodiments of the present disclosure, the pharmaceutical composition comprises an effective amount of the immunoconjugate and a pharmaceutically acceptable excipient for the immunoconjugate.

In still another aspect, the present disclosure is directed to a method for treating a subject in need thereof, comprising the step of administering to the subject an effective amount of an immunoconjugate or pharmaceutical composition according to any aspect/embodiment of the present disclosure.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

Materials and Methods

Cell Lines

N87, SKBR3, BT474, and MCF7 cells were obtained from the American Type Culture Collection (ATCC). The N87 gastric cancer cells (HER2-positive) were grown in RPMI 1640 medium (Invitrogen, Carlsbad, Calif.) supplemented with 10% fetal bovine serum (FBS) at 37° C. in a humidified atmosphere containing 5% $CO_2$. Maleimido-caproyl-valine-citrulline-monomethyl auristatin E (mc-vc-MMAE), a modified small molecule cytotoxic drug, was purchased from MedChem Express (Princeton, N.J., USA).

SKBR3 cells were cultured in RPMI 1640 (Gibco) with 10% fetal bovine serum (Gibco) and penicillin-streptomycin (100×; Gibco). BT474 cells were cultured in Hybri-Care Medium (ATCC) with 10% fetal bovine serum and Penicillin/Streptomycin/Glutamine (100×; Gibco). MCF7 cells were cultured in RPMI 1640 with 10% fetal bovine serum and penicillin-streptomycin (100×). Suspension HEK293 Freestyle (293-F, Life Technologies, USA) cells were grown in serum free Freestyle 293 expression media (Gibco) at 37° C. shaken with 110 rpm in 8% $CO_2$ incubator (Thermo Scientific).

AL1-PE38KDEL and AL2-PE38KDEL Gene Construction and Protein Expression/Purification AL1-PE38KDEL gene (SEQ ID No. 99) and AL2-PE38KDEL gene (SEQ ID No. 100) based on the published structure of protein A/L fragments (PDB code:4HKZ) and a truncated form of *Pseudomonas aeruginosa* Exotoxin A (PDB code:1IKQ) were synthesized.

For plasmid construction, the synthesized genes were subcloned into pET32a expression vector (Novagen) encoding a N-terminal thioredoxin fusion protein to the AL1-/AL2-PE38KDEL via SfiI and NotI restriction sites, and the resultant fusion protein contains a hexa-His tag C-terminal to the thioredoxin, followed by a TEV protease cutting site before the AL1-/AL2-PE38KDEL.

For protein expression, the constructed plasmids were transformed into *E. coli* Rosetta-gami B (DE3) strain (Novagen), and selected colonies were grown in 2×YT medium (Tryptone 16 g/L, Yeast extract 10 g/L, NaCl 5 g/L) with ampicillin (200 μg/L), tetracycline (12.5 μg/L) chloramphenicol (37.5 μg/L) and kanamycin (15 μg/L) at 37° C. until a cell density of $OD_{600}$ reached 1.0, and were then incubated at 16° C. for another 1 hour. The cultures were induced with 0.5 mM IPTG overnight at 16° C. After centrifugation, the harvested cells were resuspended in buffer A (500 mM NaCl and 5 mM imidazole in 20 mM Tris-HCl, pH 8.0), lysed by Microfluidizer (Microfluidics, MA), and then centrifuged at 40,000×g for 1 hour. The supernatant was loaded onto a HisTrap HP column (GE Healthcare) equilibrated with buffer A. After washing with 30 mL buffer A, the column was eluted by a linear gradient of 0-50% buffer B (the same recipe as that in A, except for 1000 mM imidazole). The eluted AL1-/AL2-PE38KDEL fractions at 0.14-0.24 M imidazole were pooled and digested with His-tagged TEV protease ($A_{280}$ ratio 50:1) at 30° C. for 3 hours, and then dialyzed against buffer A. The cleaved thioredoxin and TEV protease, both containing hexa-His tag, were removed by HisTrap HP column. The AL1-PE38KDEL protein (SEQ ID No. 101) and AL2-PE38KDEL protein (SEQ ID No. 102) in the flow-through were collected and further purified with a Superdex 200 size-exclusion column (GE Healthcare) in SEC buffer (150 mM NaCl in 50 mM Tris-HCl, pH 8.0). Isolated proteins were further analyzed by SDS-PAGE to check their purity and molecular mass.

Gene Construction and Protein Expression/Purification of AL2-RFP/GFP

The expression and purification of the AL2-RFP followed the standard *E. coli* expression and purification methods. In brief, the coding region of AL2-GGGSG-RFP/GFP (red fluorescence protein (SEQ ID No. 103) or green fluorescence protein (SEQ ID No. 104)) with a 6×His-tag at N-terminus was codon-optimized for *E. coli* expression and cloned into pET-32b expression vector. Cultures of *E. coli* BL21 (DE3) strain (Merck) transformed with the AL2-RFP/GFP construct in pET32b expression vector were grown in 2×YT medium (Tryptone 16 g/L, Yeast extract 10 g/L, NaCl 5 g/L) with ampicillin (150 μg/L) at 37° C. until $OD_{600}$ reached 1.0~2.0, and then incubated at 16° C. for another 1 hour before adding 0.5 mM IPTG. After overnight (at least 16 hours) expression, the cells were centrifuged and the pellets were resuspended in lysis buffer (Tris-HCl 20 mM, NaCl 150 mM, imidazole 10 mM, pH 8.0) and the suspended cells were then lysed by Microfluidizer (Microfluidics, MA). The recombinant AL2-RFP/GFP fusion proteins are purified by $Ni^{2+}$-IMAC column (GE Healthcare Life Sciences) with imidazole gradient from 10 mM to 500 mM in TS solution (Tris-HCl 20 mM, NaCl 150 mM, pH 8.0). The AL2-RFP/GFP fusion protein (SEQ ID No. 105, SEQ ID No. 106) was further purified by Superdex200 size-exclusion column (GE Healthcare Life Sciences) in PBS buffer and stored at −80° C. The purified protein was analyzed by SDS-PAGE and Coomassie blue staining.

scFv Expression/Purification

For preparation of secreted scFv, ER2738 was infected with phage harboring the phagemid pCANTABSE containing the scFv gene for 30 minutes. The infected ER2738 were amplified in 2×YT with 100 μg/mL ampicillin for 5-6 hours before adding 10 mM IPTG. After overnight culture, the culture supernatant containing the secreted soluble scFv was filtrated by 0.22 μm filter.

For preparing the purified Trastuzumab scFv with E-tag, the gene sequence derived from Trastuzumab Fab (PDB code:4HKZ) was synthesized and constructed by connecting two variable domains with a linker polypeptide, $(G)_4S(G)_4S(G)_4S$ (SEQ ID No. 91), and introducing the E-tag oligopeptide (GAPVPYPDPLEPRAA; SEQ ID No. 92) to the C-terminal end. The resulting gene was then cloned into pET32a expression vector (Novagen) via SfiI and NotI restriction sites. The detailed procedures of scFv protein expression and purification were performed as previously described by Yu, C. M. et al. in "Rationalization and design of the complementarity determining region sequences in an antibody-antigen recognition interface" (*PLoS One* 7, e33340 (2012)).

Concentration Determination of scFv in Culture Medium

The concentration of the secreted scFv in the culture medium was determined by comparing the ELISA signal to purified standard scFv with known concentration. In brief, the protein L antigen (0.2 μg per well) were coated in PBS buffer (pH7.4) on NUNC 96-well Maxisorb immunoplates overnight at 4° C., and blocked with 5% skim milk in PBST [0.05% (v/v) Tween 20] for 1 hour. Secreted scFvs and standard scFv were serially diluted with ER2738 cultured 2×YT. After blocking, 50 μL diluted samples were added to each well with 50 μL 5% skim milk in PBST [0.05% (v/v) Tween 20], and incubated for 1 hour under gentle shaking. The plate was washed 6 times with 300 μL PBST and then added with 100 μL of 1:20000-diluted horseradish peroxidase/anti-E-tag IgG antibody conjugate (ICL) in PBST with 5% milk for 1-hour incubation. The plates were washed six times with PBST buffer and twice with PBS, developed for 3 minutes with 3,3',5,5'-tetramethyl-benzidine peroxidase substrate (Kirkegaard & Perry Laboratories), quenched with 1.0 M HCl and read spectrophotometrically at 450 nm. Concentrations of secreted scFvs were determined with the standard curve derived with known scFv concentrations.

Surface Plasmon Resonance Measurement of Binding Kinetics of scFv to AL1-PE38KDEL and AL2-PE38KDEL BIAcore T200 (GE Healthcare) instrument was used to determine the binding affinities and kinetics parameters between scFv and AL1-/AL2-PE38KDEL. Purified AL1-/AL2-PE38KDEL protein in 10 mM acetate buffer (pH 4.5) was immobilized on a CM5 sensor chip to a response unit (RU) of 250-300 with an amine coupling kit. Association ($k_{on}$) and dissociation ($k_{off}$) constants of the interactions between AL1-/AL2-PE38KDEL and scFv were measured in HBS-EP+ running buffer (10 mM HEPES pH 7.4, 150 mM NaCl, 3 mM EDTA, 0.05% v/v Surfactant P20; GE Healthcare) with a flow rate of 30 µL/min. The sensor surface was regenerated with 10 mM Glycine, pH 2.0, prior to a new scFv injection and the signals obtained were subtracted by that obtained from the reference channel that had not been coated with ligands. Binding kinetics was determined by global fitting to 1:1 binding model using the Biacore evaluation software (GE Healthcare). Experiments were done in triplicate, and the results were expressed as the mean value with standard deviation.

Measurements of $EC_{50}$ with ELISA for scFv to AL1-PE38KDEL and AL2-PE38KDEL

For determining the $EC_{50}$ of soluble scFv binding to AL1-/AL2-PE38KDEL, ELISA assay was carried out. In brief, the HER2/ECD antigen (0.3 µg per well) were coated in PBS buffer (pH7.4) on NUNC 96-well Maxisorb immunoplates overnight at 4° C., and blocked with 5% skim milk in PBST [0.05% (v/v) Tween 20] for 1 hour. In the meantime, the secreted scFv in filtered supernatant was mixed with the AL1-/AL2-PE38KDEL at a molar ratio of 1:1 for scFv:AL fragment. After 1-hour incubation at room temperature, the scFv or scFv-AL1-/AL2-PE38KDEL mixtures were prepared at 11 concentrations by twofold serial dilutions with 2YT culture medium. 50 µL of diluted scFv samples were mixed with 50 µL of blocking buffer and then added to the blocked microtiter plate for another one hour under gently shaking. The plate was washed 6 times with 300 µL PBST and then added with 100 µL of 1:4000-diluted horseradish peroxidase/anti-E tag antibody conjugate (Abcam) in PBST with 5% milk for 1 hour incubation. The plates were washed six times with PBST buffer and twice with PBS, developed for 2 minutes with 3,3',5,5'-tetramethyl-benzidine peroxidase substrate (Kirkegaard & Perry Laboratories), quenched with 1.0 M HCl and read spectrophotometrically at 450 nm. The $EC_{50}$ (ng/mL) was calculated according to Stewart and Watson method.

Preparation of AL1- and AL2-Drug Conjugates

To conjugate the maleimide payload with AL1 or AL2 adaptor proteins, the cysteine residue was introduced into the C-terminal end of AL adaptor proteins (designated as AL1C or AL2C). After gene synthesis, the AL1C or AL2C were constructed with pET26 expression vector, and further expressed and purified using HisTrap HP and Superdex G200 columns. For AL1C-026 conjugation, 2.84 mL of 20 mM TCEP (110.4 nmole) was added into 0.5 mg (31.6 nmole) of purified AL1C protein in PBS buffer to reduce the intermolecular disulfide bond of AL1C protein and AL1C-beta-mercaptoethanol conjugate, and then incubated at 20° C. for 2 hours. After the reduction, 8.52 µL of 10 mM maleimide-vc-MMAE in DMSO was added to the TCEP containing AL1C protein solution, mixed well, and incubated at 20° C. for 16 hours. The protein solution was further concentrated with 3 kDa Centricon (Millipore Corp. Billerica, Mass., USA), and then applied to Superdex75 10/300 GL column (GE Healthcare) for gel filtration purification of AL1C-vc-MMAE conjugate. The concentration of AL1C-vc-MMAE conjugate was determined using BCA kit (Thermo SCIENTIFIC). PAGE analysis and $EC_{50}$ determination were used to confirm the integrity of AL1C-vc-MMAE conjugate. For AL1C-021, the AL1C protein was conjugated with Osu-monomethyl auristatin F (MMAF) via lysine conjugation. For AL2C-002 and AL2C-004 conjugates, the AL2C protein was conjugated with maleimide-vc-MMAE or maleimide-MMAF, respectively.

Preparation of Antibody-Drug Conjugates

The antibody-vcMMAE conjugates were prepared as previously described with some modification. Briefly, sample antibody (2 mg/mL) was reduced for 2 hours at 20° C. with the addition of EDTA to 2 mM and TCEP to a 3-fold excess relative to the antibody. The reduced antibody was conjugated by the addition of 5.25 equivalents of maleimide-vc-MMAE from a 10-mM stock in DMSO. The conjugation reaction was allowed to proceed at 20° C. for 1 hour before being quenched by the addition of N-acetylcysteine. The quenched conjugation mixture was desalted twice with 5 mL Zeba™ Spin Desalting Column (7K MWCO, Thermo SCIENTIFIC), and then concentrated by centrifugal ultrafiltration (Amicon Ultra 10K device; Millipore Corp. Billerica, Mass., USA). After quantifying its concentration using a BCA protein assay kit (Thermo SCIENTIFIC), the final conjugate was tested with binding $EC_{50}$ assay, SDS-PAGE, drug-to-antibody ratio (DAR) calculation by hydrophobic interaction chromatography (HIC; butyl-NPR column; Tosoh Bioscience, Tokyo, Japan), and then stored at 4° C.

Cell Cytotoxicity Assay

For determining the cytotoxic effects of immunotoxins, $10^4$ cells/well were seeded in 96-well plates. IgGs or scFvs were pre-incubated with AL1-PE38KDEL/AL2-PE38KDEL at a molar ratio of 1:1 for scFv:AL fragment for 1 hour at room temperature so as to form non-covalently linked immunotoxins. After serial dilution in ER2738 cultured 2YT, scFv-AL1-PE38KDEL/AL2-PE38KDEL mixtures were added to cell culture without serum. ER2738 cultured 2YT with AL1-PE38KDEL or AL2-PE38KDEL were used as negative control. After 4 hours of incubation at 37° C., the antibody toxin mixture was replaced by fresh normal medium with serum. After 4 days of culture at 37° C., the number of viable cells was quantified using WST-1 (Roche) by measuring $OD_{450}$. Percentage of cell viability was calculated per the following equation, % of cell viability=$OD_{450\ nm}$ (antibody treated cells)/ $OD_{450\ nm}$ (negative control cells)×100%.

For AL1-PE38KDEL, AL1C-Osu-MMAF (AL1C-021), and AL1C-vc-MMAE (AL1C-026), $1\times10^4$ cells/well were plated and allowed to adhere. 16-18 hours later, the medium was removed and replaced with different concentrations of AL1C conjugates and H32, Trastuzumab (Herceptin), GH2-20, GH2-41, GH2-75, and GH2-61 anti-HER2 IgGs without serum. The molar ratio of AL1C conjugates and IgGs are 2:1. After 4-16 hours of incubation at 37° C., the antibody-toxin mixture was replaced by fresh normal medium with serum. After 4 days of culture at 37° C., the cells were treated with WST-1 (Roche) per the manufacturer's instruction. $OD_{450}$ of each well were analyzed by Victor (Perkin Elmer) and the relative cell viability were analyzed by normalization to cell treated with the medium. For AL2C conjugates, the molar ration of AL2C and IgG is 1:1. The other procedure was the same as AL1C conjugates. For IgG-vc-MMAE conjugates treatment, the conjugates with different amounts were directly added into the culture medium and culture for 72 hours.

Mean Fluorescence Intensity Measurements of scFv with AL2-RFP on Cell Surface by Flowcytometry HER2-expressed cells were used for scFv-HER2-ECD bonding by FACS analysis. Cells were suspended by trypsin treatment and went through mesh 40-micron pore. About $2\times10^5$ cells were incubated with 100 µL scFv at 4° C. for 30 minutes, then washed once with 0.5% FBS 1× PBS (wash buffer), mixed with 1.2 µg AL2-RFP in 50 µL wash buffer at 4° C. for 20 minutes, and then wash twice with washer buffer. After centrifugation and resuspension, cells were analyzed for RFP signal by FACS (BD FACS Canto II).

Confocal Microscopy for IgG Internalization

SKBR-3 Cells grown on glass coverslips were incubated with 1 μg/mL Trastuzumab, M32 or H32 IgG at 37° C. for 1 hour. After washing, cells were fixed with 3.7% formaldehyde and permeabilized with 0.1% Triton-X 100. The fixed cells were incubated with rabbit anti-Rab5, Rab7 or Rab9 antibody (1:200 dilution in PBS/0.1% Triton-100/3% BSA) at room temperature for 1 hour and then incubated with Cy3-conjugated anti-rabbit secondary antibodies (1:200 dilution in PBS/0.1% Triton-100/3% BSA) at room temperature for 1 hour. The presence of Trastuzumab and H32 IgG was revealed by a Cy2-conjugated anti-human secondary antibody, M32 was revealed by a Cy2-conjugated anti-mouse antibody. Coverslips were mounted with Gel Mount aqueous mounting medium (Sigma, St. Louis, Mo., USA). Images were acquired using a Zeiss LSM 510 META confocal microscope with a 63× objective (1.4 oil).

Detection of IgG Induced Vesicle Protein Expressions by Western Blot

SKBR-3 cells that treated with 1 μg/mL Trastuzumab, M32 or H32 IgG at 37° C. for 1 hour were scraped in lysis buffer (1% NP-40, 50 mM Tris pH 7.4, 150 mM NaCl, 2 mM $MgCl_2$, 1 mM EGTA, and protease and phosphatase inhibitors). Cellular protein from lysates was separated by SDS-PAGE, and then transferred to PVDF membrane for Western blot detection with antibodies against Rab7 and Rab9, and GAPDH, followed by incubation with appropriate HRP-conjugated secondary antibodies. Blots were developed using an enhanced chemiluminescence system.

Antibody Internalization by Biotinylation Assay.

SKBR-3 cell membrane was biotinylated using EZ-link Sulfo-NHS-SS-Biotin (Pierce, IL) in PBS at 4° C. for 30 minutes. Labeled cells were washed twice in cold PBS and then incubated with 10 μg/mL Trastuzumab or H32 IgG at 37° C. for internalization, after 1 hour, biotin groups remaining on the cell surface were cleaved off at 4° C. with the reducing buffer (100 mM sodium-2-mercaptoethane sulfonate, 50 mM Tris, pH 8.6, 100 mM NaCl). The cells were then washed three times in cold PBS and scraped in lysis buffer. Biotinylated membrane complex of HER-2 receptor and internalized antibody were captured on streptavidin ELISA plates (Nunc immobilizer; Nunc, Roskilde, Denmark) from the cell lysates diluted to 10 μg/mL total protein in PBS for 1 hour of incubation at room temperature. The plates were then washed three times with PBS and incubated with horseradish peroxidase (HRP)-conjugated anti-human secondary antibody for 1 hour and washed three times in PBS, and the HRP signal was revealed by incubation with OPD color substrate (Sigma, St. Louis, Mo.). Color development was analyzed at 492 nm using an ELISA reader.

Negative Stain EM and Image Processing

The antibody-antigen complexes at approximately 8 μg/mL were applied to glow-discharged, carbon-coated copper grids. The grids were washed and stained with 0.75% (wt/vol) uranyl formate for 30 seconds. The specimens were imaged with a FEI Tecnai F20 electron microscope operated at 120 kV. Micrographs were recorded with a Gatan UltraScan 1000 CCD at 1.21 Å/pixel and at an average defocus of 1.3 μm. The images were corrected for contrast transfer function, and the defocus value was determined using CTFfind3. The projections of the particles were boxed using DoG picker in Appion, and classified to 2D classes at 3.63 Å/pixel using software packages, including ISAC and Relion. The 3D initial model was generated by EMAN2 ab initial common line method. The initial model was refined with approximately 60,000 particles using Relion to 23 Å resolution with gold standard FSC=0.5 cutoff. Crystal structures of Fab and HER2 ECD (PDB 3wsq) were fit to the 3D model to map the binding region using UCSF chimera.

IgG Expression/Purification

For IgG expression, the variable domains of light chain (VL) and heavy chain (VH) cDNAs were amplified from the scFv plasmids of binder phages by PCR and then cloned into mammalian expression vector pIgG (a gift from Dr. Tse-Wen Chang, Genomics Research Center of Academia Sinica). The VL domain cDNA was amplified by PCR with proof-reading DNA polymerase (KOD Hot Start DNA polymerase, Novagen) using primer set GH2-VL-F-KpnI (CAGGTG-CACGATGTGATGGTACCGATATTCAAAT GACCCA-GAGCCCGAGCAGCCTGAGC; SEQ ID NO. 93) with GH2-VL-R (TGCAGCCACCGTACGTTTGATTTC-CACCT$\underline{T}$GGTGCC; SEQ ID No. 94); for VH domain, using GH2-VH-F (CGTGTCGCATCTGAAGTGCAGCTGGTG-GAATCGGGA; SEQ ID NO. 95) with GH2-VH-R-NheI (GACCGATGGGCCCTTGGTGCTAGCCGAGCTCACG-GTAACAAGGGTGCC; SEQ ID No. 96). The italic letter of primers indicated the restriction enzyme sites. PCR reactions were performed in a volume of 50 μL with 100 ng DNA template and 1 μL of 10 μM of each primer for 30 cycles (30 seconds for 95° C., 30 seconds for 56° C., 30 seconds for 72° C.) followed a 10-minute final synthesis step at 72° C. The PCR products were extracted from 1.0% agarose electrophoresis gel. The linker DNA fragment between $V_L$ and $V_H$ domains was obtained from pIgG vector by PCR amplification as above, using primer set GH2-IgG-linker-F (AAGGTGGAAATCAAACGTACGGTGGCTG-CACCATCTGTC; SEQ ID No. 97) and GH2-IgG-linker-R (CTGCACTTCAGATGCGACACGCGTAGCAACAGC; SEQ ID No. 98). The linker fragment includes the constant domain of light chain, bovine growth hormone (BGH) polyA signal, and human cytomegalovirus (CMV) promoter followed by the signal peptide of IgG heavy chain. The above three DNA fragments (VL domain, linker, and VH domain) were assembled by PCR amplification using primer set GH2-VL-F-KpnI and GH2-VH-R-NheI for 30 cycles (30 seconds for 95° C., 30 seconds for 58° C., 90 seconds for 72° C.). The PCR products were extracted from 1% agarose electrophoresis gel and cloned into pIgG vector by Gibson assembly methods. In brief, 2 μL (20 ng) of linearized pIgG vector (digested by KpnI and NheI previously) and 2 μL (20 ng) insert DNA were mixed with 4 μL Gibson Assembly Master Mix (New England BioLabs Inc. Ipswich, Mass., USA) and incubated at 50° C. for 1 hour. After then, half volume of ligation mixture was transformed with *Escherichia coli* JM109 competent cells. The DNA insertion of plasmid was confirmed by restriction enzyme digestion and nucleotide sequencing. The constructed vector contains both light chain and heavy chain of IgG, controlled by human cytomegalovirus (CMV) promoter separately.

Transfection of HEK293 F cells and IgG expression were carried as follows. For 500 mL culture transfection, suspension 293-F cells in 2-L Erlenmeyer flasks were adjusted to the density of $1.0 \times 10^6$ cells/mL. The plasmid DNA (500 μg), diluted in 25 mL serum free medium and sterile with 0.2 μm syringe filter, was mixed vigorously with 25 mL medium containing 1 mg of cationic polymer polyethylenimine (PEI, Polysciences). After 20 minutes incubation at room temperature, the mixture was added dropwise to the cells with slight shaking, and then the cells were grown in reach-in incubator at 37° C. Tryptone N1 (ST Bio, Inc, Taipei, Taiwan) was added to a final concentration of 0.5% at the $24^{th}$ hour of post-transfection. After 5 days' culture, the supernatant was collected by centrifugation at 8000×g for 30 minutes and filtered with 0.8 μm membrane filter (Pall Corporation, Michigan). The supernatant was loaded on HiTrap Protein A affinity column (GE Healthcare, Uppsala, Sweden), and eluted with 0.2 N glycine-HCl at pH 2.50 into 1/10 volume of 1 M Tris-HCl buffer at pH 9.1. The IgG proteins were further purified with Superdex 200 gel filtration column (10/300 GL, GE Healthcare, Uppsala, Sweden) to remove high molecular weight aggregates.

Tumor Xenograft Studies

The mouse experiments were performed in accordance with the Guidelines of the Academia Sinica Institutional Animal Care and Use Committee.

The N87 tumor-bearing mouse model was established by subcutaneously inoculating 1×10$^6$ cells into the right flank of 6-week-old male NOD.CB17-Prkdcscid/NcrCrlBltw NOD/SCID mice (BioLASCO Taiwan Co. Ltd). When tumor size reached approximately 100-200 mm$^3$, the mice were assigned into the following treatment groups (n=6), and treated with indicated concentration of GH2-61 IgG-AL1-PE38KDEL immunotoxins (0.375, 0.75, 1.5, 3 mg/kg). To monitor the tumor growth, the longest and shortest diameters of the tumors were measured using a digital caliper twice weekly. Tumor volume (mm$^3$) was computed according to the following formula: tumor volume=(length×width2)×0.523. Before each treatment, mice were weighed to monitor the systemic toxicity of the treatments. Mice were intraperitoneally injected twice a week with PBS or GH2-61 IgG-AL1-PE38KDEL immunotoxins in a total volume of 100 μL. To evaluate the anti-tumor efficacy of GH2-61 IgG-AL1C-026 complexes and GH2-61 IgG-vcMMAE conjugates in N87 xenograft tumor model, GH2-61 IgG-AL1C-026 complexes (2.5, 5 mg/kg), or GH2-61 IgG-vcMMAE conjugates (2.5, 5 mg/kg) was given i.v. once a week for 3 weeks.

Example 1

High-Throughput Screening Platform for Non-Covalently Assembled Immunotoxins in Combination with Phage-Displayed Synthetic Antibody Libraries High-throughput screening tests a large number of monoclonal antibodies for their biological function in parallel. Conventional tests of the function of immunotoxins require labor- and material-intensive sub-cloning and purification of the immunotoxins, limiting the throughput rate in discovering and optimizing the targeting antibodies. Monoclonal GH2 synthetic antibodies can be consistently expressed to the concentration on the order of 10 nM to 100 nM in soluble scFv form secreted by host *E. coli* cells into about 1 ml of medium in 96-deepwell plates. To enable a high-throughput screening platform for the soluble scFvs in culture media without purification of the scFvs, we constructed the adaptor-toxin fusion proteins: AL1-PE38KDEL and AL2-PE38KDEL, according to the structure of Protein A and Protein L in complex with a scFv of IGKV1-NL1*01/IGHV3-23*04 framework (PDB code: 4HKZ).

Specifically, the AL1-PE38KDEL adaptor-toxin fusion protein has composite structure of the AL1-PE38KDEL immunoconjugate and Trastuzumab scFv complex. The complex structure of the Trastuzumab scFv variable domain in complex with protein A and protein L is derived from PDB code: 4HKZ. There is a distance of about 37.3 Å Between the C-terminal residue of the VL domain and the N-terminal residue of the VH domain; whereas there is a distance of about 39.8 Å between the C-terminal residue of the Protein A and the N-terminal residue of the protein L. The PE38KDEL is a truncated form of *Pseudomonas* exotoxin (PDB code: 1IKQ) comprising the domain II and domain III of the exotoxin.

Regarding the AL2-PE38KDEL adaptor-toxin fusion protein, it has one additional AL fragment linked by a 5-residue linker (Linker2) to the N-terminus of the AL1-PE38KDEL as described above.

These adaptor-toxin fusion proteins bind to recombinant scFv or IgG with the IGKV1-NL1*01/IGHV3-23*04 framework, self-assembling into non-covalently-linked immunotoxin complexes in crude mixture of culture media, allowing the self-assembled immunotoxin complexes to be tested on cells cultures in micro-titer plates for cytotoxicity assay in high-throughput format without the rate-limiting processes of subcloning and purification.

Example 2

Non-Covalently Assembled Immunotoxins with Monovalent Targeting Modules

Figure 1:
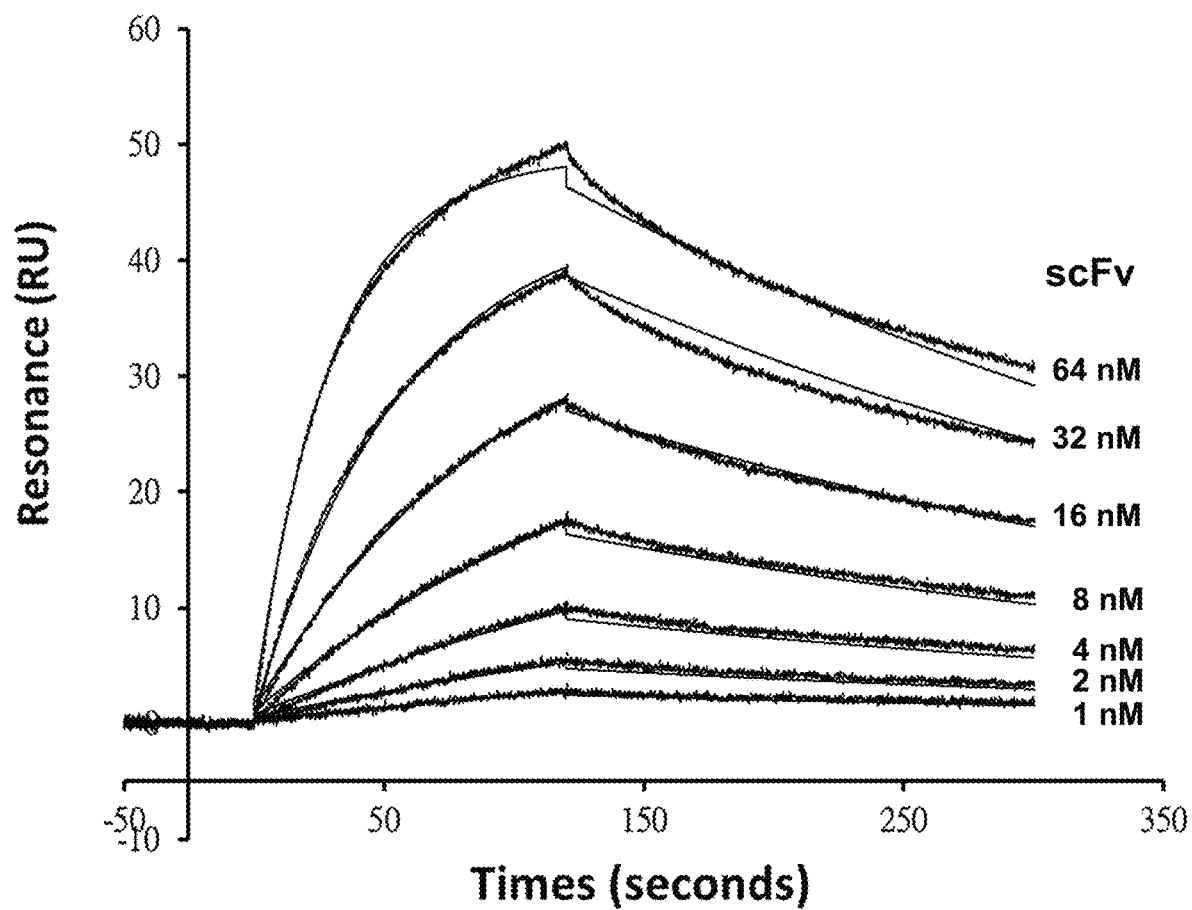
FIG. 1 is a line graph summarizing SPR measurements of immobilized AL1-PE38KDEL passed over with 1, 2, 4, 8, 16, 32 and 64 nM Trastuzumab scFv, in which the SPR measurements are shown in bold lines with global fit (thin lines) to the experimental data with $K_d=5.64\pm0.03\times10^{-9}$ M; $k_{on}=4.54\pm0.06\times10^5$ M$^{-1}$ S$^{-1}$, and $k_{off}=2.56\pm0.04\times10^{-3}$ S$^{-1}$.

AL1-PE38KDEL binds to scFv of IGKV1-NL1*01/IGHV3-23*04 framework in high affinity. The N-to-C sequential arrangement of the Protein A and Protein L in the AL fragment of the adaptor-toxin fusion protein AL1-PE38KDEL is essential to avoid the clash between the Linker3 and the VL-VH linker, which is a 15-residue polypeptide linking the N-to-C sequential arrangement of the VL and VH domains in the scFv construct of the GH2 library. Linker3 is a 15-residue polypeptide linker, providing enough length to accommodate a scFv molecule simultaneously binding to the Protein A and the Protein L in the AL fragment. Linker4 is a 5-residue linker connecting the AL fragment to the toxin PE38KDEL. The adaptor-toxin fusion protein AL1-PE38KDEL has one high affinity scFv binding site, enabling binding of Protein A to the VH domain and Protein L to the VL domain simultaneously. Alternative binding configurations with only one Protein A/L interacting with the scFv molecule are of relatively low affinity with dissociation constant $K_d$ on the order of $10^{-6}$~$10^{-7}$ M. Hence, these monovalent complex configurations are not expected to be significantly populated in the scFv-AL1-PE38KDEL complexes. This anticipation has been validated with the binding affinity and binding kinetics of scFv to AL1-PE38KDEL measured with surface plasmon resonance (scFv solution flows over immobilized AL1-PE38KDEL), from which the results indicated $K_d$=5.64±0.03×10$^{-9}$ M with $k_{on}$=4.54±0.06×10$^5$ M$^{-1}$ S$^{-1}$ and $k_{off}$=2.56±0.04×10$^{-3}$ S$^{-1}$ (FIG. 1).

Example 3

Non-Covalently Assembled Immunotoxins with Bivalent Targeting Modules

Figure 2:
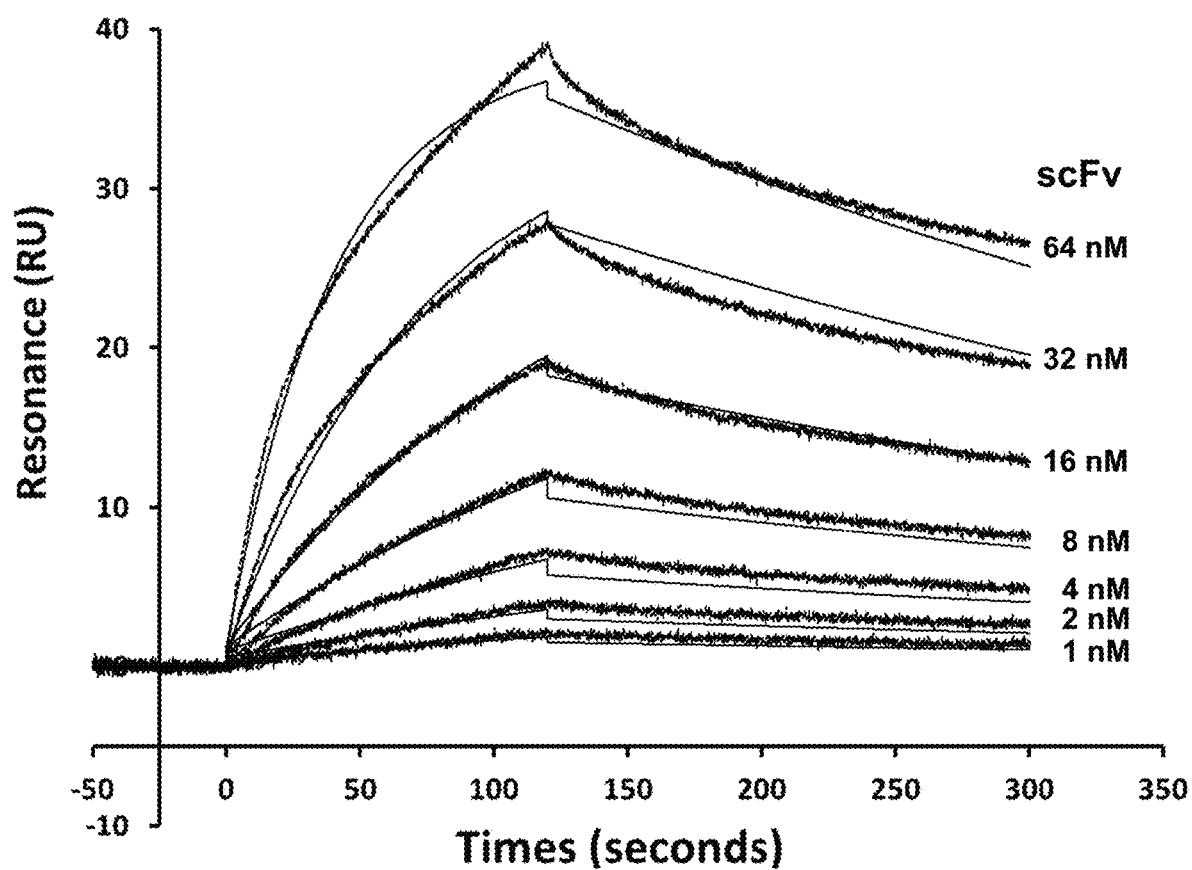
FIG. 2 is a line graph summarizing SPR measurements of immobilized AL2-PE38KDEL passed over with 1, 2, 4, 8, 16, 32 and 64 nM Trastuzumab scFv, in which the SPR measurements are shown in bold lines with global fit (thin lines) to the experimental data with $K_d=5.52\pm0.03\times10^{-9}$ M; $k_{on}=3.60\pm0.06\times10^5$ M$^{-1}$ S$^{-1}$, and $k_{off}=1.99\pm0.04\times10^{-3}$ S$^{-1}$.
Figure 3A:
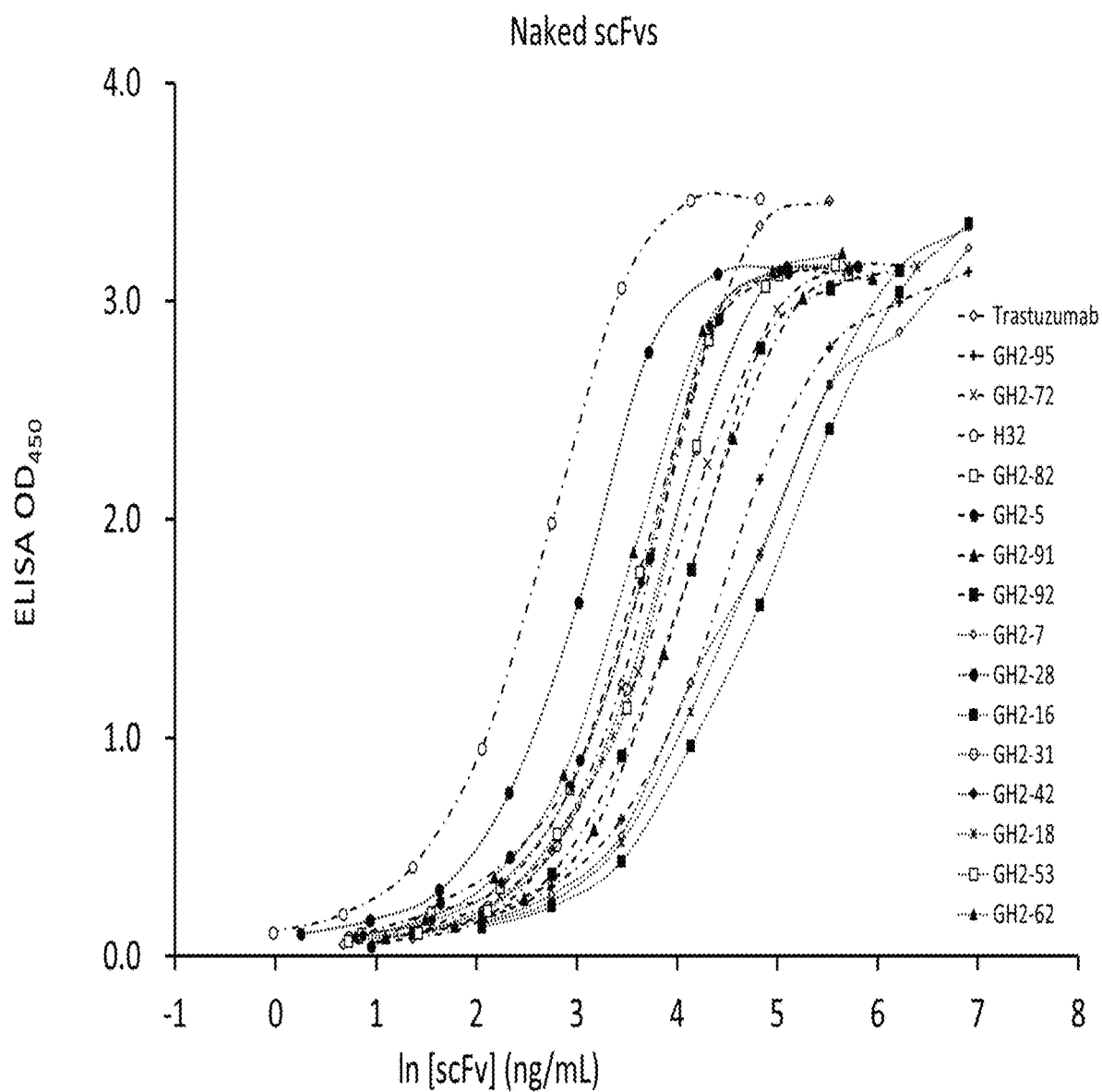
FIG. 3A to FIG. 3E show binding affinities of scFvs to the antigen HER2-ECD. 16 scFvs with IGKV1-NL1*01/IGHV3-23*04 germline framework were used to measure the $EC_{50}$ for HER2-ECD binding in the absence (FIG. 3A) and presence of AL1-PE38KDEL (FIG. 3B) or AL2-PE38KDEL (FIG. 3C) with 1:1 molar ratio of the scFv:AL fragment. The $EC_{50}$ value for each scFv is showed in Table 1. The HER2-ECD-binding $EC_{50}$'s for the scFv-AL1-PE38KDEL (FIG. 3D) or scFv-AL2-PE38KDEL (FIG. 3E) complexes are versus those for the naked scFvs.
Figure 3B:
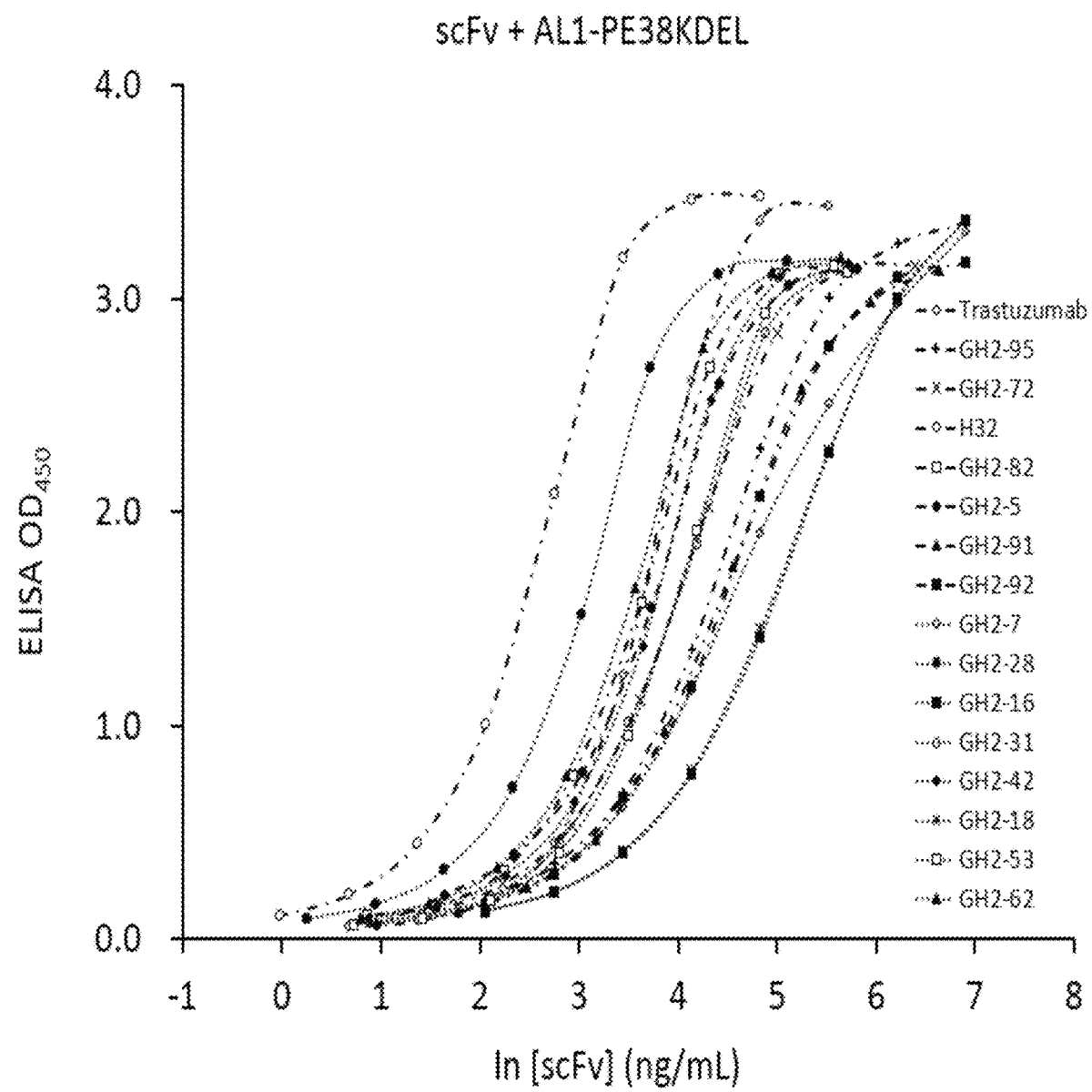
Figure 3C:
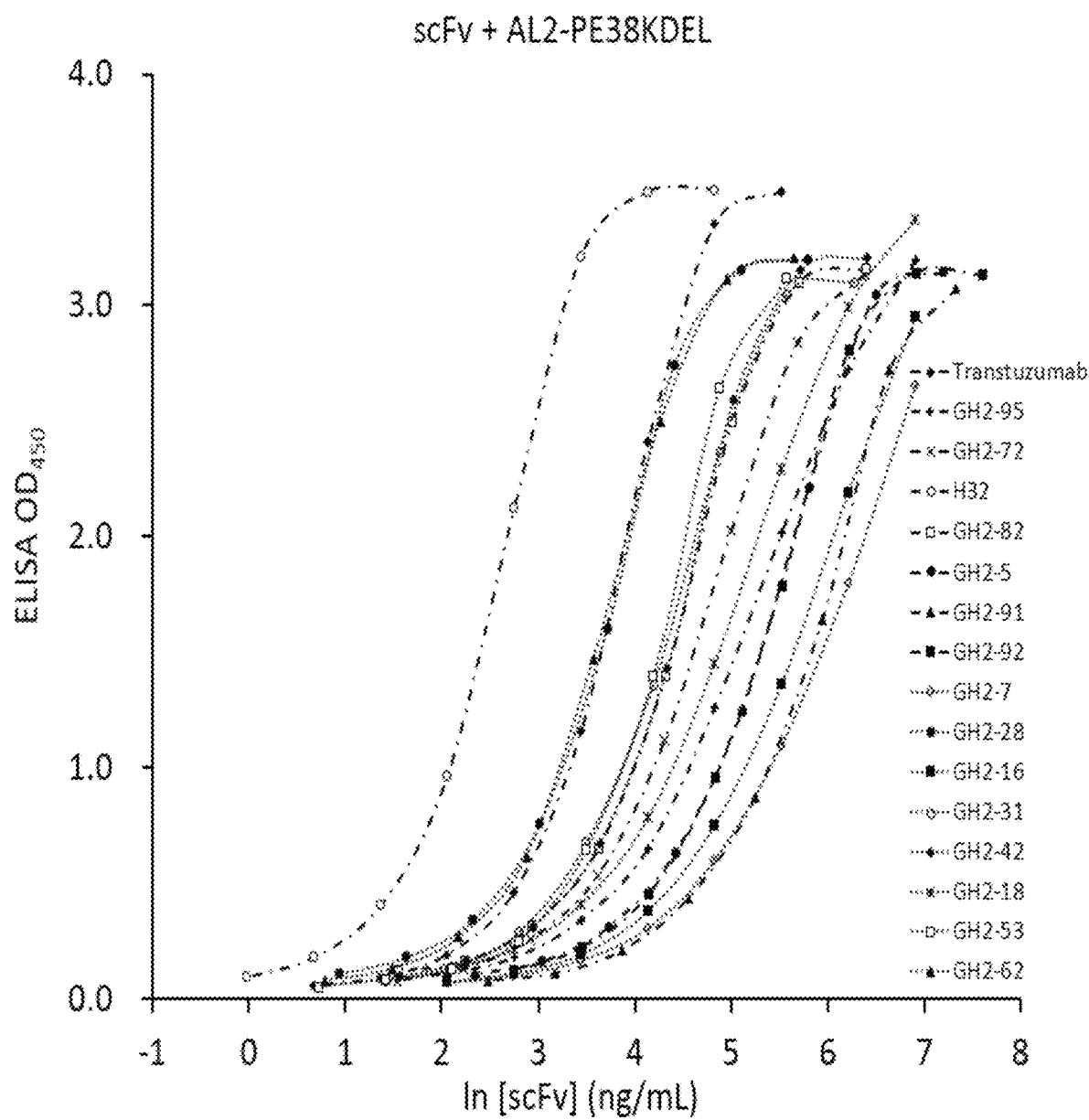
Figure 3D:
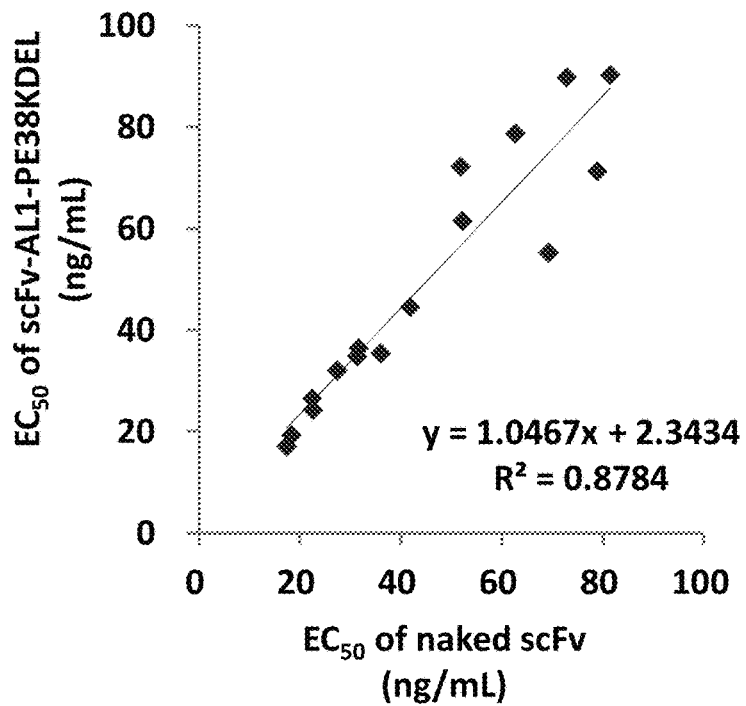
Figure 3E:
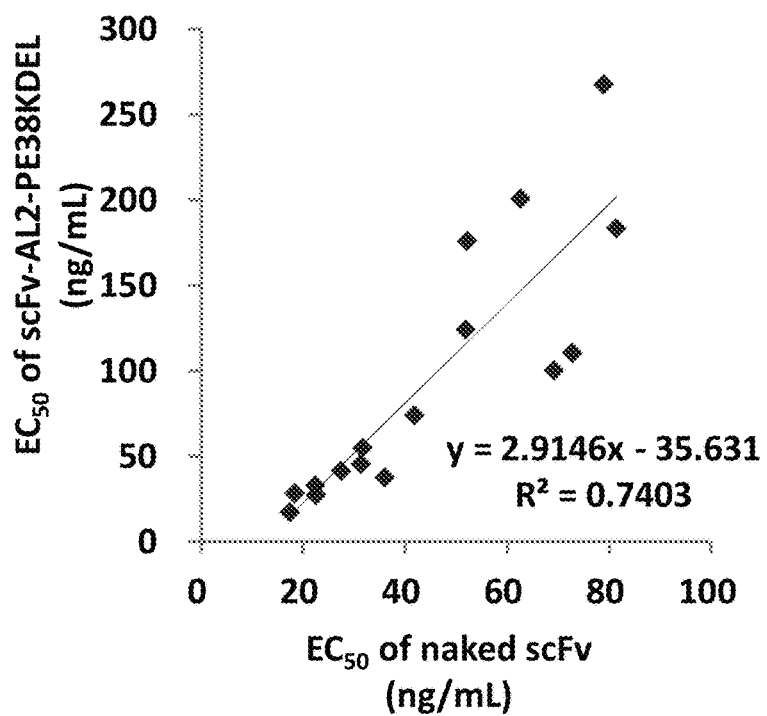

The adaptor-toxin fusion protein AL2-PE38KDEL is expected to bind to two scFvs of IGKV1-NL1*01/IGHV3-23*04 framework with two consecutive AL fragments. The two AL fragments are linked by Linker2, which is a 5-residue linker to prevent the formation of a scFv-binding site composed of the Protein L from the first AL fragment and the Protein A from the second AL fragment. As such, the AL2-PE38KDEL adaptor-toxin fusion protein is expected to contain two independent scFv binding sites with nano-molar affinity. Although the complex configuration binding to one scFv could occur by forming the complex with the Protein A from the first AL fragment and the Protein L from the second AL fragment, this configuration is anticipated to have lower affinity to the scFv in comparison with the binding configuration as described above. This anticipation arises on the basis that the entropy cost of forming the complex fixing the N- and C-termini encompassing the long intervening fragments (the Protein L and Protein A from the first and the second AL fragment respectively) is much higher than that of forming per scFv-AL complex as described above. This anticipation has been validated by the measurement of the binding affinity and binding kinetics of scFv to AL2-PE38KDEL (scFv flows over immobilized AL2-PE38KDEL) with surface plasmon resonance: $K_d=5.52\pm0.03\times10^{-9}$ M with $k_{on}=3.60\pm0.06\times10^5$ M$^{-1}$ S$^{-1}$ and $k_{off}=1.99\pm0.04\times10^{-3}$ S$^{-1}$ (FIG. 2). These measurements are similar to those for scFv binding to AL1-PE38KDEL (FIG. 1), indicating that the AL2-PE38KDEL has two independent scFv-binding sites, each of which has binding thermodynamics and kinetics measurements similar to those of the AL fragment in the AL1-PE38KDEL; the complex configuration as described above is expected to be the main state of the complex configurations for the scFv-AL2-PE38KDEL complexes.

Example 4

AL-scFv Complex Formation does not Interfere with scFv-HER2-ECD Interaction

Protein A and Protein L binding to the scFvs of the IGKV1-NL1*01/IGHV3-23*04 framework have been known to have little impact on the binding of the scFvs to their corresponding antigens. Quantitative comparisons of the scFv-antigen binding affinities in the presence and absence of AL1-PE38KDEL and AL2-PE38KDEL are shown in FIGS. 3A to 3E. 16 HER2-ECD-specific scFvs with diverse affinity to HER2-ECD were used to measure the $EC_{50}$ for the scFv-HER2-ECD binding in the absence (FIG. 3A) and presence of AL1-PE38KDEL (FIG. 3B) or AL2-PE38KDEL (FIG. 3C) (data shown in Table 1).

Plotting HER2-ECD-binding $EC_{50}$'s for the scFv-AL1-PE38KDEL complexes versus those for the same set of 'naked' scFvs shows slope of 1.0 and $R^2=0.88$ (Pearson's correlation coefficient=0.94) (FIG. 3D), indicating that quantitatively, the binding of AL1-PE38KDEL to each of the 16 scFvs does not affect the scFv-HER2-ECD interactions. Plotting HER2-ECD-binding $EC_{50}$'s for the scFv-AL2-PE38KDEL complexes versus those for the 'naked' scFvs shows slope of 2.9 and $R^2=0.74$ (Pearson's correlation coefficient=0.86) (FIG. 3E), indicating that the effective concentration of the scFv in the scFv-AL2-PE38KDEL system was reduced by three folds, perhaps because the scFv-AL2-PE38KDEL complexes are less effective to generate the equivalent ELISA signal strength comparing with the corresponding 'naked' scFv or scFv-AL1-PE38KDEL complex. The high linear correlations between the affinities of the 'naked' scFvs with those of the scFvs in the scFv-AL1-PE38KDEL (FIG. 3D) or scFv-AL2-PE38KDEL (FIG. 3E) complexes indicate that the complex formation does not affect the relative affinities of the scFvs binding to the antigen molecule.

TABLE 1

| scFv | $EC_{50}$ (ng/mL) | | |
|---|---|---|---|
| | Naked | scFv-AL1-PE38KDEL | scFv-AL2-PE38KDEL |
| Trastuzumab | 35.99 | 35.49 | 37.9 |
| GH2-95 | 69.24 | 55.2 | 100.14 |
| GH2-7 | 79.04 | 71.27 | 267.91 |

TABLE 1-continued

| scFv | $EC_{50}$ (ng/mL) | | |
|---|---|---|---|
| | Naked | scFv-AL1-PE38KDEL | scFv-AL2-PE38KDEL |
| GH2-16 | 81.43 | 90.29 | 183.47 |
| GH2-18 | 72.92 | 89.82 | 110.71 |
| H32 | 17.39 | 17.02 | 17.11 |
| GH2-5 | 52.13 | 61.42 | 176 |
| GH2-28 | 18.37 | 19.33 | 28.43 |
| GH2-31 | 27.4 | 32.04 | 41.48 |
| GH2-42 | 31.68 | 36.45 | 54.8 |
| GH2-53 | 22.39 | 26.52 | 33.18 |
| GH2-62 | 22.63 | 24.18 | 27.3 |
| GH2-72 | 31.42 | 34.81 | 45.77 |
| GH2-82 | 41.83 | 44.45 | 74.07 |
| GH2-91 | 62.64 | 78.87 | 200.9 |
| GH2-92 | 51.84 | 72.24 | 124.42 |

Example 5

Figure 4A:
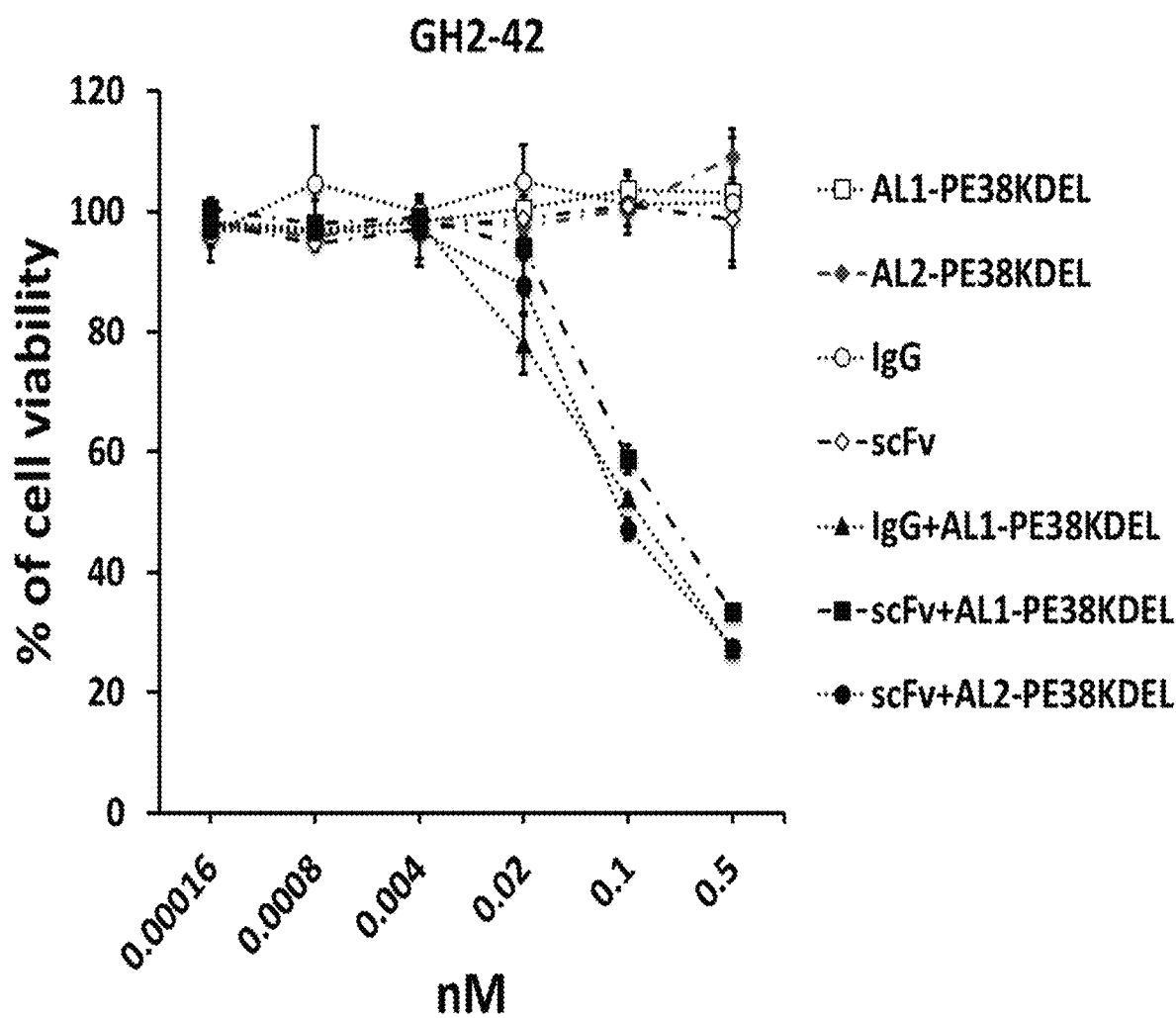
FIGS. 4A to 4C show the cytotoxicity of scFv or IgG complexed with the adaptor-toxin fusion protein AL1-PE38KDEL or AL2-PE38KDEL. N87 cells were treated with controls (AL1-PE38KDEL, AL2-PE38KDEL, scFv, and IgG) or non-covalently assembled immunotoxins (IgG-AL1-PE38KDEL, scFv-AL1-PE38KDEL, and scFv-AL2-PE38KDEL), for which the cytotoxicity was determined. The y-axis of the plots shows the percentage of cell viability of N87 cells; the x-axis shows the concentration of the VL-VH variable domain or the AL fragment in the controls or immunotoxin complexes; the antibody (IgG or scFv) and the adaptor-toxin fusion protein (AL1-PE38KDEL or AL2-PE38KDEL) were mixed in 1:1 molar ratio for VL-VH:AL fragment. The error bars were determined with three independent repeats of the measurements. Cytotoxicity test results for the antibodies GH2-42, G2-61, and G2-75 in scFv or IgG form are respectively provided in FIGS. 4A, 4B, and 4C.
Figure 4B:
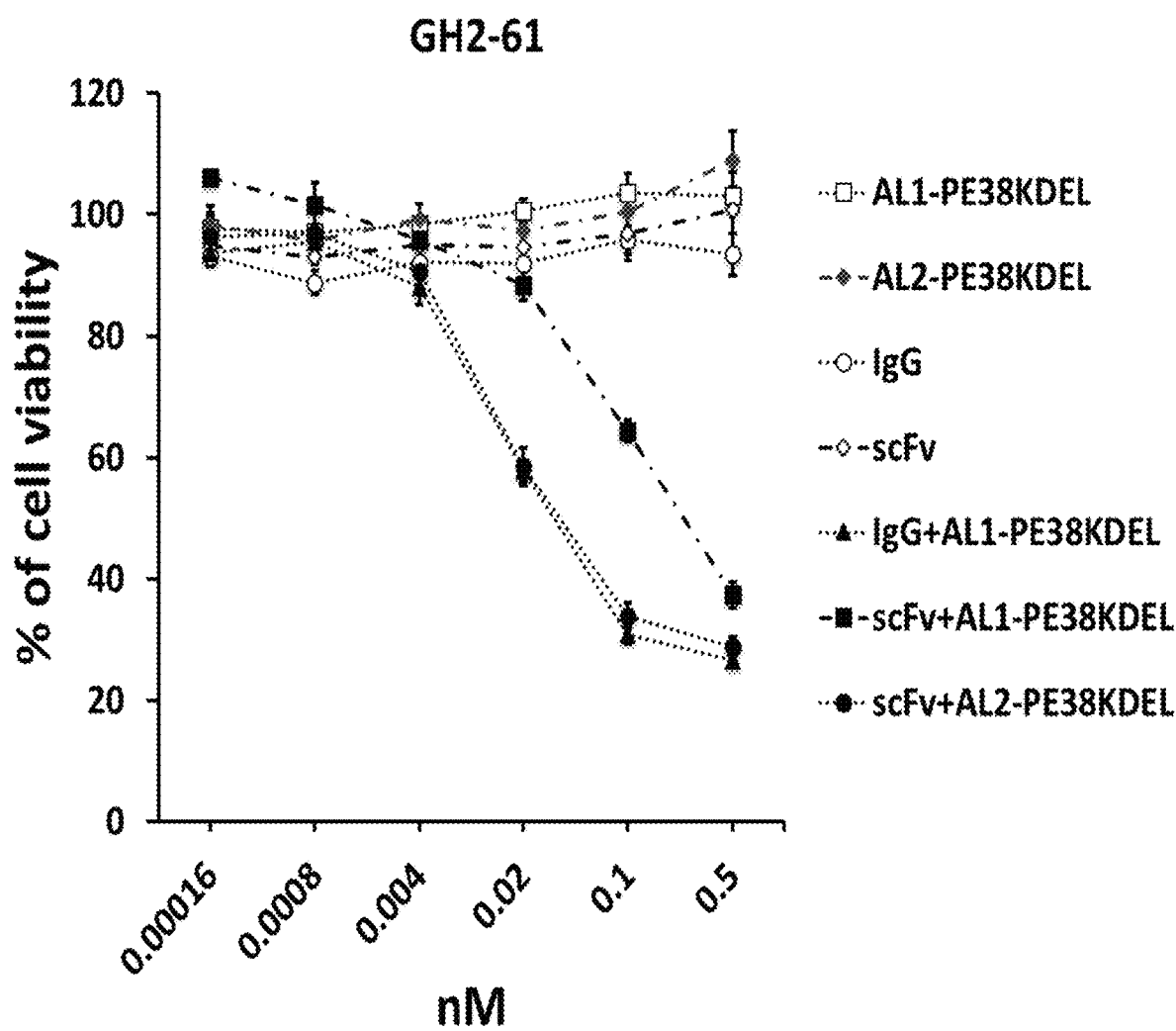
Figure 4C:
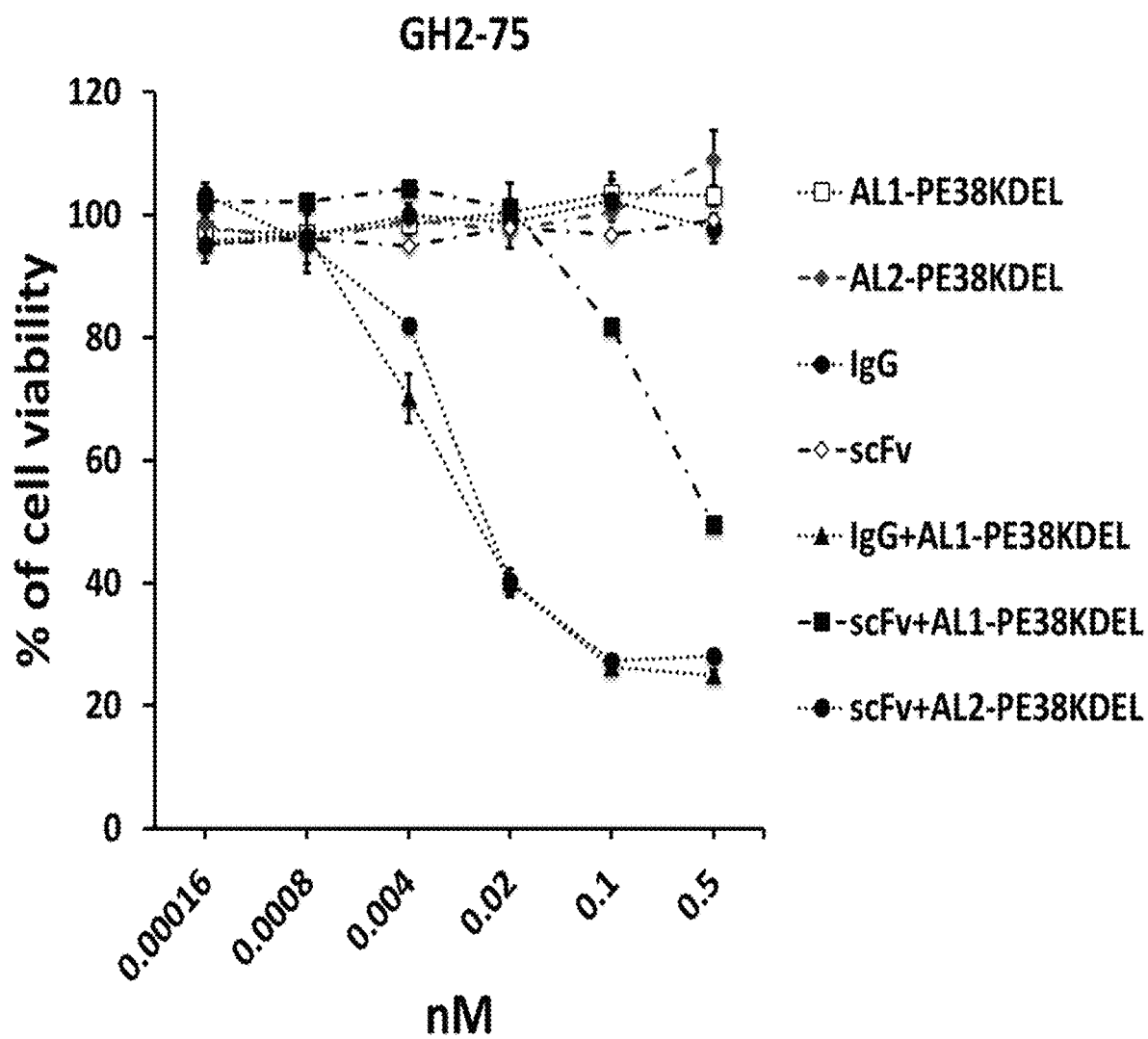

Non-Covalently Assembled scFv-AL1-PE38KDEL and scFv-AL2-PE38KDEL can be Potent Immunotoxins with Subnano-Molar $IC_{50}$ Both types of scFv-AL2-PE38KDEL and scFv-AL1-PE38KDEL complexes are potent immunotoxins. IgGs with the IGKV1-NL1*01/IGHV3-23*04 framework for the VL and VH variable domains complexed with AL1-PE38KDEL were comparable immunotoxins as the corresponding scFv-AL2-PE38KDEL (FIGS. 4A to 4C). The scFv(GH2-42)-AL1-PE38KDEL, scFv(GH2-61)-AL1-PE38KDEL, and scFv(GH2-75)-AL1-PE38KDEL are similar in potency as immunotoxins, with $IC_{50} \cong 0.1$ nM—the concentration of the scFv-AL1-PE38KDEL at which 50% of the cells tested were killed by the immunotoxin (FIGS. 4A to 4C). The IgG-AL1-PE38KDEL immunotoxins are equally potent as the corresponding scFv-AL2-PE38KDEL complexes for the three representative antibodies (FIGS. 4A to 4C), most likely because these two types of immunotoxins have bivalent antibody targeting modules. The immunotoxins with bivalent targeting modules are more cytotoxic comparing with the corresponding immunotoxins with monovalent targeting modules (FIGS. 4A to 4C); the extent of the bivalent effect varies depending on the details of the antibody-antigen interactions (FIGS. 4A to 4C). The results suggest that although the scFv-AL2-PE38KDEL complexes reduce the effective concentration of scFv in ELISA measurements (FIG. 3E), the cell-based cytotoxicity measurements nevertheless indicate the superior potency of the immunotoxins with bivalent antigen binding sites. The ELISA measurements were not indicative for the potency of the immunotoxins; direct measurements of cell-based cytotoxicity are essential for screening the potency of the immunotoxins. Overall, the technical platform provided herein is feasible for high-throughput screening of scFv/IgG as targeting modules in non-covalently assembled immunotoxins with mono- or bi-valent targeting modules.

Example 6

High-Throughput Screening of Non-Covalently Assembled Immunotoxins

92 HER2-ECD-specific scFvs selected from the GH2 synthetic antibody library were tested as the targeting modules in the non-covalently assembled immunotoxins with the present high-throughput screening platform. The CDR sequences of this set of scFvs, as we as the cytotoxicities thereof, are listed in Table 2, whereas the yield, EC50 and Biacore assay results of some randomly selected scFvs are summarized in Table 3.

In particular, epitope group 1 represents the grouping results from the competition assay of 92 GH2 scFv against 6 mouse IgGs (M32, M41, M61, M62, M63, and M64); M32-M62 epitope is situated on domains I of HER2-ECD, M41-M61 on domain IV and M63-M64 on domain III, whereas epitope group 2 represents the grouping result from the competition assay of 92 GH2 scFvs against 5 IgGs of known antibody-antigen complex structures: Trastuzumab (epitope: HER2-ECD domain IV), Pertuzumab (epitope: HER2-ECD domain II), A21 (epitope: HER2-ECD domain I), Fab37 (epitope: HER2-ECD domain III), and M32 (epitope: HER2-ECD domain I). The sequence range of corresponding CDR are indicated by the Kabat numbering, and the ranking order is based on the ranking of the cytotoxicity of the corresponding scFv-AL1-PE38KDEL. Specifically, the CDR-L1 region is the L30 to L32 residues, the CDR-L2 region is the L49 to L53 residues, the CDR-L3 region is the L91 to L96 residues, CDR-H1 region is the H30 to H33 residues, the CDR-H2 region is the H50 to H58 residues, and the CDR-H3 region is the H96 to H100B residues.

TABLE 2

| scFv | SEQ ID No. | Epitope Group 1 | Epitope Group 2 | Cytotoxicity (% of cell viability) AL1-PE38KDEL | Cytotoxicity (% of cell viability) AL2-PE38KDEL |
|---|---|---|---|---|---|
| GH2-41 | 33 | M41-M61 | — | 42.3 (4.0) | 37.4 (3.3) |
| GH2-32 | 25 | M32-M62 | A21/M32 | 42.4 (1.7) | 38.7 (3.4) |
| GH2-50 | 41 | — | M32 | 43.0 (1.9) | 39.7 (1.6) |
| GH2-61 | 50 | M32-M62 | A21/M32 | 44.0 (3.2) | 39.6 (2.0) |
| GH2-42 | 34 | M32-M62 | A21/M32 | 45.6 (2.0) | 40.1 (5.9) |
| GH2-72 | 59 | M32-M62 | M32 | 45.7 (4.2) | 52.5 (2.4) |
| GH2-20 | 15 | M41-M61 | — | 46.7 (1.7) | 34.8 (2.6) |
| GH2-82 | 68 | M32-M62 | A21/M32 | 48.0 (3.9) | 43.1 (2.2) |
| GH2-83 | 69 | M32-M62 | M32 | 48.2 (4.2) | 41.6 (2.5) |
| GH2-92 | 76 | M32-M62 | A21/M32 | 49.4 (1.9) | 55.5 (3.7) |
| GH2-56 | 46 | M41-M61 | — | 49.5 (3.2) | 47.7 (1.4) |
| GH2-62 | 51 | M32-M62 | A21/M32 | 49.6 (2.5) | 45.1 (2.9) |
| GH2-75 | 61 | M32-M62 | M32 | 50.1 (3.1) | 38.9 (1.9) |
| GH2-24 | 18 | M32-M62 | A21/M32 | 50.4 (3.9) | 47.0 (3.9) |
| GH2-28 | 21 | M32-M62 | A21/M32 | 50.8 (2.3) | 39.9 (3.5) |
| GH2-89 | 73 | M32-M62 | A21/M32 | 50.9 (1.6) | 69.9 (6.5) |
| GH2-31 | 24 | M32-M62 | A21/M32 | 52.0 (3.4) | 44.7 (3.8) |
| GH2-33 | 26 | M32-M62 | A21/M32 | 52.3 (2.6) | 43.8 (4.8) |
| GH2-43 | 35 | M32-M62 | A21/M32 | 52.9 (3.1) | 53.9 (3.8) |
| GH2-51 | 42 | M32-M62 | M32 | 53.4 (2.7) | 40.1 (3.4) |
| GH2-101 | 84 | M32-M62 | A21/M32 | 55.1 (3.9) | 57.9 (4.2) |
| GH2-69 | 57 | M32-M62 | A21/M32 | 58.4 (1.5) | 64.7 (3.9) |
| GH2-103 | 86 | M32-M62 | A21/M32 | 58.4 (1.5) | 44.5 (2.4) |
| GH2-93 | 77 | M32-M62 | A21/M32 | 58.5 (5.2) | 60.3 (1.5) |
| GH2-94 | 78 | M32-M62 | A21/M32 | 58.6 (0.4) | 53.4 (3.6) |
| GH2-23 | 17 | M41-M61 | — | 59.3 (2.1) | 60.1 (4.0) |
| GH2-68 | 56 | M32-M62 | A21/M32 | 59.5 (4.1) | 71.5 (3.5) |
| GH2-13 | 9 | M32-M62 | M32 | 60.3 (1.3) | 47.7 (3.2) |
| GH2-7 | 4 | M32-M62 | M32 | 60.4 (0.8) | 67.9 (3.3) |
| GH2-104 | 87 | M32-M62 | M32 | 61.3 (6.0) | 56.4 (2.6) |
| GH2-57 | 47 | M32-M62 | A21/M32 | 63.1 (6.7) | 46.5 (2.5) |
| GH2-98 | 82 | M32-M62 | A21/M32 | 63.6 (4.1) | 55.6 (4.0) |
| GH2-66 | 55 | M32-M62 | M32 | 63.7 (3.3) | 54.9 (0.6) |
| GH2-97 | 81 | M32-M62 | A21/M32 | 64.2 (6.1) | 75.5 (4.0) |
| GH2-76 | 62 | M32-M62 | A21/M32 | 64.5 (3.1) | 53.3 (2.4) |
| GH2-90 | 74 | M32-M62 | A21/M32 | 64.6 (7.1) | 60.4 (2.7) |
| GH2-46 | 37 | M32-M62 | A21/M32 | 65.7 (1.4) | 50.2 (2.8) |
| GH2-84 | 70 | M32-M62 | A21/M32 | 65.9 (5.9) | 53.3 (2.1) |
| GH2-71 | 58 | M32-M62 | A21/M32 | 66.3 (7.0) | 65.8 (1.5) |
| GH2-5 | 3 | M32-M62 | A21/M32 | 66.5 (1.6) | 84.6 (6.2) |
| GH2-30 | 23 | M32-M62 | A21/M32 | 66.5 (2.8) | 85.8 (1.5) |
| GH2-47 | 38 | M32-M62 | A21/M32 | 67.5 (4.6) | 49.7 (1.8) |
| GH2-95 | 79 | M32-M62 | M32 | 67.7 (6.0) | 37.6 (1.4) |
| GH2-19 | 14 | M32-M62 | A21/M32 | 68.7 (2.9) | 62.6 (9.2) |
| GH2-100 | 83 | M32-M62 | A21/M32 | 68.7 (5.6) | 63.1 (0.8) |
| GH2-105 | 88 | M32-M62 | A21/M32 | 68.9 (1.8) | 51.1 (4.2) |
| GH2-80 | 66 | M32-M62 | A21/M32 | 70.7 (3.3) | 86.2 (3.8) |
| GH2-54 | 44 | M32-M62 | M32 | 71.5 (8.5) | 56.3 (3.1) |
| GH2-91 | 75 | M32-M62 | A21/M32 | 71.7 (0.7) | 94.8 (1.5) |
| GH2-81 | 67 | M32-M62 | A21/M32 | 72.3 (7.9) | 65.4 (3.3) |
| GH2-96 | 80 | M32-M62 | A21/M32 | 72.7 (4.1) | 61.6 (2.4) |
| GH2-79 | 65 | M32-M62 | A21/M32 | 75.8 (4.5) | 73.5 (5.9) |
| GH2-25 | 19 | M41-M61 | — | 76.8 (3.1) | 63.7 (3.5) |
| GH2-77 | 63 | M32-M62 | A21/M32 | 77.0 (10.1) | 64.8 (5.6) |
| GH2-106 | 89 | M32-M62 | A21/M32 | 77.3 (5.0) | 61.8 (6.1) |
| GH2-39 | 31 | M32-M62 | A21/M32 | 77.7 (2.3) | 35.6 (2.6) |
| GH2-78 | 64 | M32-M62 | A21/M32 | 77.9 (2.7) | 79.6 (2.3) |
| GH2-14 | 10 | M32-M62 | M32 | 78.7 (4.4) | 78.5 (8.6) |
| GH2-59 | 48 | M32-M62 | A21/M32 | 78.7 (5.9) | 71.8 (3.1) |
| GH2-85 | 71 | M32-M62 | A21/M32 | 79.6 (11.4) | 52.0 (1.4) |

TABLE 2-continued

| scFv | SEQ ID No. | Epitope Group 1 | Epitope Group 2 | Cytotoxicity (% of cell viability) AL1-PE38KDEL | Cytotoxicity (% of cell viability) AL2-PE38KDEL |
|---|---|---|---|---|---|
| GH2-16 | 11 | — | — | 79.6 (2.1) | 80.6 (7.4) |
| GH2-60 | 49 | M32-M62 | A21/M32 | 80.1 (3.8) | 38.9 (2.7) |
| GH2-73 | 60 | M32-M62 | A21/M32 | 81.3 (9.2) | 35.2 (2.3) |
| GH2-3 | 1 | M63-M64 | Trastuzumab | 82.3 (5.4) | 71.9 (2.0) |
| GH2-9 | 6 | M32-M62 | A21/M32 | 83.0 (3.6) | 78.9 (3.9) |
| GH2-45 | 36 | M32-M62 | A21/M32 | 84.8 (1.4) | 90.7 (4.6) |
| GH2-65 | 54 | M32-M62 | M32 | 85.1 (7.0) | 84.3 (1.2) |
| GH2-53 | 43 | M41-M61 | — | 86.0 (8.8) | 86.6 (6.2) |
| GH2-64 | 53 | M41-M61 | — | 87.0 (13.3) | 69.1 (3.2) |
| GH2-11 | 7 | M32-M62 | A21/M32 | 88.2 (1.3) | 77.2 (0.9) |
| H32 | 107 | M32-M62 | M32 | 88.9 (13.0) | 40.0 (5.5) |
| GH2-102 | 85 | M32-M62 | A21/M32 | 89.0 (11.1) | 91.6 (6.7) |
| GH2-36 | 28 | M32-M62 | A21/M32 | 89.9 (6.6) | 81.9 (4.9) |
| GH2-40 | 32 | M32-M62 | A21/M32 | 90.1 (8.7) | 42.9 (6.0) |
| GH2-87 | 72 | M63-M64 | Fab37 | 90.9 (7.2) | 90.6 (4.7) |
| GH2-107 | 90 | M32-M62 | A21/M32 | 92.5 (5.6) | 101.1 (8.0) |
| GH2-38 | 30 | M32-M62 | A21/M32 | 93.3 (5.7) | 79.1 (2.9) |
| GH2-8 | 5 | M32-M62 | M32 | 93.4 (3.0) | 40.1 (1.0) |
| GH2-49 | 40 | M41-M61 | — | 94.6 (10.9) | 87.6 (5.5) |
| Trastuzumab | N/A | — | Trastuzumab | 94.7 (5.8) | 86.8 (7.9) |
| GH2-63 | 52 | M41-M61 | — | 96.0 (9.9) | 105.1 (7.8) |
| GH2-12 | 8 | M32-M62 | A21/M32 | 96.3 (7.0) | 88.7 (2.6) |
| GH2-55 | 45 | M32-M62 | A21/M32 | 97.1 (16.6) | 111.2 (6.7) |
| GH2-4 | 2 | M32-M62 | A21/M32 | 97.4 (3.9) | 83.4 (5.5) |
| GH2-35 | 27 | M32-M62 | A21/M32 | 97.5 (2.5) | 110.1 (9.7) |
| GH2-18 | 13 | — | Trastuzumab | 98.4 (7.6) | 104.6 (6.3) |
| GH2-26 | 20 | M32-M62 | A21/M32 | 100.2 (0.9) | 83.3 (4.1) |
| GH2-29 | 22 | M32-M62 | A21/M32 | 100.2 (8.0) | 87.4 (4.8) |
| GH2-37 | 29 | M32-M62 | A21/M32 | 101.0 (9.1) | 102.5 (6.6) |
| GH2-21 | 16 | M41-M61 | — | 102.8 (7.6) | 93.0 (5.2) |
| GH2-17 | 12 | M63-M64 | Trastuzumab | 106.1 (4.9) | 106.0 (6.5) |
| GH2-48 | 39 | M32-M62 | — | 107.8 (2.8) | 101.3 (2.9) |

TABLE 3

| scFv | Yield (mg/L) | EC$_{50}$ (ng/mL) | BIAcore assay $k_{on}$ (M$^{-1}$S$^{-1}$) | BIAcore assay $k_{off}$ (S$^{-1}$) | BIAcore assay $K_D$ (M) |
|---|---|---|---|---|---|
| GH2-61 | 10 | 3.5 | $3.866 \times 10^5$ | $1.044 \times 10^{-4}$ | $2.700 \times 10^{-10}$ |
| GH2-42 | 19.3 | 2.7 | $1.393 \times 10^6$ | $2.354 \times 10^{-4}$ | $1.690 \times 10^{-10}$ |
| GH2-72 | 12.6 | 13.7 | $9.152 \times 10^8$ | 10.89 | $1.189 \times 10^{-8}$ |
| GH2-75 | 18.3 | 2.2 | $8.399 \times 10^5$ | $1.486 \times 10^{-4}$ | $1.769 \times 10^{-10}$ |
| GH2-23 | 11 | 4.5 | $2.174 \times 10^5$ | $1.797 \times 10^{-4}$ | $8.266 \times 10^{-10}$ |
| GH2-13 | 7.7 | 3 | $3.103 \times 10^6$ | $8.179 \times 10^{-3}$ | $2.636 \times 10^{-9}$ |
| GH2-7 | 11 | 3.3 | $6.179 \times 10^6$ | $6.082 \times 10^{-2}$ | $9.842 \times 10^{-9}$ |
| GH2-104 | 41.7 | 2.8 | $8.515 \times 10^5$ | $8.841 \times 10^{-4}$ | $1.035 \times 10^{-9}$ |
| GH2-98 | 29.7 | 82.3 | $2.536 \times 10^5$ | $2.243 \times 10^{-2}$ | $8.847 \times 10^{-8}$ |
| GH2-66 | 12.3 | 7.9 | $6.026 \times 10^6$ | $3.284 \times 10^{-1}$ | $5.453 \times 10^{-8}$ |
| GH2-95 | 29.8 | 3.2 | $5.466 \times 10^4$ | $2.441 \times 10^{-4}$ | $4.466 \times 10^{-9}$ |
| GH2-54 | 27 | 8 | $3.387 \times 10^5$ | $1.282 \times 10^{-2}$ | $3.785 \times 10^{-8}$ |
| GH2-91 | 14.2 | 4.2 | $2.747 \times 10^5$ | $6.790 \times 10^{-3}$ | $2.472 \times 10^{-9}$ |
| GH2-81 | 28.1 | 5 | $9.750 \times 10^5$ | $1.309 \times 10^{-2}$ | $1.343 \times 10^{-8}$ |
| GH2-96 | 20.1 | 3.4 | $2.537 \times 10^5$ | $1.375 \times 10^{-3}$ | $5.422 \times 10^{-9}$ |
| GH2-78 | 12.1 | 24.4 | $3.302 \times 10^4$ | $1.632 \times 10^{-3}$ | $4.942 \times 10^{-8}$ |
| GH2-14 | 41.1 | 9.2 | $3.365 \times 10^5$ | $5.735 \times 10^{-3}$ | $1.704 \times 10^{-8}$ |
| GH2-59 | 5.8 | 31.2 | $4.778 \times 10^4$ | $2.877 \times 10^{-4}$ | $6.022 \times 10^{-9}$ |
| GH2-16 | 18.8 | 4.2 | $8.571 \times 10^4$ | $1.025 \times 10^{-4}$ | $1.196 \times 10^{-9}$ |
| GH2-60 | 15.8 | 3.4 | $3.636 \times 10^6$ | $5.557 \times 10^{-3}$ | $1.529 \times 10^{-9}$ |
| GH2-3 | 8 | 7 | $2.425 \times 10^5$ | $5.024 \times 10^{-4}$ | $2.071 \times 10^{-9}$ |
| GH2-65 | 6.8 | 7.6 | $3.497 \times 10^5$ | $1.110 \times 10^{-2}$ | $3.175 \times 10^{-8}$ |
| H32 | 6.8 | 3.1 | $2.941 \times 10^5$ | $7.147 \times 10^{-5}$ | $2.430 \times 10^{-10}$ |
| GH2-102 | 8.1 | 23.1 | $1.371 \times 10^6$ | $3.902 \times 10^{-2}$ | $2.845 \times 10^{-8}$ |
| GH2-36 | 10.1 | 3.9 | $8.681 \times 10^8$ | 7.7 | $8.852 \times 10^{-9}$ |
| GH2-40 | 8.7 | 4 | $7.118 \times 10^4$ | $2.165 \times 10^{-4}$ | $3.042 \times 10^{-9}$ |
| GH2-87 | 40.2 | 14.7 | $3.948 \times 10^5$ | $5.248 \times 10^{-3}$ | $1.329 \times 10^{-8}$ |
| GH2-8 | 9.3 | 5.1 | $5.988 \times 10^5$ | $1.551 \times 10^{-4}$ | $2.590 \times 10^{-10}$ |
| Trastuzumab | — | 4.5 | $2.543 \times 10^6$ | $2.157 \times 10^{-5}$ | $8.482 \times 10^{-12}$ |
| GH2-18 | 13.8 | 3.3 | $1.563 \times 10^5$ | $1.086 \times 10^{-5}$ | $6.948 \times 10^{-11}$ |
| GH2-21 | 15.8 | 4.1 | $4.435 \times 10^5$ | $6.228 \times 10^{-4}$ | $1.404 \times 10^{-9}$ |

Figure 5:
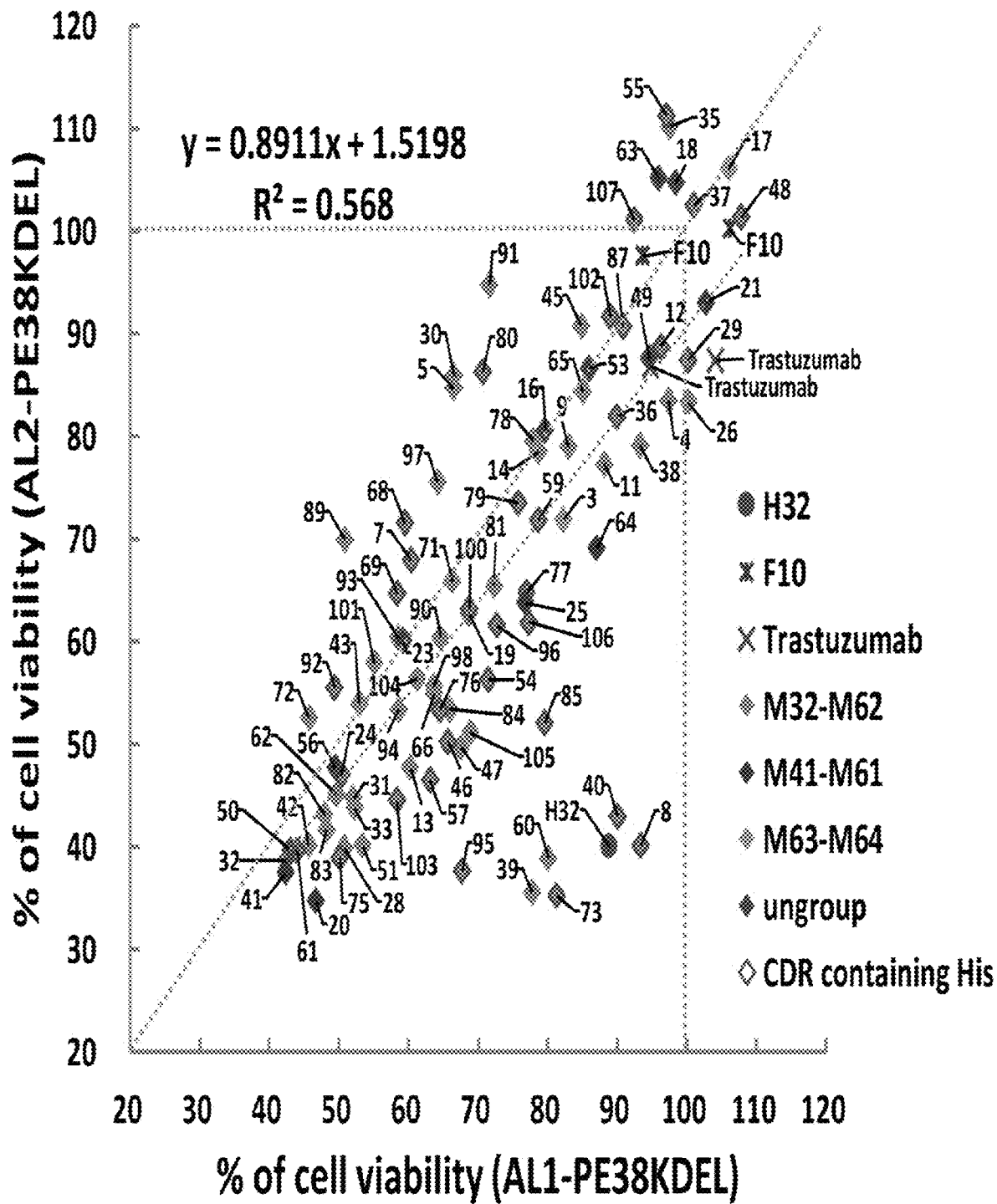
FIG. 5 shows the cytotoxicity screening of 92 HER2-ECD-specific scFv-AL1/AL2-PE38KDEL immunotoxins. The percentages of cell viability for N87 cells treated with scFv-AL1-PE38KDEL or scFv-AL2-PE38KDEL were determined and shown in the x-axis and y-axis respectively. Four epitope groups of these GH2 scFvs are marked in gray (M32-M62), green (M41-M61), yellow (M63-M64), and purple (ungrouped). GH2 scFvs with histidine(s) in CDR H3 are indicated by the red frame over the symbol. The detailed data for each of the scFvs are listed in Tables 2 and 3.
Figure 6A:
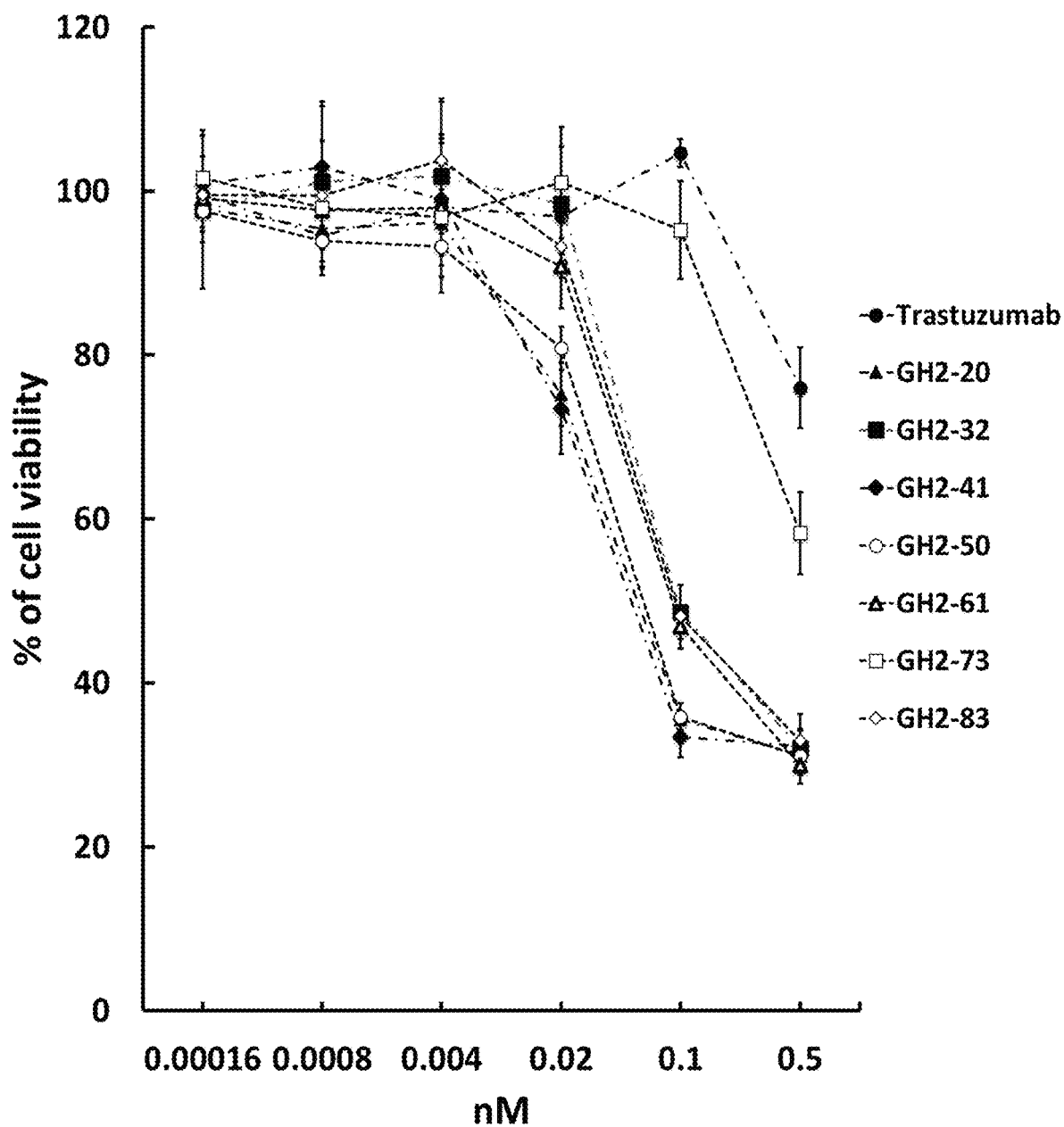
FIG. 6A and FIG. 6B respectively shows the $IC_{50}$ measurements of selected GH2 scFvs for the scFv-AL1-PE38KDEL complexes and scFv-AL2-PE38KDEL complexes, where the y-axis shows the percentage of the cell viability of the treated N87 cells and the x-axis shows the concentration of the scFv. The error bars were calculated with three independent repeats of the measurements.
Figure 6B:
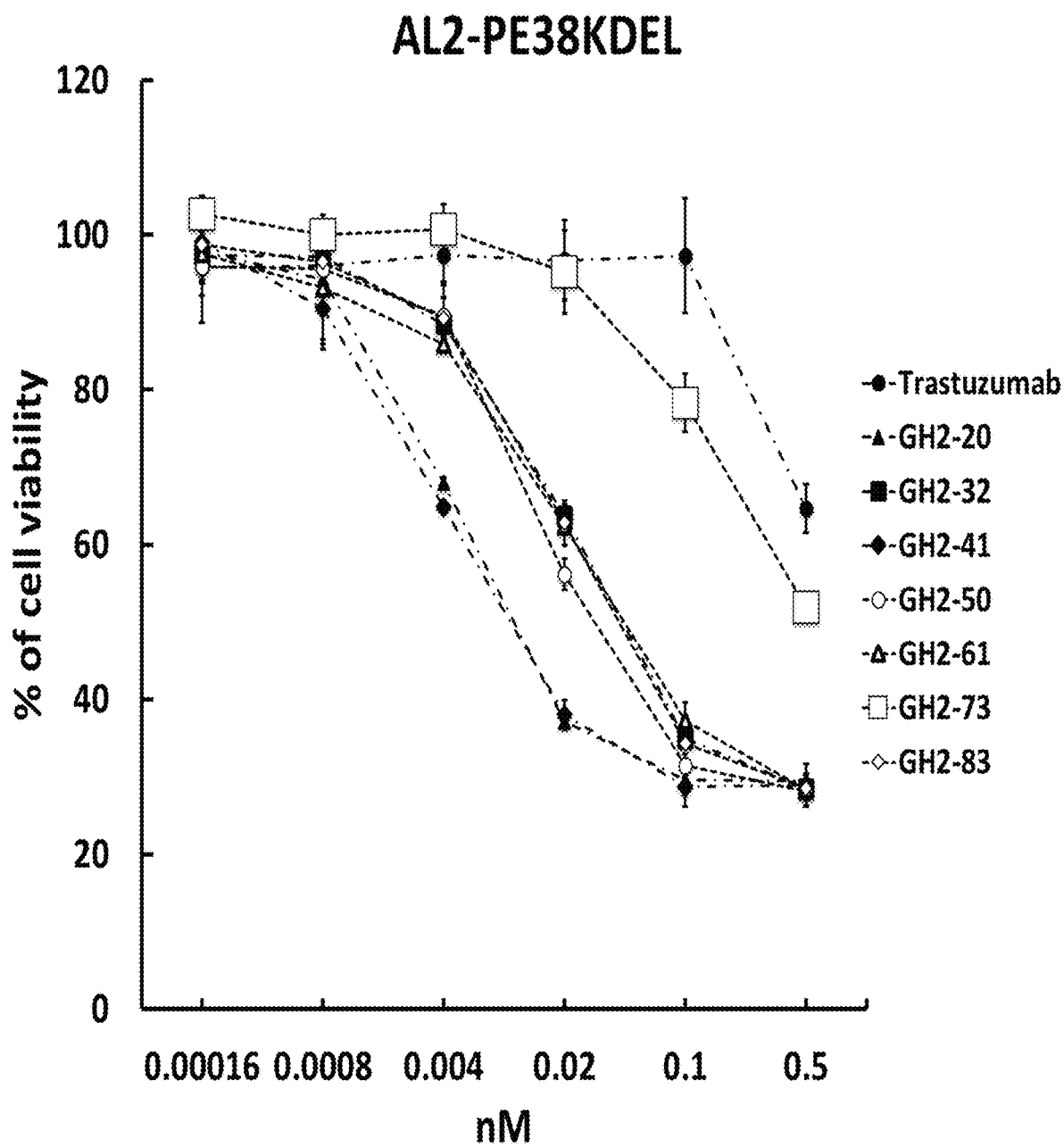
Figure 7A:
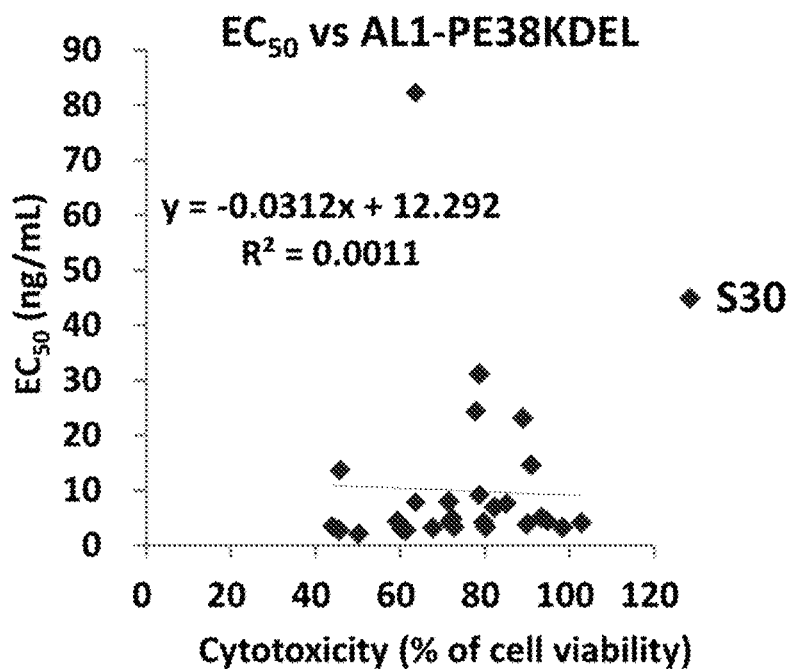
FIG. 7A to FIG. 7D show the $EC_{50}$, $K_D$, $k_{on}$, and $k_{off}$ vs. cytotoxicity of scFv-AL1-PE38KDEL immunotoxins, respectively. The $EC_{50}$, $K_D$, $k_{on}$, and $k_{off}$ for the scFvs were plotted against the cytotoxicity of the corresponding scFv-AL1-PE38KDEL immunotoxins. The detailed information for these scFvs (data set S30) are shown in Tables 2 and 3.
Figure 7B:
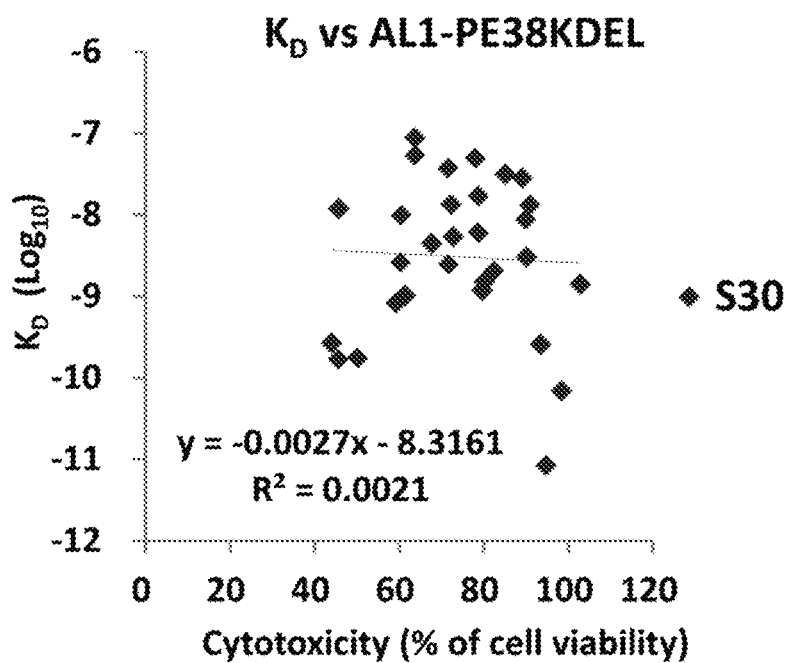
Figure 7C:
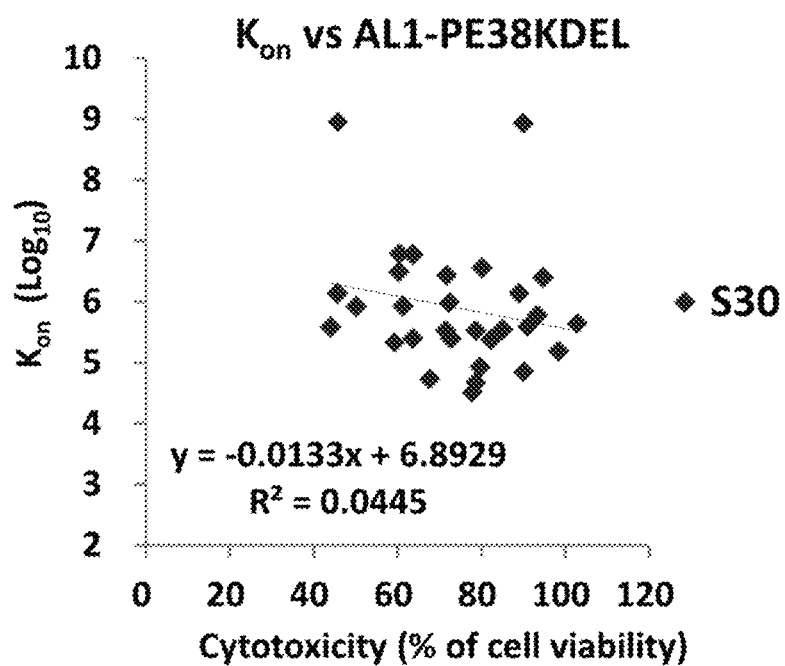
Figure 7D:
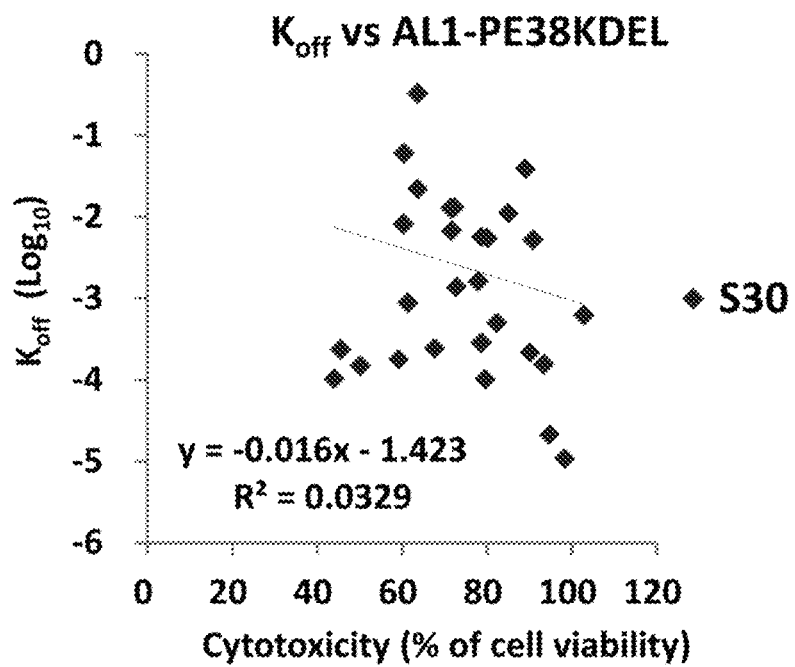
Figure 8A:
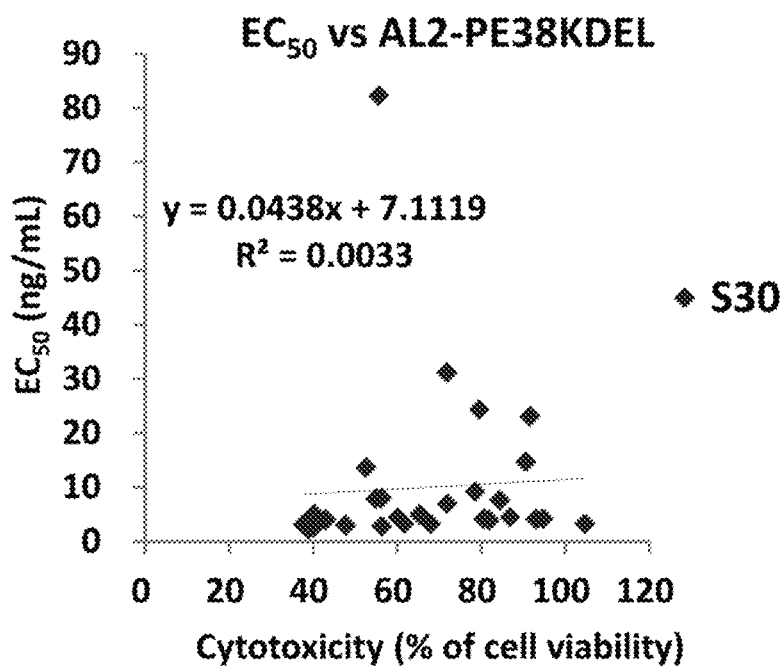
FIG. 8A to FIG. 8D show the $EC_{50}$, $K_D$, $k_{on}$, and $k_{off}$ vs. cytotoxicity of scFv-AL2-PE38KDEL immunotoxins. The $EC_{50}$, $K_D$, $k_{on}$, and $k_{off}$ for the scFvs were plotted against the cytotoxicity of the corresponding scFv-AL2-PE38KDEL immunotoxins. The detailed information for these scFvs (data set S30) are shown in Tables 2 and 3.
Figure 8B:
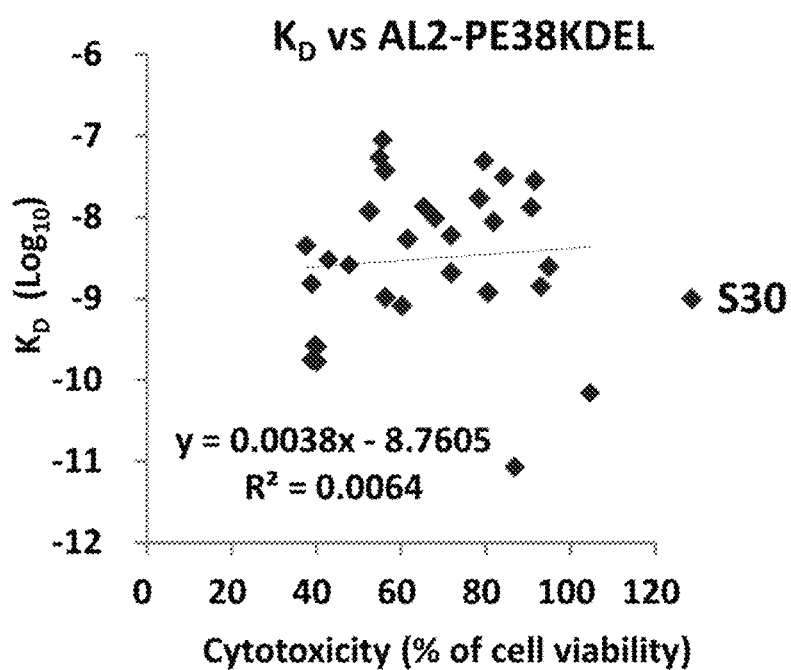
Figure 8C:
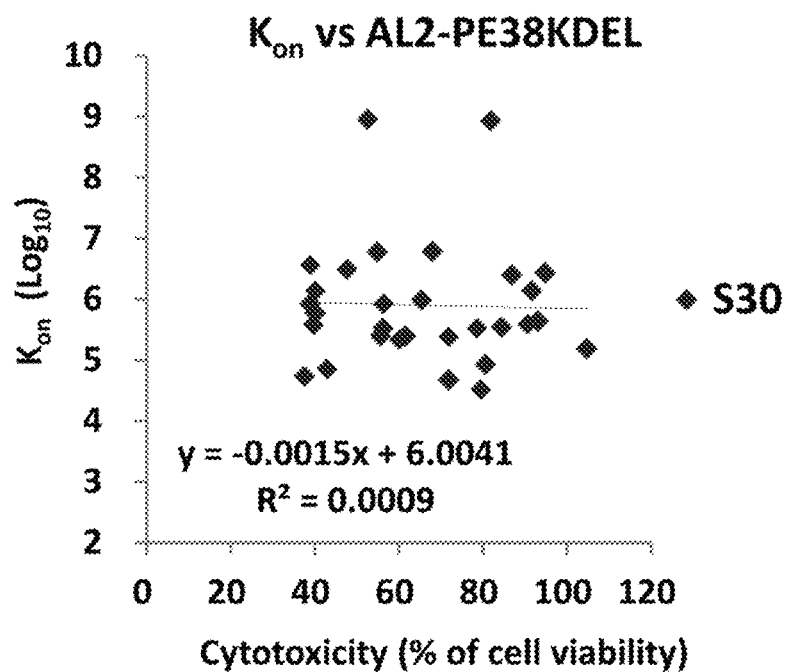
Figure 8D:
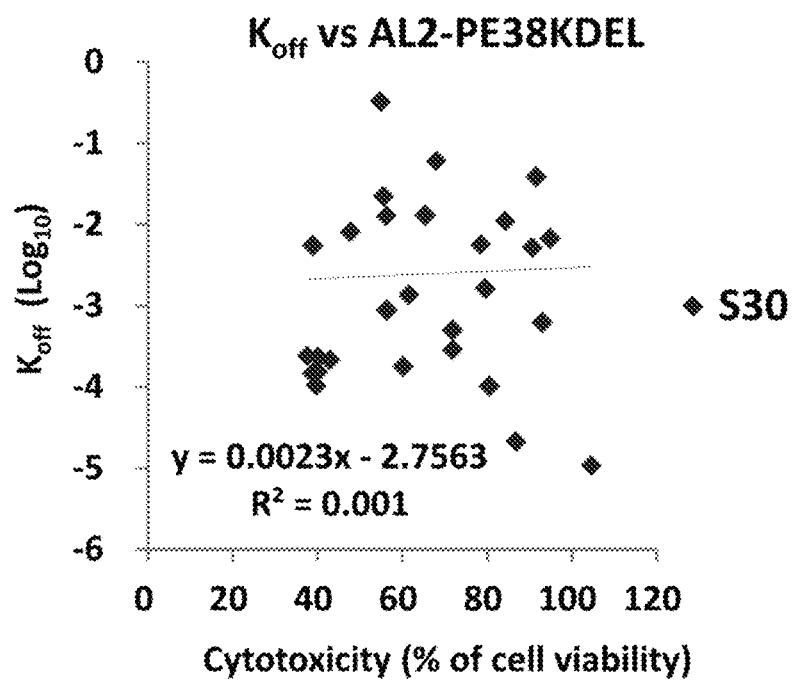

The soluble scFv in culture medium was adjusted to concentration of 0.5 nM in the presence of corresponding concentration of AL1-PE38KDEL or AL2-PE38KDEL for 1:1 molar ratio of scFv:AL fragment. The immunotoxin solutions were applied to test the cytotoxicity in micro-titer plate; the cell viability readouts showed wide-range of cytotoxicity of the immunotoxins at the concentration of 0.5 nM of scFv for both types of immunotoxins (FIG. 5). The IC$_{50}$'s of a few of the most potent immunotoxins were determined by cytotoxicity measurements for cells treated with serial dilutions of the scFv-AL1-PE38KDEL (FIG. 6A) and scFv-AL2-PE38KDEL immunotoxins (FIG. 6B). The GH2-41 and GH2-20 scFvs appear as the most effective targeting modules from the set of the 92 scFvs in both form of immunotoxins, and the bivalent form is superior to the monovalent form in terms of cytotoxicity by about 10 folds, with IC$_{50}$<10 pico-molar. By comparison, Trastuzumab scFv as a targeting module is about 100 folds inferior in terms of IC$_{50}$ to the best scFvs in the set of scFvs tested (FIGS. 6A and 6B).

The epitopes and binding affinity/kinetics of the tested scFvs are not the major determinants for the potency of the immunotoxins. The cytotoxicity of the scFv-AL1-PE38KDEL immunotoxins is largely linearly correlated with the cytotoxicity of the corresponding scFv-AL2-

PE38KDEL immunotoxins with slope=0.89 and $R^2$=0.57 (Pearson's correlation coefficient=0.75) (FIG. 5). A slope less than one in the plot indicates that bivalent immunotoxins are in general more potent than single valent immunotoxins; the bivalent effect is dependent on the details of the scFv-antigen interaction (FIGS. 4A to 4C), explaining the scattering of the data points in the plot. Moderate linear correlation in the plot suggests that intrinsic properties of the scFv determine the potency of the mono- and bivalent immunotoxins. However, the predominant determinants for the potency of the immunotoxins are not obvious: scFvs from the same epitope group (color coded as shown in the data points in FIG. 5, see also Tables 2 and 3) have wide range of cytotoxicity, suggesting that the cytotoxicity of the immunotoxins depends on parameters not limited by the epitope locations on the antigen surface. $EC_{50}$, $K_d$, $k_{on}$, and $k_{off}$ for the scFvs plotted against the cytotoxicity of the corresponding scFv-AL1-PE38KDEL immunotoxins (FIGS. 7A to 7D) and the cytotoxicity of the corresponding scFv-AL2-PE38KDEL immunotoxins (FIGS. 8A to 8D) show correlation coefficient close to zero, indicating that these binding affinity and binding kinetics parameters of the scFvs are not predominant determinants for the immunotoxins' potency.

The amino acid types on the CDR regions of the scFvs could be an important determinant affecting the cytotoxicity of the immunotoxins. Only CDRH3 of the GH2 synthetic scFvs are distributed with ionizable residue His (see the data points with black outline in FIG. 5), which might affect the cytotoxic potency of the immunotoxins because the His sidechain is expected to change charge state (pKa=6.5) when the immunotoxins are internalized from environment of pH 7 to expose to increasingly acidified environment with the pH approaching 5 in late endosomes. If the CDRH3 contains His residues and the His residues are involved in antibody-antigen interactions, these His residues could determine the subcellular locations where the immunotoxins dissociated from the target receptors at acidic pH. This dissociation location could decide if the immunotoxins get transferred to cytosol. We divide the 92 scFvs into 4 quarters according to the scFv-AL1-PE38KDEL cytotoxicity (Tables 2 and 3) and find that the ratios for scFvs containing His in CDRH3 are 6/23, 8/23, 10/23, and 13/23 respectively for the four quarters of the set of 92 scFv-AL1-PE38KDEL immunotoxins with decreasing cytotoxicity (FIG. 5 and Tables 2 and 3). This monotonic trend suggests that the His sidechains involving antibody-antigen interactions could be a determinant for the toxin payload trafficking routes, which in turn determine the cytotoxicity of the immunotoxins.

Figure 9A:
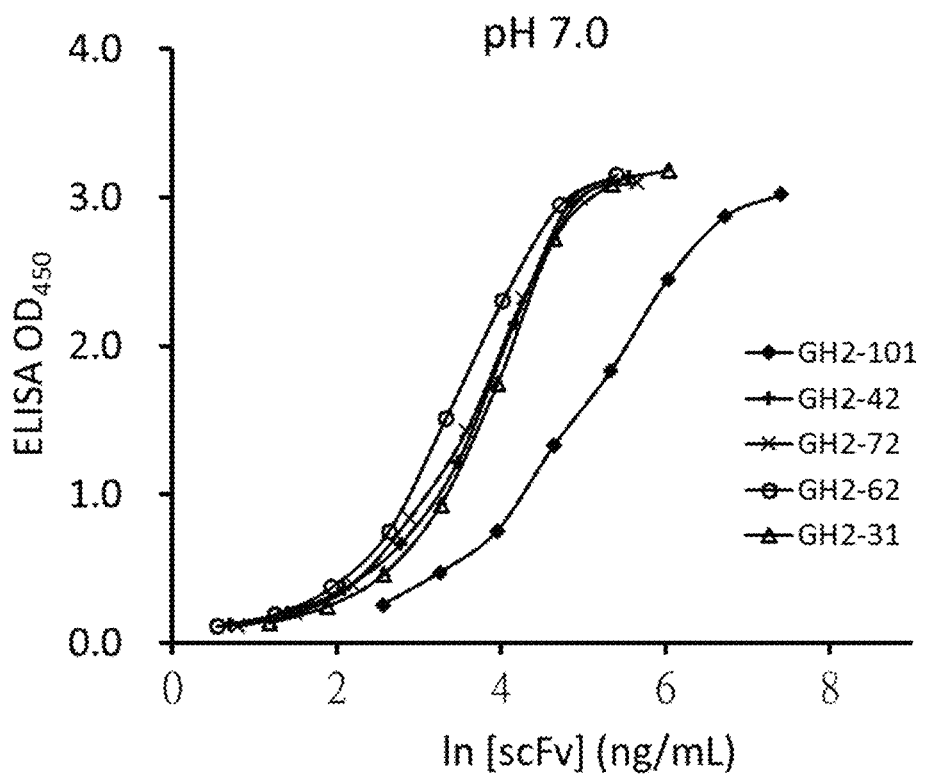
FIG. 9A to FIG. 9D respectively show the $EC_{50}$ of selected scFvs for scFv-AL1-PE38KDEL at pH 7 and pH 5.
Figure 9A:
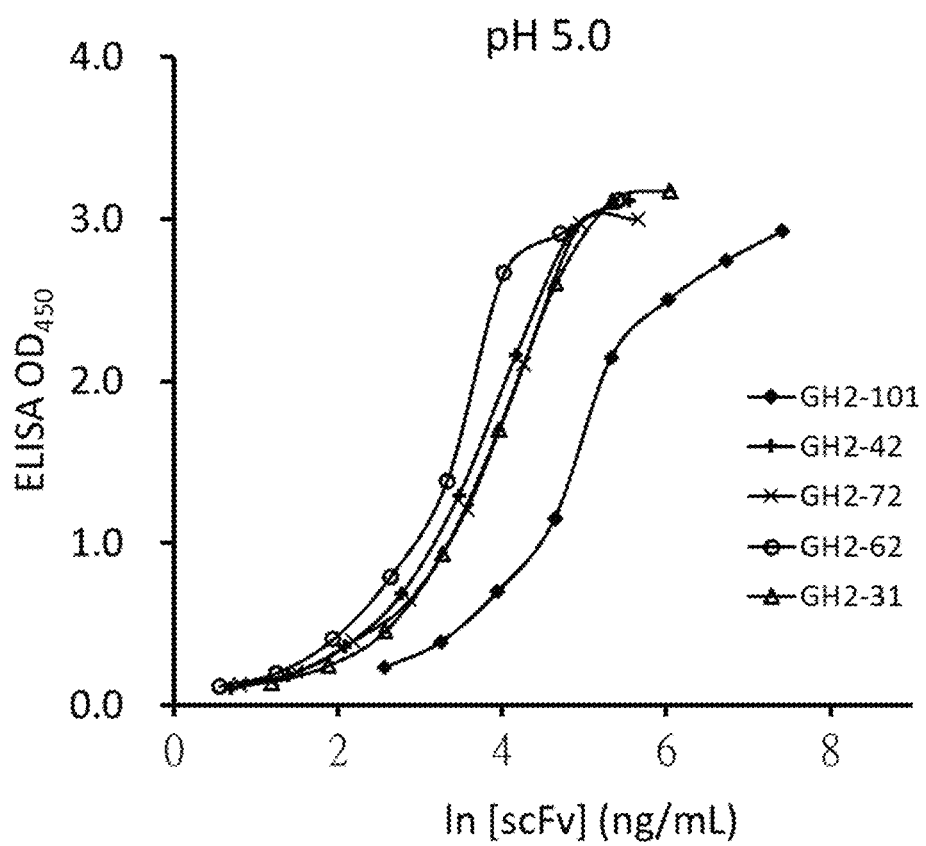
Figure 9B:
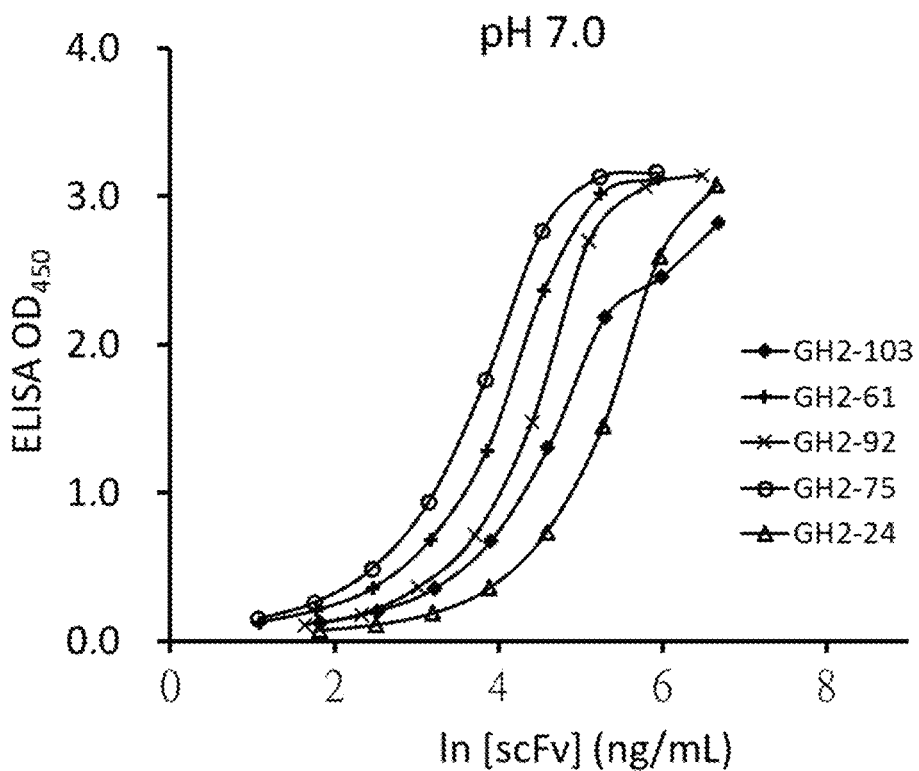
Figure 9B:
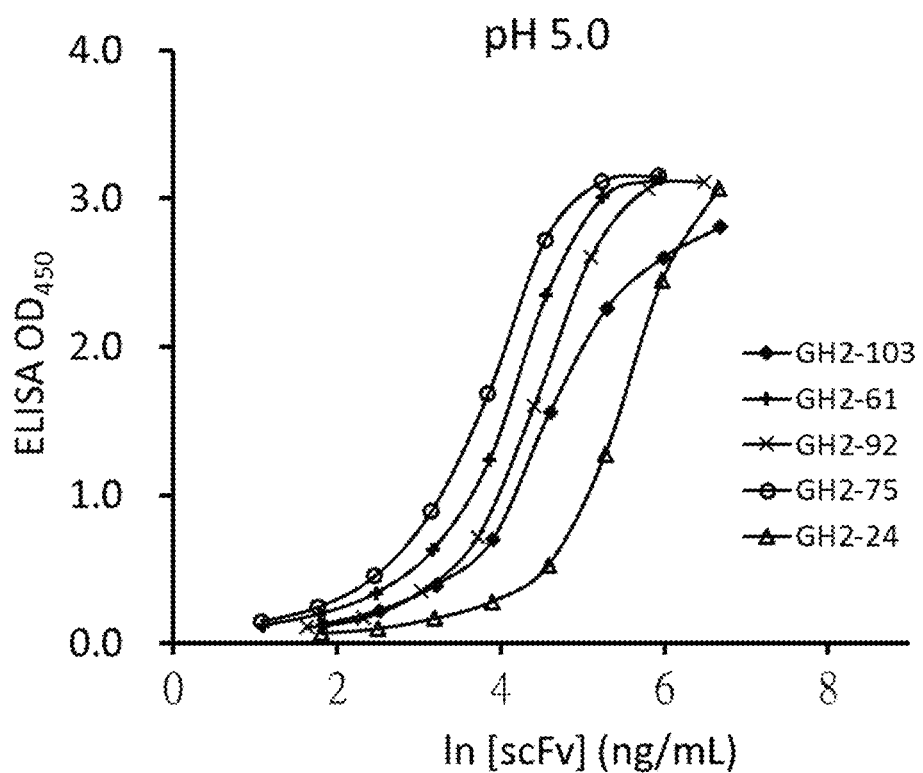
Figure 9C:
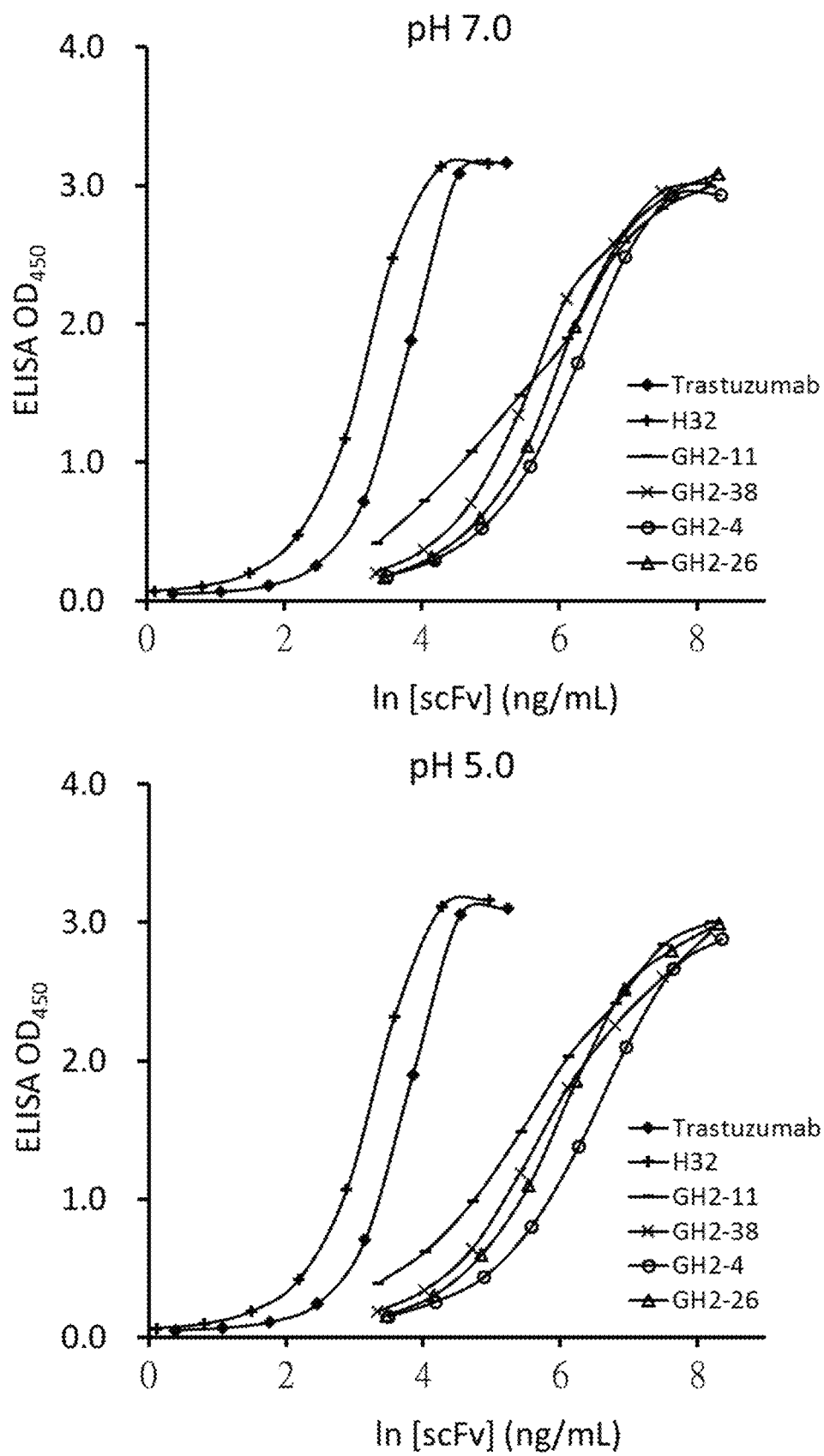
Figure 9D:
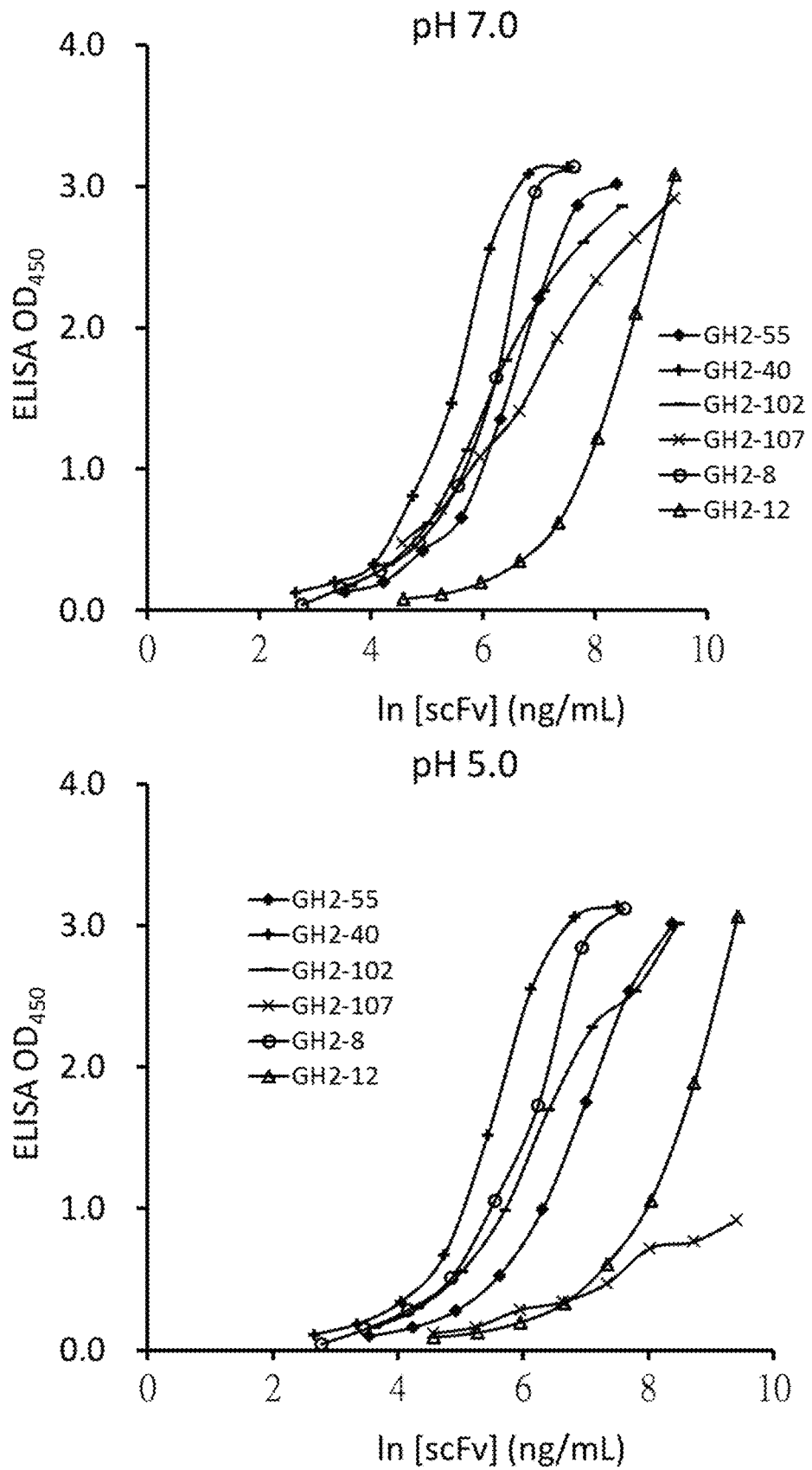

To test the effect of CDR His sidechains in determining the cytotoxicity of the immunotoxins, the pH-dependency of the immunotoxin-HER2 binding affinities for four subsets of scFv-AL1-PE38KDEL with diverse cytotoxicities and His residue distributions in the CDR regions was determined. Four subsets of scFv-AL1-PE38KDEL from the set of immunotoxins belonging to the M32-M62 epitope group were randomly grouped; see FIG. 5 (gray diamond data points with red outline (His in CDR) or without red outline (no His in CDR)): the first set scFv-AL1-PE38KDEL (GH2-42,72,62,31,101) were among the top 25% in terms of cytotoxicity and without His residue in the CDR regions (FIG. 9A); the second set (GH2-61, 92, 75, 24, 103) were also among the top 25% in terms of cytotoxicity but with His residue(s) in the CDR regions (FIG. 9B); the third set (GH2-11, 38, 4, 26, and H32) were among the bottom 25% in terms of cytotoxicity and without His residue in the CDR regions (FIG. 9C); the fourth set (GH2-102, 40, 107, 8, 12, 55) were also among the bottom 25% in terms of cytotoxicity and with His residue(s) in the CDR regions (FIG. 9D). Only the fourth group contained members for which the HER2-ECD affinities were substantially compromised at pH5 in comparison with those at pH7 (FIG. 9A to FIG. 9D and Table 4, below). The first and the third groups did not contain His residue in the CDR regions and thus the pH-independency of the affinities to their antigen was as expected. The pH-independency of the affinities of the second group (FIG. 9B) and the pH-dependency of the affinities of the fourth group (FIG. 9D) indicated that the interruption of the antibody-antigen interactions due to the ionization of His sidechains at the acidic environment of the endosome could be one of the factors attributing to the low cytotoxicity of the immunotoxins, in agreement with the conclusion in the previous paragraph. The affinity of scFv (trastuzumab)-AL1-PE38KDEL to HER-ECD is high and pH-independent (FIG. 9C), and thus the low cytotoxicity of this immunotoxin is most likely attributable to the epitope of trastuzumab on HER2-ECD domain IV, which is distant to the M32-M62 epitope group on domain I of HER2-ECD.

TABLE 4

| scFv | $EC_{50}$ of scFv-AL1-PE38KDEL (ng/mL) | | Ratio |
|---|---|---|---|
| | pH 7.0 | pH 5.0 | (pH 5/pH 7) |
| GH2-61 | 47.12 | 48.70 | 1.03 |
| GH2-42 | 41.61 | 41.17 | 0.99 |
| GH2-72 | 37.27 | 37.54 | 1.01 |
| GH2-92 | 77.35 | 77.08 | 1.00 |
| GH2-62 | 26.25 | 26.18 | 1.00 |
| GH2-75 | 37.79 | 39.61 | 1.05 |
| GH2-24 | 95.95 | 105.53 | 1.10 |
| GH2-31 | 33.30 | 34.10 | 1.02 |
| GH2-101 | 95.90 | 98.47 | 1.03 |
| GH2-103 | 65.99 | 58.44 | 0.89 |
| GH2-11 | 174.01 | 177.91 | 1.02 |
| H32 | 18.66 | 19.38 | 1.04 |
| GH2-102 | 423.30 | 417.27 | 0.99 |
| GH2-40 | 132.38 | 134.76 | 1.02 |
| GH2-107 | 787.74 | 380874.90 | 483.50 |
| GH2-38 | 232.35 | 276.80 | 1.19 |
| GH2-8 | 528.30 | 506.42 | 0.96 |
| GH2-12 | 1191.12 | 2106.96 | 1.77 |
| GH2-55 | 352.19 | 476.76 | 1.35 |
| GH2-4 | 259.81 | 348.50 | 1.34 |
| GH2-26 | 389.84 | 411.86 | 1.06 |
| Trastuzumab | 38.95 | 38.65 | 0.99 |

The scFvs were randomly selected from those listed in Table 3. The scFvs in the upper half of the Table 4 were selected from the first quarter of Table 3, which were the top 25% of scFvs in Table 3, ranked by cytotoxicity of the corresponding scFv-AL1-PE38KDEL; the scFvs in the lower half of the Table 4 were selected from the fourth quarter of Table 3, which were the bottom 25% of scFvs in Table 3, ranked by cytotoxicity of the corresponding scFv-AL1-PE38KDEL. The ratio was calculated by dividing the $EC_{50}$(pH5) with the $EC_{50}$(pH7).

Example 7

Figure 10A:
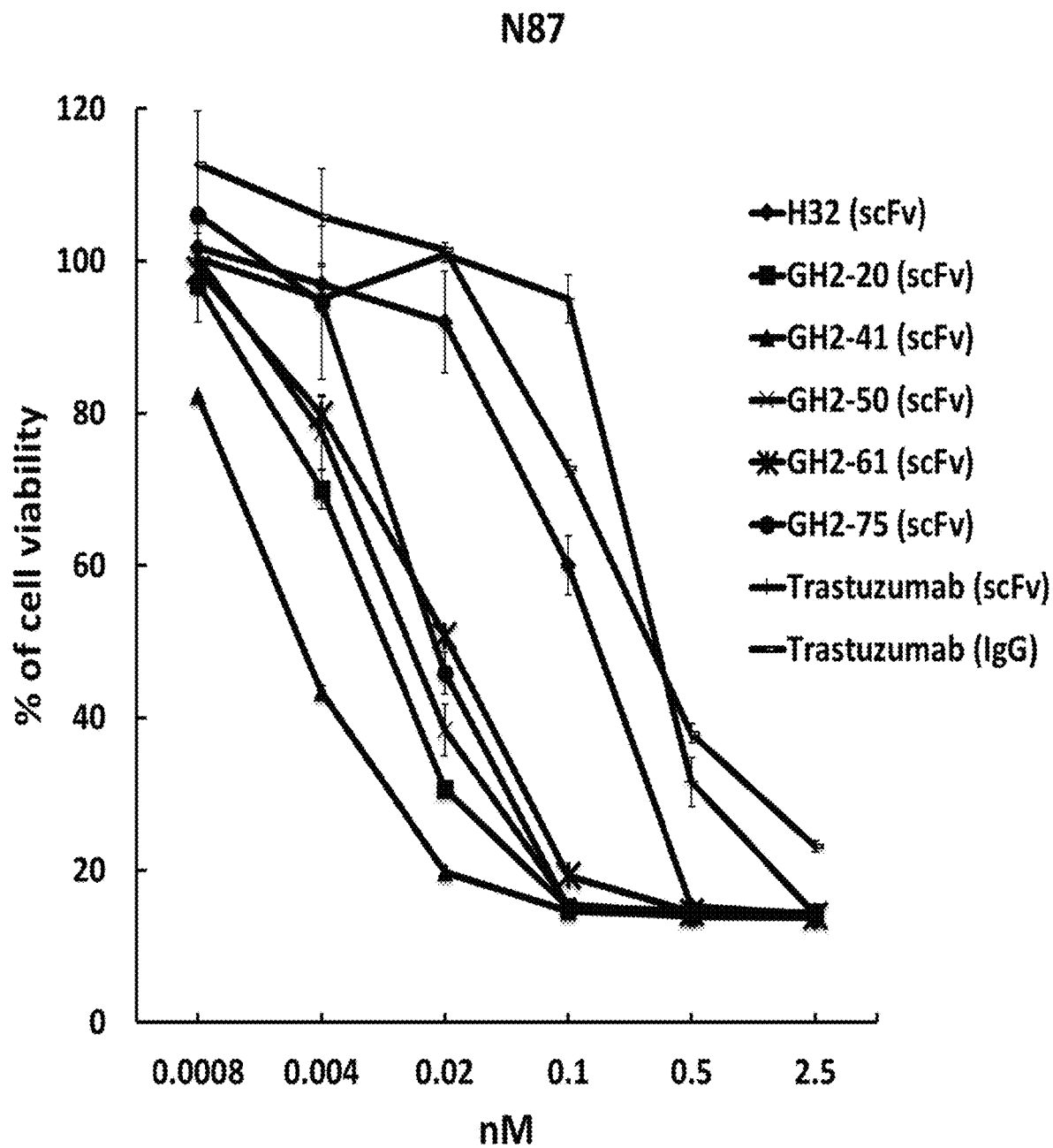
FIG. 10A to FIG. 10H show the cytotoxicity and mean fluorescence intensity of immunotoxins on cells with different HER2 expression level. The $IC_{50}$'s for N87 (FIG. 10A), SKBR3 (FIG. 10C), BT474 (FIG. 10E) and MCF7 (FIG. 10G) cells were measured with selected GH2 scFvs complexed with AL2-PE38KDEL in 1:1 ratio of the scFv:AL fragment. The error bars were calculated with three independent repeats of the measurements. Mean fluorescence intensities (MFIs) for the same set of scFvs complexed with AL2-RFP in 1:1 ratio of the scFv:AL fragment were measured with N87 (FIG. 10B), SKBR3 (FIG. 10D), BT474 (FIG. 10F), and MCF7 (FIG. 10H) cells by flow cytometry, where the MFIs shown in the y-axis were adjusted over the background value by the cells treated with AL2-RFP without scFv. The x-axis shows the concentration of the VL-VH variable domain or the AL fragment.
Figure 10B:
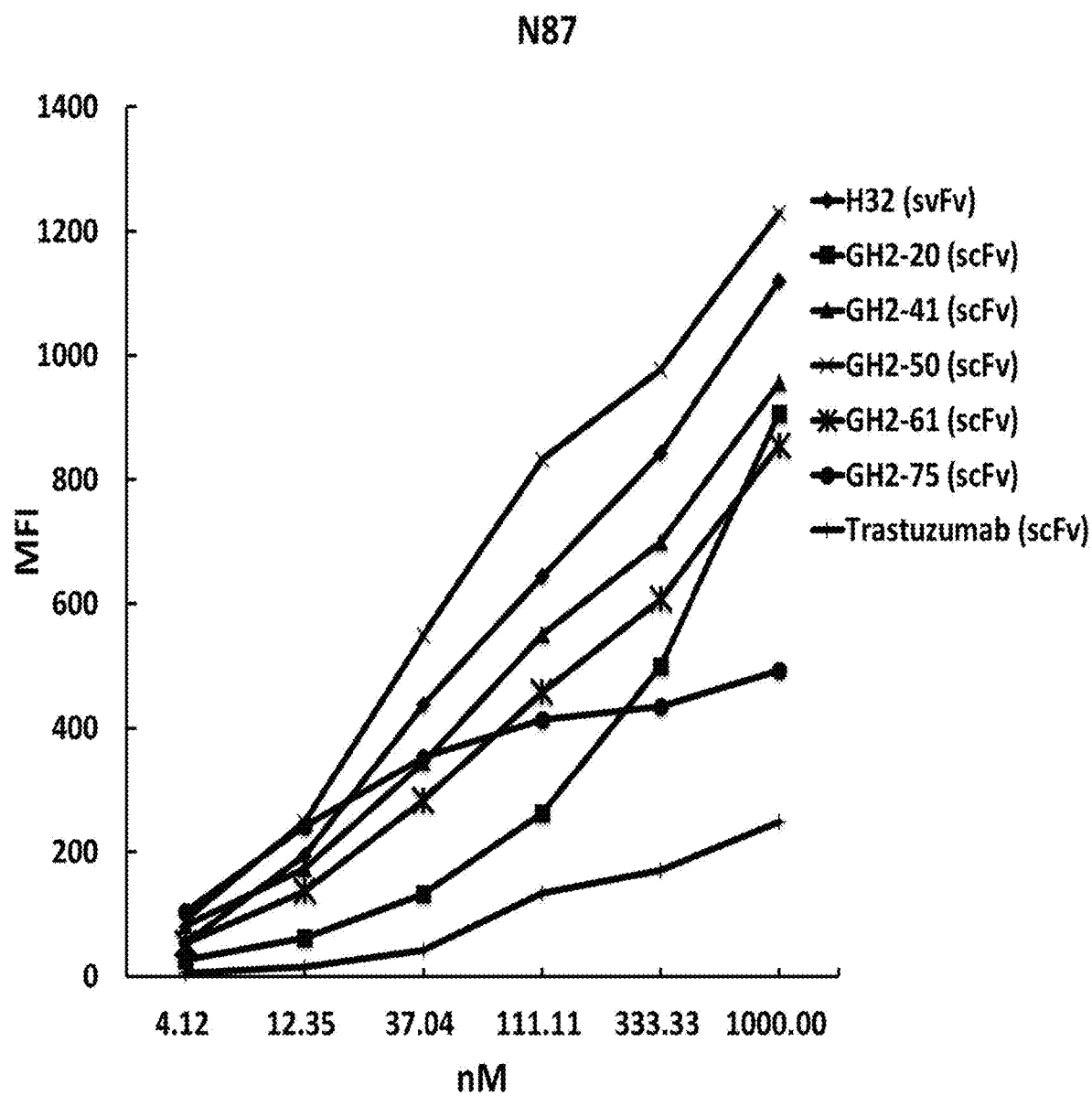
Figure 10C:
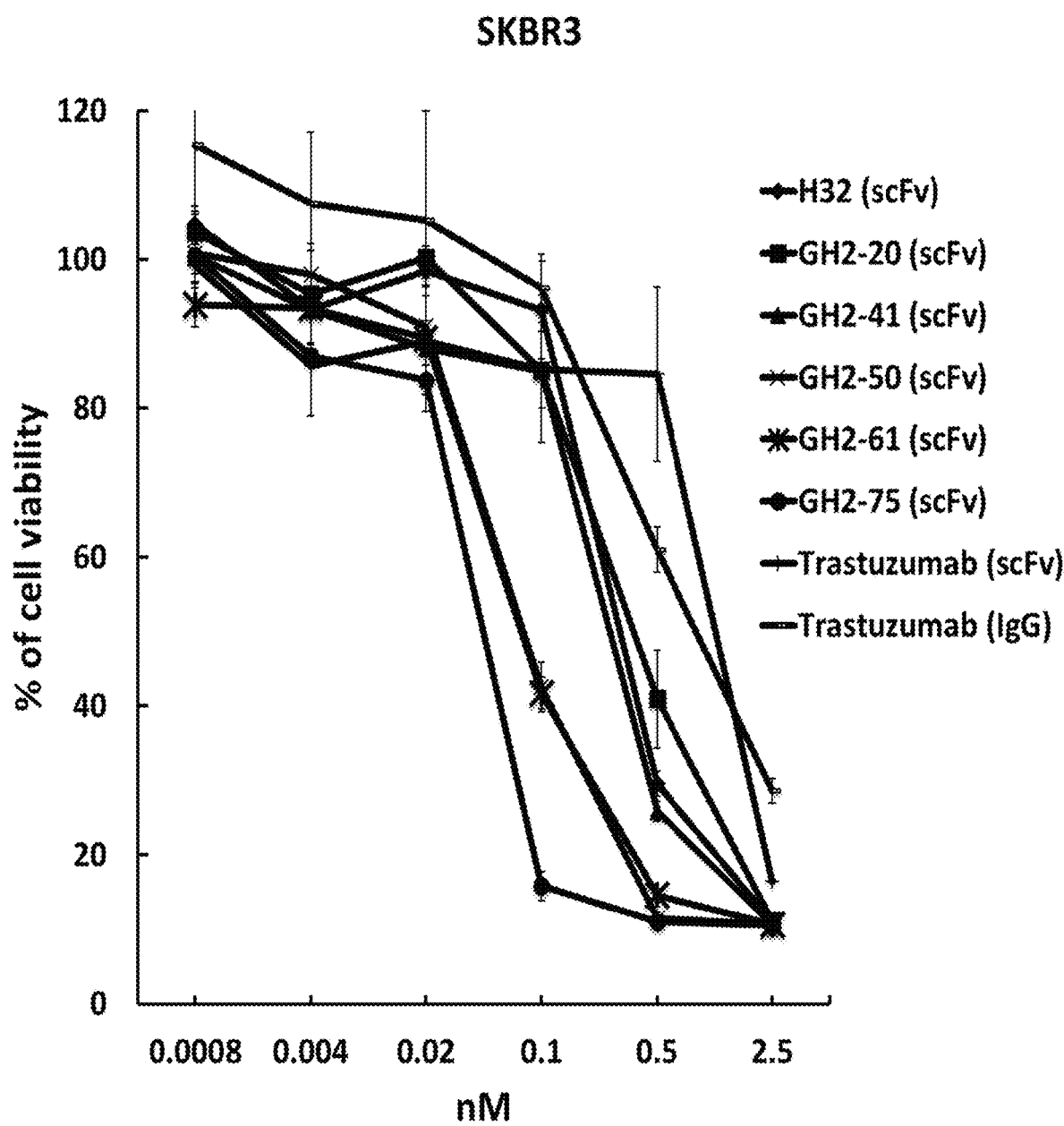
Figure 10D:
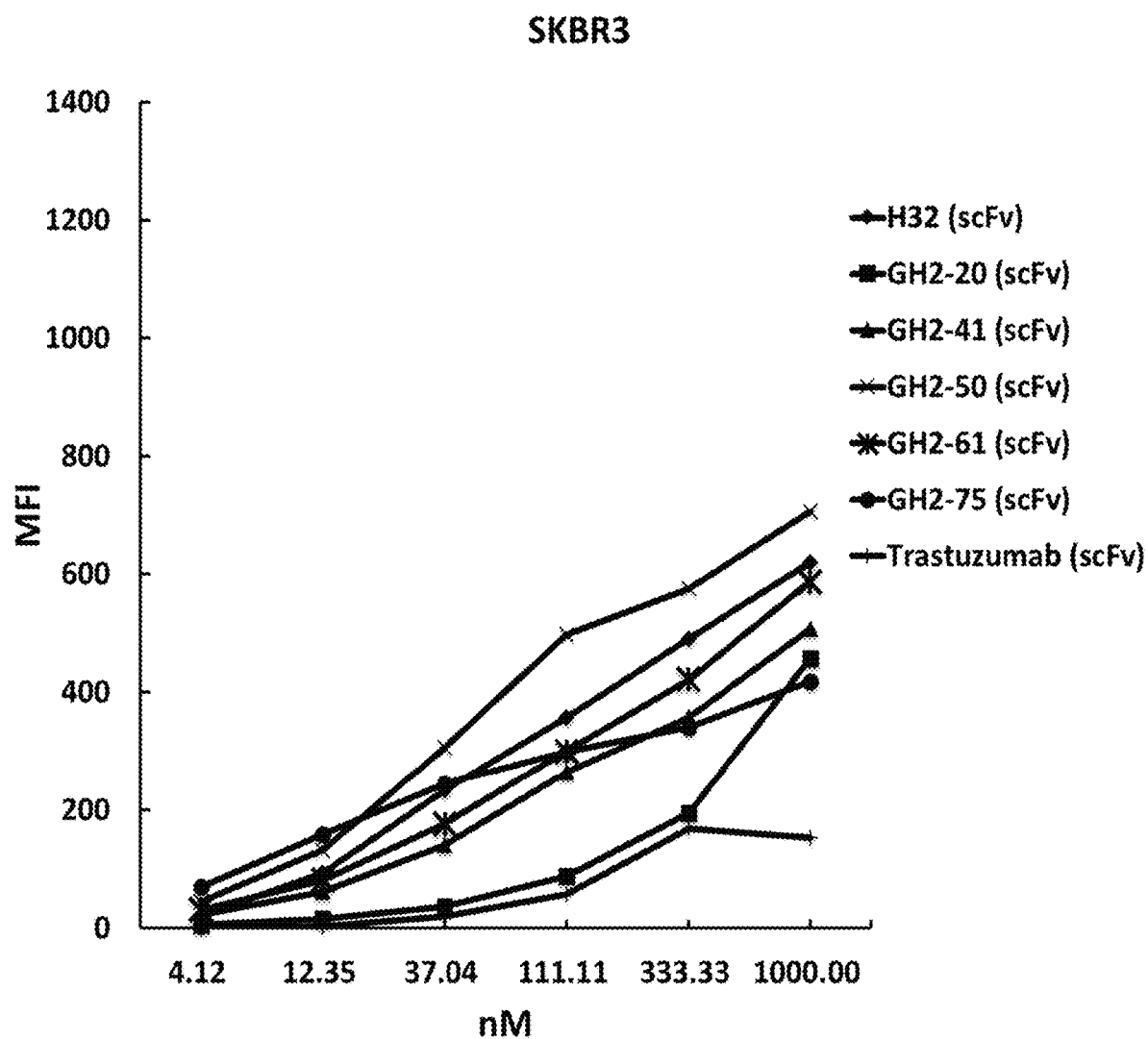
Figure 10E:
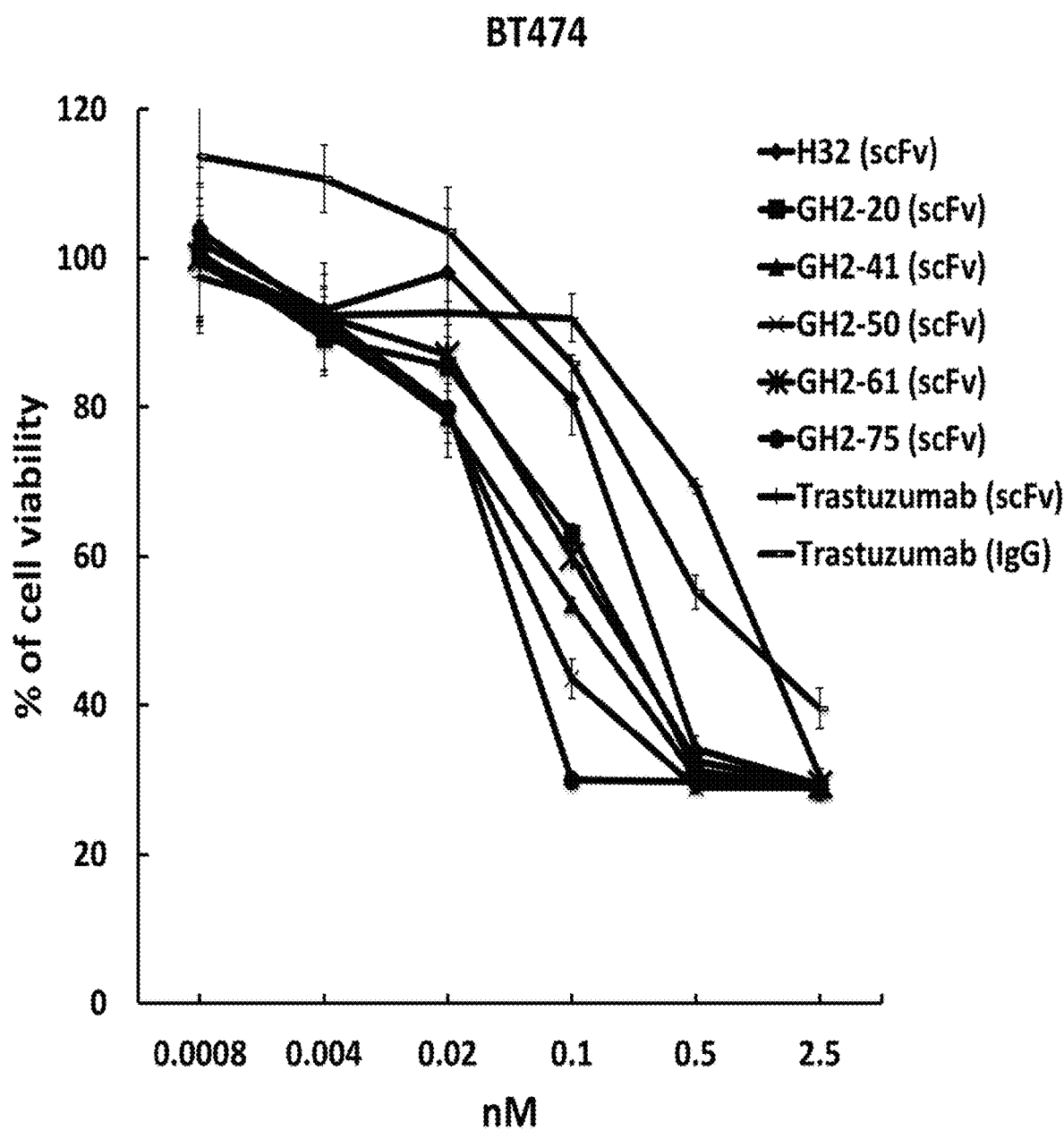
Figure 10F:
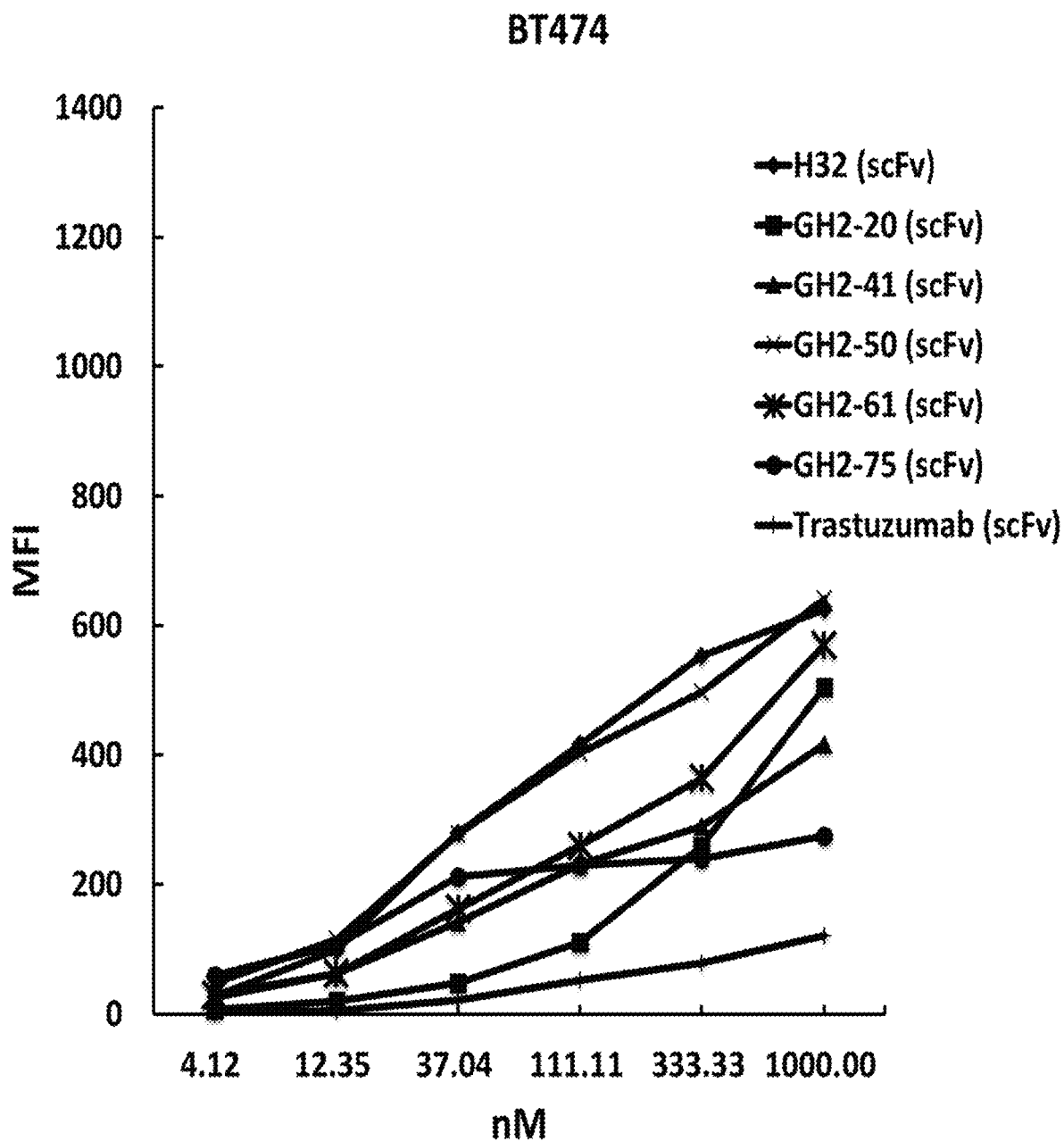
Figure 10G:
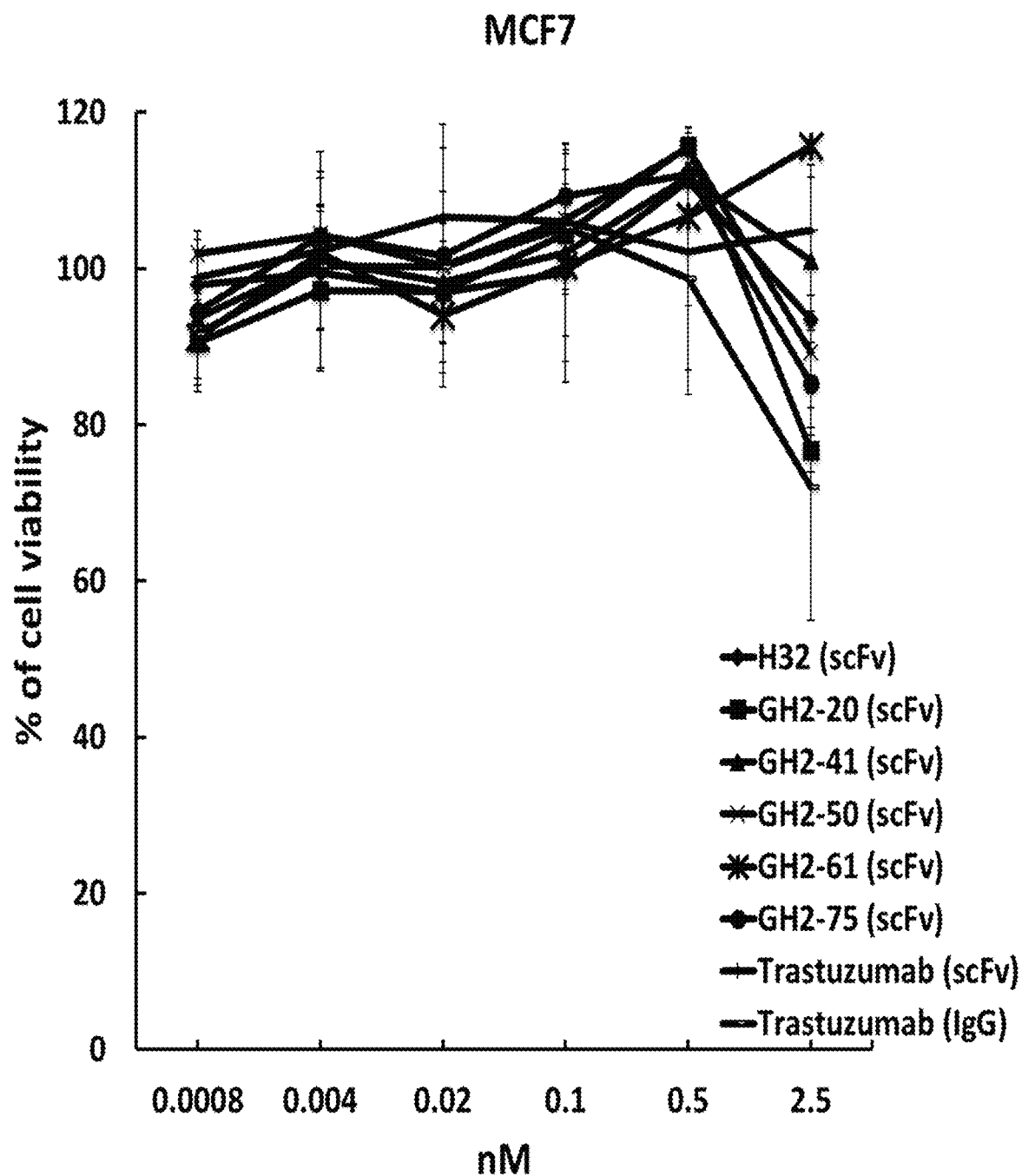
Figure 10H:
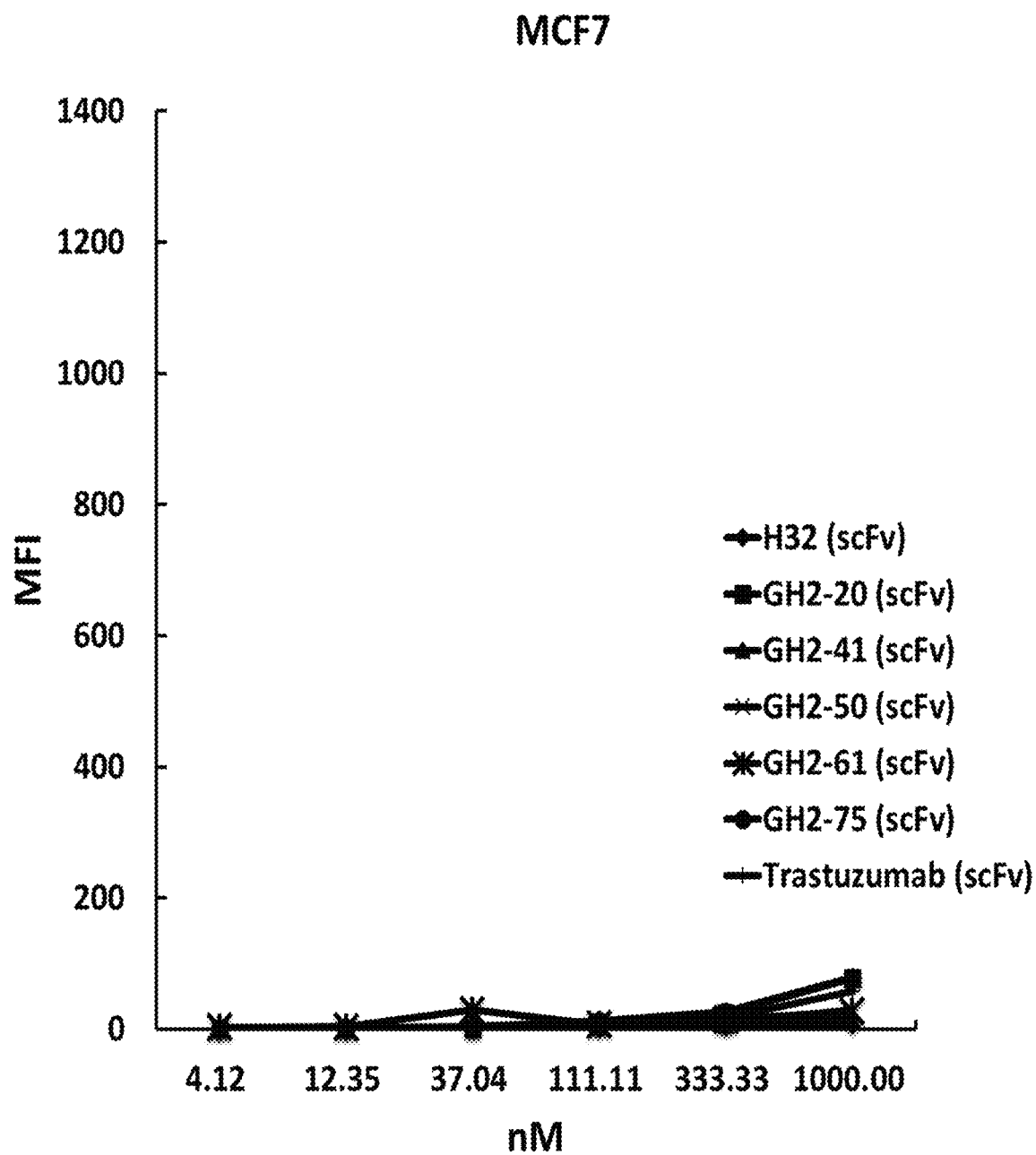

Cell Surface Target Receptor Expression Level Determines the Potency of the Immunotoxins The distribution density of the target receptor HER2 (FIGS. 10B, 10D, 10F, and 10H) affects the cytotoxicity of the immunotoxins (FIGS. 10A, 10C, 10E, and 10G). The N87 cell line has the highest HER2 receptor density on the cell surface (FIG. 10B) among the cell lines tested in FIGS. 10A-10H, and the immunotoxins (in scFv-AL2-PE38KDEL form) are the most potent, with the lowest $IC_{50}$'s for this cell line (FIG. 10A). The SKBR3 and BT474 cell lines have less HER2 receptor density (FIGS. 10D and 10F) in comparison with that of N87; the cytotoxicity of the corresponding immunotoxins measured with these cell lines are also less potent (FIGS. 10C and 10E). In the negative control cell line MCF7, where only negligible density of HER2 shows on the cell surface (FIG. 10H), the cells are not sensitive to the immunotoxins (FIG. 10G). Note that the affinity ranking of the scFvs to the cell surface receptor is not correlated with the ranking of the cytotoxicity of the immunotoxin (FIGS. 10A to 10H). Moreover, the potency ranks of the scFv as targeting modules are also dependent on the cell line tested (FIGS. 10A, 10C, and 10E), indicating that differences between cells could affect the cytotoxicity of the immunotoxins.

Example 10

Figure 11:
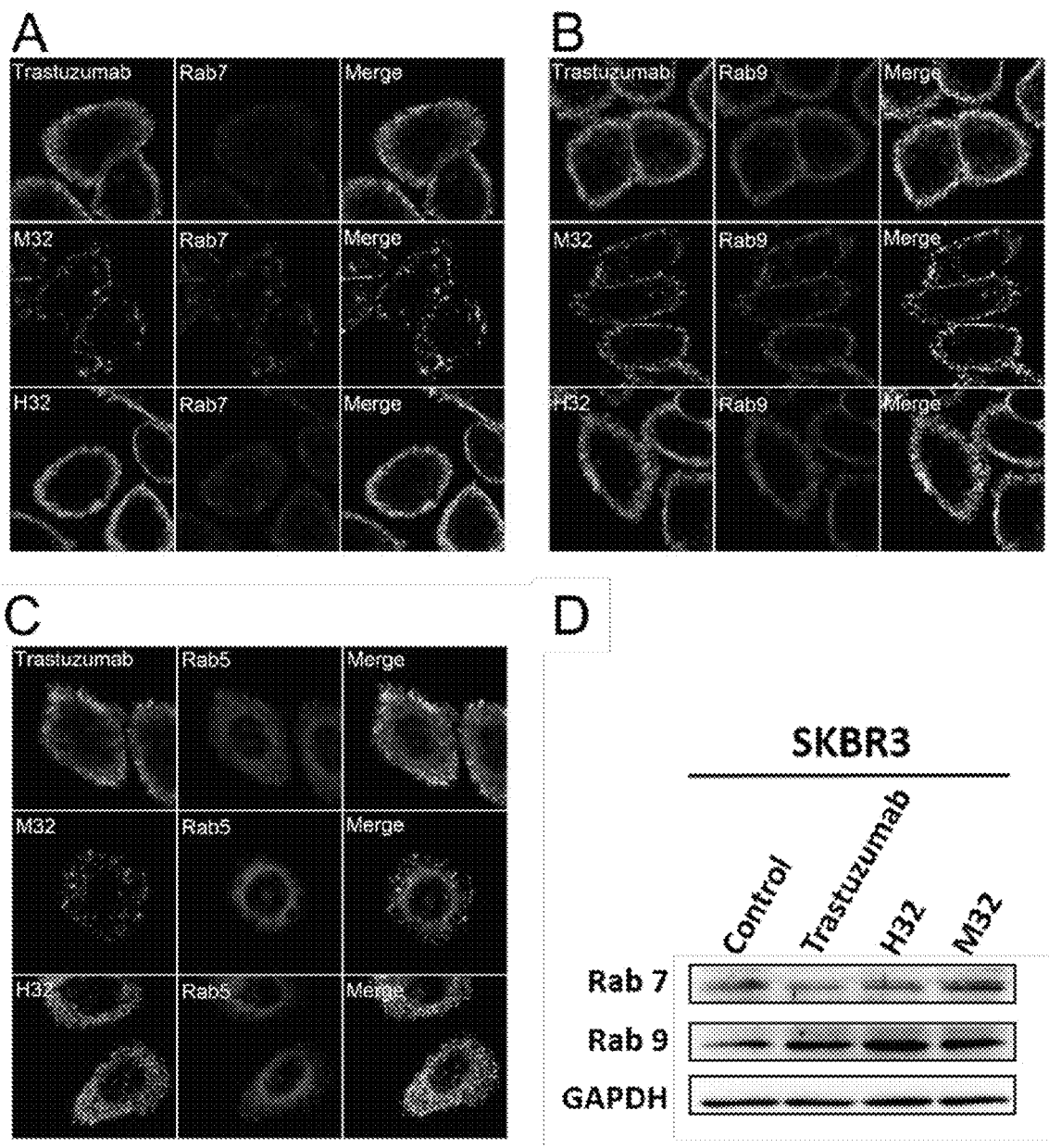
FIG. 11 shows the comparison of the internalization pathways of M32, H32, and Trastuzumab IgGs binding to HER2-ECD on cell surface. SKBR-3 cells were incubated with Trastuzumab, M32 or H32 IgG for 1 hour, and the localizations of the internalized IgGs in relation to that of Rab7 (panel A), Rab9 (panel B), and Rab5 (panel C) were revealed by immunofluorescence microscopy. Panel D shows the relative expression level of Rab7 and Rab9 in the SKBR-3 cells treated with Trastuzumab, M32, or H32 IgG.

Antibody Binding to HER2-ECD on Cell Surface Leads Endocytic Trafficking of the Antibody to Late Endosome and Golgi Complex The endocytic mechanism of the antibody-HER2 complexes was further investigated by following the antibody (H32, M32, and Trastuzumab) internalization locations in relation to the Rab5, Rab7, and Rab9 GTPases (FIG. 11). Antibody H32 is the humanized version of antibody M32, which is a control mouse anti-HER2 antibody, for which the epitope on HER2-ECD is representative for the majority of the antibodies in FIG. 5; more than three quarters of the 92 scFvs in Table 2 and Table 3 belong to this epitope group (dubbed M32-M62 epitope group). The internalization of H32 IgG upon binding to HER2 is 1.4-fold more efficient than that of Trastuzumab based on the biotinylation assay (see materials and methods), explaining in part the superior potency of H32 comparing with Trastuzumab as targeting modules in immunotoxins (FIG. 5). FIG. 11 shows that the trafficking routes for these two HER2-binding IgGs are identical in terms of their subcellular locations relative to Rab5, Rab7 and Rab9. Rab5 is associated with early endocytic pathway and Rab7 and Rab9 function on the late endocytic pathway. Rab5 can be detected around clathrin-coated vesicles near cytoplasm membrane and early endosomes, whereas Rab7 and Rab9 are located around late endosomes. Co-localization of the antibody M32, H32, and Trastuzumab with Rab7 (FIG. 11, panel A) and Rab9 (FIG. 11, panel B) but not with Rab5 (FIG. 11, panel C) suggests that the antibodies were internalized following the late endocytic pathway after binding to HER2-ECD on cell surface. The antibody-associated receptor endocytosis also enhanced expression of Rab9, especially by antibody H32 (FIG. 11, panel D). Rab9 has been known to regulate the recycling of mannose-6-phosphate receptor from late endosomes to the Golgi complex. The better-enhanced Rab9 expression due to antibody H32 binding to HER2 could explain the high potency of scFv(H32)-AL2-PE38KDEL, for which the potency as an immunotoxin is much higher than that of scFv(Trastuzumab)-AL2-PE38KDEL (FIG. 5). The enhanced expression of Rab9 also supports the notion that the trafficking of the endocytic antibody-associated receptors could be driven to the Golgi complex following the retrograde trafficking pathway.

Example 11

Fab H32 Binds to Domain I in HER2-ECD

Fab H32-HER2-ECD complexes were analyzed by negative stain EM and single particle reconstruction (FIG. 12A). 2D class averages suggested that the specimens were relatively homogeneous and dominantly in forms of 1:1 antibody-antigen complexes (FIG. 12B). Domains of Fab H32 can be clearly identified in some 2D class averages depending on their orientations. Domains of HER2-ECD can as well be identified in some 2D class averages viewing from the sides where domain I, II, III, and smaller tail domain IV can be assigned. The densities of HER2-ECD, especially domain IV, in some 2D classes were less clear than those of Fab H32, suggesting structural flexibility and variations among HER2-ECD domain relative locations. Particles of selected 2D classes were subsequently subjected to 3D reconstruction and refined to 23 Å resolution with gold standard FSC=0.5 cutoff (FIG. 12C). The 3D map was fit with model Fab and the crystallographic structure of HER2 ECD (PDB 3wsq) (data not shown). The data suggested that Fab H32 interacted with HER2-ECD through region next to the epitope of A21 in domain I (data not shown), which agreed well with the analysis of 2D projection images, the HDX-MS and competition data (FIG. 6 of Chen, H. S. et al. Predominant structural configuration of natural antibody repertoires enables potent antibody responses against protein antigens. Sci Rep 5, 12411 (2015)). The epitope of H32 is different from any observed epitopes on HER2 (data not shown). The epitope difference between the antibody H32 and Trastuzumab could explain the potency difference of the immunotoxins based on these two antibodies.

Example 12

Cytotoxicity Measurements Comparison of IgG-AL1-PE38KDEL Immunotoxin, IgG-AL1C-/AL2C-Drug Conjugates and IgG-vcMMAE Conjugates The analyses of 6 anti-HER2 IgG-vc-MMAE conjugates were summarized in Table 5. The yield was calculated as follows: Yields=(output antibody-drug conjugate/input naked IgG)×100%. The drug-to-antibody ratio (DAR) of each conjugate was determined by butyl-NPR hydrophobic column. The $EC_{50}$ ratio was calculated as follows: $EC_{50}$ ratio=$EC_{50}$(conjugation)/$EC_{50}$ (unconjugation).

TABLE 5

| IgG sample | Yield (%) | DAR | $EC_{50}$ (ng/mL) Conjugation | Unconjugation | $EC_{50}$ ratio |
|---|---|---|---|---|---|
| Herceptin | 103.7 | 2.90 | 3.23 | 1.70 | 1.90 |
| H32 | 91.7 | 3.58 | 2.35 | 1.43 | 1.64 |
| G2-75 | 51.3 | 1.24 | 1.72 | 1.44 | 1.19 |
| G2-61 | 34.8 | 1.99 | 3.67 | 2.28 | 1.61 |
| G2-41 | 63.6 | 2.49 | 85.69 | 57.95 | 1.48 |
| G2-20 | 31.9 | 1.31 | 4.52 | 3.70 | 1.22 |

The capacity of immunotoxin in cytotoxicity can be delivered by adaptor-toxin fusion protein AL1-PE38KDEL. The immunotoxin construction rate is limited and thus low-throughput. Anti-HER2 IgGs or scFvs bound with AL1-PE38KDEL could verify the cytotoxicity capacity of antibodies leads and thus shorten the timeline of drug development. In three high HER expressing cell lines, GH2-75 IgG showed the highest potency in the cytotoxicity of gastric cancer N87 cells and so did H32 in breast cancer SKBR3 cells respectively; see FIGS. 13A to 13C). Thus, different anti-HER2 IgGs show distinct degree of cytotoxicity in different cancer cells and could be selected for a specific cancer therapy.

Antibody-drug conjugates are consistent of monoclonal antibodies, cytotoxic chemicals, and synthetic linker. The selection of liker and cytotoxic chemicals determines the potency of cytotoxicity. The selection of linker and chemicals could be conducted by conjugating the linker and drugs to AL1C/AL2C and then testing the cytotoxicity of IgG-AL1C/AL2C-linker-drug complexes in target cancer cells. The result was elucidated by the treatment of AL1C-Osu-MMAF (AL1C-021) and AL1C-vc-MMAE (AL1C-026) bound with anti-HER2 IgGs in N87 (FIGS. 14A and 14B) and SKBR3 cells (FIGS. 14C and 14D). The result showed that GH2-75 IgG had the most potent cytotoxicity among IgGs-AL1C-Osu-MMAF, but H32 IgG was the most potent IgG among IgGs-AL1C-vc-MMAE complexes in SKBR3 cells (FIGS. 14C and 14D). Accordingly, the ranking of the cytotoxicity potency of IgGs was different in N87 and BT-474 cells when cells were treated with IgG-AL2C-vc-MMAE (AL2C-002) (FIGS. 15A and 15B) and IgG-AL2C-MMAF (AL2C-004) complexes (FIGS. 15C and 15D). The ranking of IgGs cytotoxicity is accordant when anti-HER2 IgGs were conjugated with vc-MMAE in the gastric cancer N87 cell line and the breast cancer BT-474 cell line (FIGS. 16A and 16B).

Thus, AL1C/AL2C-drug adaptor proteins provide a high-throughput platform to select linker-chemicals for different indications before IgG-drug conjugation which is time-consuming and low-throughput.

Example 13

Comparison of In Vivo Anti-Tumor Activity of Two Types of GH2-61 IgG-AL1-PE38KDEL Immunotoxin with GH2-61 IgG-Vc-MMAE Conjugates Anti-tumor activities of GH2-61 IgG-AL1-PE38KDEL immunotoxins were first evaluated in N87 tumor model in NOD/SCID mice. The results demonstrated that the treatment of tumor-bearing mice with GH2-61 IgG-AL1-PE38KDEL immunotoxins exhibited a significant tumor regression in a dose-dependent manner (FIG. 17A). There was no significant difference in body weights among treated groups compared with the PBS-treated group during the treatment course (FIG. 17B). The anti-tumor activities of two systems of ADCs were then evaluated in the same in vivo model of N87. The results indicated that conjugations of MMAE resulted in an increased anti-tumor potency in vivo than GH2-61 IgG-AL1C-026 complexes (FIG. 18A). There was no weight loss observed in each treatment groups, indicating that the treatments were well tolerated (FIG. 18B).

The above experimental data highlight three aspects in developing an optimally functional immunotoxin.

First, immunotoxins with bivalent antibody-based targeting module are generally superior to those with corresponding monovalent targeting module in term of cytotoxic potency by up to 10 folds (FIGS. 4A to 4C and FIGS. 6A and 6B), although most of the immunotoxins currently under development adopt monovalent design. Bivalent targeting modules could result in cross-linked cell surface receptors, which could in turn accelerate receptor-mediated endocytosis and decrease the off rate of the immunotoxins. Both could assist the trafficking of the toxin to cytosol. However, the data also suggest that the bivalent enhancement of immunotoxin cytotoxicity is antibody-dependent, i.e. the bivalent binding promotes superior toxin delivery in some scFvs but shows no obvious difference comparing with monovalent binding in other scFvs (FIGS. 4A to 4C and FIGS. 6A and 6B). Consequently, since prediction of the potency of an immunotoxin based on the valence, epitope and binding affinity of the antibody targeting module is unlikely to be accurate, experimental tests in high throughput format as described in this work can provide substantial information in optimizing the functional immunotoxins.

Second, the potency of the immunotoxins is positively correlated with the densities of the cell surface antigen (FIGS. 10A to 10H). But the correlation level could range from a few folds to more than 100-fold loss of potency (e.g. antibody GH2-41, see FIGS. 10A to 10H) due to 2-fold reduction of cell surface target density, perhaps because of other differences among the cells. The implication is that the immunotoxins could be engineered to have optimal cytotoxicity towards the target cells with abundant cell surface targets while remain tolerable in terms of toxicity against off-target cells with moderately lower level of target density on the cell surface.

Third, epitope of the antibody-based targeting module is a major determinant for the potency of the immunotoxins (FIGS. 11 and 12A to 12C). However, antibodies in the same epitope group can have diverse potency in delivering the toxin payloads (FIGS. 5, 6A and 6B). Other factors, especially the amino acid types used in the paratope of the antibody, could determine the trafficking route of the toxin payload and thus affect the potency of the immunotoxin. Engineering the pH-dependency of antibody-antigen interactions has demonstrated that ionization of engineered His sidechains of the antibody-antigen interface in the acidic environment of endosome enhances cycling of antibody back to plasma, improving pharmacokinetics and duration of the antibody. By contrast, the results shown in FIG. 5, FIGS. 9A to 9D and Table 4 indicate that the ionization of the His sidechains involving the antibody-antigen interactions in the increasingly acidic environment of endosome could interrupt the immunotoxin trafficking, thereby compromising the cytotoxicity of the toxin payloads.

These experimental data reveal the complex function of the antibody as the targeting module in an immunotoxin, highlighting the need of multifaceted optimization of the toxin delivery capability of the targeting antibody according to the specifics of the target receptor, the target cell, and the cytotoxic payload. Natural antibodies have been the main source for the targeting modules in immunotoxins, but the diversity of the natural antibodies is restricted by predominant clonal selections governed by germline gene usage and by clonal elimination resulting from immune-tolerance of self-antigens, which are frequently the targets of immunotoxins. As such, natural antibodies as the targeting modules for the immunotoxins could be suboptimal because of limited pool of suitable candidates from natural antibody repertoires. By contrast, properly designed and constructed synthetic antibody libraries could provide more diverse selections of antibodies with epitope-paratope combinations better-suited for developing immunotoxins or other types immunoconjugates against self-antigens with optimal cytotoxicity. The work herein provides the evidence supporting the implications of high-throughput discovering and optimizing antibodies as the targeting modules for immunoconjugates with the synthetic antibody libraries.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for high-throughput screening of a functional antibody fragment for an immunoconjugate that targets a target antigen, comprising the steps of,
   (a) providing a phage-displayed synthetic single-chain variable fragment (scFv) library that comprises a plurality of phage-displayed scFvs, wherein the VH domain of each of the plurality of phage-displayed scFvs has a binding affinity to protein A, and the VL domain of each of the plurality of phage-displayed scFvs has a binding affinity to protein L;
   (b) selecting, from the phage-displayed synthetic scFv library of the step (a), a plurality of phages that express scFvs specific for the target antigen;
   (c) preparing a plurality of secreted scFvs respectively from the plurality of phages selected in the step (b);
   (d) allowing the formation of a plurality of scFv-adaptor-drug complexes by contacting an adaptor-drug conjugate with the plurality of secreted scFvs prepared in the step (c), respectively, wherein the adaptor-drug conjugate comprises a drug and an adaptor that comprises at least one AL module comprising a protein A fragment at the N-terminus, a protein L fragment at the C-terminus, and a first polypeptide linker connecting the protein A fragment and the protein L fragment;
   (e) culturing a plurality of cells presenting the target antigen in the presence of the plurality of scFv-adaptor-drug complexes formed in the step (d), respectively;
   (f) determining the respective cytotoxic efficacy of the plurality of scFv-adaptor-drug complexes on the plurality of cells presenting the target antigen cultured in the step (e); and (g) selecting the functional antibody fragment for the immunoconjugate based on the results determined in the step (f), wherein the respective scFv of one or more scFv-adaptor-drug complexes of the plurality of scFv-adaptor-drug complexes that exhibit superior efficacy over the other scFv-adaptor-drug complexes of the plurality of scFv-adaptor-drug complexes is selected as the functional antibody fragment for the immunoconjugate.

2. The method of claim 1, wherein the target antigen is human epidermal growth factor receptor 2 (HER2), maltose-binding protein, bovine serum albumin, human serum albumin, lysozyme, interleukin-1 beta (IL-1β), hemagglutinin of influenza virus, vascular endothelial growth factor (VEGF), epidermal growth factor receptor 1 (EGFR1), epidermal growth factor receptor 3 (EGFR3), glucagon receptor, programmed death-ligand 1 (PD-L1), sialic acid binding Ig-like lectin 3 (SIGLEC 3), or rituximab.

3. The method of claim 2, wherein the target antigen is HER2.

4. The method of claim 1, wherein the drug is selected from the group consisting of an immunotoxin, an immunoliposome, and a cytotoxic drug.

5. The method of claim 4, wherein the drug further comprises a sequence of KDEL connected thereto.

6. The method of claim 5, wherein the immunotoxin is an exotoxin.

7. The method of claim 6, wherein the exotoxin is *Pseudomonas* Exotoxin (PE) A, or a truncated form of PE A subunit toxin.

8. The method of claim 7, wherein the sequence of KDEL is connected to the C-terminus of the truncated form of PE A subunit toxin.

9. The method of claim 1, wherein the adaptor-drug conjugate further comprises a second polypeptide linker connecting the drug to the C-terminus of the adaptor.

10. The method of claim 1, wherein the adaptor comprises two AL modules and further comprises a second polypeptide linker connecting the two AL modules.

11. The method of claim 1, wherein the step (f) is determined by measuring the respective cell viability of the plurality of cells presenting the target antigen cultured in the step (e).

* * * * *

SEQUENCE LISTING

```
<160> NUMBER OF SEQ ID NOS: 107

<210> SEQ ID NO 1
<211> LENGTH: 248
<212> TYPE: PRT
<213> ORGANISM: Artificial Sequence
<220> FEATURE:
<223> OTHER INFORMATION: Antibody GH2-3-amino acid sequence

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Asn
            20                  25                  30

Val Ala Trp Tyr Gln Gln Lys Pro Gly Lys Ala Pro Lys Leu Leu Ile
        35                  40                  45

Tyr Gly Ala Arg Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Gly Gly Gly Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Ser Gly Gly Trp Ile His Trp Val
145                 150                 155                 160

Arg Gln Ala Pro Gly Lys Gly Leu Glu Trp Val Ala Gly Ile Trp Pro
                165                 170                 175

Ser Gly Gly Ser Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Tyr Phe
    210                 215                 220

Gly Phe Gly Asp Leu Met Asp Tyr Trp Gly Gln Gly Thr Leu Val Thr
225                 230                 235                 240

Val Ser Ser Ala Ser Ala Ala Ala
                245

<210> SEQ ID NO 2
<211> LENGTH: 248
<212> TYPE: PRT
<213> ORGANISM: Artificial Sequence
<220> FEATURE:
<223> OTHER INFORMATION: Antibody GH2-4-amino acid sequence

<400> SEQUENCE: 2

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Phe Gly Gly
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asp Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Ser Gly Ser Ile His Trp Val
145                 150                 155                 160

Arg Gln Ala Pro Gly Lys Gly Leu Glu Trp Val Ala Phe Ile Gly Pro
                165                 170                 175

Phe Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Trp
    210                 215                 220

Asn Asp Tyr Asp Phe Met Asp Tyr Trp Gly Gln Gly Thr Leu Val Thr
225                 230                 235                 240

Val Ser Ser Ala Ser Ala Ala Ala
            245

<210> SEQ ID NO 3
<211> LENGTH: 248
<212> TYPE: PRT
<213> ORGANISM: Artificial Sequence
<220> FEATURE:
<223> OTHER INFORMATION: Antibody GH2-5-amino acid sequence

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Ser Gly Ala Pro Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Gly Ser Glu Val Gln Leu Val
            115                 120                 125
```

Glu Ser Gly Gly Leu Val Gln Pro Gly Gly Ser Leu Arg Leu Ser
    130             135             140

Cys Ala Ala Ser Gly Phe Thr Ile Asn Asn Trp Gly Ile His Trp Val
145             150             155             160

Arg Gln Ala Pro Gly Lys Gly Leu Glu Trp Val Ala Gly Ile Gly Pro
                165             170             175

Phe Gly Gly Tyr Thr Ser Tyr Ala Asp Ser Val Lys Gly Arg Phe Thr
            180             185             190

Ile Ser Ala Asp Thr Ser Lys Asn Thr Ala Tyr Leu Gln Met Asn Ser
        195             200             205

Leu Arg Ala Glu Asp Thr Ala Val Tyr Tyr Cys Ala Arg Phe Gly Val
    210             215             220

Val Tyr Asp Gly Ile Met Asp Tyr Trp Gly Gln Gly Thr Leu Val Thr
225             230             235             240

Val Ser Ser Ala Ser Ala Ala Ala
                245

<210> SEQ ID NO 4
<211> LENGTH: 248
<212> TYPE: PRT
<213> ORGANISM: Artificial Sequence
<220> FEATURE:
<223> OTHER INFORMATION: Antibody GH2-7-amino acid sequence

<400> SEQUENCE: 4

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Val Ser Gly Trp
            20              25              30

Val Ala Trp Tyr Gln Gln Lys Pro Gly Lys Ala Pro Lys Leu Leu Ile
        35              40              45

Ser Gly Thr Ala Gly Leu Tyr Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Tyr Asp Phe Pro Val
            85              90              95

Thr Phe Gly Gln Gly Thr Lys Val Glu Ile Lys Arg Gly Gly Ser Ser
        100             105             110

Arg Phe Pro Pro Leu Val Ala Gly Gly Gly Glu Val Gln Leu Val
            115             120             125

Glu Ser Gly Gly Gly Leu Val Gln Pro Gly Gly Ser Leu Arg Leu Ser
    130             135             140

Cys Ala Ala Ser Gly Phe Thr Ile Asp Asp Tyr Phe Ile His Trp Val
145             150             155             160

Arg Gln Ala Pro Gly Lys Gly Leu Glu Trp Val Ala Gly Ile Gly Pro
                165             170             175

Ser Trp Gly Tyr Thr Phe Tyr Ala Asp Ser Val Lys Gly Arg Phe Thr
            180             185             190

Ile Ser Ala Asp Thr Ser Lys Asn Thr Ala Tyr Leu Gln Met Asn Ser
        195             200             205

Leu Arg Ala Glu Asp Thr Ala Val Tyr Tyr Cys Ala Arg Phe Gly His
    210             215             220

Asn Phe Val Asn Gly Met Asp Tyr Trp Gly Gln Gly Thr Leu Val Thr
225             230             235             240

Val Ser Ser Ala Ser Ala Ala Ala
            245

<210> SEQ ID NO 5
<211> LENGTH: 251
<212> TYPE: PRT
<213> ORGANISM: Artificial Sequence
<220> FEATURE:
<223> OTHER INFORMATION: Antibody GH2-8-amino acid sequence

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Trp Trp
            20                  25                  30

Val Ala Trp Tyr Gln Gln Lys Pro Gly Lys Ala Pro Lys Leu Leu Ile
        35                  40                  45

Ser Gly Ala Thr Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Asp Ser Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Gly Gly Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Gly Ser Ser Gly Ile
145                 150                 155                 160

His Trp Val Arg Gln Ala Pro Gly Lys Gly Leu Glu Trp Val Ala Gly
                165                 170                 175

Ile Trp Pro Tyr Trp Gly Ser Thr Tyr Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Gly Val Gly Tyr His Tyr Tyr Met Asp Tyr Trp Gly Gln Gly Thr
225                 230                 235                 240

Leu Val Thr Val Ser Ser Ala Ser Ala Ala Ala
                245                 250

<210> SEQ ID NO 6
<211> LENGTH: 251
<212> TYPE: PRT
<213> ORGANISM: Artificial Sequence
<220> FEATURE:
<223> OTHER INFORMATION: Antibody GH2-9-amino acid sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Asp Gly
            20                  25                  30

Val Ala Trp Tyr Gln Gln Lys Pro Gly Lys Ala Pro Lys Leu Leu Ile

```
                35                  40                  45
Ser Gly Ser Ser Trp Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Gly Tyr Pro Ile
                 85                  90                  95

Thr Phe Gly Gln Gly Thr Lys Val Glu Ile Lys Arg Gly Gly Ser Ser
                100                 105                 110

Arg Ser Ser Ser Gly Gly Gly Ser Gly Gly Gly Glu Val
            115                 120                 125

Gln Leu Val Glu Ser Gly Gly Leu Val Gln Pro Gly Gly Ser Leu
            130                 135                 140

Arg Leu Ser Cys Ala Ala Ser Glu Phe Thr Ile Gly Ser Trp Gly Ile
145                 150                 155                 160

His Trp Val Arg Gln Ala Pro Gly Lys Gly Leu Glu Trp Val Ala Gly
                165                 170                 175

Ile Gly Pro Tyr Gly Gly Tyr Thr Ser Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
            210                 215                 220

Phe Asp Ile Trp Asn Tyr Phe Gly Met Asp Tyr Trp Gly Gln Gly Thr
225                 230                 235                 240

Leu Val Thr Val Ser Ser Ala Ser Ala Ala Ala
                245                 250

<210> SEQ ID NO 7
<211> LENGTH: 251
<212> TYPE: PRT
<213> ORGANISM: Artificial Sequence
<220> FEATURE:
<223> OTHER INFORMATION: Antibody GH2-11-amino acid sequence

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Gly Asp Gly
                 20                  25                  30

Val Ala Trp Tyr Gln Gln Lys Pro Gly Lys Ala Pro Lys Leu Leu Ile
                 35                  40                  45

Tyr Ser Ala Gly Trp Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Ile
                 85                  90                  95

Thr Phe Gly Gln Gly Thr Lys Val Glu Ile Lys Arg Gly Gly Ser Ser
                100                 105                 110

Arg Ser Ser Ser Gly Gly Gly Gly Ser Gly Gly Gly Glu Val
            115                 120                 125

Gln Leu Val Glu Ser Gly Gly Gly Leu Val Gln Pro Gly Gly Ser Leu
            130                 135                 140

Arg Leu Ser Cys Ala Ala Ser Gly Phe Thr Ile Asn Asp Trp Gly Ile
```

```
                145                 150                 155                 160
His Trp Val Arg Gln Ala Pro Gly Lys Gly Leu Glu Trp Val Ala Gly
                    165                 170                 175

Ile Gly Pro Tyr Gly Gly Tyr Thr Ser Tyr Ala Asp Ser Val Arg Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
            210                 215                 220

Phe Val Asn Trp Asp Phe Tyr Gly Met Asp Tyr Trp Gly Gln Gly Thr
225                 230                 235                 240

Leu Val Thr Val Ser Ser Ala Ser Ala Ala Ala
                245                 250

<210> SEQ ID NO 8
<211> LENGTH: 250
<212> TYPE: PRT
<213> ORGANISM: Artificial Sequence
<220> FEATURE:
<223> OTHER INFORMATION: Antibody GH2-12-amino acid sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Asn
                20                  25                  30

Val Ala Trp Tyr Gln Gln Lys Pro Gly Lys Ala Pro Lys Leu Leu Ile
            35                  40                  45

Tyr Gly Pro Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Tyr Pro Ile
                85                  90                  95

Thr Phe Gly Gln Gly Thr Lys Val Glu Ile Lys Arg Gly Gly Ser Ser
                100                 105                 110

Arg Ser Ser Ser Gly Gly Gly Ser Gly Gly Gly Glu Val
            115                 120                 125

Gln Leu Val Glu Ser Gly Gly Gly Leu Val Gln Pro Gly Gly Ser Leu
            130                 135                 140

Arg Leu Ser Cys Ala Ala Ser Gly Phe Thr Ile Asn Asp Trp Gly Ile
145                 150                 155                 160

His Trp Val Arg Gln Ala Pro Gly Lys Gly Leu Glu Trp Val Ala Gly
                    165                 170                 175

Ile Trp Pro Tyr Trp Gly Tyr Thr Ser Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
            210                 215                 220

Tyr His Val Tyr Phe Trp Trp Met Asp Tyr Trp Gly Gln Gly Thr Leu
225                 230                 235                 240

Val Thr Val Ser Ser Ala Ser Ala Ala Ala
                245                 250
```

```
<210> SEQ ID NO 9
<211> LENGTH: 251
<212> TYPE: PRT
<213> ORGANISM: Artificial Sequence
<220> FEATURE:
<223> OTHER INFORMATION: Antibody GH2-13-amino acid sequence

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Phe Gly
            20                  25                  30

Val Ala Trp Tyr Gln Gln Lys Pro Gly Lys Ala Pro Lys Leu Leu Ile
        35                  40                  45

Ser Gly Thr Thr Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asp Gly Gly Ile
145                 150                 155                 160

His Trp Val Arg Gln Ala Pro Gly Lys Gly Leu Glu Trp Val Ala Gly
                165                 170                 175

Ile Trp Pro Tyr Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Asp Asn Asn Trp Val Gly Asn Met Asp Tyr Trp Gly Gln Gly Thr
225                 230                 235                 240

Leu Val Thr Val Ser Ser Ala Ser Ala Ala Ala
                245                 250

<210> SEQ ID NO 10
<211> LENGTH: 251
<212> TYPE: PRT
<213> ORGANISM: Artificial Sequence
<220> FEATURE:
<223> OTHER INFORMATION: Antibody GH2-14-amino acid sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Gly Gly
            20                  25                  30

Val Ala Trp Tyr Gln Gln Lys Pro Gly Lys Ala Pro Lys Leu Leu Ile
        35                  40                  45

Ser Gly Pro Pro Tyr Leu Tyr Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
            115                 120                 125

Gln Leu Val Glu Ser Gly Gly Leu Val Gln Pro Gly Gly Ser Leu
        130                 135                 140

Arg Leu Ser Cys Ala Ala Ser Gly Phe Thr Ile Asn Asp His Gly Ile
145                 150                 155                 160

His Trp Val Arg Gln Ala Pro Gly Lys Gly Leu Glu Trp Val Ala Gly
                165                 170                 175

Ile Gly Pro Phe Gly Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
    210                 215                 220

Phe Asn Phe Asn Asp Val Gly Met Asp Tyr Trp Gly Gln Gly Thr
225                 230                 235                 240

Leu Val Thr Val Ser Ser Ala Ser Ala Ala Ala
                245                 250

<210> SEQ ID NO 11
<211> LENGTH: 250
<212> TYPE: PRT
<213> ORGANISM: Artificial Sequence
<220> FEATURE:
<223> OTHER INFORMATION: Antibody GH2-16-amino acid sequence

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Ser Ser
            20                  25                  30

Val Ala Trp Tyr Gln Gln Lys Pro Gly Lys Ala Pro Lys Leu Leu Ile
        35                  40                  45

Ser Tyr Thr Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Gly Pro Met
                85                  90                  95

Thr Phe Gly Gln Gly Thr Lys Val Glu Ile Lys Arg Gly Gly Ser Ser
            100                 105                 110

Arg Ser Ser Ser Leu Trp Arg Gly Ser Gly Gly Gly Glu Val Gln
            115                 120                 125

Leu Val Glu Ser Gly Gly Gly Leu Val Gln Pro Gly Gly Ser Leu Arg
        130                 135                 140

Leu Ser Cys Ala Ala Ser Gly Phe Thr Ile Asn Asn Trp Gly Ile His
145                 150                 155                 160

Trp Val Arg Gln Ala Pro Gly Lys Gly Leu Glu Trp Val Ala Gly Ile
                165                 170                 175

```
Trp Pro Phe Gly Gly Tyr Thr Tyr Tyr Ala Asp Ser Val Lys Gly Arg
                180                 185                 190

Phe Thr Ile Ser Ala Asp Thr Ser Lys Asn Thr Ala Tyr Leu Gln Met
            195                 200                 205

Asn Ser Leu Arg Ala Glu Asp Thr Ala Val Tyr Tyr Cys Ala Arg Phe
        210                 215                 220

Asp Tyr Leu Asn Asn Gly Gly Met Asp Tyr Trp Gly Gln Gly Thr Leu
225                 230                 235                 240

Val Thr Val Ser Ser Ala Ser Ala Ala Ala
                245                 250

<210> SEQ ID NO 12
<211> LENGTH: 244
<212> TYPE: PRT
<213> ORGANISM: Artificial Sequence
<220> FEATURE:
<223> OTHER INFORMATION: Antibody GH2-17-amino acid sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Ser Ser
            20                  25                  30

Val Ala Trp Tyr Gln Gln Lys Pro Gly Lys Ala Pro Lys Leu Leu Ile
        35                  40                  45

Ser Tyr Thr Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Gly Ser Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Ile Asn Asn Ser Gly Ile His Trp Val Arg Gln Ala Pro
145                 150                 155                 160

Gly Lys Gly Leu Glu Trp Val Ala Gly Ile Trp Pro Tyr Gly Gly Tyr
                165                 170                 175

Thr Ser Tyr Ala Asp Ser Val Lys Gly Arg Phe Thr Ile Ser Ala Asp
            180                 185                 190

Thr Ser Lys Asn Thr Ala Tyr Leu Gln Met Asn Ser Leu Arg Ala Glu
        195                 200                 205

Asp Thr Ala Val Tyr Tyr Cys Ala Arg Phe Asp Tyr Phe Asn Ile Gly
    210                 215                 220

Gly Met Asp Tyr Trp Gly Gln Gly Thr Leu Val Thr Val Ser Ser Ala
225                 230                 235                 240

Ser Ala Ala Ala

<210> SEQ ID NO 13
<211> LENGTH: 247
<212> TYPE: PRT
<213> ORGANISM: Artificial Sequence
<220> FEATURE:
<223> OTHER INFORMATION: Antibody GH2-18-amino acid sequence
```

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Lys Pro Gly Lys Ala Pro Lys Leu Leu Ile
        35                  40                  45

Tyr Trp Thr Thr Gly Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Ser Gly Pro Ile
                85                  90                  95

Thr Phe Gly Gln Gly Thr Lys Val Glu Ile Lys Arg Gly Gly Ser Ser
            100                 105                 110

Arg Ser Pro Ser Gly Ser Gly Gly Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Phe Thr Ile Ser Asn Trp Gly Ile His Trp Val Arg
145                 150                 155                 160

Gln Ala Pro Gly Lys Gly Leu Glu Trp Val Ala Gly Ile Trp Pro Tyr
                165                 170                 175

Gly Gly Tyr Thr Phe Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ala Arg Phe Asn Tyr Leu
210                 215                 220

Asn Leu Gly Gly Met Asp Tyr Trp Gly Gln Gly Thr Leu Val Thr Val
225                 230                 235                 240

Ser Ser Ala Ser Ala Ala Ala
            245

<210> SEQ ID NO 14
<211> LENGTH: 251
<212> TYPE: PRT
<213> ORGANISM: Artificial Sequence
<220> FEATURE:
<223> OTHER INFORMATION: Antibody GH2-19-amino acid sequence

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Gly Trp
            20                  25                  30

Val Ala Trp Tyr Gln Gln Lys Pro Gly Lys Ala Pro Lys Leu Leu Ile
        35                  40                  45

Tyr Tyr Thr Arg Trp Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asn Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
            115                 120                 125

Gln Leu Val Glu Ser Gly Gly Gly Leu Val Gln Pro Gly Gly Ser Leu
            130                 135                 140

Arg Leu Ser Cys Ala Ala Ser Gly Phe Thr Ile Asn Asp Phe Phe Ile
145                 150                 155                 160

His Trp Val Arg Gln Ala Pro Gly Lys Gly Leu Glu Trp Val Ala Gly
                    165                 170                 175

Ile Gly Pro Phe Gly Gly Phe Thr Ser Tyr Ala Asp Ser Val Lys Gly
                180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
            210                 215                 220

Phe Tyr Trp Gly Asp Asp Phe Asp Met Asp Tyr Trp Gly Gln Gly Thr
225                 230                 235                 240

Leu Val Thr Val Ser Ser Ala Ser Ala Ala Ala
                245                 250

<210> SEQ ID NO 15
<211> LENGTH: 251
<212> TYPE: PRT
<213> ORGANISM: Artificial Sequence
<220> FEATURE:
<223> OTHER INFORMATION: Antibody GH2-20-amino acid sequence

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Asn
            20                  25                  30

Val Ala Trp Tyr Gln Gln Lys Pro Gly Lys Ala Pro Lys Leu Leu Ile
        35                  40                  45

Tyr Trp Thr Thr Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Asn Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Glu Val
            115                 120                 125

Gln Leu Val Glu Ser Gly Gly Gly Leu Val Gln Pro Gly Gly Ser Leu
            130                 135                 140

Arg Leu Ser Cys Ala Ala Ser Gly Leu Thr Ile Asn Asp Tyr Gly Ile
145                 150                 155                 160

His Trp Val Arg Gln Ala Pro Gly Lys Gly Leu Glu Trp Val Ala Ser
                    165                 170                 175

Ile Gly Pro Ser Gly Gly Phe Thr Ser Tyr Ala Asp Ser Val Lys Gly
                180                 185                 190

Arg Phe Thr Ile Ser Ala Asp Thr Ser Lys Asn Thr Ala Tyr Leu Gln
            195                 200                 205

Met Asn Ser Leu Arg Ala Glu Asp Thr Ala Val Tyr Tyr Cys Ala Arg
                210                 215                 220

Phe Val Ile Tyr Trp Gly Phe Phe Met Asp Tyr Trp Gly Gln Gly Thr
225                 230                 235                 240

Leu Val Thr Val Ser Ser Ala Ser Ala Ala Ala
                245                 250

<210> SEQ ID NO 16
<211> LENGTH: 251
<212> TYPE: PRT
<213> ORGANISM: Artificial Sequence
<220> FEATURE:
<223> OTHER INFORMATION: Antibody GH2-21-amino acid sequence

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asp Asn
            20                  25                  30

Val Ala Trp Tyr Gln Gln Lys Pro Gly Lys Ala Pro Lys Leu Leu Ile
        35                  40                  45

Tyr Trp Ala Thr Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Phe Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asn Asp Tyr Ser Ile
145                 150                 155                 160

His Trp Val Arg Gln Ala Pro Gly Lys Gly Leu Glu Trp Val Ala Ser
                165                 170                 175

Ile Trp Pro Phe Gly Gly Ser Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Asn Tyr Trp Ile Gly Ile Ile Met Asp Tyr Trp Gly Gln Gly Thr
225                 230                 235                 240

Leu Val Thr Val Ser Ser Ala Ser Ala Ala Ala
                245                 250

<210> SEQ ID NO 17
<211> LENGTH: 249
<212> TYPE: PRT
<213> ORGANISM: Artificial Sequence
<220> FEATURE:
<223> OTHER INFORMATION: Antibody GH2-23-amino acid sequence

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Trp Gly
            20                  25                  30

Val Ala Trp Tyr Gln Gln Lys Pro Gly Lys Ala Pro Lys Leu Leu Ile
        35                  40                  45

Ser Trp Ser Ala Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Phe Pro Phe
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Thr Ile Asn Gly Gly Ile His Trp
145                 150                 155                 160

Val Arg Gln Ala Pro Gly Lys Gly Leu Glu Trp Val Ala Phe Ile Gly
            165                 170                 175

Pro Phe Gly Gly Ser Thr Phe Tyr Ala Asp Ser Val Lys Gly Arg Phe
        180                 185                 190

Thr Ile Ser Ala Asp Thr Ser Lys Asn Thr Ala Tyr Leu Gln Met Asn
    195                 200                 205

Ser Leu Arg Ala Glu Asp Thr Ala Val Tyr Tyr Cys Ala Arg Phe Phe
210                 215                 220

Gly Gly Asn Ile His Val Met Asp Tyr Trp Gly Gln Gly Thr Leu Val
225                 230                 235                 240

Thr Val Ser Ser Ala Ser Ala Ala Ala
            245

<210> SEQ ID NO 18
<211> LENGTH: 251
<212> TYPE: PRT
<213> ORGANISM: Artificial Sequence
<220> FEATURE:
<223> OTHER INFORMATION: Antibody GH2-24-amino acid sequence

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Trp Gly
            20                  25                  30

Val Ala Trp Tyr Gln Gln Lys Pro Gly Lys Ala Pro Lys Leu Leu Ile
        35                  40                  45

Ser Ser Thr Arg Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Gly Glu Val
        115                 120                 125

```
Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asp Asn Gly Ser Ile
145                 150                 155                 160

His Trp Val Arg Gln Ala Pro Gly Lys Gly Leu Glu Trp Val Ala Phe
                165                 170                 175

Ile Gly Pro Ser Gly Gly Tyr Thr Phe Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
    210                 215                 220

Phe Gly Trp His Asn Val Asp Asn Met Asp Tyr Trp Gly Gln Gly Thr
225                 230                 235                 240

Leu Val Thr Val Ser Ser Ala Ser Ala Ala
                245                 250

<210> SEQ ID NO 19
<211> LENGTH: 251
<212> TYPE: PRT
<213> ORGANISM: Artificial Sequence
<220> FEATURE:
<223> OTHER INFORMATION: Antibody GH2-25-amino acid sequence

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
                20                  25                  30

Val Ala Trp Tyr Gln Gln Lys Pro Gly Lys Ala Pro Lys Leu Leu Ile
            35                  40                  45

Ser Tyr Thr Arg Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Ser Gly Gly Gly Gly Ser Gly Gly Gly Gly Glu Val
            115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asn Tyr Phe Ile
145                 150                 155                 160

His Trp Val Arg Gln Ala Pro Gly Lys Gly Leu Glu Trp Val Ala Phe
                165                 170                 175

Ile Gly Pro Ser Gly Gly Ser Thr Tyr Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
    210                 215                 220

Phe Asp Leu Tyr Asn Tyr Gly Gly Met Asp Tyr Trp Gly Gln Gly Thr
225                 230                 235                 240
```

Leu Val Thr Val Ser Ser Ala Ser Ala Ala Ala
            245                 250

<210> SEQ ID NO 20
<211> LENGTH: 251
<212> TYPE: PRT
<213> ORGANISM: Artificial Sequence
<220> FEATURE:
<223> OTHER INFORMATION: Antibody GH2-26-amino acid sequence

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Gly
            20                  25                  30

Val Ala Trp Tyr Gln Gln Lys Pro Gly Lys Ala Pro Lys Leu Leu Ile
        35                  40                  45

Tyr Gly Thr Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asp Tyr Gly Ile
145                 150                 155                 160

His Trp Val Arg Gln Ala Pro Gly Lys Gly Leu Glu Trp Val Ala Phe
                165                 170                 175

Ile Gly Pro Tyr Trp Gly Tyr Thr Tyr Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Tyr Phe Phe Gly Asp Gly Leu Met Asp Tyr Trp Gly Gln Gly Thr
225                 230                 235                 240

Leu Val Thr Val Ser Ser Ala Ser Ala Ala Ala
            245                 250

<210> SEQ ID NO 21
<211> LENGTH: 251
<212> TYPE: PRT
<213> ORGANISM: Artificial Sequence
<220> FEATURE:
<223> OTHER INFORMATION: Antibody GH2-28-amino acid sequence

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Gly
            20                  25                  30

Val Ala Trp Tyr Gln Gln Lys Pro Gly Lys Ala Pro Lys Leu Leu Ile

```
            35                  40                  45
Phe Tyr Thr Arg Trp Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Phe Ser Trp Pro Leu
                 85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
        115                 120                 125

Gln Leu Val Glu Ser Gly Gly Leu Val Gln Pro Gly Gly Ser Leu
    130                 135                 140

Arg Leu Ser Cys Ala Ala Ser Gly Phe Thr Ile Asn Asn Gly Gly Ile
145                 150                 155                 160

His Trp Val Arg Gln Ala Pro Gly Lys Gly Leu Glu Trp Val Ala Ser
                165                 170                 175

Ile Gly Pro Ser Trp Gly Ser Thr Val Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Gly Phe Asp Tyr Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 22
<211> LENGTH: 251
<212> TYPE: PRT
<213> ORGANISM: Artificial Sequence
<220> FEATURE:
<223> OTHER INFORMATION: Antibody GH2-29-amino acid sequence

<400> SEQUENCE: 22

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Phe Gly Gly
                20                  25                  30

Val Ala Trp Tyr Gln Gln Lys Pro Gly Lys Ala Pro Lys Leu Leu Ile
            35                  40                  45

Ser Tyr Pro Gly Trp Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Trp Pro Ile
                 85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
        115                 120                 125

Gln Leu Val Glu Ser Gly Gly Leu Val Gln Pro Gly Gly Ser Leu
    130                 135                 140

Arg Leu Ser Cys Ala Ala Ser Gly Phe Thr Ile Asn Asn Tyr Gly Ile
```

```
                145                 150                 155                 160
His Trp Val Arg Gln Ala Pro Gly Lys Gly Leu Glu Trp Val Ala Phe
                    165                 170                 175
Ile Gly Pro Ser Trp Gly Tyr Thr Tyr Tyr Ala Asp Ser Val Lys Gly
                    180                 185                 190
Arg Phe Thr Ile Ser Ala Asp Thr Ser Lys Asn Thr Ala Tyr Leu Gln
                    195                 200                 205
Met Asn Ser Leu Arg Ala Glu Asp Thr Ala Val Tyr Tyr Cys Ala Arg
                    210                 215                 220
Phe Gly Ile His Tyr Asp Gly Val Met Asp Tyr Trp Gly Gln Gly Thr
225                 230                 235                 240
Leu Val Thr Val Ser Ser Ala Ser Ala Ala Ala
                    245                 250

<210> SEQ ID NO 23
<211> LENGTH: 251
<212> TYPE: PRT
<213> ORGANISM: Artificial Sequence
<220> FEATURE:
<223> OTHER INFORMATION: Antibody GH2-30-amino acid sequence

<400> SEQUENCE: 23

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Phe Gly Gly
                    20                  25                  30
Val Ala Trp Tyr Gln Gln Lys Pro Gly Lys Ala Pro Lys Leu Leu Ile
                    35                  40                  45
Ser Gly Thr Ser Ser Leu Tyr Ser Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Ser Phe Pro Ile
                    85                  90                  95
Thr Phe Gly Gln Gly Thr Lys Val Glu Ile Lys Arg Gly Gly Ser Ser
                    100                 105                 110
Arg Ser Ser Ser Ser Gly Gly Gly Gly Ser Gly Gly Gly Gly Glu Val
            115                 120                 125
Gln Leu Val Glu Ser Gly Gly Gly Leu Val Gln Pro Gly Gly Ser Arg
            130                 135                 140
Arg Leu Ser Cys Ala Ala Ser Gly Phe Thr Ile Asn Asn Phe Gly Ile
145                 150                 155                 160
His Trp Val Arg Gln Ala Pro Gly Lys Gly Leu Glu Trp Val Ala Ser
                    165                 170                 175
Ile Gly Pro Phe Trp Gly Tyr Thr Ser Tyr Ala Asp Ser Val Lys Gly
                    180                 185                 190
Arg Phe Thr Ile Ser Ala Asp Thr Ser Lys Asn Thr Ala Tyr Leu Gln
                    195                 200                 205
Met Asn Ser Leu Arg Ala Glu Asp Thr Ala Val Tyr Tyr Cys Ala Arg
                    210                 215                 220
Phe Gly Asn Asp Tyr Asp Gly Val Met Asp Tyr Trp Gly Gln Gly Thr
225                 230                 235                 240
Leu Val Thr Val Ser Ser Ala Ser Ala Ala Ala
                    245                 250
```

```
<210> SEQ ID NO 24
<211> LENGTH: 251
<212> TYPE: PRT
<213> ORGANISM: Artificial Sequence
<220> FEATURE:
<223> OTHER INFORMATION: Antibody GH2-31-amino acid sequence

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Trp Gly
            20                  25                  30

Val Ala Trp Tyr Gln Gln Lys Pro Gly Lys Ala Pro Lys Leu Leu Ile
        35                  40                  45

Tyr Ser Pro Pro Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asn Asn Phe Gly Ile
145                 150                 155                 160

His Trp Val Arg Gln Ala Pro Gly Lys Gly Leu Glu Trp Val Ala Ser
                165                 170                 175

Ile Gly Pro Phe Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Gly Asn Asp Tyr Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 25
<211> LENGTH: 251
<212> TYPE: PRT
<213> ORGANISM: Artificial Sequence
<220> FEATURE:
<223> OTHER INFORMATION: Antibody GH2-32-amino acid sequence

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Gly
            20                  25                  30

Val Ala Trp Tyr Gln Gln Lys Pro Gly Lys Ala Pro Lys Leu Leu Ile
        35                  40                  45

Ser Gly Pro Ser Ser Leu Tyr Ser Gly Val Pro Ser Arg Phe Ser Gly
    50                  55                  60
```

```
Ser Gly Gly Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Trp Pro Ile
                 85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
        115                 120                 125

Gln Leu Val Glu Ser Gly Gly Leu Val Gln Pro Gly Gly Ser Leu
        130                 135                 140

Arg Leu Ser Cys Ala Ala Ser Gly Phe Thr Ile Ser Asn Trp Gly Ile
145                 150                 155                 160

His Trp Val Arg Gln Ala Pro Gly Lys Gly Leu Glu Trp Val Ala Gly
                165                 170                 175

Ile Gly Pro Ser Trp Gly Tyr Thr Ser Tyr Ala Asp Ser Val Lys Gly
                180                 185                 190

Arg Phe Thr Ile Ser Ala Asp Ser Lys Asn Thr Ala Tyr Leu Gln
            195                 200                 205

Met Asn Ser Leu Arg Ala Glu Asp Thr Ala Val Tyr Tyr Cys Ala Arg
        210                 215                 220

Phe Gly Asn Val Tyr Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 26
<211> LENGTH: 251
<212> TYPE: PRT
<213> ORGANISM: Artificial Sequence
<220> FEATURE:
<223> OTHER INFORMATION: Antibody GH2-33-amino acid sequence

<400> SEQUENCE: 26

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Gly Tyr Gly
             20                  25                  30

Val Ala Trp Tyr Gln Gln Lys Pro Gly Lys Ala Pro Lys Leu Leu Ile
             35                  40                  45

Tyr Gly Thr Thr Tyr Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Trp Pro Leu
                 85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Arg Gly Glu Val
        115                 120                 125

Gln Leu Val Glu Ser Gly Gly Leu Val Gln Pro Gly Gly Ser Leu
        130                 135                 140

Arg Leu Ser Cys Ala Ala Ser Gly Phe Thr Ile Asn Asn Phe Gly Ile
145                 150                 155                 160

His Trp Val Arg Gln Ala Pro Gly Lys Gly Leu Glu Trp Val Ala Gly
                165                 170                 175
```

Ile Gly Pro Phe Trp Gly Tyr Thr Tyr Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Gly Asp Tyr Tyr Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 27
<211> LENGTH: 251
<212> TYPE: PRT
<213> ORGANISM: Artificial Sequence
<220> FEATURE:
<223> OTHER INFORMATION: Antibody GH2-35-amino acid sequence

<400> SEQUENCE: 27

Asp Ile Gln Val Thr Gln Ser Pro Ser Ser Leu Ser Val Ser Val Gly
1               5                   10                  15

Asp Arg Val Thr Ile Thr Cys Arg Ala Ser Gln Asp Val Gly Ser Tyr
            20                  25                  30

Val Ala Trp Tyr Gln Gln Lys Pro Gly Lys Ala Pro Lys Leu Leu Ile
        35                  40                  45

Ser Ser Pro Ser Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Ile
                85                  90                  95

Thr Phe Gly Gln Gly Thr Lys Val Glu Ile Lys Arg Gly Gly Ser Ser
            100                 105                 110

Arg Ser Ser Ser Ser Gly Gly Gly Gly Ser Gly Gly Gly Gly Glu Val
        115                 120                 125

Gln Leu Val Glu Ser Gly Gly Gly Leu Val Gln Pro Gly Ser Ser Leu
    130                 135                 140

Arg Leu Ser Cys Ala Ala Ser Gly Phe Thr Ile Asn Asn Phe Gly Ile
145                 150                 155                 160

His Trp Val Arg Gln Ala Pro Gly Lys Gly Leu Glu Trp Val Ala Tyr
                165                 170                 175

Ile Trp Pro Phe Gly Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Asn Gly Asp Tyr Val Gly Leu Met Asp Tyr Trp Gly Gln Gly Thr
225                 230                 235                 240

Leu Val Thr Val Ser Ser Ala Ser Ala Ala Ala
                245                 250

<210> SEQ ID NO 28
<211> LENGTH: 251
<212> TYPE: PRT
<213> ORGANISM: Artificial Sequence
<220> FEATURE:

<223> OTHER INFORMATION: Antibody GH2-36-amino acid sequence

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Glu Pro Gly Lys Ala Pro Lys Leu Leu Ile
        35                  40                  45

Tyr Phe Ser Ser Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Gly Glu Val
        115                 120                 125

Gln Leu Val Glu Ser Gly Gly Leu Val Gln Pro Gly Gly Ser Leu
    130                 135                 140

Arg Leu Ser Cys Ala Ala Ser Gly Phe Thr Ile Gly Gly Gly Ile
145                 150                 155                 160

His Trp Val Arg Gln Ala Pro Gly Lys Gly Leu Glu Trp Val Ala Tyr
                165                 170                 175

Ile Gly Pro Tyr Gly Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe His Asp His Ile Gly Gly Ile Met Asp Tyr Trp Gly Gln Gly Thr
225                 230                 235                 240

Leu Val Thr Val Ser Ser Ala Ser Ala Ala Ala
            245                 250

<210> SEQ ID NO 29
<211> LENGTH: 250
<212> TYPE: PRT
<213> ORGANISM: Artificial Sequence
<220> FEATURE:
<223> OTHER INFORMATION: Antibody GH2-37-amino acid sequence

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Gly Gly
            20                  25                  30

Val Ala Trp Tyr Gln Gln Lys Pro Gly Lys Ala Pro Lys Leu Leu Ile
        35                  40                  45

Ser Ser Pro Arg Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Leu
                85                  90                  95

```
Thr Phe Gly Gln Gly Thr Lys Val Glu Ile Lys Arg Gly Gly Ser Ser
            100                 105                 110

Arg Ser Ser Ser Gly Gly Gly Gly Gly Gly Gly Gly Glu Val Gln
            115                 120                 125

Leu Val Glu Thr Gly Gly Leu Val Gln Pro Gly Gly Ser Leu Arg
    130                 135                 140

Leu Ser Cys Ala Ala Ser Gly Phe Thr Ile Gly Asn Phe Gly Ile His
145                 150                 155                 160

Trp Val Arg Gln Ala Pro Gly Lys Gly Leu Glu Trp Val Ala Tyr Ile
                165                 170                 175

Gly Pro Tyr Gly Gly Tyr Thr Phe Tyr Ala Asp Ser Val Lys Gly Arg
                180                 185                 190

Phe Thr Ile Ser Ala Asp Thr Ser Lys Asn Thr Ala Tyr Leu Gln Met
            195                 200                 205

Asn Ser Leu Arg Ala Glu Asp Thr Ala Val Tyr Tyr Cys Ala Arg Phe
210                 215                 220

Gly Asp His Phe Asp Gly Val Met Asp Tyr Trp Gly Gln Gly Thr Leu
225                 230                 235                 240

Val Thr Val Ser Ser Ala Ser Ala Ala Ala
            245                 250

<210> SEQ ID NO 30
<211> LENGTH: 251
<212> TYPE: PRT
<213> ORGANISM: Artificial Sequence
<220> FEATURE:
<223> OTHER INFORMATION: Antibody GH2-38-amino acid sequence

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Gly Gly
            20                  25                  30

Val Ala Trp Tyr Gln Gln Lys Pro Gly Lys Ala Pro Lys Leu Leu Ile
        35                  40                  45

Tyr Gly Pro Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Ser Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
            115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asp Gly Gly Ile
145                 150                 155                 160

His Trp Val Arg Gln Ala Pro Gly Lys Gly Leu Glu Trp Val Ala Gly
                165                 170                 175

Ile Gly Pro Tyr Gly Gly Tyr Thr Ser Tyr Ala Asp Ser Val Lys Gly
                180                 185                 190

Arg Phe Thr Ile Ser Ala Asp Thr Ser Lys Asn Thr Ala Tyr Leu Gln
            195                 200                 205
```

```
Met Asn Ser Leu Arg Ala Glu Asp Thr Ala Val Tyr Tyr Cys Ala Arg
        210                 215                 220

Phe Gly Asp Asn Phe Ile Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 31
<211> LENGTH: 251
<212> TYPE: PRT
<213> ORGANISM: Artificial Sequence
<220> FEATURE:
<223> OTHER INFORMATION: Antibody GH2-39-amino acid sequence

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Asp Gly
            20                  25                  30

Val Ala Trp Tyr Gln Gln Lys Pro Gly Lys Ala Pro Lys Leu Leu Ile
        35                  40                  45

Tyr Tyr Pro Gly Tyr Leu Tyr Ser Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
130                 135                 140

Arg Leu Ser Cys Ala Ala Ser Gly Phe Thr Ile Ser Asp Trp Gly Ile
145                 150                 155                 160

His Trp Val Arg Gln Ala Pro Gly Lys Gly Leu Glu Trp Val Ala Gly
                165                 170                 175

Ile Gly Pro Tyr Gly Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Ser Ala Val Tyr Tyr Cys Ala Arg
    210                 215                 220

Phe Gly Val Asn Tyr Asp Gly Asn Met Asp Tyr Trp Gly Gln Gly Thr
225                 230                 235                 240

Leu Val Thr Val Ser Ser Ala Ser Ala Ala Ala
                245                 250

<210> SEQ ID NO 32
<211> LENGTH: 251
<212> TYPE: PRT
<213> ORGANISM: Artificial Sequence
<220> FEATURE:
<223> OTHER INFORMATION: Antibody GH2-40-amino acid sequence

<400> SEQUENCE: 32

Asp Ile Gln Met Thr Gln Ser Pro Ser Ser Leu Ser Ala Ser Val Gly
```

```
            1               5                  10                 15
    Asp Arg Val Thr Ile Thr Cys Arg Ala Ser Gln Asp Val Asn Asn Gly
                    20                  25                 30

Val Ala Trp Tyr Gln Gln Lys Pro Gly Lys Ala Pro Lys Leu Leu Ile
                    35                  40                 45

Ser Gly Thr Pro Trp Leu Tyr Ser Gly Val Pro Ser Arg Phe Ser Gly
                    50                  55                 60

Ser Gly Ser Gly Thr Asp Phe Thr Leu Thr Ile Ser Ser Leu Gln Pro
    65                  70                  75                 80

Glu Asp Phe Ala Thr Tyr Tyr Cys Gln Gln Tyr Phe Asp Trp Pro Leu
                    85                  90                 95

Thr Phe Gly Gln Gly Thr Lys Val Glu Ile Lys His Gly Gly Ser Ser
                    100                 105                110

Arg Ser Ser Ser Gly Gly Gly Ser Gly Gly Gly Glu Val
                    115                 120                125

Gln Leu Val Glu Ser Gly Gly Leu Val Gln Pro Gly Gly Ser Leu
        130                 135                 140

Arg Leu Ser Cys Ala Ala Ser Gly Phe Thr Ile Asn Ser Trp Gly Ile
    145                 150                 155                160

His Trp Val Arg Gln Ala Pro Gly Lys Gly Leu Glu Trp Val Ala Trp
                    165                 170                175

Ile Gly Pro Tyr Trp Gly Phe Thr Ser Tyr Ala Asp Ser Val Lys Gly
                    180                 185                190

Arg Phe Thr Ile Ser Ala Asp Thr Ser Lys Asn Thr Ala Tyr Leu Gln
                    195                 200                205

Met Asn Ser Leu Arg Ala Glu Asp Thr Ala Val Tyr Tyr Cys Ala Arg
        210                 215                 220

Phe Asp Gly His Phe Asp Gly Val Met Asp Tyr Trp Gly Gln Gly Thr
    225                 230                 235                240

Leu Val Thr Val Ser Ser Ala Ser Ala Ala Ala
                    245                 250

<210> SEQ ID NO 33
<211> LENGTH: 251
<212> TYPE: PRT
<213> ORGANISM: Artificial Sequence
<220> FEATURE:
<223> OTHER INFORMATION: Antibody GH2-41-amino acid sequence

<400> SEQUENCE: 33

Asp Ile Gln Met Thr Gln Ser Pro Ser Ser Leu Ser Ala Ser Val Gly
    1               5                  10                 15

Asp Arg Val Thr Ile Thr Cys Arg Ala Ser Gln Asp Val Ser Asn Ser
                    20                  25                 30

Val Ala Trp Tyr Gln Gln Lys Pro Gly Lys Ala Pro Lys Leu Leu Ile
                    35                  40                 45

Ser Gly Ala Ala Trp Leu Tyr Ser Gly Val Pro Ser Arg Phe Ser Gly
                    50                  55                 60

Ser Gly Ser Gly Thr Asp Phe Thr Leu Thr Ile Ser Ser Leu Gln Pro
    65                  70                  75                 80

Glu Asp Phe Ala Thr Tyr Tyr Cys Gln Gln Ser Gly Asn Phe Pro Leu
                    85                  90                 95

Thr Phe Gly Gln Gly Thr Lys Val Glu Ile Lys Arg Gly Gly Ser Ser
                    100                 105                110

Arg Ser Ser Ser Ser Gly Gly Gly Gly Ser Gly Gly Gly Gly Glu Val
```

```
                115                 120                 125
Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asn Trp Gly Ile
145                 150                 155                 160

His Trp Val Arg Gln Ala Pro Gly Lys Gly Leu Glu Trp Val Ala Ser
                165                 170                 175

Ile Gly Pro Ser Gly Gly Phe Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Tyr Ile Tyr Gly Gly Val Ile Met Asp Tyr Trp Gly Gln Gly Thr
225                 230                 235                 240

Leu Val Thr Val Ser Ser Ala Ser Ala Ala Ala
                245                 250
```

<210> SEQ ID NO 34
<211> LENGTH: 249
<212> TYPE: PRT
<213> ORGANISM: Artificial Sequence
<220> FEATURE:
<223> OTHER INFORMATION: Antibody GH2-42-amino acid sequence

<400> SEQUENCE: 34

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Gly
            20                  25                  30

Val Ala Trp Tyr Gln Gln Lys Pro Gly Lys Ala Pro Lys Leu Leu Ile
        35                  40                  45

Ser Gly Pro Thr Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Leu
                85                  90                  95

Thr Phe Gly Gln Gly Thr Lys Val Lys Arg Gly Ser Ser Arg Ser
            100                 105                 110

Ser Ser Ser Gly Gly Gly Ser Gly Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Ile Ser Asn Trp Gly Ile His Trp
145                 150                 155                 160

Val Arg Gln Ala Pro Gly Lys Gly Leu Glu Trp Val Ala Gly Ile Gly
                165                 170                 175

Pro Tyr Gly Gly Tyr Thr Ser Tyr Ala Asp Ser Val Lys Gly Arg Phe
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Ala Arg Phe Gly
    210                 215                 220

Phe Tyr Phe Asp Gly Ile Met Asp Tyr Trp Gly Gln Gly Thr Leu Val
```

```
                225                 230                 235                 240

Thr Val Ser Ser Ala Ser Ala Ala Ala
                245

<210> SEQ ID NO 35
<211> LENGTH: 251
<212> TYPE: PRT
<213> ORGANISM: Artificial Sequence
<220> FEATURE:
<223> OTHER INFORMATION: Antibody GH2-43-amino acid sequence

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
            20                  25                  30

Val Ala Trp Tyr Gln Gln Lys Pro Gly Lys Ala Pro Lys Leu Leu Ile
        35                  40                  45

Ser Gly Thr Pro Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Ile
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Gly Trp Gly Ile
145                 150                 155                 160

His Trp Val Arg Gln Ala Pro Gly Lys Gly Leu Glu Trp Val Ala Ser
                165                 170                 175

Ile Gly Pro Phe Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Gly Val Asp Val Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 36
<211> LENGTH: 251
<212> TYPE: PRT
<213> ORGANISM: Artificial Sequence
<220> FEATURE:
<223> OTHER INFORMATION: Antibody GH2-45-amino acid sequence

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Gly
            20                  25                  30
```

Val Ala Trp Tyr Gln Gln Lys Pro Gly Lys Ala Pro Lys Leu Leu Ile
            35                  40                  45

Ser Trp Pro Gly Tyr Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Ser Ser
                100                 105                 110

Arg Ser Ser Ser Gly Gly Gly Ser Gly Gly Gly Glu Val
            115                 120                 125

Gln Leu Val Glu Ser Gly Gly Gly Leu Val Gln Pro Gly Gly Ser Leu
130                 135                 140

Arg Leu Ser Cys Ala Ala Ser Gly Phe Thr Ile Asp Asp Tyr Gly Ile
145                 150                 155                 160

His Trp Val Arg Gln Ala Pro Gly Lys Gly Leu Glu Trp Val Ala Phe
                165                 170                 175

Ile Gly Pro Phe Gly Gly Tyr Thr Tyr Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
                210                 215                 220

Phe Asp Asn Asn Val Trp Gly Met Asp Tyr Trp Gly Gln Gly Thr
225                 230                 235                 240

Leu Val Thr Val Ser Ser Ala Ser Ala Ala Ala
                245                 250

<210> SEQ ID NO 37
<211> LENGTH: 251
<212> TYPE: PRT
<213> ORGANISM: Artificial Sequence
<220> FEATURE:
<223> OTHER INFORMATION: Antibody GH2-46-amino acid sequence

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Ser
                20                  25                  30

Val Ala Trp Tyr Gln Gln Lys Pro Gly Lys Ala Pro Lys Leu Leu Ile
            35                  40                  45

Tyr Trp Ala Gly Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Trp Pro Ile
                85                  90                  95

Thr Phe Gly Gln Gly Thr Lys Val Glu Ile Lys Arg Gly Gly Ser Ser
                100                 105                 110

Arg Ser Ser Ser Gly Gly Gly Leu Gly Gly Gly Glu Val
            115                 120                 125

Gln Leu Val Glu Ser Gly Gly Gly Leu Val Gln Pro Gly Gly Ser Leu
130                 135                 140

```
Arg Leu Ser Cys Ala Ala Ser Gly Phe Thr Ile Gly Ser Tyr Gly Ile
145                 150                 155                 160

His Trp Val Arg Gln Ala Pro Gly Lys Gly Leu Glu Trp Val Ala Gly
                165                 170                 175

Ile Gly Pro Tyr Gly Gly Tyr Thr Phe Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
210                 215                 220

Phe Gly Tyr His Val Asp Gly Ile Met Asp Tyr Trp Gly Gln Gly Thr
225                 230                 235                 240

Leu Val Thr Val Ser Ser Ala Ser Ala Ala Ala
                245                 250

<210> SEQ ID NO 38
<211> LENGTH: 244
<212> TYPE: PRT
<213> ORGANISM: Artificial Sequence
<220> FEATURE:
<223> OTHER INFORMATION: Antibody GH2-47-amino acid sequence

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Ser Phe
            20                  25                  30

Val Ala Trp Tyr Gln Gln Lys Pro Gly Lys Ala Pro Lys Leu Leu Ile
        35                  40                  45

Tyr Tyr Thr Ser Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Glu Val Gln Leu Val Glu Ser Gly Gly Gly
        115                 120                 125

Gly Leu Val Gln Pro Gly Gly Ser Leu Arg Leu Ser Cys Ala Ala Ser
    130                 135                 140

Gly Phe Thr Ile Asn Asp Tyr Gly Ile His Trp Val Arg Gln Ala Pro
145                 150                 155                 160

Gly Lys Gly Leu Glu Trp Val Ala Gly Ile Gly Pro Phe Gly Gly Tyr
                165                 170                 175

Thr Ser Tyr Ala Asp Ser Val Lys Gly Arg Phe Thr Ile Ser Ala Asp
            180                 185                 190

Thr Ser Lys Asn Thr Ala Tyr Leu Gln Met Asn Ser Leu Arg Ala Glu
        195                 200                 205

Asp Thr Ala Val Tyr Tyr Cys Ala Arg Phe Gly Val Leu Phe Asp Gly
    210                 215                 220

Val Met Asp Tyr Trp Gly Gln Gly Thr Leu Val Thr Val Ser Ser Ala
225                 230                 235                 240

Ser Ala Ala Ala
```

```
<210> SEQ ID NO 39
<211> LENGTH: 251
<212> TYPE: PRT
<213> ORGANISM: Artificial Sequence
<220> FEATURE:
<223> OTHER INFORMATION: Antibody GH2-48-amino acid sequence

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Trp Gly
            20                  25                  30

Val Ala Trp Tyr Gln Gln Lys Pro Gly Lys Ala Pro Lys Leu Leu Ile
        35                  40                  45

Ser Ser Thr Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Val
                85                  90                  95

Thr Phe Gly Gln Gly Thr Lys Val Glu Ile Lys Arg Gly Gly Ser Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asn Gly Gly Gly Ile
145                 150                 155                 160

His Trp Val Arg Gln Ala Pro Gly Lys Gly Leu Glu Trp Val Ala Phe
                165                 170                 175

Ile Trp Pro Tyr Gly Gly Phe Thr Phe Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Asn Tyr Asn His Gly Trp Phe Met Asp Tyr Trp Gly Gln Gly Thr
225                 230                 235                 240

Leu Val Thr Val Ser Ser Ala Ser Ala Ala Ala
                245                 250

<210> SEQ ID NO 40
<211> LENGTH: 251
<212> TYPE: PRT
<213> ORGANISM: Artificial Sequence
<220> FEATURE:
<223> OTHER INFORMATION: Antibody GH2-49-amino acid sequence

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Ser Gly
            20                  25                  30

Val Ala Trp Tyr Gln Gln Lys Pro Gly Lys Ala Pro Lys Leu Leu Ile
        35                  40                  45

Ser Ser Thr Tyr Leu Tyr Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asp Tyr Pro Phe
                85                  90                  95

Thr Phe Gly Gln Gly Thr Lys Val Glu Ile Lys His Gly Gly Ser Ser
            100                 105                 110

Arg Ser Ser Ser Gly Gly Gly Ser Gly Gly Gly Glu Val
        115                 120                 125

Gln Leu Val Glu Ser Gly Gly Leu Val Gln Pro Gly Gly Ser Leu
        130                 135                 140

Arg Leu Ser Cys Ala Ala Ser Gly Phe Thr Ile Asn Gly Phe Ser Ile
145                 150                 155                 160

His Trp Val Arg Gln Ala Pro Gly Lys Gly Leu Glu Trp Val Ala Trp
                165                 170                 175

Ile Trp Pro Ser Gly Gly Tyr Thr Ser Tyr Ala Asp Ser Val Lys Gly
                180                 185                 190

Arg Phe Thr Ile Ser Ala Asp Thr Ser Lys Asn Thr Ala Tyr Leu Gln
                195                 200                 205

Met Asn Ser Leu Arg Ala Glu Asp Thr Ala Val Tyr Tyr Cys Ala Arg
    210                 215                 220

Phe Asn His His His His Trp Gly Met Asp Tyr Trp Gly Gln Gly Thr
225                 230                 235                 240

Leu Val Thr Val Ser Ser Ala Ser Ala Ala Ala
                245                 250

<210> SEQ ID NO 41
<211> LENGTH: 251
<212> TYPE: PRT
<213> ORGANISM: Artificial Sequence
<220> FEATURE:
<223> OTHER INFORMATION: Antibody GH2-50-amino acid sequence

<400> SEQUENCE: 41

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Phe Tyr Gly
                20                  25                  30

Val Ala Trp Tyr Gln Gln Lys Pro Gly Lys Ala Pro Lys Leu Leu Ile
            35                  40                  45

Phe Trp Thr Thr Tyr Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Ser Ser
            100                 105                 110

Arg Ser Ser Ser Gly Gly Gly Ser Gly Gly Gly Glu Val
        115                 120                 125

Gln Leu Val Glu Ser Gly Gly Leu Val Gln Pro Gly Gly Ser Leu
        130                 135                 140

Arg Leu Ser Cys Ala Ala Ser Gly Phe Thr Ile Asn Asn Asp Gly Ile
145                 150                 155                 160

His Trp Val Arg Gln Ala Pro Gly Lys Gly Leu Glu Trp Val Ala Ala
                165                 170                 175
```

Ile Gly Pro Phe Trp Gly Ser Thr Asp Tyr Ala Asp Ser Val Lys Gly
            180                 185                 190

Arg Phe Thr Ile Ser Ala Asp Thr Ser Asn Thr Ala Tyr Leu His
        195                 200                 205

Met Asn Ser Leu Arg Ala Glu Asp Thr Ala Leu Tyr Tyr Cys Ala Arg
    210                 215                 220

Phe Gly Asn Tyr Tyr Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 42
<211> LENGTH: 251
<212> TYPE: PRT
<213> ORGANISM: Artificial Sequence
<220> FEATURE:
<223> OTHER INFORMATION: Antibody GH2-51-amino acid

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Gly
            20                  25                  30

Val Ala Trp Tyr Gln Gln Lys Pro Gly Lys Ala Pro Lys Leu Leu Ile
        35                  40                  45

Ser Trp Thr Thr Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Trp Pro Leu
                85                  90                  95

Thr Phe Gly Gln Gly Thr Lys Val Glu Ile Lys Arg Gly Gly Pro Ser
            100                 105                 110

Arg Ser Ser Ser Gly Gly Gly Gly Ser Gly Gly Gly Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asp Gly Tyr Gly Ile
145                 150                 155                 160

His Trp Val Arg Gln Ala Pro Gly Lys Gly Leu Glu Trp Val Ala Ser
                165                 170                 175

Ile Gly Pro Phe Trp Gly Tyr Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Gly Asp Tyr Tyr Asp Gly Val Met Asp Tyr Trp Gly Gln Gly Thr
225                 230                 235                 240

Leu Val Thr Val Ser Ser Ala Ser Ala Ala Ala
                245                 250

<210> SEQ ID NO 43
<211> LENGTH: 248
<212> TYPE: PRT
<213> ORGANISM: Artificial Sequence
<220> FEATURE:

<223> OTHER INFORMATION: Antibody GH2-53-amino acid sequence

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Asn Asn
            20                  25                  30

Val Ala Trp Tyr Gln Gln Lys Pro Gly Lys Ala Pro Lys Leu Leu Ile
        35                  40                  45

Phe Trp Ser Arg Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Tyr Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Asp Tyr Trp Ile His Trp Val
145                 150                 155                 160

Arg Gln Ala Pro Gly Lys Gly Leu Glu Trp Val Ala Gly Ile Gly Pro
                165                 170                 175

Phe Gly Gly Phe Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe His Tyr
    210                 215                 220

Tyr Trp Gly His Phe Met Asp Tyr Trp Gly Gln Gly Thr Leu Val Thr
225                 230                 235                 240

Val Ser Ser Ala Ser Ala Ala Ala
            245

<210> SEQ ID NO 44
<211> LENGTH: 248
<212> TYPE: PRT
<213> ORGANISM: Artificial Sequence
<220> FEATURE:
<223> OTHER INFORMATION: Antibody GH2-54-amino acid sequence

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Asn
            20                  25                  30

Val Ala Trp Tyr Gln Gln Lys Pro Gly Lys Ala Pro Lys Leu Leu Ile
        35                  40                  45

Phe Gly Ser Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Asn Tyr Pro Phe
                85                  90                  95

```
Thr Phe Gly Gln Gly Thr Lys Val Glu Ile Lys Arg Gly Gly Gly
                100                 105                 110

Ser Ile Glu Gly Arg Ser Gly Gly Gly Ser Glu Val Gln Leu Val
                115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Asp Gly Ser Ile His Trp Val
145                 150                 155                 160

Arg Gln Ala Pro Gly Lys Gly Leu Glu Trp Val Ala Phe Ile Gly Pro
                165                 170                 175

Tyr Trp Gly Phe Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205

Leu Arg Ala Glu Asp Thr Ala Val Tyr Tyr Cys Ala Arg Phe Val Asn
                210                 215                 220

Trp Val His Tyr Gly Met Asp Tyr Trp Gly Gln Gly Thr Leu Val Thr
225                 230                 235                 240

Val Ser Ser Ala Ser Ala Ala Ala
                245

<210> SEQ ID NO 45
<211> LENGTH: 248
<212> TYPE: PRT
<213> ORGANISM: Artificial Sequence
<220> FEATURE:
<223> OTHER INFORMATION: Antibody GH2-55-amino acid sequence

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Gly Asn
                20                  25                  30

Val Ala Trp Tyr Gln Gln Lys Pro Gly Lys Ala Pro Lys Leu Leu Ile
                35                  40                  45

Ser Ser Ala Gly Ser Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Ser Trp Pro Leu
                85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
                115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asp Gly Phe Ser Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205
```

```
Leu Arg Ala Glu Asp Thr Ala Val Tyr Tyr Cys Ala Arg Phe Asp Ile
        210                 215                 220

Trp His Asn Phe Gly Met Asp Tyr Trp Gly Gln Gly Thr Leu Val Thr
225                 230                 235                 240

Val Ser Ser Ala Ser Ala Ala Ala
                245

<210> SEQ ID NO 46
<211> LENGTH: 248
<212> TYPE: PRT
<213> ORGANISM: Artificial Sequence
<220> FEATURE:
<223> OTHER INFORMATION: Antibody GH2-56-amino acid sequence

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Asn Asn
            20                  25                  30

Val Ala Trp Tyr Gln Gln Lys Pro Gly Lys Ala Pro Lys Leu Leu Ile
        35                  40                  45

Tyr Gly Ala Ala Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gly Asn Phe Pro Val
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Gly Gly Ser Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Phe Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Asn Ile
    210                 215                 220

Trp Tyr Gly Val Asn Met Asp Tyr Trp Gly Gln Gly Thr Leu Val Thr
225                 230                 235                 240

Val Ser Ser Ala Ser Ala Ala Ala
                245

<210> SEQ ID NO 47
<211> LENGTH: 248
<212> TYPE: PRT
<213> ORGANISM: Artificial Sequence
<220> FEATURE:
<223> OTHER INFORMATION: Antibody GH2-57-amino acid sequence

<400> SEQUENCE: 47

Asp Ile Gln Met Thr Gln Ser Pro Ser Ser Leu Ser Ala Ser Val Gly
```

```
            1               5                  10                 15
         Asp Arg Val Thr Ile Thr Cys Arg Ala Ser Gln Asp Val Asn Asn Gly
                        20                  25                 30

Val Ala Trp Tyr Gln Gln Lys Pro Gly Lys Ala Pro Lys Leu Leu Ile
                        35                  40                 45

Tyr Tyr Thr Gly Gly Leu Tyr Ser Gly Val Pro Ser Arg Phe Ser Gly
                        50                  55                 60

Ser Gly Ser Gly Thr Asp Phe Thr Leu Thr Ile Ser Ser Leu Gln Pro
          65                 70                  75                 80

Glu Asp Phe Ala Thr Tyr Tyr Cys Gln Gln Tyr Ser Ser Tyr Pro Leu
                        85                  90                 95

Thr Phe Gly Gln Gly Thr Lys Val Glu Ile Lys Arg Gly Gly Gly Gly
                        100                 105                110

Ser Ile Glu Gly Arg Ser Gly Gly Gly Ser Glu Val Gln Leu Val
                        115                 120                125

Glu Ser Gly Gly Gly Leu Val Gln Pro Gly Gly Ser Leu Arg Leu Ser
          130                135                 140

Cys Ala Ala Ser Gly Phe Thr Ile Ser Ser Gly Ser Ile His Trp Val
          145                150                 155                160

Arg Gln Ala Pro Gly Lys Gly Leu Glu Trp Val Ala Gly Ile Gly Pro
                        165                 170                175

Tyr Trp Gly Tyr Thr Ser Tyr Ala Asp Ser Val Lys Gly Arg Phe Thr
                        180                 185                190

Ile Ser Ala Asp Thr Ser Lys Asn Thr Ala Tyr Leu Gln Met Asn Ser
                        195                 200                205

Leu Arg Ala Glu Asp Thr Ala Glu Tyr Tyr Cys Ala Arg Phe Leu His
          210                215                 220

Gly Asp Ile Phe Gly Met Asp Tyr Trp Gly Gln Gly Thr Leu Val Thr
          225                230                 235                240

Val Ser Ser Ala Ser Ala Ala Ala
                        245

<210> SEQ ID NO 48
<211> LENGTH: 248
<212> TYPE: PRT
<213> ORGANISM: Artificial Sequence
<220> FEATURE:
<223> OTHER INFORMATION: Antibody GH2-59-amino acid sequence

<400> SEQUENCE: 48

Asp Ile Gln Met Thr Gln Ser Pro Ser Ser Leu Ser Ala Ser Val Gly
          1                  5                  10                 15

Asp Arg Val Thr Ile Thr Cys Arg Ala Ser Gln Asp Val Ser Gly Gly
                        20                  25                 30

Val Ala Trp Tyr Gln Gln Lys Pro Gly Lys Ala Pro Lys Leu Leu Ile
                        35                  40                 45

Ser Trp Thr Gly Ser Leu Tyr Ser Gly Val Pro Ser Arg Phe Ser Gly
                        50                  55                 60

Ser Gly Ser Gly Thr Asp Phe Thr Leu Thr Ile Ser Ser Leu Gln Pro
          65                 70                  75                 80

Glu Asp Phe Ala Thr Tyr Tyr Cys Gln Gln Trp Ser Asp Phe Pro Ile
                        85                  90                 95

Thr Phe Gly Gln Gly Thr Lys Val Glu Ile Lys Arg Gly Gly Gly Gly
                        100                 105                110

Ser Ile Glu Gly Arg Ser Gly Gly Gly Gly Ser Glu Val Gln Leu Val
```

```
                   115                 120                 125
Glu Ser Gly Gly Gly Leu Val Arg Pro Gly Gly Ser Leu Arg Leu Ser
            130                 135                 140

Cys Ala Ala Ser Gly Phe Thr Ile Gly Asp Trp Tyr Ile His Trp Val
145                 150                 155                 160

Arg Gln Ala Pro Gly Lys Gly Leu Glu Trp Val Ala Gly Ile Gly Pro
                165                 170                 175

Tyr Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Val Gly
            210                 215                 220

Asp Val Trp His Asp Met Asp Tyr Trp Gly Gln Gly Thr Leu Val Ala
225                 230                 235                 240

Val Ser Ser Ala Ser Ala Ala Ala
                245

<210> SEQ ID NO 49
<211> LENGTH: 248
<212> TYPE: PRT
<213> ORGANISM: Artificial Sequence
<220> FEATURE:
<223> OTHER INFORMATION: Antibody GH2-60-amino acid sequence

<400> SEQUENCE: 49

Asp Ile Gln Met Thr Gln Gly Pro Ser Ser Leu Ser Ala Ser Val Gly
1               5                   10                  15

Asp Arg Val Thr Ile Thr Cys Arg Ala Ser Gln Asp Val Gly Ser Trp
            20                  25                  30

Val Ala Trp Tyr Gln Gln Lys Pro Gly Lys Ala Pro Lys Leu Leu Ile
        35                  40                  45

Ser Ser Pro Pro Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Asp Ser Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
            130                 135                 140

Cys Ala Ala Ser Gly Phe Thr Ile Ser Asp Phe Gly Ile His Trp Val
145                 150                 155                 160

Arg Gln Ala Pro Gly Lys Gly Leu Glu Trp Val Ala Gly Ile Trp Pro
                165                 170                 175

Tyr Trp Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Trp Asn
            210                 215                 220

Ile Tyr Trp Asn Val Met Asp Tyr Trp Gly Gln Gly Thr Leu Val Thr
```

```
                225                 230                 235                 240

Val Ser Ser Ala Ser Ala Ala Ala
                245

<210> SEQ ID NO 50
<211> LENGTH: 248
<212> TYPE: PRT
<213> ORGANISM: Artificial Sequence
<220> FEATURE:
<223> OTHER INFORMATION: Antibody GH2-61-amino acid sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Asn
            20                  25                  30

Val Ala Trp Tyr Gln Gln Lys Pro Gly Lys Ala Pro Lys Leu Leu Ile
        35                  40                  45

Ser Trp Ser Thr Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Gly Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asn Trp Gly Ile His Trp Val
145                 150                 155                 160

Arg Gln Ala Pro Gly Lys Gly Leu Glu Trp Val Ala Gly Ile Trp Pro
                165                 170                 175

Tyr Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Tyr Asn
    210                 215                 220

His His Gly Gly Val Met Asp Tyr Trp Gly Gln Gly Thr Leu Val Thr
225                 230                 235                 240

Val Ser Ser Ala Ser Ala Ala Ala
                245

<210> SEQ ID NO 51
<211> LENGTH: 248
<212> TYPE: PRT
<213> ORGANISM: Artificial Sequence
<220> FEATURE:
<223> OTHER INFORMATION: Antibody GH2-62-amino acid sequence

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Gly Tyr
            20                  25                  30
```

Val Ala Trp Tyr Gln Gln Lys Pro Gly Lys Ala Pro Lys Leu Leu Ile
         35                  40                  45

Phe Gly Ala Ser Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Ser Ser Pro Leu
                 85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asn Trp Gly Ile His Trp Val
145                 150                 155                 160

Arg Gln Ala Pro Gly Lys Gly Leu Glu Trp Val Ala Gly Ile Trp Pro
                165                 170                 175

Phe Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Asp Tyr
    210                 215                 220

Leu Asn Asn Gly Gly Met Asp Tyr Trp Gly Gln Gly Thr Leu Val Thr
225                 230                 235                 240

Val Ser Ser Ala Ser Ala Ala Ala
                245

<210> SEQ ID NO 52
<211> LENGTH: 248
<212> TYPE: PRT
<213> ORGANISM: Artificial Sequence
<220> FEATURE:
<223> OTHER INFORMATION: Antibody GH2-63-amino acid sequence

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Ser Asp
            20                  25                  30

Val Ala Trp Tyr Gln Gln Lys Pro Gly Lys Ala Pro Lys Leu Leu Ile
         35                  40                  45

Ser Phe Thr Arg Ser Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Leu
                 85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

```
Cys Ala Ala Ser Gly Phe Thr Ile Gly Asn Trp Ser Ile His Trp Val
145                 150                 155                 160

Arg Gln Ala Pro Gly Lys Gly Leu Glu Trp Val Ala Gly Ile Trp Pro
                165                 170                 175

Tyr Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe His Tyr
    210                 215                 220

Trp Trp His Asn Ile Met Asp Tyr Trp Gly Gln Gly Thr Leu Val Thr
225                 230                 235                 240

Val Ser Ser Ala Ser Ala Ala Ala
                245
```

<210> SEQ ID NO 53
<211> LENGTH: 248
<212> TYPE: PRT
<213> ORGANISM: Artificial Sequence
<220> FEATURE:
<223> OTHER INFORMATION: Antibody GH2-64-amino acid sequence

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Asp
                20                  25                  30

Val Ala Trp Tyr Gln Gln Lys Pro Gly Lys Ala Pro Lys Leu Leu Ile
            35                  40                  45

Phe Phe Ser Ser Trp Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asn Tyr Pro Leu
                85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Gly Asp Trp Ser Ile His Trp Val
145                 150                 155                 160

Arg Gln Ala Pro Gly Lys Gly Leu Glu Trp Val Ala Gly Ile Trp Pro
                165                 170                 175

Ser Gly Gly Ser Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Asn Tyr
    210                 215                 220

Trp Ile Asn Gly Ile Met Asp Tyr Trp Gly Gln Gly Thr Leu Val Thr
225                 230                 235                 240

Val Ser Ser Ala Ser Ala Ala Ala
                245
```

<210> SEQ ID NO 54
<211> LENGTH: 248
<212> TYPE: PRT
<213> ORGANISM: Artificial Sequence
<220> FEATURE:
<223> OTHER INFORMATION: Antibody GH2-65-amino acid sequence

<400> SEQUENCE: 54

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Trp
            20                  25                  30

Val Ala Trp Tyr Gln Gln Lys Pro Gly Lys Ala Pro Lys Leu Leu Ile
        35                  40                  45

Ser Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Phe Pro Val
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asp Asp Trp Gly Ile His Trp Val
145                 150                 155                 160

Arg Gln Ala Pro Gly Lys Gly Leu Glu Trp Val Ala Trp Ile Trp Pro
                165                 170                 175

Tyr Trp Gly Tyr Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Leu Asp
    210                 215                 220

Trp Asn Asn Asn Trp Met Asp Tyr Trp Gly Gln Gly Thr Leu Val Thr
225                 230                 235                 240

Val Ser Ser Ala Ser Ala Ala Ala
                245
```

<210> SEQ ID NO 55
<211> LENGTH: 248
<212> TYPE: PRT
<213> ORGANISM: Artificial Sequence
<220> FEATURE:
<223> OTHER INFORMATION: Antibody GH2-66-amino acid sequence

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Ser Tyr
            20                  25                  30

Val Ala Trp Tyr Gln Gln Lys Pro Gly Lys Ala Pro Lys Leu Leu Ile
        35                  40                  45

Ser Tyr Ala Ser Gly Leu Tyr Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Ser Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Gly Asn Trp Gly Ile His Trp Val
145                 150                 155                 160

Arg Gln Ala Pro Gly Lys Gly Leu Glu Trp Val Ala Tyr Ile Trp Pro
                165                 170                 175

Tyr Trp Gly Phe Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Leu Asp
210                 215                 220

Trp Asn Leu Leu Trp Met Asp Tyr Trp Gly Gln Gly Thr Leu Val Thr
225                 230                 235                 240

Val Ser Ser Ala Ser Ala Ala Ala
                245

<210> SEQ ID NO 56
<211> LENGTH: 248
<212> TYPE: PRT
<213> ORGANISM: Artificial Sequence
<220> FEATURE:
<223> OTHER INFORMATION: Antibody GH2-68-amino acid sequence

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Ser
                20                  25                  30

Val Ala Trp Tyr Gln Gln Lys Pro Gly Lys Ala Pro Lys Leu Leu Ile
            35                  40                  45

Phe Ser Pro Arg Tyr Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asn Phe Gly Ile His Trp Val
145                 150                 155                 160

Arg Gln Ala Pro Gly Lys Gly Leu Glu Trp Val Ala Gly Ile Gly Pro
                165                 170                 175

-continued

Tyr Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Ile
210                 215                 220

His His Asp Gly Val Met Asp Tyr Trp Gly Gln Gly Thr Leu Val Thr
225                 230                 235                 240

Val Ser Ser Ala Ser Ala Ala Ala
            245

<210> SEQ ID NO 57
<211> LENGTH: 248
<212> TYPE: PRT
<213> ORGANISM: Artificial Sequence
<220> FEATURE:
<223> OTHER INFORMATION: Antibody GH2-69-amino acid sequence

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Tyr Ser
            20                  25                  30

Val Ala Trp Tyr Gln Gln Lys Pro Gly Lys Ala Pro Lys Leu Leu Ile
            35                  40                  45

Phe Gly Thr Thr Gly Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Asn Ser Trp Gly Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Asp
        210                 215                 220

Asp His Asp Gly Leu Met Asp Tyr Trp Gly Gln Gly Thr Leu Val Thr
225                 230                 235                 240

Val Ser Ser Ala Ser Ala Ala Ala
            245

<210> SEQ ID NO 58
<211> LENGTH: 248
<212> TYPE: PRT
<213> ORGANISM: Artificial Sequence

```
<220> FEATURE:
<223> OTHER INFORMATION: Antibody GH2-71-amino acid sequence

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Gly
            20                  25                  30

Val Ala Trp Tyr Gln Gln Lys Pro Gly Lys Ala Pro Lys Leu Leu Ile
        35                  40                  45

Phe Ser Thr Gly Gly Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Leu
                85                  90                  95

Thr Phe Ser Gln Gly Thr Lys Val Glu Ile Lys Arg Gly Gly Gly Gly
            100                 105                 110

Ser Ile Glu Gly Arg Ser Gly Arg Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Asn Phe Gly Ile His Trp Val
145                 150                 155                 160

Arg Gln Ala Pro Gly Lys Gly Leu Glu Trp Val Ala Gly Ile Gly Pro
                165                 170                 175

Ser Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Asn Asn
210                 215                 220

Trp Asp Ile Phe Gly Met Asp Tyr Trp Gly Gln Gly Thr Leu Val Thr
225                 230                 235                 240

Val Ser Ser Ala Ser Ala Ala Ala
                245

<210> SEQ ID NO 59
<211> LENGTH: 248
<212> TYPE: PRT
<213> ORGANISM: Artificial Sequence
<220> FEATURE:
<223> OTHER INFORMATION: Antibody GH2-72-amino acid sequence

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Tyr Phe
            20                  25                  30

Val Ala Trp Tyr Gln Gln Lys Pro Gly Lys Ala Pro Lys Leu Leu Ile
        35                  40                  45

Ser Gly Thr Thr Trp Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asn Trp Pro Leu
```

```
                    85                  90                  95
Thr Phe Gly Gln Gly Thr Lys Val Glu Ile Lys Arg Gly Gly Gly
                100                 105                 110
Ser Ile Glu Gly Arg Ser Gly Gly Gly Ser Glu Val Gln Leu Val
                115                 120                 125
Glu Ser Gly Gly Gly Leu Val Gln Pro Gly Gly Ser Leu Arg Leu Ser
    130                 135                 140
Cys Ala Ala Ser Gly Phe Thr Ile Ser Asn Gly Gly Ile His Trp Val
145                 150                 155                 160
Arg Gln Ala Pro Gly Lys Gly Leu Glu Trp Val Ala Tyr Ile Trp Pro
                165                 170                 175
Ser Gly Gly Tyr Thr Phe Tyr Ala Asp Ser Val Lys Gly Arg Phe Thr
                180                 185                 190
Ile Ser Ala Asp Thr Ser Lys Asn Thr Ala Tyr Leu Gln Met Asn Ser
                195                 200                 205
Leu Arg Ala Glu Asp Thr Ala Val Tyr Tyr Cys Ala Arg Phe Phe Asn
    210                 215                 220
Asn Asp Trp Ile Gly Met Asp Tyr Trp Gly Gln Gly Thr Leu Val Thr
225                 230                 235                 240

Val Ser Ser Ala Ser Ala Ala Ala
                245

<210> SEQ ID NO 60
<211> LENGTH: 248
<212> TYPE: PRT
<213> ORGANISM: Artificial Sequence
<220> FEATURE:
<223> OTHER INFORMATION: Antibody GH2-73-amino acid sequence

<400> SEQUENCE: 60

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Ser Asn
                20                  25                  30
Val Ala Trp Tyr Gln Gln Lys Pro Gly Lys Ala Pro Lys Leu Leu Ile
            35                  40                  45
Ser Ser Pro Thr Gly Leu Tyr Ser Gly Val Pro Ser Arg Phe Ser Gly
50                  55                  60
Ser Gly Ser Gly Thr Asp Phe Thr Leu Ala Ile Ser Ser Leu Gln Pro
65                  70                  75                  80
Glu Asp Phe Ala Thr Tyr Tyr Cys Gln Gln Tyr Ser Asn Trp Pro Phe
                85                  90                  95
Thr Phe Gly Gln Gly Thr Lys Val Glu Ile Lys Arg Gly Gly Gly
                100                 105                 110
Ser Ile Glu Gly Arg Ser Gly Ser Gly Gly Ser Glu Val Arg Leu Val
                115                 120                 125
Glu Ser Gly Gly Gly Leu Val Gln Pro Gly Gly Ser Leu Arg Leu Ser
    130                 135                 140
Cys Ala Ala Ser Gly Phe Thr Ile Ser Asn Trp Gly Ile His Trp Val
145                 150                 155                 160
Arg Gln Ala Pro Gly Lys Gly Leu Glu Trp Val Ala Gly Ile Trp Pro
                165                 170                 175
Phe Gly Gly Ser Thr Ser Tyr Ala Asp Ser Val Lys Gly Arg Phe Thr
                180                 185                 190
Ile Ser Ala Asp Thr Ser Lys Asn Thr Ala Tyr Leu Gln Met Asn Ser
```

-continued

```
            195                 200                 205
Leu Arg Ala Glu Asp Thr Ala Val Tyr Tyr Cys Ala Arg Phe His His
    210                 215                 220

Phe Val Trp Tyr Gly Met Asp Tyr Trp Gly Gln Gly Thr Leu Val Thr
225                 230                 235                 240

Val Ser Ser Ala Ser Ala Ala Ala
                245

<210> SEQ ID NO 61
<211> LENGTH: 243
<212> TYPE: PRT
<213> ORGANISM: Artificial Sequence
<220> FEATURE:
<223> OTHER INFORMATION: Antibody GH2-75-amino acid sequence

<400> SEQUENCE: 61

Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Asp Val Ser Gly Tyr
            20                  25                  30

Val Ala Trp Tyr Gln Gln Lys Pro Gly Lys Ala Pro Lys Leu Leu Ile
        35                  40                  45

Tyr Ser Ser Gly Val Pro Ser Arg Phe Ser Gly Ser Gly Ser Gly Thr
    50                  55                  60

Asp Phe Thr Leu Thr Ile Ser Ser Leu Gln Pro Glu Asp Phe Ala Thr
65                  70                  75                  80

Tyr Tyr Cys Gln Gln Tyr Tyr Asn Trp Pro Val Thr Phe Gly Gln Gly
                85                  90                  95

Thr Lys Val Glu Ile Lys Arg Gly Gly Gly Gly Ser Ile Glu Gly Arg
            100                 105                 110

Ser Gly Gly Gly Gly Ser Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Ser Thr Ile Gly Asn Ser Gly Ile His Trp Val Arg Gln Ala Pro Gly
145                 150                 155                 160

Lys Gly Leu Glu Trp Val Ala Tyr Ile Gly Pro Tyr Gly Gly Tyr Thr
                165                 170                 175

Ser Tyr Ala Asp Ser Val Lys Gly Arg Phe Thr Ile Ser Ala Asp Thr
            180                 185                 190

Ser Lys Asn Thr Ala Tyr Leu Gln Met Asn Ser Leu Arg Ala Glu Asp
        195                 200                 205

Thr Ala Val Tyr Tyr Cys Ala Arg Phe Asp Asp Tyr His Trp Asp Gly
    210                 215                 220

Met Asp Tyr Trp Gly Gln Gly Thr Leu Val Thr Val Ser Ser Ala Ser
225                 230                 235                 240

Ala Ala Ala

<210> SEQ ID NO 62
<211> LENGTH: 248
<212> TYPE: PRT
<213> ORGANISM: Artificial Sequence
<220> FEATURE:
<223> OTHER INFORMATION: Antibody GH2-76-amino acid sequence

<400> SEQUENCE: 62

Asp Ile Gln Met Thr Gln Ser Pro Ser Ser Leu Ser Ala Ser Val Gly
```

```
                1               5                   10                  15
        Asp Arg Val Thr Ile Thr Cys Arg Ala Ser Gln Asp Val Ser Asp Gly
                        20                  25                  30

Val Ala Trp Tyr Gln Gln Lys Pro Gly Lys Ala Pro Lys Leu Leu Ile
                        35                  40                  45

Phe Ser Thr Ser Trp Leu Tyr Ser Gly Val Pro Ser Arg Phe Ser Gly
                        50                  55                  60

Ser Gly Ser Gly Thr Asp Phe Thr Leu Ala Ile Ser Ser Leu Gln Pro
        65                      70                  75                  80

Glu Asp Phe Ala Thr Tyr Tyr Cys Gln Gln Tyr Tyr Asn Trp Pro Ile
                        85                  90                  95

Thr Phe Gly Gln Gly Thr Lys Val Glu Ile Lys Arg Gly Gly Gly Gly
                        100                 105                 110

Ser Ile Glu Gly Arg Ser Gly Gly Gly Ser Glu Val Gln Leu Val
                        115                 120                 125

Glu Ser Gly Gly Gly Leu Val Gln Pro Gly Gly Ser Leu Arg Leu Ser
                130                     135                 140

Cys Ala Ala Ser Gly Phe Thr Ile Gly Asn Ser Gly Ile His Trp Val
        145                     150                 155                 160

Arg Gln Ala Pro Gly Lys Gly Leu Glu Trp Val Ala Phe Ile Gly Pro
                        165                 170                 175

Tyr Gly Gly Tyr Thr Ser Tyr Ala Asp Ser Val Lys Gly Arg Phe Thr
                        180                 185                 190

Ile Ser Ala Asp Thr Ser Lys Asn Thr Ala Tyr Leu Gln Met Asn Ser
                        195                 200                 205

Leu Arg Ala Glu Asp Thr Ala Val Tyr Tyr Cys Ala Arg Phe Asn Leu
                210                     215                 220

Asp His Gly Tyr Gly Met Asp Tyr Trp Gly Gln Gly Thr Leu Val Thr
        225                     230                 235                 240

Val Ser Ser Ala Ser Ala Ala Ala
                        245
```

<210> SEQ ID NO 63
<211> LENGTH: 248
<212> TYPE: PRT
<213> ORGANISM: Artificial Sequence
<220> FEATURE:
<223> OTHER INFORMATION: Antibody GH2-77-amino acid sequence

<400> SEQUENCE: 63

```
        Asp Ile Gln Met Ser Gln Ser Pro Ser Ser Leu Ser Ala Ser Val Gly
        1               5                   10                  15

Asp Arg Val Thr Ile Thr Cys Arg Ala Ser Gln Asp Val Ser Gly Gly
                        20                  25                  30

Val Ala Trp Tyr Gln Gln Lys Pro Gly Lys Ala Pro Lys Leu Leu Ile
                        35                  40                  45

Phe Ser Pro Ala Gly Leu Tyr Ser Gly Val Pro Ser Arg Phe Ser Gly
                        50                  55                  60

Ser Gly Ser Gly Thr Asp Phe Thr Leu Thr Ile Ser Ser Leu Gln Pro
        65                      70                  75                  80

Glu Asp Phe Ala Thr Tyr Tyr Cys Gln Gln Tyr Tyr Asn Trp Pro Ile
                        85                  90                  95

Thr Phe Gly Gln Gly Thr Lys Val Glu Ile Lys Arg Gly Gly Gly Gly
                        100                 105                 110

Ser Ile Glu Gly Arg Ser Gly Gly Gly Gly Ser Glu Val Gln Leu Val
```

```
            115                 120                 125
Glu Ser Gly Gly Gly Leu Val Gln Pro Gly Gly Ser Leu Arg Leu Ser
        130                 135                 140

Cys Ala Ala Ser Gly Phe Thr Ile Gly Asn Trp Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly His
    210                 215                 220

Asn Tyr Asp Gly Ile Met Asp Tyr Trp Gly Gln Gly Thr Leu Val Thr
225                 230                 235                 240

Val Ser Ser Ala Ser Ala Ala Ala
                245

<210> SEQ ID NO 64
<211> LENGTH: 248
<212> TYPE: PRT
<213> ORGANISM: Artificial Sequence
<220> FEATURE:
<223> OTHER INFORMATION: Antibody GH2-78-amino acid sequence

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Ser
            20                  25                  30

Val Ala Trp Tyr Gln Gln Lys Pro Gly Lys Ala Pro Lys Leu Leu Ile
        35                  40                  45

Ser Trp Pro Thr Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Ser Gly Ser Glu Val Gln Leu Val
        115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Asn Asn Trp Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Val
    210                 215                 220

Ile Ile Asp Gly Ile Met Asp Tyr Trp Gly Gln Gly Thr Leu Val Thr
```

```
                     225                 230                 235                 240

Val Ser Ser Ala Ser Ala Ala Ala
                245

<210> SEQ ID NO 65
<211> LENGTH: 248
<212> TYPE: PRT
<213> ORGANISM: Artificial Sequence
<220> FEATURE:
<223> OTHER INFORMATION: Antibody GH2-79-amino acid sequence

<400> SEQUENCE: 65

Asp Ile Gln Met Thr Gln Ser Pro Ser Ser Leu Ser Ala Ser Val Gly
1               5                   10                  15

Asp Arg Ala Thr Ile Thr Cys Arg Ala Ser Gln Asp Val Ser Tyr Gly
            20                  25                  30

Val Ala Trp Tyr Gln Gln Lys Pro Gly Lys Ala Pro Lys Leu Leu Ile
        35                  40                  45

Ser Gly Pro Ala Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Asn Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Ser Tyr Gly Ile His Trp Val
145                 150                 155                 160

Arg Gln Ala Pro Gly Lys Gly Leu Glu Trp Val Ala Phe Ile Gly Pro
                165                 170                 175

Phe Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe His Asp
    210                 215                 220

Asp Ile Asn Trp Gly Met Asp Tyr Trp Gly Gln Gly Thr Leu Val Thr
225                 230                 235                 240

Val Ser Ser Ala Ser Ala Ala Ala
                245

<210> SEQ ID NO 66
<211> LENGTH: 248
<212> TYPE: PRT
<213> ORGANISM: Artificial Sequence
<220> FEATURE:
<223> OTHER INFORMATION: Antibody GH2-80-amino acid sequence

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Gly
            20                  25                  30
```

Val Ala Trp Tyr Gln Gln Lys Pro Gly Lys Ala Pro Lys Leu Leu Ile
            35                  40                  45

Ser Phe Pro Thr Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asn Trp Gly Ile His Trp Val
145                 150                 155                 160

Arg Gln Ala Pro Gly Lys Gly Leu Glu Trp Val Ala Gly Ile Gly Pro
                165                 170                 175

Tyr Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Asn
210                 215                 220

His His Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 67
<211> LENGTH: 248
<212> TYPE: PRT
<213> ORGANISM: Artificial Sequence
<220> FEATURE:
<223> OTHER INFORMATION: Antibody GH2-81-amino acid sequence

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Gly
            20                  25                  30

Val Ala Trp Tyr Gln Gln Lys Pro Gly Lys Ala Pro Lys Leu Leu Ile
            35                  40                  45

Ser Phe Thr Thr Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

```
Cys Ala Ala Ser Gly Phe Thr Ile Asn Asp Tyr Gly Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Val
    210                 215                 220

Leu Phe Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 68
<211> LENGTH: 248
<212> TYPE: PRT
<213> ORGANISM: Artificial Sequence
<220> FEATURE:
<223> OTHER INFORMATION: Antibody GH2-82-amino acid sequence

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Gly
            20                  25                  30

Val Ala Trp Tyr Gln Gln Lys Pro Gly Lys Ala Pro Lys Leu Leu Ile
        35                  40                  45

Ser Gly Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Ser Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Ser Gly Tyr Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Ile
    210                 215                 220

Asp Tyr Asp Gly Ile Met Asp Tyr Trp Gly Gln Gly Thr Leu Val Thr
225                 230                 235                 240

Val Ser Ser Ala Ser Ala Ala Ala
                245
```

-continued

```
<210> SEQ ID NO 69
<211> LENGTH: 248
<212> TYPE: PRT
<213> ORGANISM: Artificial Sequence
<220> FEATURE:
<223> OTHER INFORMATION: Antibody GH2-83-amino acid sequence

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Gly
            20                  25                  30

Val Ala Trp Tyr Gln Gln Lys Pro Gly Lys Ala Pro Lys Leu Leu Ile
        35                  40                  45

Ser Gly Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
            100                 105                 110

Ser Ile Gln Gly Arg Ser Gly Gly Ser Glu Val Gln Leu Val
            115                 120                 125

Glu Ser Gly Gly Gly Leu Val Gln Pro Gly Gly Ser Leu Arg Leu Ile
130                 135                 140

Cys Ala Ala Ser Gly Phe Thr Ile Ser Gly Tyr Gly Ile His Trp Met
145                 150                 155                 160

Arg Arg Ala Pro Gly Lys Gly Leu Glu Trp Val Ala Gly Ile Gly Pro
                165                 170                 175

Tyr Gly Gly Tyr Thr Ser Tyr Ala Tyr Ser Val Lys Gly Arg Phe Thr
            180                 185                 190

Ile Ser Ala Asp Thr Thr Lys Asn Thr Ala Tyr Leu Gln Met Asn Ser
        195                 200                 205

Leu Arg Ala Glu His Thr Ala Val Tyr Tyr Cys Ala Arg Phe Ala Ile
    210                 215                 220

Asp Tyr Asp Gly Ile Met Asp Tyr Trp Gly Gln Gly Thr Leu Val Thr
225                 230                 235                 240

Val Ser Ser Ala Ser Ala Ala Ala
                245

<210> SEQ ID NO 70
<211> LENGTH: 248
<212> TYPE: PRT
<213> ORGANISM: Artificial Sequence
<220> FEATURE:
<223> OTHER INFORMATION: Antibody GH2-84-amino acid sequence

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Phe Gly
            20                  25                  30

Val Ala Trp Tyr Gln Gln Lys Pro Gly Lys Ala Pro Lys Leu Leu Ile
        35                  40                  45

Ser Ser Thr Ser Trp Leu Tyr Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Ser Gly Gly Ser Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Thr Ile Gly Asp Tyr Gly Ile His Trp Val
145                 150                 155                 160

Arg Gln Ala Pro Gly Lys Gly Leu Glu Trp Val Ala Gly Ile Gly Pro
                165                 170                 175

Ser Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Phe
            210                 215                 220

Asp Ile Ile Gly Val Met Asp Tyr Trp Gly Gln Gly Thr Leu Val Thr
225                 230                 235                 240

Val Ser Ser Ala Ser Ala Ala Ala
                245

<210> SEQ ID NO 71
<211> LENGTH: 248
<212> TYPE: PRT
<213> ORGANISM: Artificial Sequence
<220> FEATURE:
<223> OTHER INFORMATION: Antibody GH2-85-amino acid sequence

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Asp Gly
                20                  25                  30

Val Ala Trp Tyr Gln Gln Lys Pro Gly Lys Ala Pro Lys Leu Leu Ile
            35                  40                  45

Ser Gly Thr Ser Tyr Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Asp Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Ser Gly Gly Ser Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Thr Ile Ser Asn Tyr Gly Ile His Trp Val
145                 150                 155                 160

Arg Gln Ala Pro Gly Lys Gly Leu Glu Trp Val Ala Gly Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Tyr Val
210                 215                 220

Asp Leu Gly Gly His Met Asp Tyr Trp Gly Gln Gly Thr Leu Val Thr
225                 230                 235                 240

Val Ser Ser Ala Ser Ala Ala Ala
                245

<210> SEQ ID NO 72
<211> LENGTH: 248
<212> TYPE: PRT
<213> ORGANISM: Artificial Sequence
<220> FEATURE:
<223> OTHER INFORMATION: Antibody GH2-87-amino acid sequence

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Ser
            20                  25                  30

Val Ala Trp Tyr Gln Gln Lys Pro Gly Lys Ala Pro Lys Leu Leu Ile
        35                  40                  45

Phe Gly Thr Arg Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Tyr Pro Leu
                85                  90                  95

Thr Phe Gly Gln Gly Thr Lys Val Glu Ile Lys Arg Gly Gly Gly Gly
            100                 105                 110

Ser Val Glu Gly Arg Ser Gly Ser Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Ser Ser Tyr Gly Ile His Trp Val
145                 150                 155                 160

Arg Gln Ala Pro Gly Lys Gly Leu Glu Trp Val Ala Gly Ile Gly Pro
                165                 170                 175

Phe Gly Gly Phe Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Leu Asn
    210                 215                 220

Ile His Leu Gly Trp Met Asp Tyr Trp Gly Gln Gly Thr Leu Val Thr
225                 230                 235                 240

Val Ser Ser Ala Ser Ala Ala Ala
                245

<210> SEQ ID NO 73
<211> LENGTH: 248
<212> TYPE: PRT
<213> ORGANISM: Artificial Sequence
<220> FEATURE:
<223> OTHER INFORMATION: Antibody GH2-89-amino acid sequence

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ser
            20                  25                  30

Val Ala Trp Tyr Gln Gln Lys Pro Gly Lys Ala Pro Lys Leu Leu Ile
        35                  40                  45

Phe Phe Ala Gly Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Arg Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Asp Trp Gly Ile His Trp Val
145                 150                 155                 160

Arg Gln Ala Pro Gly Lys Gly Leu Glu Trp Val Ala Ser Ile Gly Pro
                165                 170                 175

Phe Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Ala Tyr Tyr Cys Ala Arg Phe Gly Asn
    210                 215                 220

Tyr Val Asp Gly Ile Met Asp Tyr Trp Gly Gln Gly Thr Leu Val Thr
225                 230                 235                 240

Val Ser Ser Ala Ser Ala Ala Ala
            245

<210> SEQ ID NO 74
<211> LENGTH: 248
<212> TYPE: PRT
<213> ORGANISM: Artificial Sequence
<220> FEATURE:
<223> OTHER INFORMATION: Antibody GH2-90-amino acid sequence

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Tyr Gly
            20                  25                  30

Val Ala Trp Tyr Gln Gln Lys Pro Gly Glu Ala Pro Lys Leu Leu Ile
        35                  40                  45

Phe Phe Ser Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Ser Ser Trp Pro Ile

```
                    85                  90                  95
Thr Phe Gly Gln Gly Thr Lys Val Glu Val Lys Arg Gly Gly Gly
                100                 105                 110
Ser Ile Glu Gly Arg Ser Gly Gly Gly Ser Glu Val Gln Leu Val
                115                 120                 125
Glu Ser Gly Gly Gly Leu Val Gln Pro Gly Gly Ser Leu Arg Leu Ser
    130                 135                 140
Cys Ala Ala Ser Gly Phe Thr Ile Asn Asp Trp Gly Ile His Trp Val
145                 150                 155                 160
Arg Gln Ala Pro Gly Lys Gly Leu Glu Trp Val Ala Ser Ile Gly Pro
                165                 170                 175
Phe Trp Gly Tyr Thr Ser Tyr Ala Asp Ser Val Lys Gly Arg Phe Thr
                180                 185                 190
Ile Ser Ala Asp Thr Ser Lys Asn Thr Ala Tyr Leu Gln Met Asn Ser
            195                 200                 205
Leu Arg Ala Glu Asp Thr Ala Val Tyr Tyr Cys Ala Arg Phe Gly Phe
    210                 215                 220
Asp Val Asp Gly Val Met Asp Tyr Trp Gly Gln Gly Thr Leu Val Thr
225                 230                 235                 240
Val Ser Ser Ala Ser Ala Ala Ala
            245

<210> SEQ ID NO 75
<211> LENGTH: 248
<212> TYPE: PRT
<213> ORGANISM: Artificial Sequence
<220> FEATURE:
<223> OTHER INFORMATION: Antibody GH2-91-amino acid sequence

<400> SEQUENCE: 75

Asp Ile Gln Met Thr Gln Ser Pro Ser Ser Leu Ser Ala Ser Val Gly
1               5                   10                  15
Asp Arg Val Thr Ile Thr Cys Arg Ala Ser His Asp Val Gly Trp Gly
            20                  25                  30
Val Ala Trp Tyr Gln Gln Lys Pro Gly Lys Ala Pro Lys Leu Leu Ile
        35                  40                  45
Ser Trp Pro Thr Tyr Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Phe Ser Tyr Pro Ile
                85                  90                  95
Thr Phe Gly Gln Gly Thr Lys Val Glu Ile Lys Arg Gly Gly Gly
                100                 105                 110
Ser Ile Glu Gly Arg Ser Gly Gly Gly Ser Glu Val Gln Leu Val
                115                 120                 125
Glu Ser Gly Gly Gly Leu Val Gln Pro Gly Gly Ser Leu Arg Leu Ser
    130                 135                 140
Cys Ala Ala Ser Gly Phe Thr Ile Asn Asn Phe Gly Ile His Trp Val
145                 150                 155                 160
Arg Gln Ala Pro Gly Lys Gly Leu Glu Trp Val Ala Ser Ile Gly Pro
                165                 170                 175
Phe Trp Gly Tyr Thr Ser Tyr Ala Asp Ser Val Lys Gly Arg Phe Thr
                180                 185                 190
Ile Ser Ala Asp Thr Ser Lys Asn Thr Ala Tyr Leu Gln Met Asn Ser
```

```
                195                 200                 205
Leu Arg Ala Glu Asp Thr Ala Val Tyr Tyr Cys Ala Arg Phe Gly Asn
    210                 215                 220

Asp Tyr Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 76
<211> LENGTH: 248
<212> TYPE: PRT
<213> ORGANISM: Artificial Sequence
<220> FEATURE:
<223> OTHER INFORMATION: Antibody GH2-92-amino acid sequence

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Gly
            20                  25                  30

Val Ala Trp Tyr Gln Gln Lys Pro Gly Lys Ala Pro Lys Leu Leu Ile
        35                  40                  45

Phe Gly Ser Pro Tyr Leu Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Trp Pro Ile
                85                  90                  95

Thr Phe Gly Gln Gly Thr Gln Val Gly Ile Lys Arg Gly Gly Gly Gly
            100                 105                 110

Ser Ile Glu Gly Arg Ser Gly Ser Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Gly Asn Trp Gly Ile His Trp Val
145                 150                 155                 160

Arg Gln Ala Pro Gly Lys Gly Leu Glu Trp Val Ala Ser Ile Gly Pro
                165                 170                 175

Phe Trp Gly Tyr Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Asn
    210                 215                 220

His Tyr Asp Gly Ile Met Asp Tyr Trp Gly Gln Gly Thr Leu Val Thr
225                 230                 235                 240

Val Ser Ser Ala Ser Ala Ala Ala
                245

<210> SEQ ID NO 77
<211> LENGTH: 248
<212> TYPE: PRT
<213> ORGANISM: Artificial Sequence
<220> FEATURE:
<223> OTHER INFORMATION: Antibody GH2-93-amino acid sequence

<400> SEQUENCE: 77
```

-continued

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Trp Gly
            20                  25                  30

Val Ala Trp Tyr Gln Gln Lys Pro Gly Lys Ala Pro Lys Leu Leu Ile
        35                  40                  45

Phe Gly Ala Ser Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Gly Asn Trp Gly Ile His Trp Val
145                 150                 155                 160

Arg Gln Ala Pro Gly Lys Gly Leu Glu Trp Val Ala Gly Ile Gly Pro
                165                 170                 175

Tyr Trp Gly Ser Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Asn
    210                 215                 220

Ile Val Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 78
<211> LENGTH: 248
<212> TYPE: PRT
<213> ORGANISM: Artificial Sequence
<220> FEATURE:
<223> OTHER INFORMATION: Antibody GH2-94-amino acid sequence

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
            20                  25                  30

Val Ala Trp Tyr Gln Gln Lys Pro Gly Lys Ala Pro Lys Leu Leu Ile
        35                  40                  45

Ser Gly Ser Gly Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Asp Asn Trp Gly Ile His Trp Val
145                 150                 155                 160

Arg Gln Ala Pro Gly Lys Gly Leu Glu Trp Val Ala Ser Ile Gly Pro
                165                 170                 175

Ser Trp Gly Phe Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Val
        210                 215                 220

Asp Ile Asp Gly Ile Met Asp Tyr Trp Gly Gln Gly Thr Leu Val Thr
225                 230                 235                 240

Val Ser Ser Ala Ser Ala Ala Ala
                245

<210> SEQ ID NO 79
<211> LENGTH: 248
<212> TYPE: PRT
<213> ORGANISM: Artificial Sequence
<220> FEATURE:
<223> OTHER INFORMATION: Antibody GH2-95-amino acid sequence

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
            20                  25                  30

Val Ala Trp Tyr Gln Gln Lys Pro Gly Lys Ala Pro Lys Leu Leu Ile
        35                  40                  45

Phe Gly Ser Thr Trp Leu Tyr Ser Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Leu
                85                  90                  95

Thr Phe Gly Gln Gly Thr Lys Val Glu Ile Lys Arg Gly Gly Gly Gly
                100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Thr Ile Asp Ser Trp Gly Ile His Trp Val
145                 150                 155                 160

Arg Gln Ala Pro Gly Lys Gly Leu Glu Trp Val Ala Gly Ile Gly Pro
                165                 170                 175

Phe Trp Gly Tyr Thr Ser Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Ile
        210                 215                 220

```
His Phe Asp Gly Ile Met Asp Tyr Trp Gly Gln Gly Thr Leu Val Thr
225                 230                 235                 240

Val Ser Ser Ala Ser Ala Ala Ala
                245
```

<210> SEQ ID NO 80
<211> LENGTH: 248
<212> TYPE: PRT
<213> ORGANISM: Artificial Sequence
<220> FEATURE:
<223> OTHER INFORMATION: Antibody GH2-96-amino acid sequence

<400> SEQUENCE: 80

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Gly Gly
            20                  25                  30

Val Ala Trp Tyr Gln Gln Lys Pro Gly Lys Ala Pro Lys Leu Leu Ile
        35                  40                  45

Tyr Gly Ser Ser Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asp Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Gly Tyr Gly Ile His Trp Val
145                 150                 155                 160

Arg Gln Ala Pro Gly Lys Gly Leu Glu Trp Val Ala Gly Ile Gly Pro
                165                 170                 175

Phe Trp Gly Tyr Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly His
    210                 215                 220

Ile Val Asp Gly Leu Met Asp Tyr Trp Gly Gln Gly Thr Leu Val Thr
225                 230                 235                 240

Val Ser Ser Ala Ser Ala Ala Ala
                245
```

<210> SEQ ID NO 81
<211> LENGTH: 248
<212> TYPE: PRT
<213> ORGANISM: Artificial Sequence
<220> FEATURE:
<223> OTHER INFORMATION: Antibody GH2-97-amino acid sequence

<400> SEQUENCE: 81

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Gly
            20                  25                  30
```

Val Ala Trp Tyr Gln Gln Lys Pro Gly Lys Ala Pro Lys Leu Leu Ile
            35                  40                  45

Tyr Ser Ser Thr Trp Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Asn Asn Tyr Gly Ile His Trp Val
145                 150                 155                 160

Arg Gln Ala Pro Gly Lys Gly Leu Glu Trp Val Ala Gly Ile Gly Pro
                165                 170                 175

Tyr Trp Gly Tyr Thr Phe Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Asp
    210                 215                 220

Val Ile Asp Gly Ile Met Asp Tyr Trp Gly Gln Gly Thr Leu Val Thr
225                 230                 235                 240

Val Ser Ser Ala Ser Ala Ala Ala
            245

<210> SEQ ID NO 82
<211> LENGTH: 248
<212> TYPE: PRT
<213> ORGANISM: Artificial Sequence
<220> FEATURE:
<223> OTHER INFORMATION: Antibody GH2-98-amino acid sequence

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Gly
            20                  25                  30

Val Ala Trp Tyr Gln Gln Lys Pro Gly Lys Ala Pro Lys Leu Leu Ile
            35                  40                  45

Tyr Phe Ser Ala Ser Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Asn Asn Tyr Gly Ile His Trp Val
145                 150                 155                 160

Arg Gln Ala Pro Gly Lys Gly Leu Glu Trp Val Ala Gly Ile Gly Pro
            165                 170                 175

Ser Trp Gly Phe Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Phe
    210                 215                 220

Tyr Asn Asp Gly Phe Met Asp Tyr Trp Gly Gln Gly Thr Leu Val Thr
225                 230                 235                 240

Val Ser Ser Ala Ser Ala Ala Ala
                245

<210> SEQ ID NO 83
<211> LENGTH: 248
<212> TYPE: PRT
<213> ORGANISM: Artificial Sequence
<220> FEATURE:
<223> OTHER INFORMATION: Antibody GH2-100-amino acid sequence

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Ser Gly
            20                  25                  30

Val Ala Trp Tyr Gln Gln Lys Pro Gly Lys Thr Pro Lys Leu Leu Ile
        35                  40                  45

Tyr Gly Thr Thr Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Gly Asn Phe Gly Ile His Trp Val
145                 150                 155                 160

Arg Gln Ala Pro Gly Lys Gly Leu Glu Trp Val Ala Tyr Ile Gly Pro
            165                 170                 175

Tyr Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe His Asn
    210                 215                 220

Asp Ile Gly Gly Ile Met Asp Tyr Trp Gly Gln Gly Thr Leu Val Thr
225                 230                 235                 240

Val Ser Ser Ala Ser Ala Ala Ala
                245

```
<210> SEQ ID NO 84
<211> LENGTH: 248
<212> TYPE: PRT
<213> ORGANISM: Artificial Sequence
<220> FEATURE:
<223> OTHER INFORMATION: Antibody GH2-101-amino acid sequence

<400> SEQUENCE: 84
```

Asp Ile Gln Met Ala Gln Ser Pro Ser Ser Leu Ser Ala Ser Val Gly
1               5                   10                  15

Asp Arg Val Thr Ile Thr Cys Arg Ala Ser Gln Asp Val Ser Asn Gly
            20                  25                  30

Val Ala Trp Tyr Gln Gln Lys Pro Gly Lys Ala Pro Lys Leu Leu Ile
        35                  40                  45

Tyr Gly Thr Thr Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asn Ser Tyr Gly Ile His Trp Val
145                 150                 155                 160

Arg Gln Ala Pro Gly Lys Gly Leu Glu Trp Val Ala Ser Ile Gly Pro
                165                 170                 175

Tyr Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Tyr Ile
    210                 215                 220

Trp Phe Asp Gly Leu Met Asp Tyr Trp Gly Gln Gly Thr Leu Val Thr
225                 230                 235                 240

Val Ser Ser Ala Ser Ala Ala Ala
                245

```
<210> SEQ ID NO 85
<211> LENGTH: 248
<212> TYPE: PRT
<213> ORGANISM: Artificial Sequence
<220> FEATURE:
<223> OTHER INFORMATION: Antibody GH2-102-amino acid sequence

<400> SEQUENCE: 85
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Asn
            20                  25                  30

Val Ala Trp Tyr Gln Gln Lys Pro Gly Lys Ala Pro Lys Leu Leu Ile
        35                  40                  45

Tyr Gly Ala Pro Tyr Leu Tyr Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Trp Pro Leu
                 85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Asn Gly Gly Ile His Trp Val
145                 150                 155                 160

Arg Gln Ala Pro Gly Lys Gly Leu Glu Trp Val Ala Ser Ile Gly Pro
                165                 170                 175

Tyr Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Gly Asp Thr Ala Val Tyr Tyr Cys Ala Arg Phe Gly His
    210                 215                 220

His Tyr Asp Gly His Met Asp Tyr Trp Gly Gln Gly Thr Leu Val Thr
225                 230                 235                 240

Val Ser Ser Ala Ser Ala Ala Ala
                245

<210> SEQ ID NO 86
<211> LENGTH: 248
<212> TYPE: PRT
<213> ORGANISM: Artificial Sequence
<220> FEATURE:
<223> OTHER INFORMATION: Antibody GH2-103-amino acid sequence

<400> SEQUENCE: 86

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Phe Ser Gly
            20                  25                  30

Val Ala Trp Tyr Gln Gln Lys Pro Gly Lys Ala Pro Lys Leu Leu Ile
        35                  40                  45

Ser Gly Thr Pro Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Trp Pro Ile
                 85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Asp Glu Tyr Gly Ile His Trp Val
145                 150                 155                 160

Arg Gln Ala Pro Gly Lys Gly Leu Glu Trp Val Ala Phe Ile Gly Pro
```

```
                165                 170                 175
Tyr Trp Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly His
    210                 215                 220

Leu His Asp Gly Leu Met Asp Tyr Trp Gly Gln Gly Thr Leu Val Thr
225                 230                 235                 240

Val Ser Ser Ala Ser Ala Ala Ala
                245

<210> SEQ ID NO 87
<211> LENGTH: 248
<212> TYPE: PRT
<213> ORGANISM: Artificial Sequence
<220> FEATURE:
<223> OTHER INFORMATION: Antibody GH2-104-amino acid sequence

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Lys Pro Gly Lys Ala Pro Lys Leu Leu Ile
        35                  40                  45

Tyr Gly Ser Pro Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Trp Pro Leu
                85                  90                  95

Thr Phe Gly Gln Gly Thr Lys Val Glu Ile Lys Arg Gly Gly Gly Gly
            100                 105                 110

Ser Ile Glu Gly Arg Ser Gly Arg Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Asp Ser Trp Gly Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Asp
    210                 215                 220

Tyr Ile Asp Gly Val Met Asp Tyr Trp Gly Gln Gly Thr Leu Val Thr
225                 230                 235                 240

Val Ser Ser Ala Ser Ala Ala Ala
                245

<210> SEQ ID NO 88
<211> LENGTH: 248
<212> TYPE: PRT
```

<213> ORGANISM: Artificial Sequence
<220> FEATURE:
<223> OTHER INFORMATION: Antibody GH2-105-amino acid sequence

<400> SEQUENCE: 88

Asp Thr Gln Met Thr Gln Ser Pro Ser Leu Ser Ala Ser Val Gly
1               5                   10                  15

Asp Arg Val Thr Ile Thr Cys Arg Ala Ser Gln Asp Val Cys Ser Gly
            20                  25                  30

Val Ala Trp Tyr Gln Gln Lys Pro Gly Lys Ala Pro Lys Leu Leu Ile
            35                  40                  45

Ser Gly Ser Pro Phe Leu Tyr Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Trp Pro Met
                85                  90                  95

Thr Phe Gly Gln Gly Thr Lys Val Glu Ile Lys Arg Gly Gly Gly Gly
            100                 105                 110

Ser Ile Glu Gly Arg Ser Gly Ser Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Asp Asn Trp Trp Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Asn Asn
    210                 215                 220

Cys Gly Ile Tyr Val Met Asp Tyr Trp Gly Gln Gly Thr Leu Val Thr
225                 230                 235                 240

Val Ser Ser Ala Ser Ala Ala Ala
                245

<210> SEQ ID NO 89
<211> LENGTH: 248
<212> TYPE: PRT
<213> ORGANISM: Artificial Sequence
<220> FEATURE:
<223> OTHER INFORMATION: Antibody GH2-106-amino acid sequence

<400> SEQUENCE: 89

Asp Ile Gln Met Thr Gln Ser Pro Ser Leu Ser Ala Ser Val Gly
1               5                   10                  15

Asn Arg Val Thr Ile Thr Cys Arg Ala Ser Gln Asp Val Ser Tyr Gly
            20                  25                  30

Val Ala Trp Tyr Gln Gln Lys Pro Gly Lys Ala Pro Lys Leu Leu Ile
            35                  40                  45

Ser Gly Ala Gly Tyr Leu Tyr Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Ser Trp Pro Ile
                85                  90                  95

Thr Phe Gly Gln Gly Thr Lys Val Glu Ile Lys Arg Gly Gly Gly
            100                 105                 110

Ser Ile Glu Gly Arg Ser Gly Ser Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Ser Ser Tyr Ile His Trp Val
145                 150                 155                 160

Arg Gln Ala Pro Gly Lys Gly Leu Glu Trp Val Ala Gly Ile Gly Pro
                165                 170                 175

Phe Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ala Arg Phe Gly Trp
210                 215                 220

His His Leu His Leu Met Asp Tyr Trp Gly Gln Gly Thr Leu Val Thr
225                 230                 235                 240

Val Ser Ser Ala Ser Ala Ala Ala
                245

<210> SEQ ID NO 90
<211> LENGTH: 248
<212> TYPE: PRT
<213> ORGANISM: Artificial Sequence
<220> FEATURE:
<223> OTHER INFORMATION: Antibody GH2-107-amino acid sequence

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asp Gly
            20                  25                  30

Val Ala Trp Tyr Gln Gln Lys Pro Gly Lys Ala Pro Lys Leu Leu Ile
            35                  40                  45

Ser Gly Ala Gly Tyr Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Ser Trp Pro Ile
                85                  90                  95

Thr Phe Gly Gln Gly Thr Lys Val Glu Ile Lys Arg Gly Gly Gly Gly
            100                 105                 110

Ser Ile Glu Gly Arg Ser Gly Ser Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Asn Phe Gly Ile His Trp Val
145                 150                 155                 160

Arg Gln Ala Pro Gly Lys Gly Leu Glu Trp Val Ala Tyr Ile Gly Pro
                165                 170                 175

Tyr Gly Gly Tyr Thr Ser Tyr Ala Asp Ser Val Lys Gly Arg Phe Thr
            180                 185                 190
```

Ile Ser Ala Asp Thr Ser Lys Asn Thr Ala Tyr Leu Gln Met Asn Ser
195                 200                 205

Leu Arg Ala Glu Asp Ala Ala Val Tyr Tyr Cys Ala Arg Phe His Ile
    210                 215                 220

His Asn Leu Trp Gly Met Asp Tyr Trp Gly Gln Gly Thr Leu Val Thr
225                 230                 235                 240

Val Ser Ser Ala Ser Ala Ala Ala
                245

<210> SEQ ID NO 91
<211> LENGTH: 15
<212> TYPE: PRT
<213> ORGANISM: Artificial Sequence
<220> FEATURE:
<223> OTHER INFORMATION: Synthetized

<400> SEQUENCE: 91

Gly Gly Gly Gly Ser Gly Gly Gly Gly Ser Gly Gly Gly Gly Ser
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthesized

<400> SEQUENCE: 92

Gly Ala Pro Val Pro Tyr Pro Asp Pro Leu Glu Pro Arg Ala Ala
1               5                   10                  15

<210> SEQ ID NO 93
<211> LENGTH: 59
<212> TYPE: PRT
<213> ORGANISM: Artificial Sequence
<220> FEATURE:
<223> OTHER INFORMATION: Synthesized

<400> SEQUENCE: 93

Cys Ala Gly Gly Thr Gly Cys Ala Cys Gly Ala Thr Gly Thr Gly Ala
1               5                   10                  15

Thr Gly Gly Thr Ala Cys Cys Gly Ala Thr Ala Thr Thr Cys Ala Ala
                20                  25                  30

Ala Thr Gly Ala Cys Cys Ala Gly Ala Gly Cys Cys Ala Gly Gly Ala
            35                  40                  45

Gly Cys Ala Gly Cys Cys Thr Gly Ala Gly Cys
            50                  55

<210> SEQ ID NO 94
<211> LENGTH: 36
<212> TYPE: PRT
<213> ORGANISM: Artificial Sequence
<220> FEATURE:
<223> OTHER INFORMATION: Synthesized

<400> SEQUENCE: 94

Thr Gly Cys Ala Gly Cys Cys Ala Cys Cys Gly Thr Ala Cys Gly Thr
1               5                   10                  15

Thr Thr Gly Ala Thr Thr Thr Cys Cys Ala Cys Cys Thr Thr Gly Gly
                20                  25                  30

Thr Gly Cys Cys
            35

<210> SEQ ID NO 95
<211> LENGTH: 36
<212> TYPE: PRT
<213> ORGANISM: Artificial Sequence
<220> FEATURE:
<223> OTHER INFORMATION: Synthesized

<400> SEQUENCE: 95

Cys Gly Thr Gly Thr Cys Gly Cys Ala Thr Cys Thr Gly Ala Ala Gly
1               5                   10                  15

Thr Gly Cys Ala Gly Cys Thr Gly Gly Thr Gly Gly Ala Ala Thr Cys
                20                  25                  30

Gly Gly Gly Ala
        35

<210> SEQ ID NO 96
<211> LENGTH: 48
<212> TYPE: PRT
<213> ORGANISM: Artificial Sequence
<220> FEATURE:
<223> OTHER INFORMATION: Synthesized

<400> SEQUENCE: 96

Gly Ala Cys Cys Gly Ala Thr Gly Gly Gly Cys Cys Cys Thr Thr Gly
1               5                   10                  15

Gly Thr Gly Cys Thr Ala Gly Cys Cys Gly Ala Gly Cys Thr Cys Ala
                20                  25                  30

Cys Gly Gly Thr Ala Ala Cys Ala Ala Gly Gly Thr Gly Cys Cys
        35                  40                  45

<210> SEQ ID NO 97
<211> LENGTH: 39
<212> TYPE: PRT
<213> ORGANISM: Artificial Sequence
<220> FEATURE:
<223> OTHER INFORMATION: Synthesized

<400> SEQUENCE: 97

Ala Ala Gly Gly Thr Gly Gly Ala Ala Ala Thr Cys Ala Ala Ala Cys
1               5                   10                  15

Gly Thr Ala Cys Gly Gly Thr Gly Gly Cys Thr Gly Cys Ala Cys Cys
                20                  25                  30

Ala Thr Cys Thr Gly Thr Cys
        35

<210> SEQ ID NO 98
<211> LENGTH: 33
<212> TYPE: PRT
<213> ORGANISM: Artificial Sequence
<220> FEATURE:
<223> OTHER INFORMATION: Synthesized

<400> SEQUENCE: 98

Cys Thr Gly Cys Ala Cys Thr Thr Cys Ala Gly Ala Thr Gly Cys Gly
1               5                   10                  15

Ala Cys Ala Cys Gly Cys Gly Thr Ala Gly Cys Ala Ala Cys Ala Gly
                20                  25                  30

Cys

<210> SEQ ID NO 99
<211> LENGTH: 1491
<212> TYPE: DNA

<213> ORGANISM: Artificial Sequence
<220> FEATURE:
<223> OTHER INFORMATION: Synthesized

<400> SEQUENCE: 99

```
ggagccatgg cccagccggc cggatcctac aataaagatc agcagagcgc cttctatgaa      60
attctgaata tgccgaatct gaacgaagaa cagcgcaatg gttttattca gagcctgaaa     120
gatgatccga gccagagcac caatgttctg ggtgaagcaa aaaaactgaa tgaaagccag     180
gcaccgaaag cagataatgg tggtggtagc ggtggtggtt caggtggtgg cagtggagga     240
ggttctggcg gtagcgaagt taccattaaa gttaatctga ttttcgccga tgcaaaatt     300
cagaccgcag aatttaaagg cacctttgaa gaagcaacag ccgaagcata tcgttatgca     360
gcactgctgg caaaagttaa tggtgaatat accgctgatc tggaagatgg tggtaatcac     420
atgaatatca aatttgcagg cggtggtagt ggtaccggag gtagcctggc agcactgacc     480
gcacatcagg catgtcatct gccgctggaa acctttaccc gtcatcgtca gcctcgtggt     540
tgggaacagc tggaacagtg tggttatccg gttcagcgtc tggttgcact gtatctggca     600
gcccgtctga gctggaatca ggttgatcag gttattcgta atgcactggc aagtccgggt     660
agcggtggtg atctgggtga agcaattcgt gaacagcctg aacaggcacg tctggcactg     720
accctggcag ccgcagaaag cgaacgtttt gttcgtcagg gtacaggtaa tgatgaagcc     780
ggtgcagcaa atggtccggc agatagcggt gatgcactgc tggaacgtaa ttatccgaca     840
ggtgcagaat ttctgggtga tggtggtgat gttagcttta gcacccgtgg cacccagaat     900
tggaccgttg aacgtctgct gcaggcacac cgtcagctgg aagaacgtgg ttatgttttt     960
gttggttatc atggcacctt tctggaagca gcacagagca ttgttttttgg tggtgttcgt    1020
gcacgtagcc aggatctgga tgcaatttgg cgtggttct atattgccgg tgatccggca    1080
ctggcctatg gttatgcaca ggatcaagaa ccggatgcac gtggtcgtat cgcaatggt    1140
gccctgctgc gtgttttatgt tccgcgtagc agcctgcctg gttttatcg taccagcctg    1200
acactggctg cacctgaagc agcgggtgaa gtggaacgtc tgattggtca tccgctgccg    1260
ctgcgtctgg atgccattac aggtccggaa gaagaaggcg gtcgtctgga aaccattctg    1320
ggttggcctc tggcagaacg taccgttgtt attccgagcg caattccgac cgatccgcgt    1380
aatgttggtg gcgatctgga cccgagcagc attccggata agaacaggc aattagcgca    1440
ctgccggatt atgcaagcca gcctggtaaa ccgcctaaag atgagctgta a              1491
```

<210> SEQ ID NO 100
<211> LENGTH: 1920
<212> TYPE: DNA
<213> ORGANISM: Artificial Sequence
<220> FEATURE:
<223> OTHER INFORMATION: Synthesized

<400> SEQUENCE: 100

```
ggagccatgg cccagccggc cggatcctac aataaagatc agcagagcgc cttctatgaa      60
attctgaata tgccgaatct gaacgaagaa cagcgcaatg gttttattca gagcctgaaa     120
gatgatccga gccagagcac caatgttctg ggtgaagcaa aaaaactgaa tgaaagccag     180
gcaccgaaag cagataatgg tggtggtagc ggtggtggtt caggtggtgg cagtggagga     240
ggttctggcg gtagcgaagt taccattaaa gttaatctga ttttcgccga tgcaaaatt     300
cagaccgcag aatttaaagg cacctttgaa gaagcaacag ccgaagcata tcgttatgca     360
gcactgctgg caaaagttaa tggtgaatat accgctgatc tggaagatgg tggtaatcac     420
```

```
atgaatatca aatttgcagg cggaggtagc ggtggatata acaaagatca gcagagtgcc    480
ttctatgaaa ttctgaatat gccgaatctg aacgaagaac agcgcaatgg ttttattcag    540
agcctgaaag atgatccgag ccagagcacc aatgttctgg gtgaagcaaa aaaactgaat    600
gaaagccagg caccgaaagc agataatggt ggtggtagcg gtggtggttc aggtggtggc    660
agtggaggag ttctggcgg tagcgaagtt accattaaag ttaatctgat tttcgccgat    720
ggcaaaattc agaccgcaga atttaaaggc acctttgaag aagcaacagc cgaagcatat    780
cgttatgcag cactgctggc aaaagttaat ggtgaatata ccgctgatct ggaagatggt    840
ggtaatcaca tgaacattaa attcgccggt ggtggcagtg gtaccggagg tagcctggca    900
gcactgaccg cacatcaggc atgtcatctg ccgctggaaa cctttacccg tcatcgtcag    960
cctcgtggtt gggaacagct ggaacagtgt ggttatccgg ttcagcgtct ggttgcactg   1020
tatctggcag cccgtctgag ctggaatcag gttgatcagg ttattcgtaa tgcactggca   1080
agtccgggta gcggtggtga tctgggtgaa gcaattcgtg aacagcctga acaggcacgt   1140
ctggcactga ccctggcagc cgcagaaagc gaacgttttg ttcgtcaggg tacaggtaat   1200
gatgaagccg gtgcagcaaa tggtccggca gatagcggtg atgcactgct ggaacgtaat   1260
tatccgacag gtgcagaatt tctgggtgat ggtggtgatg ttagctttag cacccgtggc   1320
acccagaatt ggaccgttga acgtctgctg caggcacacc gtcagctgga gaacgtggt    1380
tatgttttg ttggttatca tggcacccttt ctggaagcag cacagagcat tgttttggt    1440
ggtgttcgtg cacgtagcca ggatctggat gcaatttggc gtggtttcta tattgccggt   1500
gatccggcac tggcctatgg ttatgcacag gatcaagaac cggatgcacg tggtcgtatt   1560
cgcaatggtg ccctgctgcg tgtttatgtt ccgcgtagca gcctgcctgg tttttatcgt   1620
accagcctga cactggctgc acctgaagca gcgggtgaag tggaacgtct gattggtcat   1680
ccgctgccgc tgcgtctgga tgccattaca ggtccggaag aagaaggcgg tcgtctggaa   1740
accattctgg gttggcctct ggcagaacgt accgttgtta ttccgagcgc aattccgacc   1800
gatccgcgta tgttggtgg cgatctggac ccgagcagca ttccggataa agaacaggca   1860
attagcgcac tgccggatta tgcaagccag cctggtaaac cgcctaaaga tgagctgtaa   1920
```

<210> SEQ ID NO 101
<211> LENGTH: 496
<212> TYPE: PRT
<213> ORGANISM: Artificial Sequence
<220> FEATURE:
<223> OTHER INFORMATION: synthesized

<400> SEQUENCE: 101

Gly Ala Met Ala Gln Pro Ala Gly Ser Tyr Asn Lys Asp Gln Gln Ser
1               5                   10                  15

Ala Phe Tyr Glu Ile Leu Asn Met Pro Asn Leu Asn Glu Glu Gln Arg
            20                  25                  30

Asn Gly Phe Ile Gln Ser Leu Lys Asp Asp Pro Ser Gln Ser Thr Asn
        35                  40                  45

Val Leu Gly Glu Ala Lys Lys Leu Asn Glu Ser Gln Ala Pro Lys Ala
    50                  55                  60

Asp Asn Gly Gly Gly Ser Gly Gly Gly Ser Gly Gly Ser Gly Gly
65                  70                  75                  80

Gly Ser Gly Gly Ser Glu Val Thr Ile Lys Val Asn Leu Ile Phe Ala
                85                  90                  95

Asp Gly Lys Ile Gln Thr Ala Glu Phe Lys Gly Thr Phe Glu Ala
            100                 105                 110

Thr Ala Glu Ala Tyr Arg Tyr Ala Ala Leu Leu Ala Lys Val Asn Gly
        115                 120                 125

Glu Tyr Thr Ala Asp Leu Glu Asp Gly Gly Asn His Met Asn Ile Lys
    130                 135                 140

Phe Ala Gly Gly Ser Gly Thr Gly Gly Ser Leu Ala Ala Leu Thr
145                 150                 155                 160

Ala His Gln Ala Cys His Leu Pro Leu Glu Thr Phe Thr Arg His Arg
                165                 170                 175

Gln Pro Arg Gly Trp Glu Gln Leu Glu Gln Cys Gly Tyr Pro Val Gln
            180                 185                 190

Arg Leu Val Ala Leu Tyr Leu Ala Ala Arg Leu Ser Trp Asn Gln Val
        195                 200                 205

Asp Gln Val Ile Arg Asn Ala Leu Ala Ser Pro Gly Ser Gly Gly Asp
    210                 215                 220

Leu Gly Glu Ala Ile Arg Glu Gln Pro Glu Gln Ala Arg Leu Ala Leu
225                 230                 235                 240

Thr Leu Ala Ala Ala Glu Ser Glu Arg Phe Val Arg Gln Gly Thr Gly
                245                 250                 255

Asn Asp Glu Ala Gly Ala Ala Asn Gly Pro Ala Asp Ser Gly Asp Ala
            260                 265                 270

Leu Leu Glu Arg Asn Tyr Pro Thr Gly Ala Glu Phe Leu Gly Asp Gly
        275                 280                 285

Gly Asp Val Ser Phe Ser Thr Arg Gly Thr Gln Asn Trp Thr Val Glu
    290                 295                 300

Arg Leu Leu Gln Ala His Arg Gln Leu Glu Glu Arg Gly Tyr Val Phe
305                 310                 315                 320

Val Gly Tyr His Gly Thr Phe Leu Glu Ala Ala Gln Ser Ile Val Phe
                325                 330                 335

Gly Gly Val Arg Ala Arg Ser Gln Asp Leu Asp Ala Ile Trp Arg Gly
            340                 345                 350

Phe Tyr Ile Ala Gly Asp Pro Ala Leu Ala Tyr Gly Tyr Ala Gln Asp
        355                 360                 365

Gln Glu Pro Asp Ala Arg Gly Arg Ile Arg Asn Gly Ala Leu Leu Arg
    370                 375                 380

Val Tyr Val Pro Arg Ser Ser Leu Pro Gly Phe Tyr Arg Thr Ser Leu
385                 390                 395                 400

Thr Leu Ala Ala Pro Glu Ala Gly Glu Val Glu Arg Leu Ile Gly
                405                 410                 415

His Pro Leu Pro Leu Arg Leu Asp Ala Ile Thr Gly Pro Glu Glu Glu
            420                 425                 430

Gly Gly Arg Leu Glu Thr Ile Leu Gly Trp Pro Leu Ala Glu Arg Thr
        435                 440                 445

Val Val Ile Pro Ser Ala Ile Pro Thr Asp Pro Arg Asn Val Gly Gly
    450                 455                 460

Asp Leu Asp Pro Ser Ser Ile Pro Asp Lys Glu Gln Ala Ile Ser Ala
465                 470                 475                 480

Leu Pro Asp Tyr Ala Ser Gln Pro Gly Lys Pro Lys Asp Glu Leu
                485                 490                 495

<210> SEQ ID NO 102
<211> LENGTH: 639
<212> TYPE: PRT

<213> ORGANISM: Artificial Sequence
<220> FEATURE:
<223> OTHER INFORMATION: synthesized

<400> SEQUENCE: 102

```
Gly Ala Met Ala Gln Pro Ala Gly Ser Tyr Asn Lys Asp Gln Gln Ser
1               5                   10                  15

Ala Phe Tyr Glu Ile Leu Asn Met Pro Asn Leu Asn Glu Glu Gln Arg
            20                  25                  30

Asn Gly Phe Ile Gln Ser Leu Lys Asp Asp Pro Ser Gln Ser Thr Asn
        35                  40                  45

Val Leu Gly Glu Ala Lys Lys Leu Asn Glu Ser Gln Ala Pro Lys Ala
50                  55                  60

Asp Asn Gly Gly Ser Gly Gly Ser Gly Gly Ser Gly Gly
65                  70                  75              80

Gly Ser Gly Gly Ser Glu Val Thr Ile Lys Val Asn Leu Ile Phe Ala
                85                  90                  95

Asp Gly Lys Ile Gln Thr Ala Glu Phe Lys Gly Thr Phe Glu Glu Ala
                100                 105                 110

Thr Ala Glu Ala Tyr Arg Tyr Ala Ala Leu Leu Ala Lys Val Asn Gly
            115                 120                 125

Glu Tyr Thr Ala Asp Leu Glu Asp Gly Gly Asn His Met Asn Ile Lys
130                 135                 140

Phe Ala Gly Gly Gly Ser Gly Gly Tyr Asn Lys Asp Gln Gln Ser Ala
145                 150                 155                 160

Phe Tyr Glu Ile Leu Asn Met Pro Asn Leu Asn Glu Glu Gln Arg Asn
                165                 170                 175

Gly Phe Ile Gln Ser Leu Lys Asp Asp Pro Ser Gln Ser Thr Asn Val
            180                 185                 190

Leu Gly Glu Ala Lys Lys Leu Asn Glu Ser Gln Ala Pro Lys Ala Asp
        195                 200                 205

Asn Gly Gly Gly Ser Gly Gly Gly Ser Gly Gly Gly Ser Gly Gly Gly
210                 215                 220

Ser Gly Gly Ser Glu Val Thr Ile Lys Val Asn Leu Ile Phe Ala Asp
225                 230                 235                 240

Gly Lys Ile Gln Thr Ala Glu Phe Lys Gly Thr Phe Glu Glu Ala Thr
                245                 250                 255

Ala Glu Ala Tyr Arg Tyr Ala Ala Leu Leu Ala Lys Val Asn Gly Glu
            260                 265                 270

Tyr Thr Ala Asp Leu Glu Asp Gly Gly Asn His Met Asn Ile Lys Phe
        275                 280                 285

Ala Gly Gly Gly Ser Gly Thr Gly Gly Ser Leu Ala Ala Leu Thr Ala
290                 295                 300

His Gln Ala Cys His Leu Pro Leu Glu Thr Phe Thr Arg His Arg Gln
305                 310                 315                 320

Pro Arg Gly Trp Glu Gln Leu Glu Gln Cys Gly Tyr Pro Val Gln Arg
                325                 330                 335

Leu Val Ala Leu Tyr Leu Ala Ala Arg Leu Ser Trp Asn Gln Val Asp
            340                 345                 350

Gln Val Ile Arg Asn Ala Leu Ala Ser Pro Gly Ser Gly Gly Asp Leu
        355                 360                 365

Gly Glu Ala Ile Arg Glu Gln Pro Glu Gln Ala Arg Leu Ala Leu Thr
370                 375                 380

Leu Ala Ala Ala Glu Ser Glu Arg Phe Val Arg Gln Gly Thr Gly Asn
```

```
                385                 390                 395                 400
Asp Glu Ala Gly Ala Ala Asn Gly Pro Ala Asp Ser Gly Asp Ala Leu
                    405                 410                 415

Leu Glu Arg Asn Tyr Pro Thr Gly Ala Glu Phe Leu Gly Asp Gly Gly
                420                 425                 430

Asp Val Ser Phe Ser Thr Arg Gly Thr Gln Asn Trp Thr Val Glu Arg
                435                 440                 445

Leu Leu Gln Ala His Arg Gln Leu Glu Glu Arg Gly Tyr Val Phe Val
            450                 455                 460

Gly Tyr His Gly Thr Phe Leu Glu Ala Ala Gln Ser Ile Val Phe Gly
465                 470                 475                 480

Gly Val Arg Ala Arg Ser Gln Asp Leu Asp Ala Ile Trp Arg Gly Phe
                485                 490                 495

Tyr Ile Ala Gly Asp Pro Ala Leu Ala Tyr Gly Tyr Ala Gln Asp Gln
                500                 505                 510

Glu Pro Asp Ala Arg Gly Arg Ile Arg Asn Gly Ala Leu Leu Arg Val
                515                 520                 525

Tyr Val Pro Arg Ser Ser Leu Pro Gly Phe Tyr Arg Thr Ser Leu Thr
            530                 535                 540

Leu Ala Ala Pro Glu Ala Ala Gly Glu Val Glu Arg Leu Ile Gly His
545                 550                 555                 560

Pro Leu Pro Leu Arg Leu Asp Ala Ile Thr Gly Pro Glu Glu Glu Gly
                565                 570                 575

Gly Arg Leu Glu Thr Ile Leu Gly Trp Pro Leu Ala Glu Arg Thr Val
                580                 585                 590

Val Ile Pro Ser Ala Ile Pro Thr Asp Pro Arg Asn Val Gly Gly Asp
            595                 600                 605

Leu Asp Pro Ser Ser Ile Pro Asp Lys Glu Gln Ala Ile Ser Ala Leu
                610                 615                 620

Pro Asp Tyr Ala Ser Gln Pro Gly Lys Pro Pro Lys Asp Glu Leu
625                 630                 635

<210> SEQ ID NO 103
<211> LENGTH: 1584
<212> TYPE: DNA
<213> ORGANISM: Artificial Sequence
<220> FEATURE:
<223> OTHER INFORMATION: Synthetic

<400> SEQUENCE: 103
atgcatcatc accaccatca tgatcctac aataaagatc agcagagcgc cttctatgaa      60
attctgaata tgccgaatct gaacgaagaa cagcgcaatg gttttattca gagcctgaaa     120
gatgatccga gccagagcac caatgttctg ggtgaagcaa aaaaactgaa tgaaagccag     180
gcaccgaaag cagataatgg tggtggtagc ggtggtggtt caggtggtgg cagtggagga     240
ggttctggcg gtagcgaagt taccattaaa gttaatctga ttttcgccga tgcaaaatt      300 cagaccgcag aatttaaagg cacctttgaa gaagcaacag ccgaagcata tcgttatgca     360
gcactgctgg caaaagttaa tggtgaatat accgctgatc tggaagatgg tggtaatcac     420
atgaatatca aatttgcagg cggagtagc ggtggatata caaagatca gcagagtgcc      480 ttctatgaaa ttctgaatat gccgaatctg aacgaagaac agcgcaatgg ttttattcag     540
agcctgaaaa tgatccgag ccagagcacc aatgttctgg gtgaagcaaa aaaactgaat      600
gaaagccagg caccgaaagc agataatggt ggtggtagcg gtggtggttc aggtggtggc     660
```

```
agtggaggag gttctggcgg tagcgaagtt accattaaag ttaatctgat tttcgccgat    720
ggcaaaattc agaccgcaga atttaaaggc acctttgaag aagcaacagc cgaagcatat    780
cgttatgcag cactgctggc aaaagttaat ggtgaatata ccgctgatct ggaagatggt    840
ggtaatcaca tgaacattaa attcgccggt ggtggcggca cggtaccat gagcgagctg     900 atcaaggaga acatgcacat gaagctgtac atggagggca ccgtgaacaa ccaccacttc    960
aagtgcacat ccgagggcga aggcaagccc tacgagggca cccagaccat gaagatcaag   1020
gtggtcgagg gcggccctct cccttcgcc ttcgacatcc tggctaccag cttcatgtac    1080
ggcagcaaag ccttcatcaa ccacacccag ggcatcccg acttctttaa gcagtccttc    1140
cctgagggct tcacatggga gagaatcacc acatacgaag acggggcgt gctgaccgct   1200 acccaggaca ccagcttcca gaacggctgc atcatctaca cgtcaagat caacggggtg    1260 aacttcccat ccaacggccc tgtgatgcag aagaaaacac gcggctggga ggccaacacc   1320
gagatgctgt accccgctga cggcggcctg agaggccaca gccagatggc cctgaagctc   1380
gtgggcgggg gctacctgca ctgctccttc aagaccacat acagatccaa gaaacccgct    1440
aagaacctca agatgcccgg cttccacttc gtggaccaca gactggaaag aatcaaggag    1500
gccgacaaag agacctacgt cgagcagcac gagatggctg tggccaagta ctgcgacctc    1560
cctagcaaac tggggcacag ataa                                          1584

<210> SEQ ID NO 104
<211> LENGTH: 1608
<212> TYPE: DNA
<213> ORGANISM: Artificial Sequence
<220> FEATURE:
<223> OTHER INFORMATION: Synthesized

<400> SEQUENCE: 104
atgcatcatc accaccatca tggatcctac aataaagatc agcagagcgc cttctatgaa     60
attctgaata tgccgaatct gaacgaagaa cagcgcaatg gttttattca gagcctgaaa    120
gatgatccga ccagagcac caatgttctg ggtgaagcaa aaaaactgaa tgaaagccag     180
gcaccgaaag cagataatgg tggtggtagc ggtggtggtt caggtggtgg cagtggagga    240
ggttctggcg gtagcgaagt taccattaaa gttaatctga ttttcgccga tggcaaaatt    300
cagaccgcag aatttaaagg cacctttgaa gaagcaacag ccgaagcata tcgttatgca    360
gcactgctgg caaaagttaa tggtgaatat accgctgatc tggaagatgg tggtaatcac    420
atgaatatca aatttgcagg cggaggtagc ggtggatata caaagatca gcagagtgcc    480 ttctatgaaa ttctgaatat gccgaatctg aacgaagaac agcgcaatgg ttttattcag    540
agcctgaaag atgatccgag ccagagcacc aatgttctgg gtgaagcaaa aaaactgaat    600
gaaagccagg caccgaaagc agataatggt ggtggtagcg gtggtggttc aggtggtggc    660
agtggaggag gttctggcgg tagcgaagtt accattaaag ttaatctgat tttcgccgat    720
ggcaaaattc agaccgcaga atttaaaggc acctttgaag aagcaacagc cgaagcatat    780
cgttatgcag cactgctggc aaaagttaat ggtgaatata ccgctgatct ggaagatggt    840
ggtaatcaca tgaacattaa attcgccggt ggtggcggca cggtaccat ggtgagcaag     900 ggcgaggagc tgttcaccgg ggtggtgccc atcctggtcg agctggacgg cgacgtaaac    960
ggccacaagt tcagcgtgtc cggcgagggc gagggcgatg ccacctacgg caagctgacc   1020
ctgaagttca tctgcaccac cggcaagctg cccgtgccct ggcccaccct cgtgaccacc   1080
ctgacctacg gcgtgcagtg cttcagccgc taccccgacc acatgaagca gcacgacttc   1140
```

```
ttcaagtccg ccatgcccga aggctacgtc caggagcgca ccatcttctt caaggacgac    1200
ggcaactaca agacccgcgc cgaggtgaag ttcgagggcg acaccctggt gaaccgcatc    1260
gagctgaagg gcatcgactt caaggaggac ggcaacatcc tggggcacaa gctggagtac    1320
aactacaaca gccacaacgt ctatatcatg gccgacaagc agaagaacgg catcaaggtg    1380
aacttcaaga tccgccacaa catcgaggac ggcagcgtgc agctcgccga ccactaccag    1440
cagaacaccc ccatcggcga cggccccgtg ctgctgcccg acaaccacta cctgagcacc    1500
cagtccgccc tgagcaaaga ccccaacgag aagcgcgatc acatggtcct gctggagttc    1560
gtgaccgccg ccgggatcac tctcggcatg gacgagctgt acaagtaa                 1608
```

<210> SEQ ID NO 105
<211> LENGTH: 527
<212> TYPE: PRT
<213> ORGANISM: Artificial Sequence
<220> FEATURE:
<223> OTHER INFORMATION: symthesized

<400> SEQUENCE: 105

```
Met His His His His His Gly Ser Tyr Asn Lys Asp Gln Gln Ser
1               5                   10                  15

Ala Phe Tyr Glu Ile Leu Asn Met Pro Asn Leu Asn Glu Glu Gln Arg
            20                  25                  30

Asn Gly Phe Ile Gln Ser Leu Lys Asp Asp Pro Ser Gln Ser Thr Asn
        35                  40                  45

Val Leu Gly Glu Ala Lys Lys Leu Asn Glu Ser Gln Ala Pro Lys Ala
    50                  55                  60

Asp Asn Gly Gly Gly Ser Gly Gly Gly Ser Gly Gly Ser Gly Gly
65                  70                  75                  80

Gly Ser Gly Gly Ser Glu Val Thr Ile Lys Val Asn Leu Ile Phe Ala
                85                  90                  95

Asp Gly Lys Ile Gln Thr Ala Glu Phe Lys Gly Thr Phe Glu Glu Ala
            100                 105                 110

Thr Ala Glu Ala Tyr Arg Tyr Ala Ala Leu Leu Ala Lys Val Asn Gly
        115                 120                 125

Glu Tyr Thr Ala Asp Leu Glu Asp Gly Gly Asn His Met Asn Ile Lys
    130                 135                 140

Phe Ala Gly Gly Gly Ser Gly Gly Tyr Asn Lys Asp Gln Gln Ser Ala
145                 150                 155                 160

Phe Tyr Glu Ile Leu Asn Met Pro Asn Leu Asn Glu Glu Gln Arg Asn
                165                 170                 175

Gly Phe Ile Gln Ser Leu Lys Asp Asp Pro Ser Gln Ser Thr Asn Val
            180                 185                 190

Leu Gly Glu Ala Lys Lys Leu Asn Glu Ser Gln Ala Pro Lys Ala Asp
        195                 200                 205

Asn Gly Gly Gly Ser Gly Gly Gly Ser Gly Gly Gly Ser Gly Gly Gly
    210                 215                 220

Ser Gly Gly Ser Glu Val Thr Ile Lys Val Asn Leu Ile Phe Ala Asp
225                 230                 235                 240

Gly Lys Ile Gln Thr Ala Glu Phe Lys Gly Thr Phe Glu Glu Ala Thr
                245                 250                 255

Ala Glu Ala Tyr Arg Tyr Ala Ala Leu Leu Ala Lys Val Asn Gly Glu
            260                 265                 270

Tyr Thr Ala Asp Leu Glu Asp Gly Gly Asn His Met Asn Ile Lys Phe
```

```
            275                 280                 285
Ala Gly Gly Gly Ser Gly Thr Met Ser Glu Leu Ile Lys Glu Asn
        290                 295                 300
Met His Met Lys Leu Tyr Met Glu Gly Thr Val Asn Asn His His Phe
305                 310                 315                 320
Lys Cys Thr Ser Glu Gly Gly Lys Pro Tyr Glu Gly Thr Gln Thr
            325                 330                 335
Met Lys Ile Lys Val Val Glu Gly Gly Pro Leu Pro Phe Ala Phe Asp
                340                 345                 350
Ile Leu Ala Thr Ser Phe Met Tyr Gly Ser Lys Ala Phe Ile Asn His
                355                 360                 365
Thr Gln Gly Ile Pro Asp Phe Phe Lys Gln Ser Phe Pro Glu Gly Phe
            370                 375                 380
Thr Trp Glu Arg Ile Thr Thr Tyr Glu Asp Gly Gly Val Leu Thr Ala
385                 390                 395                 400
Thr Gln Asp Thr Ser Phe Gln Asn Gly Cys Ile Ile Tyr Asn Val Lys
            405                 410                 415
Ile Asn Gly Val Asn Phe Pro Ser Asn Gly Pro Val Met Gln Lys Lys
                420                 425                 430
Thr Arg Gly Trp Glu Ala Asn Thr Glu Met Leu Tyr Pro Ala Asp Gly
                435                 440                 445
Gly Leu Arg Gly His Ser Gln Met Ala Leu Lys Leu Val Gly Gly Gly
            450                 455                 460
Tyr Leu His Cys Ser Phe Lys Thr Thr Tyr Arg Ser Lys Lys Pro Ala
465                 470                 475                 480
Lys Asn Leu Lys Met Pro Gly Phe His Phe Val Asp His Arg Leu Glu
                485                 490                 495
Arg Ile Lys Glu Ala Asp Lys Glu Thr Tyr Val Glu Gln His Glu Met
                500                 505                 510
Ala Val Ala Lys Tyr Cys Asp Leu Pro Ser Lys Leu Gly His Arg
            515                 520                 525

<210> SEQ ID NO 106
<211> LENGTH: 535
<212> TYPE: PRT
<213> ORGANISM: Artificial Sequence
<220> FEATURE:
<223> OTHER INFORMATION: Synthesized

<400> SEQUENCE: 106

Met His His His His His Gly Ser Tyr Asn Lys Asp Gln Gln Ser
1               5                   10                  15
Ala Phe Tyr Glu Ile Leu Asn Met Pro Asn Leu Asn Glu Gly Gln Arg
                20                  25                  30
Asn Gly Phe Ile Gln Ser Leu Lys Asp Asp Pro Ser Gln Ser Thr Asn
            35                  40                  45
Val Leu Gly Glu Ala Lys Lys Leu Asn Glu Ser Gln Ala Pro Lys Ala
        50                  55                  60
Asp Asn Gly Gly Gly Ser Gly Gly Gly Ser Gly Gly Gly Ser Gly Gly
65                  70                  75                  80
Gly Ser Gly Gly Ser Glu Val Thr Ile Lys Val Asn Leu Ile Phe Ala
                85                  90                  95
Asp Gly Lys Ile Gln Thr Ala Glu Phe Lys Gly Thr Phe Glu Glu Ala
                100                 105                 110
Thr Ala Glu Ala Tyr Arg Tyr Ala Ala Leu Leu Ala Lys Val Asn Gly
```

```
            115                 120                 125
Glu Tyr Thr Ala Asp Leu Glu Asp Gly Gly Asn His Met Asn Ile Lys
    130                 135                 140

Phe Ala Gly Gly Gly Ser Gly Gly Tyr Asn Lys Asp Gln Gln Ser Ala
145                 150                 155                 160

Phe Tyr Glu Ile Leu Asn Met Pro Asn Leu Asn Glu Glu Gln Arg Asn
                165                 170                 175

Gly Phe Ile Gln Ser Leu Lys Asp Asp Pro Ser Gln Ser Thr Asn Val
            180                 185                 190

Leu Gly Glu Ala Lys Lys Leu Asn Glu Ser Gln Ala Pro Lys Ala Asp
        195                 200                 205

Asn Gly Gly Gly Ser Gly Gly Gly Ser Gly Gly Ser Gly Gly Gly
    210                 215                 220

Ser Gly Gly Ser Glu Val Thr Ile Lys Val Asn Leu Ile Phe Ala Asp
225                 230                 235                 240

Gly Lys Ile Gln Thr Ala Glu Phe Lys Gly Thr Phe Glu Glu Ala Thr
                245                 250                 255

Ala Glu Ala Tyr Arg Tyr Ala Ala Leu Leu Ala Lys Val Asn Gly Glu
            260                 265                 270

Tyr Thr Ala Asp Leu Glu Asp Gly Gly Asn His Met Asn Ile Lys Phe
        275                 280                 285

Ala Gly Gly Gly Ser Gly Thr Met Val Ser Lys Gly Glu Glu Leu
    290                 295                 300

Phe Thr Gly Val Val Pro Ile Leu Val Glu Leu Asp Gly Asp Val Asn
305                 310                 315                 320

Gly His Lys Phe Ser Val Ser Gly Glu Gly Glu Gly Asp Ala Thr Tyr
                325                 330                 335

Gly Lys Leu Thr Leu Lys Phe Ile Cys Thr Thr Gly Lys Leu Pro Val
            340                 345                 350

Pro Trp Pro Thr Leu Val Thr Thr Leu Thr Tyr Gly Val Gln Cys Phe
        355                 360                 365

Ser Arg Tyr Pro Asp His Met Lys Gln His Asp Phe Phe Lys Ser Ala
    370                 375                 380

Met Pro Glu Gly Tyr Val Gln Glu Arg Thr Ile Phe Phe Lys Asp Asp
385                 390                 395                 400

Gly Asn Tyr Lys Thr Arg Ala Glu Val Lys Phe Glu Gly Asp Thr Leu
                405                 410                 415

Val Asn Arg Ile Glu Leu Lys Gly Ile Asp Phe Lys Glu Asp Gly Asn
            420                 425                 430

Ile Leu Gly His Lys Leu Glu Tyr Asn Tyr Asn Ser His Asn Val Tyr
        435                 440                 445

Ile Met Ala Asp Lys Gln Lys Asn Gly Ile Lys Val Asn Phe Lys Ile
    450                 455                 460

Arg His Asn Ile Glu Asp Gly Ser Val Gln Leu Ala Asp His Tyr Gln
465                 470                 475                 480

Gln Asn Thr Pro Ile Gly Asp Gly Pro Val Leu Leu Pro Asp Asn His
                485                 490                 495

Tyr Leu Ser Thr Gln Ser Ala Leu Ser Lys Asp Pro Asn Glu Lys Arg
            500                 505                 510

Asp His Met Val Leu Leu Glu Phe Val Thr Ala Ala Gly Ile Thr Leu
        515                 520                 525

Gly Met Asp Glu Leu Tyr Lys
    530                 535
```

```
<210> SEQ ID NO 107
<211> LENGTH: 249
<212> TYPE: PRT
<213> ORGANISM: Artificial Sequence
<220> FEATURE:
<223> OTHER INFORMATION: Synthesized

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Ala Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Lys Ala Ser Gly Phe Asn Ile Lys Asp Tyr Phe Met Tyr Trp Val
145                 150                 155                 160

Arg Gln Ala Pro Gly Lys Gly Leu Glu Trp Val Gly Trp Ile Asp Pro
            165                 170                 175

Glu Asn Gly Asn Thr Ile Tyr Asp Pro Lys Phe Gln Gly Arg Phe Thr
        180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Thr Arg Gly Tyr Tyr
    210                 215                 220

Gly Ser Arg Val Leu Ala Met Asp Tyr Trp Gly Gln Gly Thr Leu Val
225                 230                 235                 240

Thr Val Ser Ser Ala Ser Ala Ala Ala
                245
```